(12) United States Patent
Mautino et al.

(10) Patent No.: US 9,260,434 B2
(45) Date of Patent: Feb. 16, 2016

(54) FUSED IMIDAZOLE DERIVATIVES USEFUL AS IDO INHIBITORS

(71) Applicant: NewLink Genetics Corporation, Ames, IA (US)

(72) Inventors: Mario Mautino, Ankeny, IA (US); Sanjeev Kumar, Ames, IA (US); Jesse Waldo, Huxley, IA (US); Firoz Jaipuri, Ames, IA (US); Tanay Kesharwani, Ames, IA (US); Xiaoxia Zhang, Hayward, CA (US)

(73) Assignee: NewLink Genetics Corporation, Ames, IA (US)

( * ) Notice: Subject to any disclaimer, the term of this patent is extended or adjusted under 35 U.S.C. 154(b) by 0 days.

(21) Appl. No.: 14/053,440

(22) Filed: Oct. 14, 2013

(65) Prior Publication Data

US 2014/0066625 A1    Mar. 6, 2014

Related U.S. Application Data

(63) Continuation of application No. PCT/US2012/033245, filed on Apr. 12, 2012.

(60) Provisional application No. 61/475,788, filed on Apr. 15, 2011.

(51) Int. Cl.
*C07D 487/04* (2006.01)

(52) U.S. Cl.
CPC .................. *C07D 487/04* (2013.01)

(58) Field of Classification Search
CPC .................................. C07D 487/14
USPC ...................................... 548/428
See application file for complete search history.

(56) References Cited

U.S. PATENT DOCUMENTS

| | | |
|---|---|---|
| 7,598,287 B2 | 10/2009 | Munn |
| 7,705,022 B2 | 4/2010 | Prendergast |
| 7,714,139 B2 | 5/2010 | Prendergast |
| 8,476,454 B2 | 7/2013 | Prendergast |
| 8,846,726 B2 | 9/2014 | Combs |
| 8,951,536 B2 | 2/2015 | Combs |
| 8,993,605 B2 | 3/2015 | Combs |

FOREIGN PATENT DOCUMENTS

| | | | |
|---|---|---|---|
| WO | 2008115804 A1 | 9/2008 | |
| WO | 2009085185 A1 | 7/2009 | |
| WO | 2009/132238 A2 | 10/2009 | |
| WO | WO 2009/132238 | * 10/2009 | ........... A61K 31/538 |
| WO | 2009073620 A9 | 3/2010 | |
| WO | 2009132238 A3 | 2/2011 | |
| WO | 2011056652 A1 | 5/2011 | |
| WO | 2012142237 A8 | 10/2012 | |
| WO | 2014081689 A1 | 5/2014 | |
| WO | 2014150646 A1 | 9/2014 | |
| WO | 2014150677 A1 | 9/2014 | |
| WO | 2014159248 A1 | 10/2014 | |
| WO | 2014186035 A1 | 11/2014 | |
| WO | 2015002918 A1 | 1/2015 | |
| WO | 2015006520 A1 | 1/2015 | |
| WO | 2014141110 A3 | 4/2015 | |

OTHER PUBLICATIONS

Kumar, S. et al., "Structure based development of phenylimidazole-derived inhibitors of indoleamine 2,3-dioxygenase", Journal of Medicinal Chemistry, 2008, 51(16), 4968-4977.

* cited by examiner

*Primary Examiner* — Erich A Leeser
(74) *Attorney, Agent, or Firm* — McDonnell Boehnen Hulbert & Berghoff LLP

(57) ABSTRACT

Presently provided are IDO inhibitors and pharmaceutical compositions thereof, useful for modulating an activity of indoleamine 2,3-dioxygenase; treating indoleamine 2,3-dioxygenase (IDO) mediated immunosuppression; treating a medical conditions that benefit from the inhibition of enzymatic activity of indoleamine-2,3-dioxygenase; enhancing the effectiveness of an anti-cancer treatment comprising administering an anti-cancer agent; treating tumor-specific immunosuppression associated with cancer; and treating immunosupression associated with an infectious disease.

29 Claims, 1 Drawing Sheet

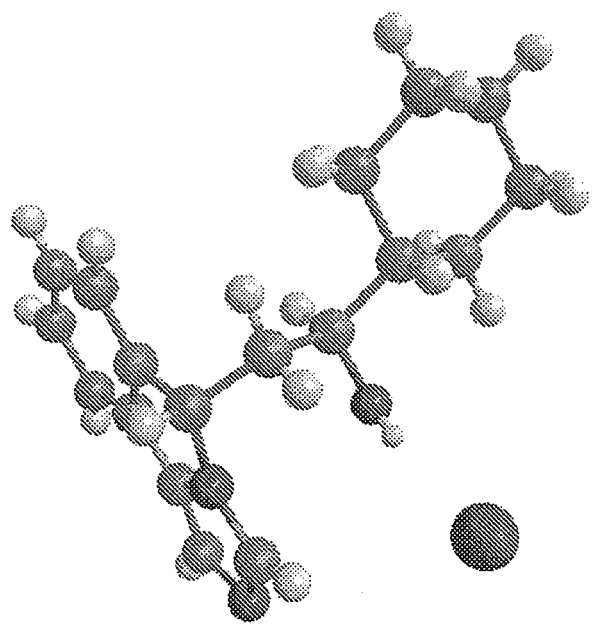

FUSED IMIDAZOLE DERIVATIVES USEFUL AS IDO INHIBITORS

CROSS-REFERENCE TO RELATED APPLICATIONS

This application is a continuation of International Application No. PCT/US2012/033245 filed Apr. 12, 2012, which claims the benefit of the filing date of U.S. Provisional Application Ser. No. 61/475,788, filed Apr. 15, 2011, which are hereby incorporated by reference in their entirety.

BACKGROUND OF THE INVENTION

1. Field of the Invention

The present disclosure relates to compounds and methods for inhibition of indoleamine 2,3-dioxygenase; further the disclosure relates to method of treatment of diseases and disorders mediated by indoleamine 2,3-dioxygenase.

2. Summary of the Related Art

Tryptophan (Trp) is an essential amino acid required for the biosynthesis of proteins, niacin and the neurotransmitter 5-hydroxytryptamine (serotonin). The enzyme indoleamine 2,3-dioxygenase (also known as INDO or IDO) catalyzes the first and rate limiting step in the degradation of L-tryptophan to N-formyl-kynurenine. In human cells, IFN-y stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process.

It has been observed that HeLa cells co-cultured with peripheral blood lymphocytes (PBLs) acquire an immunoinhibitory phenotype through up-regulation of IDO activity. A reduction in PBL proliferation upon treatment with interleukin-2 (IL-2) was believed to result from IDO released by the tumor cells in response to IFN-y secretion by the PBLs. This effect was reversed by treatment with 1-methyl-tryptophan (1MT), a specific IDO inhibitor. It was proposed that IDO activity in tumor cells may serve to impair antitumor responses (Logan, et al., 2002, Immunology, 105: 478-87).

Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. It was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol., 294: 425-35). To this end, it has recently been shown that IDO inhibition can enhance the levels of virus-specific T cells and, concomitantly, reduce the number of virally infected macrophages in a mouse model of HIV (Portula et al., 2005, Blood, 106:2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to 1MT, and a rapid, T cell-induced rejection of all allogeneic concepti was observed. Thus, by catabolizing tryptophan, the mammalian conceptus appears to suppress T-cell activity and defends itself against rejection, and blocking tryptophan catabolism during murine pregnancy allows maternal T cells to provoke fetal allograft rejection (Munn, et al., 1998, Science 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, Nature Med., 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al., 2005, Nature Med., 11:312-9).

One mechanism contributing to immunologic unresponsiveness toward tumors may be presentation of tumor antigens by tolerogenic host APCs. A subset of human IDO-expressing antigen-presenting cells (APCs) that coexpressed CD123 (IL3RA) and CCR6 and inhibited T-cell proliferation have also been described. Both mature and immature CD123-positive dendritic cells suppressed T-cell activity, and this IDO suppressive activity was blocked by 1MT (Munn, et al., 2002, Science 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, J. Clin. Invest., 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al., 2003, Trends Immunol., 24: 242-8).

Small molecule inhibitors of IDO are being developed to treat or prevent IDO-related diseases such as those described above. For example, PCT Publication WO 99/29310 reports methods for altering T cell-mediated immunity comprising altering local extracellular concentrations of tryptophan and tryptophan metabolites, using an inhibitor of IDO such as 1-methyl-DL-tryptophan, p-(3-benzofuranyl)-DL-alanine, p-[3-benzo[b]thienyl]-DL-alanine, and 6-nitro-L-tryptophan) (Munn, 1999). Reported in WO 03/087347, also published as European Patent 1501918, are methods of making antigen-presenting cells for enhancing or reducing T cell tolerance (Munn, 2003). Compounds having indoleamine-2,3-dioxygenase (IDO) inhibitory activity are further reported in WO 2004/094409; and U.S. Patent Application Publication No. 2004/0234623 is directed to methods of treating a subject with a cancer or an infection by the administration of an inhibitor of indoleamine-2,3-dioxygenase in combination with other therapeutic modalities.

In light of the experimental data indicating a role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. The compounds, compositions and methods herein help meet the current need for IDO modulators.

SUMMARY OF THE INVENTION

In one aspect, the invention comprises compounds according to the formula (I),

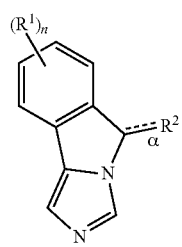
(I)

wherein $R^1$, $R^2$, n and α are each defined herein.

In another aspect, the invention comprises compounds according to the formula (II),

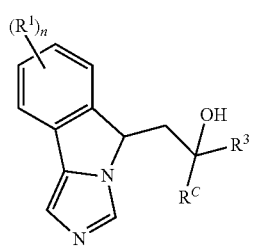
(II)

wherein $R^1$, $R^3$, $R^C$, and n are each defined herein.

In another aspect pharmaceutical compositions are provided comprising a pharmaceutically acceptable excipient, diluent, or carrier, and a compound according to formula (I) or (II).

In another aspect methods are provided for (a) modulating an activity of indoleamine 2,3-dioxygenase comprising contacting an indoleamine 2,3-dioxygenase with a modulation effective amount of a compound according to formula (I) or (II), or a pharmaceutical composition comprising a compound according to formula (I) or (II); (b) treating indoleamine 2,3-dioxygenase (IDO) mediated immunosuppression in a subject in need thereof, comprising administering an effective indoleamine 2,3-dioxygenase inhibiting amount of a compound according to formula (I) or (II), or a pharmaceutical composition comprising a compound according to formula (I) or (II); (c) treating a medical condition that benefits from the inhibition of enzymatic activity of indoleamine-2,3-dioxygenase comprising administering an effective indoleamine 2,3-dioxygenase inhibiting amount of a compound according to formula (I) or (II), or a pharmaceutical composition comprising a compound according to formula (I) or (II); (d) enhancing the effectiveness of an anti-cancer treatment comprising administering an anti-cancer agent and a compound according to formula (I) or (II), or a pharmaceutical composition comprising a compound according to formula (I) or (II); (e) treating tumor-specific immunosuppression associated with cancer comprising administering an effective indoleamine 2,3-dioxygenase inhibiting amount of a compound according to formula (I) or (II), or a pharmaceutical composition comprising a compound according to formula (I) or (II); and (f) treating immunosupression associated with an infectious disease, e.g., HIV-1 infection, comprising administering an effective indoleamine 2,3-dioxygenase inhibiting amount of a compound according to formula (I) or (II), or a pharmaceutical composition comprising a compound according to formula (I) or (II).

BRIEF DESCRIPTION OF THE DRAWINGS

FIG. 1 shows the absolute configuration of a diasteromer of the HBr salt of compound 1417 as confirmed by X-ray crystallography.

DETAILED DESCRIPTION OF THE INVENTION

In one aspect, the invention provides compounds of formula (I),

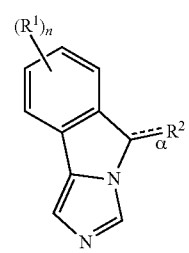
(I)

or a pharmaceutically acceptable salt thereof, wherein bond α is a single or double bond;
n is 0, 1, 2, 3, or 4;
each $R^1$ is independently halogen, cyano, nitro, $C_{1-6}$alkyl, $C_{1-6}$haloalkyl, —OR, —N(R)$_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, or —N(R)C(O)N(R)$_2$;

R$^2$ is —C$_{1-4}$alkyl-R$^A$ or —C$_{2-4}$alkenyl-R$^3$ when bond α is a single bond; and R$^2$ is =C(H)R$^A$ when bond α is a double bond;

wherein

R$^A$ is —CN, —C(O)R$^3$, —C(O)OR$^3$, —C(O)N(R$^3$)(R$^C$), —C(OR$^B$)(R$^3$)(R$^C$), —C(NHR$^B$)(R$^3$)(R$^C$), or —C(=N—OR$^C$)R$^3$, wherein R$^B$ is hydrogen, C$_{1-6}$alkyl, C$_{1-6}$haloalkyl, —C$_{1-6}$alkyl-R$^{B1}$, —C(O)R$^3$, or —S(O)$_2$R$^3$, —C(O)(CH$_2$)$_{1-4}$COOR, —C(O)CH(NH$_2$)(R$^D$), —S(O)$_2$OR$^3$, —S(O)$_2$N(R$^3$)$_2$, —CH$_2$—OP(O)$_2$(OR)$_2$, or —P(O)(OR$^3$)$_2$, wherein R$^{B1}$ is cyano, nitro, C$_{1-6}$alkyl, C$_{1-6}$haloalkyl, —OR, —N(R)$_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, or —N(R)C(O)N(R)$_2$;

R$^D$ is hydrogen, methyl, —CH(CH$_3$)$_2$, —CH$_2$CH(CH$_3$)$_2$, —CH(CH$_3$)(CH$_2$CH$_3$), benzyl, 4-hydroxybenzyl, —CH$_2$(3-indolyl), —CH$_2$SH, —CH$_2$CH$_2$SCH$_3$, —CH$_2$OH, —CH(CH$_3$)OH, —(CH$_2$)$_4$—NH$_2$, —(CH$_2$)$_3$—N(H)C(=NH)NH$_2$, —CH$_2$(4-imidazolyl), —CH$_2$COOH, —CH$_2$CH$_2$COOH, —CH$_2$CONH$_2$, —CH$_2$CH$_2$CONH$_2$;

each R$^3$ is independently hydrogen, C$_{1-6}$alkyl, C$_{1-6}$haloalkyl, aryl, heteroaryl, C$_{3-8}$cycloalkyl, C$_{3-8}$cycloalkenyl, 3-10 membered heterocyclyl, arylC$_{1-6}$alkyl-, heteroarylC$_{1-6}$alkyl-, C$_{3-8}$cycloalkylC$_{1-6}$alkyl-, C$_{3-8}$cycloalkenylC$_{1-6}$alkyl-, or (3-10 membered heterocyclyl)C$_{1-6}$alkyl-, wherein the alkyl, C$_{3-8}$cycloalkyl, C$_{3-8}$cycloalkenyl, 3-10 membered heterocyclyl, C$_{3-8}$cycloalkylC$_{1-6}$alkyl-, C$_{3-8}$cycloalkenylC$_{1-6}$alkyl-, and (3-10 membered heterocyclyl)C$_{1-6}$alkyl- are each optionally and independently substituted by one =R$^{32}$ group and each optionally substituted and independently by one, two, three, or four R$^{31}$ groups;

the aryl, heteroaryl, arylC$_{1-6}$alkyl-, and heteroarylC$_{1-6}$alkyl- groups, are each optionally substituted by one, two, three, or four R$^{31}$ groups;

wherein each R$^{31}$ is independently halogen, cyano, nitro, C$_{1-6}$alkyl, —C$_{1-6}$alkyl-R$^{33}$, C$_{1-6}$haloalkyl, —OR, —N(R)$_2$, —SR, —C(O)OR, —C(O)N(R)$_2$, —C(O)R—, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, —N(R)C(O)N(R)$_2$, wherein R$^{33}$ is cyano, —OR, —N(R)$_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, or —N(R)C(O)N(R)$_2$;

R$^{32}$ is =O, =S, =N(R), =N(OR), =C(R$^{34}$)$_2$, =(spiro-C$_{3-8}$cycloalkyl), or =(spiro-(3-10 membered heterocyclyl)), wherein each R$^{34}$ is independently hydrogen, halogen, C$_{1-6}$alkyl, C$_{1-6}$haloalkyl, C$_{3-8}$cycloalkyl, or 3-10 membered heterocyclyl;

or both R$^{34}$ taken together with the atom to which they are both attached form a monocyclic C$_{3-8}$cycloalkyl or monocyclic 3-8 membered heterocyclyl;

R$^C$ is hydrogen or C$_{1-6}$alkyl;

and each R is independently hydrogen or R$^{10}$, wherein

R$^{10}$ is C$_{1-6}$alkyl, C$_{1-6}$haloalkyl, aryl, heteroaryl, C$_{3-8}$cycloalkyl, C$_{3-8}$cycloalkenyl, 3-10 membered heterocyclyl, arylC$_{1-6}$alkyl, heteroarylC$_{1-6}$alkyl-, C$_{3-8}$cycloalkylC$_{1-6}$alkyl-, C$_{3-8}$cycloalkenylC$_{1-6}$alkyl-, or (3-10 membered heterocyclyl)C$_{1-6}$alkyl-, each R$^{10}$ optionally substituted by one, two, three, or four groups that are each independently halogen, cyano, nitro, C$_{1-6}$alkyl, C$_{1-6}$haloalkyl, —OR$^{11}$, —N(R$^{11}$)$_2$, —SR$^{11}$, —C(O)OR$^{11}$, —C(O)N(R$^{11}$)$_2$, —C(O)R$^{11}$, —S(O)R$^{11}$, —S(O)OR$^{11}$, —S(O)N(R$^{11}$)$_2$, —S(O)$_2$R$^{11}$, —S(O)$_2$OR$^{11}$, —S(O)$_2$N(R$^{11}$)$_2$, —OC(O)R$^{11}$, —OC(O)OR$^{11}$, —OC(O)N(R$^{11}$)$_2$, —N(R$^{11}$)C(O)R$^{11}$, —N(R$^{11}$)C(O)OR$^{11}$, —N(R$^{11}$)C(O)N(R$^{11}$)$_2$, wherein each R$^{11}$ is independently hydrogen or C$_{1-6}$alkyl.

In one embodiment, the compounds of formula (I) further include those compounds where, R$^B$ is additionally —C(O)N(H)R$^3$ or —C(O)(CH$_2$)$_{1-4}$(NR)COOR;

R$^3$ is additionally (heteroaryl)-(3-10 membered heterocyclyl)-;

R$^{31}$ is additionally —C(O)N(OH)R, —C(N=R$^{11}$)R, or —C(N=R$^{11}$)N(R$^{11}$)R;

R$^{34}$ is additionally cyano or —C$_{1-6}$alkyl-OR; and/or

R$^{10}$ is additionally optionally substituted by —N(R$^{11}$)S(O)$_2$R$^{11}$ or —C(O)-(3-10 membered heterocyclyl);

such compounds are referred to as compounds of formula (I').

The invention further comprises subgenera of formula (I) and formula (I') in which the substituents are selected as any and all combinations of one or more of structural formula (I), n, R$^1$, R$^2$, R$^3$, R$^A$, R$^B$, and R$^C$, as defined herein, including without limitation, the following:

Structural Formula I is One of Formulae (Ia)-(Ih):

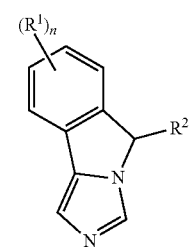

(Ia)

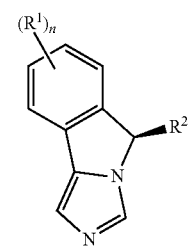

(Ib)

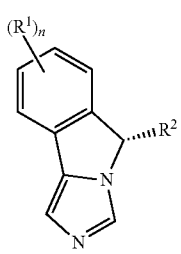
(Ic)

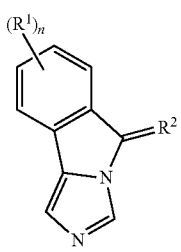
(Id)

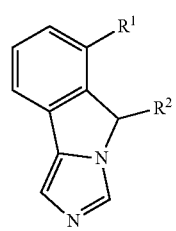
(Ie)

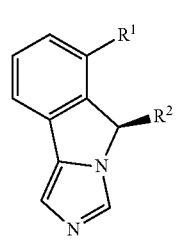
(If)

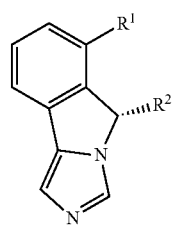
(Ig)

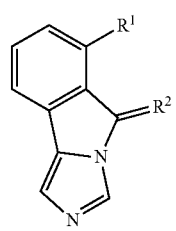
(Ih)

n and $R^1$ are Selected from One of the Following Groups (1a)-(1u):
- (1a) n is 1, 2, 3, or 4, and each $R^1$ is as defined for formula (I).
- (1b) n is 0, 1, 2, or 3, and each $R^1$ is as defined for formula (I).
- (1c) n is 0, 1, or 2 and each $R^1$ is as defined for formula (I).
- (1d) n is 0, 1, or 2 and each $R^1$ is independently halogen, —OR, —N(R)$_2$, or —SR.
- (1e) n is 0, 1, or 2 and each $R^1$ is independently halogen, —OR$^O$, —N(R$^O$)$_2$, or —SR$^O$, wherein each $R^O$ is independently hydrogen or $C_{1-6}$alkyl.
- (1f) n is 0, 1, or 2 and each $R^1$ is independently fluoro, chloro, hydroxy, or methoxy.
- (1g) n is 0, 1, or 2 and each $R^1$ is independently halogen.
- (1h) n is 0, 1, or 2 and each $R^1$ is independently fluoro or chloro.
- (1i) n is 0 or 1 and $R^1$ is as defined for formula (I).
- (1j) n is 0 or 1 and $R^1$ is halogen, —OR, —N(R)$_2$, or —SR.
- (1k) n is 0 or 1 and $R^1$ is halogen, —OR$^O$, —N(R$^O$)$_2$, or —SR; wherein each $R^O$ is independently hydrogen or $C_{1-6}$alkyl.
- (1l) n is 0 or 1 and $R^1$ is fluoro, chloro, hydroxy, or methoxy.
- (1m) n is 0 or 1 and $R^1$ is halogen.
- (1n) n is 0 or 1 and $R^1$ is fluoro or chloro.
- (1o) n is 1 and $R^1$ is as defined for formula (I).
- (1p) n is 1 and $R^1$ is halogen, —OR, —N(R)$_2$, or —SR;
- (1q) n is 1 and $R^1$ is halogen, —OR$^O$, —N(R$^O$)$_2$, or —SR$^O$; wherein each $R^O$ is independently hydrogen or $C_{1-6}$alkyl.
- (1r) n is 1 and $R^1$ is fluoro, chloro, hydroxy, or methoxy.
- (1s) n is 1 and $R^1$ is halogen.
- (1t) n is 1 and $R^1$ is fluoro or chloro.
- (1u) n is 0.

$R^2$ is Selected from One of the Following Groups (2a)-(2l):
- (2a) $R^2$ is —$C_{1-4}$alkyl-$R^A$.
- (2b) $R^2$ is —$C_{1-2}$alkyl-$R^A$.
- (2c) $R^2$ is —C(H)=C(H)$R^3$.
- (2d) $R^2$ is —C(H)=C(H)$R^{30}$, wherein $R^{30}$ is phenyl optionally substituted by one, two, three, or four $R^{31}$ groups.
- (2e) $R^2$ is —C(H)=C(H)$R^{30}$, wherein $R^{30}$ is phenyl optionally substituted by one or two $R^{31}$ groups.
- (2f) $R^2$ is —CH$_2$—$R^A$, —CH$_2$CH$_2$—$R^A$, —C(H)(CH$_3$)CH$_2$—$R^A$, or —C(H)=C(H)$R^3$.
- (2g) $R^2$ is —CH$_2$—$R^A$, —CH$_2$CH$_2$—$R^A$, or —C(H)(CH$_3$)CH$_2$—$R^A$.
- (2h) $R^2$ is —CH$_2$—$R^A$, —CH$_2$CH$_2$—RA, or —C(H)=C(H)$R^3$.
- (2i) $R^2$ is —CH$_2$—$R^A$.
- (2j) $R^2$ is —CH$_2$CH$_2$—$R^A$.
- (2k) $R^2$ is —C(H)(CH$_3$)CH$_2$—$R^A$.
- (2l) $R^2$ is —CH$_2$—$R^A$, —CH$_2$CH$_2$—$R^A$, or —C(H)=C(H)$R^3$.

$R^a$ is Selected from One of the Following Groups (3a)-(3n):
- (3a) $R^A$ is —CN, —C(O)OR$^3$, or —C(O)N(R$^3$)(R$^C$).
- (3b) $R^A$ is —C(O)R$^3$ or —C(OR$^B$)(R$^3$)(R$^C$).
- (3c) $R^A$ is —C(NHR$^B$)(R$^3$)(R$^C$), or —C(=N—OR$^C$)R$^3$.
- (3d) $R^A$ is —C(NHR$^B$)(R$^3$)(R$^C$), wherein $R^B$ is hydrogen, $C_{1-6}$alkyl, or —C(O)$C_{1-6}$alkyl.
- (3e) $R^A$ is —C(NH$_2$)(R$^3$)(R$^C$).
- (3f) $R^A$ is —C(O)OR$^3$.
- (3g) $R^A$ is —C(O)N(R$^3$)(R$^C$).
- (3h) $R^A$ is —C(O)R$^3$.
- (3i) $R^A$ is —C(OR$^B$)(R$^3$)(R$^C$).
- (3j) $R^A$ is —C(OH)(R$^3$)(R$^C$).
- (3k) $R^A$ is —CH(OH)(R$^3$).
- (3l) $R^A$ is —CN, —C(O)R$^3$, —C(O)OR$^3$, —C(O)N(R$^3$)(R$^C$), —C(OR$^B$)(R$^3$)(R), —C(NHR$^B$)(R$^3$)(R$^C$), or —C(=N—OR$^C$)R$^3$.
- (3m) $R^A$ is —C(O)R$^3$ or —C(OR$^B$)(R$^3$)(R$^C$), wherein $R^B$ is hydrogen and $R^C$ is hydrogen or $C_{1-6}$alkyl.
- (3n) $R^A$ is —C(OR$^B$)(R$^3$)(R$^C$), wherein $R^B$ is hydrogen and $R^C$ is hydrogen or $C_{1-6}$alkyl.

$R^B$ is Selected from One of the Following Groups (4a)-(4k):

(4a) $R^B$ is hydrogen, $C_{1-6}$alkyl, $C_{1-6}$haloalkyl, —$C_{1-6}$alkyl-$R^B1$, —C(O)(CH$_2$)$_{1-4}$COOR$^{B2}$, —C(O)C(NH$_2$)R$^D$, —P(O$_3$)(R$^{B2}$)$_2$, —CH$_2$—OP(O)$_2$(OR)$_2$, wherein R$^D$ is the side chain of natural alpha amino acids, —C(O)R$^3$, or —S(O)$_2$R$^3$, wherein R$^{B1}$ is cyano, nitro, $C_{1-6}$alkyl, $C_{1-6}$haloalkyl, —OR$^{B2}$, —N(R$^{B2}$)$_2$, —SR$^{B2}$, —C(O)OR$^{B2}$, —C(O)N(R$^{B2}$)$_2$, —C(O)R$^{B2}$, —S(O)R$^{B2}$, —S(O)OR$^{B2}$, —S(O)N(R$^{B2}$)$_2$, —S(O)$_2$R$^{B2}$, —S(O)$_2$OR$^{B2}$, —S(O)$_2$N(R$^{B2}$)$_2$, —OC(O)R$^{B2}$, —OC(O)OR$^{B2}$, —OC(O)N(R$^{B2}$)$_2$, —N(R$^{B2}$)C(O)R$^{B2}$, —N(R$^{B2}$)C(O)OR$^2$, or —N(R$^{B2}$)C(O)N(R$^{B2}$)$_2$, wherein each R$^{B2}$ is independently hydrogen or $C_{1-6}$alkyl.

(4b) $R^B$ is hydrogen, $C_{1-6}$alkyl, $C_{1-6}$haloalkyl, —$C_{1-6}$alkyl-$R^{11}$, —C(O)R$^3$, or —S(O)$_2$R$^3$, wherein R$^B1$ is cyano, nitro, $C_{1-6}$alkyl, $C_{1-6}$haloalkyl, —OR$^{B2}$, —N(R$^{B2}$)$_2$, —SR$^{B2}$, —C(O)OR$^{B2}$, —C(O)N(R$^{B2}$)$_2$, —C(O)R$^{B2}$, —S(O)R$^{B2}$, —S(O)OR$^{B2}$, —S(O)N(R$^{B2}$)$_2$, —S(O)$_2$R$^{B2}$, —S(O)$_2$OR$^{B2}$, —S(O)$_2$N(R$^{B2}$)$_2$, —OC(O)R$^{B2}$, —OC(O)OR$^{B2}$, —OC(O)N(R$^{B2}$)$_2$, —N(R$^{B2}$)C(O)R$^{B2}$, —N(R$^{B2}$)C(O)OR, or —N(R$^{B2}$)C(O)N(R$^{B2}$)$_2$, wherein each R$^{B2}$ is independently hydrogen or $C_{1-6}$alkyl.

(4c) $R^B$ is hydrogen, $C_{1-6}$alkyl, $C_{1-6}$haloalkyl, or —$C_{1-6}$alkyl-$R^{B1}$, wherein R$^{B1}$ is cyano, nitro, $C_{1-6}$alkyl, $C_{1-6}$haloalkyl, —OR$^{B2}$, —N(R$^B$)$_2$, —SR$^{B2}$, —C(O)OR$^{B2}$, —C(O)N(R$^{B2}$)$_2$, —C(O)R$^{B2}$, —S(O)R$^{B2}$, —S(O)OR$^{B2}$, —S(O)N(R$^{B2}$)$_2$, —S(O)$_2$R$^{B2}$, —S(O)$_2$OR$^{B2}$, —S(O)$_2$N(R$^{B2}$)$_2$, —OC(O)R$^{B2}$, —OC(O)OR$^{B2}$, —OC(O)N(R$^2$)$_2$, —N(R$^{B2}$)C(O)R$^{B2}$, —N(R$^{B2}$)C(O)OR$^{B2}$, or —N(R$^2$)C(O)N(R$^{B2}$)$_2$, wherein each R$^{B2}$ is independently hydrogen or $C_{1-6}$alkyl.

(4d) $R^B$ is hydrogen, $C_{1-6}$alkyl, $C_{1-6}$haloalkyl, or —$C_{1-6}$alkyl-$R^{B1}$, wherein R$^{B1}$ is cyano, —C(O)OR$^{B2}$, —C(O)N(R$^2$)$_2$, —C(O)R$^{B2}$, —S(O)$_2$R$^{B2}$, —S(O)$_2$OR$^2$, or —S(O)$_2$N(R$^{B2}$)$_2$, wherein each R$^{B2}$ is independently hydrogen or $C_{1-6}$alkyl.

(4e) $R^B$ is —$C_{1-6}$alkyl-$R^{B1}$, wherein R$^{B1}$ is cyano, —C(O)OR$^{B2}$, —C(O)N(R$^{B2}$)$_2$, —C(O)R$^2$, —S(O)$_2$R$^{B2}$, —S(O)$_2$OR$^{B2}$, or —S(O)$_2$N(R$^{B2}$)$_2$, wherein each R$^{B2}$ is independently hydrogen or $C_{1-6}$alkyl.

(4f) $R^B$ is hydrogen, $C_{1-6}$alkyl, $C_{1-6}$haloalkyl, —$C_{1-6}$alkyl-$R^{B1}$, —C(O)R$^{B2}$, or —S(O)$_2$R$^{B2}$, wherein R$^{B1}$ is —C(O)OR$^{B3}$, —C(O)N(R$^{B3}$)$_2$, —S(O)$_2$OR$^{B3}$, or —S(O)$_2$N(R$^3$)$_2$, R$^{B2}$ is $C_{1-6}$ alkyl; and R$^{B3}$ is hydrogen or $C_{1-6}$alkyl.

(4g) $R^B$ is hydrogen, $C_{1-6}$alkyl, or $C_{1-6}$haloalkyl.

(4h) $R^B$ is hydrogen or $C_{1-6}$alkyl;

(4i) $R^B$ is hydrogen.

(4j) $R^B$ is $C_{1-6}$alkyl.

(4k) $R^B$ is hydrogen, —C(O)R$^{12}$, —C(O)(CH$_2$)$_{1-4}$COOR$^{B2}$, —C(O)C(NH$_2$)RD, —P(O)(OR$^{B2}$)$_2$, —CH$_2$—OP(O)$_2$(OR)$_2$, —S(O)$_2$R$^{B2}$, —C(O)N(R$^{B2}$)$_2$, —S(O)$_2$OR$^{B2}$, —S(O)$_2$N(R$^3$)$_2$, wherein and R$^{B2}$ is hydrogen or $C_{1-6}$alkyl.

$R^C$ is Selected from One of the Following Groups (5a)-(5g):

(5a) $R^C$ is hydrogen or $C_{1-4}$alkyl.

(5b) $R^C$ is hydrogen or $C_{1-2}$alkyl.

(5c) $R^C$ is hydrogen or methyl.

(5d) $R^C$ is hydrogen.

(5e) $R^C$ is $C_{1-6}$alkyl.

(5f) $R^C$ is $C_{1-4}$alkyl.

(5g) $R^C$ is methyl.

$R^3$ is Selected from One of the Following Groups (6a)-(6z):

(6a) $R^3$ is hydrogen, $C_{1-6}$alkyl, aryl, heteroaryl, $C_{3-8}$cycloalkyl, $C_{3-8}$cycloalkenyl, 3-10 membered heterocyclyl, or $C_{3-8}$cycloalkyl$C_{1-6}$alkyl-, wherein the $C_{1-6}$alkyl, $C_{3-8}$cycloalkyl, $C_{3-8}$cycloalkenyl, 3-10 membered heterocyclyl, and $C_{3-8}$cycloalkyl$C_{1-6}$alkyl-, are each optionally substituted by one =R$^{32}$ group and one or two R$^{31}$ groups; and the aryl and heteroaryl groups, are each optionally substituted by one or two R$^{31}$ groups.

(6b) $R^3$ is aryl, heteroaryl, $C_{3-8}$cycloalkyl, $C_{3-8}$cycloalkenyl, 3-10 membered heterocyclyl, or $C_{3-8}$cycloalkyl$C_{1-6}$ alkyl-, wherein the $C_{3-8}$cycloalkyl, $C_{3-8}$cycloalkenyl, 3-10 membered heterocyclyl, and $C_{3-8}$cycloalkyl$C_{1-6}$alkyl-, are each optionally and independently substituted by one =R$^{32}$ group and each optionally and independently substituted by one or two R$^{31}$ groups; and the aryl and heteroaryl groups, are each optionally substituted by one or two R$^{31}$ groups.

(6c) $R^3$ is phenyl, a five or six membered heteroaryl, monocyclic $C_{5-8}$cycloalkyl, monocyclic $C_{5-8}$cycloalkenyl, a five or six membered monocyclic heterocyclyl, or (monocyclic $C_{5-8}$cycloalkyl)$C_{1-6}$ alkyl-, wherein the $C_{5-8}$cycloalkyl, $C_{5-8}$cycloalkenyl, 5-6 membered heterocyclyl, and $C_{5-8}$cycloalkyl$C_{1-6}$alkyl-, are each optionally and independently substituted by one =R$^{32}$ group and each optionally and independently substituted by one or two R$^{31}$ groups; and the phenyl and heteroaryl groups, are each optionally substituted by one or two R$^{31}$ groups.

(6d) $R^3$ is phenyl or a five or six membered heteroaryl, each optionally substituted by one or two R$^{31}$ groups.

(6e) $R^3$ is monocyclic $C_{5-8}$cycloalkyl, monocyclic $C_{5-8}$cycloalkenyl, a five or six membered monocyclic heterocyclyl, or (monocyclic $C_{5-8}$cycloalkyl)$C_{1-6}$alkyl-, each optionally substituted by one =R$^{32}$ group and one or two R$^{31}$ groups.

(6f) $R^3$ is

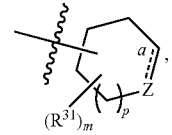

wherein bond a is a single bond or a double bond; m is 0, 1, or 2; p is 0 or 1; and wherein when bond a is a single bond, then Z is —C(R$^{36}$)$_2$—, —C(=R$^{32}$)—, —N(R$^{35}$)—, or —O—, wherein each R$^{36}$ is independently hydrogen or R$^{31}$; and R$^{35}$ is hydrogen, $C_{1-6}$alkyl, —C(O)R, —S(O)$_2$R, —C(O)OR, —C(O)N(R)$_2$, —S(O)$_2$OR, or —S(O)$_2$N(R)$_2$;

and when bond a is a double bond, then Z is —C(R$^{36}$)= or —N=.

(6g) $R^3$ is

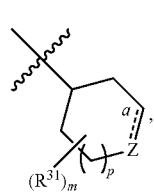

wherein bond a is a single bond or a double bond; m is 0, 1, or 2; p is 0 or 1; and wherein when bond a is a single bond, then Z is —C(R$^{36}$)$_2$—, —C(=R$^{32}$)—, —N(R$^{35}$)—, or —O—, wherein each R$^{36}$ is independently hydrogen or R$^{31}$; and $R^{35}$ is hydrogen, $C_{1-6}$alkyl, —C(O)R, —S(O)$_2$R, —C(O)OR, —C(O)N(R)$_2$, —S(O)$_2$OR, or —S(O)$_2$N(R)$_2$;

and when bond a is a double bond, then Z is —C(R$^{36}$)= or —N=.

(6h) As group (6g), wherein when bond a is a single bond, then Z is —C(R$^{36}$)$_2$— or —C(=R$^{32}$)—; and when bond a is a double bond, then Z is —C(R$^{36}$)= or —N=.

(6i) As group (6g), wherein m is 0; when bond a is a single bond, then Z is —C(R$^{36}$)$_2$— or —C(=R$^{32}$)—; and when bond a is a double bond, then Z is —C(R$^{36}$)= or —N=.

(6j) As group (6g), wherein bond a is a single bond; and Z is —C(R$^{36}$)$_2$— or —C(=R$^{32}$)—.

(6k) As group (6g), wherein bond a is a single bond; and Z is —C(R$^{36}$)$_2$—.

(6l) As group (6g), wherein bond a is a single bond; and Z is —C(=R$^{32}$)—.

(6m) As group (6g), wherein m is 0; bond a is a single bond; and Z is —C(R$^{36}$)$_2$— or —C(=R$^{32}$)—.

(6n) As group (6g), wherein m is 0; bond a is a single bond; and Z is —C(R$^{36}$)$_2$—.

(6o) As group (6g), wherein m is 0; bond a is a single bond; and Z is —C(=R$^{32}$)—.

(6p) As group (6g), wherein bond a is a single bond; and Z is —C(R$^{36}$)$_2$— or —C(=R$^{32}$)—, wherein each R$^{36}$ is independently hydrogen, halogen, $C_{1-6}$alkyl, —$C_{1-6}$alkyl-OH, $C_{1-6}$haloalkyl, or —OH, wherein
R$^{32}$ is =O, =C(R$^{34}$)$_2$, =(spiro-$C_{3-8}$cycloalkyl), or =(spiro-(3-8 membered heterocyclyl)), wherein each R$^{34}$ is independently hydrogen, halogen, $C_{1-6}$alkyl, $C_{1-6}$haloalkyl, $C_{3-8}$cycloalkyl, or 3-8 membered heterocyclyl.

(6q) As group (6g), wherein m is 0; bond a is a single bond; and Z is —C(R$^{36}$)$_2$— or —C(=R$^{32}$)—, wherein each R$^{36}$ is independently hydrogen, halogen, $C_{1-6}$alkyl, —$C_{1-6}$alkyl-OH, $C_{1-6}$haloalkyl, or —OH, wherein
R$^{32}$ is =O, =C(R$^{34}$)$_2$, =(spiro-$C_{3-8}$cycloalkyl), or =(spiro-(3-8 membered heterocyclyl)), wherein each R$^{34}$ is independently hydrogen, halogen, $C_{1-6}$alkyl, $C_{1-6}$haloalkyl, $C_{3-8}$cycloalkyl, or 3-8 membered heterocyclyl.

(6r) As group (6g), wherein bond a is a single bond; and Z is —N(R$^{35}$)— or —O—.

(6s) R$^3$ is hydrogen, $C_{1-6}$alkyl, aryl, heteroaryl, $C_{3-8}$cycloalkyl, $C_{3-8}$cycloalkenyl, 3-10 membered heterocyclyl, or $C_{3-8}$cycloalkyl$C_{1-6}$alkyl, wherein
the $C_{1-6}$alkyl, $C_{3-8}$cycloalkyl, $C_{3-8}$cycloalkenyl, 3-10 membered heterocyclyl, and $C_{3-8}$cycloalkyl$C_{1-6}$alkyl, are each optionally substituted by one =R$^{32}$ group and one or two R$^{31}$ groups;
the aryl and heteroaryl groups, are each optionally substituted by one or two R$^{31}$ groups; wherein
each R$^{31}$ is independently halogen, cyano, nitro, $C_{1-6}$alkyl, —$C_{1-6}$alkyl-R$^{33}$, $C_{1-6}$haloalkyl, —OR, —N(R)$_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, —N(R)C(O)N(R)$_2$, wherein R$^{33}$ is —OR, —N(R)$_2$, or —SR; and
R$^{32}$ is oxo, =C(R$^{34}$)$_2$, =(spiro-$C_{3-8}$cycloalkyl), or =(spiro-(3-10 membered heterocyclyl)), wherein each R$^{34}$ is independently hydrogen, halogen, $C_{1-6}$alkyl, or $C_{3-8}$cycloalkyl.

(6t) R$^3$ is hydrogen, $C_{1-6}$alkyl, aryl, heteroaryl, $C_{3-8}$cycloalkyl, $C_{3-8}$cycloalkenyl, 3-10 membered heterocyclyl, or $C_{3-8}$cycloalkyl$C_{1-6}$alkyl-, wherein
the $C_{1-6}$alkyl, $C_{3-8}$cycloalkyl, $C_{3-8}$cycloalkenyl, 3-10 membered heterocyclyl, and $C_{3-8}$cycloalkyl$C_{1-6}$alkyl-, are each optionally and independently substituted by one =R$^{32}$ group and each optionally and independently substituted by one or two R$^{31}$ groups;
the aryl and heteroaryl groups, are each optionally substituted by one or two R$^{31}$ groups;
wherein
each R$^{31}$ is independently halogen, cyano, nitro, $C_{1-6}$alkyl, —$C_{1-6}$alkyl-R$^{33}$, $C_{1-6}$haloalkyl, —OR, —N(R)$_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, —N(R)C(O)N(R)$_2$, wherein R$^{33}$ is —OR, —N(R)$_2$, or —SR;
and
R$^{32}$ is oxo, =C(R$^{34}$)$_2$, =(spiro-$C_{3-8}$cycloalkyl), or =(spiro-(3-10 membered heterocyclyl)), wherein each R$^{34}$ is independently hydrogen, halogen, $C_{1-6}$alkyl, or $C_{3-8}$cycloalkyl.

(6u) R$^3$ is aryl, heteroaryl, $C_{3-8}$cycloalkyl, $C_{3-8}$cycloalkenyl, or 3-10 membered heterocyclyl, wherein the $C_{3-8}$cycloalkyl, $C_{3-8}$cycloalkenyl, and 3-10 membered heterocyclyl are each optionally substituted by one =R$^{32}$ group and one, two, three, or four R$^{31}$ groups; and the aryl and heteroaryl are each optionally substituted by one, two, three, or four R$^{31}$ groups.

(6v) R$^3$ is phenyl, cyclopentyl, cyclohexyl, cyclohexenyl, furanyl, tetrahydropyranyl, piperidinyl, imidazolyl, thiazolyl, each optionally substituted by one, two, three, or four R$^{31}$ groups, and wherein the cyclopentyl, cyclohexyl, cyclohexenyl, andy piperidinyl groups are each optionally substituted by one =R$^{32}$ group.

(6w) R$^3$ is phenyl, cyclopentyl, cyclohexyl, cyclohex-1-en-1-yl, cyclohex-3-en-1-yl, furan-2-yl, furan-3-yl, tetrahydropyran-3-yl, tetrahydropyran-4-yl, piperidin-3-yl, piperidin-4-yl, imidazol-2-yl, imidazol-4-yl, thiazol-2-yl, thiazol-4-yl, thiazol-5-yl, each optionally substituted by one or two R$^{31}$ groups, and wherein the cyclopentyl, cyclohexyl, cyclohexenyl, andy piperidinyl groups are each optionally substituted by one =R$^{32}$ group.

(6x) Any one of groups (6a)-(6w), wherein each R is independently hydrogen, $C_{1-6}$alkyl, $C_{1-6}$haloalkyl, aryl, heteroaryl, $C_{3-8}$cycloalkyl, $C_{3-8}$cycloalkenyl, 3-10 membered heterocyclyl, aryl$C_{1-6}$alkyl, heteroaryl$C_{1-6}$alkyl-, $C_{3-8}$cycloalkyl$C_{1-6}$alkyl-, $C_{3-8}$cycloalkenyl$C_{1-6}$alkyl-, or (3-10 membered heterocyclyl)$C_{1-6}$alkyl-.

(6y) Any one of groups (6a)-(6w), wherein each R is independently hydrogen, $C_{1-6}$alkyl, $C_{1-6}$haloalkyl, phenyl, 5- or 6-membered heteroaryl, $C_{3-8}$cycloalkyl, $C_{3-8}$cycloalkenyl, 3-8 membered heterocyclyl, benzyl, (5- or 6-membered heteroaryl)$C_{1-6}$alkyl-, $C_{3-8}$ cycloalkyl$C_{1-6}$alkyl-, $C_{3-8}$cycloalkenyl$C_{1-6}$alkyl-, or (3-8 membered heterocyclyl)$C_{1-6}$alkyl-.

(6z) Any one of groups (6a)-(6w), wherein each R is independently hydrogen or $C_{1-6}$alkyl.

Particular embodiments of this aspect of the invention include compounds of any one of the formulae (I), (I'), and (Ia)-(Id), each as defined in each of the following rows, wherein each entry is a group number as defined above (e.g., (1s) refers to n is 1 and each R$^1$ is halogen), and a dash "-" indicates that the variable is as defined for formula (I) or (I')

or defined according to any one of the applicable variable definitions (1a)-(6z) [e.g., when $R^C$ is a dash, it can be either as defined for Formula (I) or (I') or any one of definitions (5a)-(5g)]:

| | n & $R^1$ | $R^2$ | $R^4$ | $R^3$ |
|---|---|---|---|---|
| (1)-1 | 1e | 2b | 3h | 6c |
| (1)-2 | 1f | 2b | 3h | 6c |
| (1)-3 | 1k | 2b | 3h | 6c |
| (1)-4 | 1l | 2b | 3h | 6c |
| (1)-5 | 1m | 2b | 3h | 6c |
| (1)-6 | 1n | 2b | 3h | 6c |
| (1)-7 | 1u | 2b | 3h | 6c |
| (1)-8 | 1e | 2b | 3h | 6f |
| (1)-9 | 1f | 2b | 3h | 6f |
| (1)-10 | 1k | 2b | 3h | 6f |
| (1)-11 | 1l | 2b | 3h | 6f |
| (1)-12 | 1m | 2b | 3h | 6f |
| (1)-13 | 1n | 2b | 3h | 6f |
| (1)-14 | 1u | 2b | 3h | 6f |
| (1)-15 | 1e | 2b | 3h | 6y |
| (1)-16 | 1f | 2b | 3h | 6y |
| (1)-17 | 1k | 2b | 3h | 6y |
| (1)-18 | 1l | 2b | 3h | 6y |
| (1)-19 | 1m | 2b | 3h | 6y |
| (1)-20 | 1n | 2b | 3h | 6y |
| (1)-21 | 1u | 2b | 3h | 6y |
| (1)-22 | 1e | 2b | 3i | 6c |
| (1)-23 | 1f | 2b | 3i | 6c |
| (1)-24 | 1k | 2b | 3i | 6c |
| (1)-25 | 1l | 2b | 3i | 6c |
| (1)-26 | 1m | 2b | 3i | 6c |
| (1)-27 | 1n | 2b | 3i | 6c |
| (1)-28 | 1u | 2b | 3i | 6c |
| (1)-29 | 1e | 2b | 3i | 6f |
| (1)-30 | 1f | 2b | 3i | 6f |
| (1)-31 | 1k | 2b | 3i | 6f |
| (1)-32 | 1l | 2b | 3i | 6f |
| (1)-33 | 1m | 2b | 3i | 6f |
| (1)-34 | 1n | 2b | 3i | 6f |
| (1)-35 | 1u | 2b | 3i | 6f |
| (1)-36 | 1e | 2b | 3i | 6y |
| (1)-37 | 1f | 2b | 3i | 6y |
| (1)-38 | 1k | 2b | 3i | 6y |
| (1)-39 | 1l | 2b | 3i | 6y |
| (1)-40 | 1m | 2b | 3i | 6y |
| (1)-41 | 1n | 2b | 3i | 6y |
| (1)-42 | 1u | 2b | 3i | 6y |
| (1)-43 | 1e | 2b | 3k | 6c |
| (1)-44 | 1f | 2b | 3k | 6c |
| (1)-45 | 1k | 2b | 3k | 6c |
| (1)-46 | 1l | 2b | 3k | 6c |
| (1)-47 | 1m | 2b | 3k | 6c |
| (1)-48 | 1n | 2b | 3k | 6c |
| (1)-49 | 1u | 2b | 3k | 6c |
| (1)-50 | 1e | 2b | 3k | 6f |
| (1)-51 | 1f | 2b | 3k | 6f |
| (1)-52 | 1k | 2b | 3k | 6f |
| (1)-53 | 1l | 2b | 3k | 6f |
| (1)-54 | 1m | 2b | 3k | 6f |
| (1)-55 | 1n | 2b | 3k | 6f |
| (1)-56 | 1u | 2b | 3k | 6f |
| (1)-57 | 1e | 2b | 3k | 6y |
| (1)-58 | 1f | 2b | 3k | 6y |
| (1)-59 | 1k | 2b | 3k | 6y |
| (1)-60 | 1l | 2b | 3k | 6y |
| (1)-61 | 1m | 2b | 3k | 6y |
| (1)-62 | 1n | 2b | 3k | 6y |
| (1)-63 | 1u | 2b | 3k | 6y |
| (1)-64 | 1e | 2i | 3h | 6c |
| (1)-65 | 1f | 2i | 3h | 6c |
| (1)-66 | 1k | 2i | 3h | 6c |
| (1)-67 | 1l | 2i | 3h | 6c |
| (1)-68 | 1m | 2i | 3h | 6c |
| (1)-69 | 1n | 2i | 3h | 6c |
| (1)-70 | 1u | 2i | 3h | 6c |
| (1)-71 | 1e | 2i | 3h | 6f |
| (1)-72 | 1f | 2i | 3h | 6f |
| (1)-73 | 1k | 2i | 3h | 6f |
| (1)-74 | 1l | 2i | 3h | 6f |
| (1)-75 | 1m | 2i | 3h | 6f |
| (1)-76 | 1n | 2i | 3h | 6f |
| (1)-77 | 1u | 2i | 3h | 6f |
| (1)-78 | 1e | 2i | 3h | 6y |
| (1)-79 | 1f | 2i | 3h | 6y |
| (1)-80 | 1k | 2i | 3h | 6y |
| (1)-81 | 1l | 2i | 3h | 6y |
| (1)-82 | 1m | 2i | 3h | 6y |
| (1)-83 | 1n | 2i | 3h | 6y |
| (1)-84 | 1u | 2i | 3h | 6y |
| (1)-85 | 1e | 2i | 3i | 6c |
| (1)-86 | 1f | 2i | 3i | 6c |
| (1)-87 | 1k | 2i | 3i | 6c |
| (1)-88 | 1l | 2i | 3i | 6c |
| (1)-89 | 1m | 2i | 3i | 6c |
| (1)-90 | 1n | 2i | 3i | 6c |
| (1)-91 | 1u | 2i | 3i | 6c |
| (1)-92 | 1e | 2i | 3i | 6f |
| (1)-93 | 1f | 2i | 3i | 6f |
| (1)-94 | 1k | 2i | 3i | 6f |
| (1)-95 | 1l | 2i | 3i | 6f |
| (1)-96 | 1m | 2i | 3i | 6f |
| (1)-97 | 1n | 2i | 3i | 6f |
| (1)-98 | 1u | 2i | 3i | 6f |
| (1)-99 | 1e | 2i | 3i | 6y |
| (1)-100 | 1f | 2i | 3i | 6y |
| (1)-101 | 1k | 2i | 3i | 6y |
| (1)-102 | 1l | 2i | 3i | 6y |
| (1)-103 | 1m | 2i | 3i | 6y |
| (1)-104 | 1n | 2i | 3i | 6y |
| (1)-105 | 1u | 2i | 3i | 6y |
| (1)-106 | 1e | 2i | 3k | 6c |
| (1)-107 | 1f | 2i | 3k | 6c |
| (1)-108 | 1k | 2i | 3k | 6c |
| (1)-109 | 1l | 2i | 3k | 6c |
| (1)-110 | 1m | 2i | 3k | 6c |
| (1)-111 | 1n | 2i | 3k | 6c |
| (1)-112 | 1u | 2i | 3k | 6c |
| (1)-113 | 1e | 2i | 3k | 6f |
| (1)-114 | 1f | 2i | 3k | 6f |
| (1)-115 | 1k | 2i | 3k | 6f |
| (1)-116 | 1l | 2i | 3k | 6f |
| (1)-117 | 1m | 2i | 3k | 6f |
| (1)-118 | 1n | 2i | 3k | 6f |
| (1)-119 | 1u | 2i | 3k | 6f |
| (1)-120 | 1e | 2i | 3k | 6y |
| (1)-121 | 1f | 2i | 3k | 6y |
| (1)-122 | 1k | 2i | 3k | 6y |
| (1)-123 | 1l | 2i | 3k | 6y |
| (1)-124 | 1m | 2i | 3k | 6y |
| (1)-125 | 1n | 2i | 3k | 6y |
| (1)-126 | 1u | 2i | 3k | 6y |
| (1)-127 | 1e | 2j | 3h | 6c |
| (1)-128 | 1f | 2j | 3h | 6c |
| (1)-129 | 1k | 2j | 3h | 6c |
| (1)-130 | 1l | 2j | 3h | 6c |
| (1)-131 | 1m | 2j | 3h | 6c |
| (1)-132 | 1n | 2j | 3h | 6c |
| (1)-133 | 1u | 2j | 3h | 6c |
| (1)-134 | 1e | 2j | 3h | 6f |
| (1)-135 | 1f | 2j | 3h | 6f |
| (1)-136 | 1k | 2j | 3h | 6f |
| (1)-137 | 1l | 2j | 3h | 6f |
| (1)-138 | 1m | 2j | 3h | 6f |
| (1)-139 | 1n | 2j | 3h | 6f |
| (1)-140 | 1u | 2j | 3h | 6f |
| (1)-141 | 1e | 2j | 3h | 6y |
| (1)-142 | 1f | 2j | 3h | 6y |
| (1)-143 | 1k | 2j | 3h | 6y |
| (1)-144 | 1l | 2j | 3h | 6y |
| (1)-145 | 1m | 2j | 3h | 6y |
| (1)-146 | 1n | 2j | 3h | 6y |
| (1)-147 | 1u | 2j | 3h | 6y |
| (1)-148 | 1e | 2j | 3i | 6c |
| (1)-149 | 1f | 2j | 3i | 6c |
| (1)-150 | 1k | 2j | 3i | 6c |

|  | n & R¹ | R² | R⁴ | R³ |
|---|---|---|---|---|
| (1)-151 | 1l | 2j | 3i | 6c |
| (1)-152 | 1m | 2j | 3i | 6c |
| (1)-153 | 1n | 2j | 3i | 6c |
| (1)-154 | 1u | 2j | 3i | 6c |
| (1)-155 | 1e | 2j | 3i | 6f |
| (1)-156 | 1f | 2j | 3i | 6f |
| (1)-157 | 1k | 2j | 3i | 6f |
| (1)-158 | 1l | 2j | 3i | 6f |
| (1)-159 | 1m | 2j | 3i | 6f |
| (1)-160 | 1n | 2j | 3i | 6f |
| (1)-161 | 1u | 2j | 3i | 6f |
| (1)-162 | 1e | 2j | 3i | 6y |
| (1)-163 | 1f | 2j | 3i | 6y |
| (1)-164 | 1k | 2j | 3i | 6y |
| (1)-165 | 1l | 2j | 3i | 6y |
| (1)-166 | 1m | 2j | 3i | 6y |
| (1)-167 | 1n | 2j | 3i | 6y |
| (1)-168 | 1u | 2j | 3i | 6y |
| (1)-169 | 1e | 2j | 3k | 6c |
| (1)-170 | 1f | 2j | 3k | 6c |
| (1)-171 | 1k | 2j | 3k | 6c |
| (1)-172 | 1l | 2j | 3k | 6c |
| (1)-173 | 1m | 2j | 3k | 6c |
| (1)-174 | 1n | 2j | 3k | 6c |
| (1)-175 | 1u | 2j | 3k | 6c |
| (1)-176 | 1e | 2j | 3k | 6f |
| (1)-177 | 1f | 2j | 3k | 6f |
| (1)-178 | 1k | 2j | 3k | 6f |
| (1)-179 | 1l | 2j | 3k | 6f |
| (1)-180 | 1m | 2j | 3k | 6f |
| (1)-181 | 1n | 2j | 3k | 6f |
| (1)-182 | 1u | 2j | 3k | 6f |
| (1)-183 | 1e | 2j | 3k | 6y |
| (1)-184 | 1f | 2j | 3k | 6y |
| (1)-185 | 1k | 2j | 3k | 6y |
| (1)-186 | 1l | 2j | 3k | 6y |
| (1)-187 | 1m | 2j | 3k | 6y |
| (1)-188 | 1n | 2j | 3k | 6y |
| (1)-189 | 1u | 2j | 3k | 6y |
| (1)-190 | 1e | 2b | — | — |
| (1)-191 | 1f | 2b | — | — |
| (1)-192 | 1k | 2b | — | — |
| (1)-193 | 1l | 2b | — | — |
| (1)-194 | 1m | 2b | — | — |
| (1)-195 | 1n | 2b | — | — |
| (1)-196 | 1u | 2b | — | — |
| (1)-197 | 1e | 2c | — | — |
| (1)-198 | 1f | 2c | — | — |
| (1)-199 | 1k | 2c | — | — |
| (1)-200 | 1l | 2c | — | — |
| (1)-201 | 1m | 2c | — | — |
| (1)-202 | 1n | 2c | — | — |
| (1)-203 | 1u | 2c | — | — |
| (1)-204 | 1e | 2i | — | — |
| (1)-205 | 1f | 2i | — | — |
| (1)-206 | 1k | 2i | — | — |
| (1)-207 | 1l | 2i | — | — |
| (1)-208 | 1m | 2i | — | — |
| (1)-209 | 1n | 2i | — | — |
| (1)-210 | 1u | 2i | — | — |
| (1)-211 | 1e | 2j | — | — |
| (1)-212 | 1f | 2j | — | — |
| (1)-213 | 1k | 2j | — | — |
| (1)-214 | 1l | 2j | — | — |
| (1)-215 | 1m | 2j | — | — |
| (1)-216 | 1n | 2j | — | — |
| (1)-217 | 1u | 2j | — | — |
| (1)-218 | 1e | 2c | — | 6c |
| (1)-219 | 1f | 2c | — | 6c |
| (1)-220 | 1k | 2c | — | 6c |
| (1)-221 | 1l | 2c | — | 6c |
| (1)-222 | 1m | 2c | — | 6c |
| (1)-223 | 1n | 2c | — | 6c |
| (1)-224 | 1u | 2c | — | 6c |
| (1)-225 | 1e | 2c | — | 6f |
| (1)-226 | 1f | 2c | — | 6f |
| (1)-227 | 1k | 2c | — | 6f |
| (1)-228 | 1l | 2c | — | 6f |
| (1)-229 | 1m | 2c | — | 6f |
| (1)-230 | 1n | 2c | — | 6f |
| (1)-231 | 1u | 2c | — | 6f |
| (1)-232 | 1e | 2c | — | 6y |
| (1)-233 | 1f | 2c | — | 6y |
| (1)-234 | 1k | 2c | — | 6y |
| (1)-235 | 1l | 2c | — | 6y |
| (1)-236 | 1m | 2c | — | 6y |
| (1)-237 | 1n | 2c | — | 6y |
| (1)-238 | 1u | 2c | — | 6y |
| (1)-239 | — | 2b | 3h | — |
| (1)-240 | — | 2b | 3i | — |
| (1)-241 | — | 2b | 3k | — |
| (1)-242 | — | 2i | 3h | — |
| (1)-243 | — | 2i | 3i | — |
| (1)-244 | — | 2i | 3k | — |
| (1)-245 | — | 2j | 3h | — |
| (1)-246 | — | 2j | 3i | — |
| (1)-247 | — | 2j | 3k | — |
| (1)-248 | — | 2b | 3h | 6c |
| (1)-249 | — | 2b | 3i | 6f |
| (1)-250 | — | 2b | 3k | 6c |
| (1)-251 | — | 2i | 3h | 6f |
| (1)-252 | — | 2i | 3i | 6y |
| (1)-253 | — | 2i | 3k | 6c |
| (1)-254 | — | 2j | 3h | 6f |
| (1)-255 | — | 2j | 3i | 6y |
| (1)-256 | — | 2j | 3k | 6c |
| (1)-257 | — | 2b | 3h | 6f |
| (1)-258 | — | 2b | 3i | 6y |
| (1)-259 | — | 2b | 3k | 6c |
| (1)-260 | — | 2i | 3h | 6f |
| (1)-261 | — | 2i | 3i | 6y |
| (1)-262 | — | 2i | 3k | 6c |
| (1)-263 | — | 2j | 3h | 6f |
| (1)-264 | — | 2j | 3i | 6y |
| (1)-265 | — | 2j | 3k | 6c |
| (1)-266 | — | 2b | 3h | 6f |
| (1)-267 | — | 2b | 3i | 6y |
| (1)-268 | — | 2b | 3k | 6c |
| (1)-269 | — | 2i | 3h | 6f |
| (1)-270 | — | 2i | 3i | 6y |
| (1)-271 | — | 2i | 3k | 6c |
| (1)-272 | — | 2j | 3h | 6f |
| (1)-273 | — | 2j | 3i | 6y |
| (1)-274 | — | 2j | 3k | 6c |

In another aspect, the invention provides the compound according to formula (II),

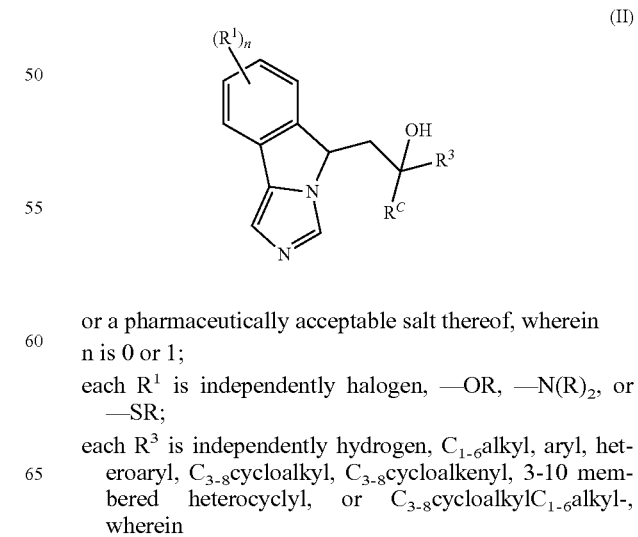

or a pharmaceutically acceptable salt thereof, wherein n is 0 or 1;

each $R^1$ is independently halogen, —OR, —N(R)$_2$, or —SR;

each $R^3$ is independently hydrogen, $C_{1-6}$alkyl, aryl, heteroaryl, $C_{3-8}$cycloalkyl, $C_{3-8}$cycloalkenyl, 3-10 membered heterocyclyl, or $C_{3-8}$cycloalkyl$C_{1-6}$alkyl-, wherein the C$_{1-6}$alkyl, C$_{3-8}$cycloalkyl, C$_{3-8}$cycloalkenyl, 3-10 membered heterocyclyl, and C$_{3-8}$cycloalkylC$_{1-6}$alkyl-, are each optionally and independently substituted by one =R$^{32}$ group and each optionally and independently substituted by one or two R$^{31}$ groups;

the aryl and heteroaryl groups, are each optionally substituted by one or two R$^{31}$ groups; wherein each R$^{31}$ is independently halogen, cyano, nitro, C$_{1-6}$alkyl, —C$_{1-6}$alkyl-R$^{33}$, C$_{1-6}$haloalkyl, —OR, —N(R)$_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, —N(R)C(O)N(R)$_2$, wherein R$^{33}$ is —OR, —N(R)$_2$, or —SR;

R$^{32}$ is oxo, =C(R$^{34}$)$_2$, =(spiro-C$_{3-8}$cycloalkyl), or =(spiro-(3-10 membered heterocyclyl)), wherein each R$^{34}$ is independently hydrogen, halogen, C$_{1-6}$alkyl, or C$_{3-8}$cycloalkyl; and R$^C$ is hydrogen or C$_{1-6}$alkyl; and each R is independently hydrogen or R$^{10}$, wherein
R$^{10}$ is C$_{1-6}$alkyl, C$_{1-6}$haloalkyl, aryl, heteroaryl, C$_{3-8}$cycloalkyl, C$_{3-8}$cycloalkenyl, 3-10 membered heterocyclyl, arylC$_{1-6}$alkyl, heteroarylC$_{1-6}$alkyl-, C$_{3-8}$cycloalkylC$_{1-6}$alkyl-, C$_{3-8}$cycloalkenylC$_{1-6}$alkyl-, or (3-10 membered heterocyclyl)C$_{1-6}$alkyl-, each R$^{10}$ optionally substituted by one, two, three, or four groups that are each independently halogen, cyano, nitro, C$_{1-6}$alkyl, C$_{1-6}$haloalkyl, —OR$^{11}$, —N(R$^{11}$)$_2$, —SR$^{11}$, —C(O)OR$^{11}$, —C(O)N(R$^{11}$)$_2$, —C(O)R$^{11}$, —S(O)R$^{11}$, —S(O)OR$^{11}$, —S(O)N(R$^{11}$)$_2$, —S(O)$_2$R$^{11}$, —S(O)$_2$OR$^1$, —S(O)$_2$N(R$^{11}$)$_2$, —OC(O)R$^{11}$, —OC(O)OR$^1$, —OC(O)N(R$^{11}$)$_2$, —N(R$^{11}$)C(O)R$^{11}$, —N(R$^{11}$)C(O)OR$^{11}$, —N(R$^{11}$)C(O)N(R$^{11}$)$_2$, wherein each R$^{11}$ is independently hydrogen or C$_{1-6}$alkyl.

In one embodiment, the compounds of formula (II) further include those compounds where, R$^3$ is additionally (heteroaryl)-(3-10 membered heterocyclyl)-;

R$^{31}$ is additionally —C(O)N(OH)R, —C(N=R$^{11}$)R, or —C(N=R$^{11}$)N(R$^{11}$)R;

R$^{34}$ is additionally cyano or —C$_{1-6}$alkyl-OR; and/or

R$^{10}$ is additionally optionally substituted by —N(R$^{11}$)S(O)$_2$R$^{11}$ or —C(O)-(3-10 membered heterocyclyl);

such compounds are referred to as compounds of formula (II').

The invention further comprises subgenera of formula (II) or (II') in which the substituents are selected as any and all combinations of one or more of structural formula (II), n, R$^1$, R$^3$, and R$^C$ as defined herein, including without limitation, the following:

Structural Formula II is One of Formulae (IIa)-(IId):

(IIa): wherein the stereoisomeric configuration of carbon-1 (C-1) and carbon-3 (C-3) of formula (II) are respectively (R, R).

(IIb): wherein the stereoisomeric configuration of carbon-1 and carbon-3 are of formula (II) respectively (R, S).

(IIc): wherein the stereoisomeric configuration of carbon-1 and carbon-3 are of formula (II) respectively (S, R).

(IId): wherein the stereoisomeric configuration of carbon-1 and carbon-3 are of formula (II) respectively (S, S).

Structural Formula II is One of Formulae (IIe)-(IIh):

(IIe): wherein the stereoisomeric configuration of carbon-1 (C-1) and carbon-3 (C-3) of formula (II) are respectively (R, R).

(IIf): wherein the stereoisomeric configuration of carbon-1 and carbon-3 are of formula (II) respectively (R, S).

(IIg): wherein the stereoisomeric configuration of carbon-1 and carbon-3 are of formula (II) respectively (S, R).

(IIh): wherein the stereoisomeric configuration of carbon-1 and carbon-3 are of formula (II) respectively (S, S).

n and R$^1$ are selected from one of the following groups (7a)-(7i):

(7a) n is 0 or 1 and R$^1$ is halogen, —OR$^0$, —N(R$^0$)$_2$, or —SR$^0$; wherein each R$^0$ is independently hydrogen or C$_{1-6}$alkyl.

(7b) n is 0 or 1 and R$^1$ is fluoro, chloro, hydroxy, or methoxy.

(7c) n is 0 or 1 and R$^1$ is halogen.

(7d) n is 0 or 1 and R$^1$ is fluoro or chloro.

(7e) n is 1 and R$^1$ is halogen, —OR$^0$, —N(R$^0$)$_2$, or —SR; wherein each R$^0$ is independently hydrogen or C$_{1-6}$alkyl.

(7f) n is 1 and R$^1$ is fluoro, chloro, hydroxy, or methoxy.

(7 g) n is 1 and R$^1$ is halogen.

(7h) n is 1 and R$^1$ is fluoro or chloro.

(7i) n is 0.

R$^C$ is Selected from One of the Following Groups (8a)-(8):

(8a) R$^C$ is hydrogen or C$_{1-4}$alkyl.

(8b) R$^C$ is hydrogen or C$_{1-2}$alkyl.

(8c) R$^C$ is hydrogen or methyl.

(8d) R$^C$ is hydrogen.

(8e) R$^C$ is C$_{1-6}$alkyl.

(8f) R$^C$ is C$_{1-4}$alkyl.

(8g) R$^C$ is methyl.

R$^3$ is Selected from One of the Following Groups (9a)-(9x):

(9a) R$^3$ is aryl, heteroaryl, C$_{3-8}$cycloalkyl, C$_{3-8}$cycloalkenyl, 3-10 membered heterocyclyl, or C$_{3-8}$cycloalkylC$_{1-6}$ alkyl-, wherein the C$_{3-8}$cycloalkyl, C$_{3-8}$cycloalkenyl, 3-10 membered heterocyclyl, and C$_{3-8}$cycloalkylC$_{1-6}$ alkyl-, are each optionally and independently substituted by one =R$^{32}$ group and each optionally and independently substituted by one or two R$^{31}$ groups; and the aryl and heteroaryl groups, are each optionally substituted by one or two R$^{31}$ groups.

(9b) R$^3$ is phenyl, a five or six membered heteroaryl, monocyclic C$_{5-8}$cycloalkyl, monocyclic C$_{5-8}$cycloalkenyl, a five or six membered monocyclic heterocyclyl, or (monocyclic C$_{5-8}$cycloalkyl)C$_{1-6}$alkyl-, wherein the C$_{5-8}$cycloalkyl, C$_{5-8}$cycloalkenyl, 5-6 membered heterocyclyl, and C$_{5-8}$cycloalkylC$_{1-6}$ alkyl-, are each optionally and independently substituted by one =R$^{32}$ group and each optionally and independently substituted by one or two R$^{31}$ groups; and the phenyl and heteroaryl groups, are each optionally substituted by one or two R$^{31}$ groups.

(9c) R$^3$ is phenyl or a five or six membered heteroaryl, each optionally substituted by one or two R$^{31}$ groups.

(9d) R$^3$ is monocyclic C$_{5-8}$cycloalkyl, monocyclic C$_{5-8}$cycloalkenyl, a five or six membered monocyclic heterocyclyl, or (monocyclic C$_{5-8}$cycloalkyl)C$_{1-6}$alkyl-, each optionally substituted by one =R$^{32}$ group and one or two R$^{31}$ groups.

(9e) R$^3$ is

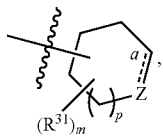

wherein bond a is a single bond or a double bond; m is 0, 1, or 2; p is 0 or 1; and wherein
when bond a is a single bond, then Z is —C(R$^{36}$)$_2$—, —C(=R$^{32}$)—, —N(R$^{35}$)—, or —O—, wherein each R$^{36}$ is independently hydrogen or R$^{31}$; and R$^{35}$ is hydrogen, C$_{1-6}$alkyl, —C(O)R, —S(O)$_2$R, —C(O)OR, —C(O)N(R)$_2$, —S(O)$_2$OR, or —S(O)$_2$N(R)$_2$;
and when bond a is a double bond, then Z is —C(R$^{36}$)= or —N=.

(9) R$^3$ is

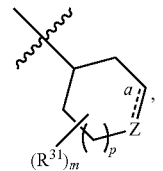

wherein bond a is a single bond or a double bond; m is 0, 1, or 2; p is 0 or 1; and wherein
when bond a is a single bond, then Z is —C(R$^{36}$)$_2$—, —C(=R$^{32}$)—, —N(R$^{35}$)—, or —O—, wherein each R$^{36}$ is independently hydrogen or R$^{31}$; and R$^{35}$ is hydrogen, C$_{1-6}$alkyl, —C(O)R, —S(O)$_2$R, —C(O)OR, —C(O)N(R)$_2$, —S(O)$_2$OR, or —S(O)$_2$N(R)$_2$;
and when bond a is a double bond, then Z is —C(R$^{36}$)= or —N=.

(9g) As group (9f), wherein when bond a is a single bond, then Z is —C(R$^{36}$)$_2$— or —C(=R$^{32}$)—; and when bond a is a double bond, then Z is —C(R$^{36}$)= or —N=.

(9h) As group (9l), wherein m is 0; when bond a is a single bond, then Z is —C(R$^{36}$)$_2$— or —C(=R$^{32}$)—; and when bond a is a double bond, then Z is —C(R$^{36}$)= or —N=.

(9I) As group (9f), wherein bond a is a single bond; and Z is —C(R$^{36}$)$_2$— or —C(=R$^{32}$)—.

(9j) As group (9f), wherein bond a is a single bond; and Z is —C(R$^{36}$)$_2$—.

(9k) As group (9f), wherein bond a is a single bond; and Z is —C(=R$^{32}$)—.

(9l) As group (9f), wherein m is 0; bond a is a single bond; and Z is —C(R$^{36}$)$_2$— or —C(=R$^{32}$)—.

(9m) As group (9f), wherein m is 0; bond a is a single bond; and Z is —C(R$^{36}$)$_2$—.

(9n) As group (9f), wherein m is 0; bond a is a single bond; and Z is —C(=R$^{32}$)—.

(9o) As group (9f), wherein bond a is a single bond; and Z is —C(R$^{36}$)$_2$— or —C(=R$^{32}$)—, wherein each R$^{36}$ is independently hydrogen, halogen, C$_{1-6}$alkyl, —C$_{1-6}$alkyl-OH, C$_{1-6}$haloalkyl, or —OH, wherein R$^{32}$ is =O, =C(R$^{34}$)$_2$, =(spiro-C$_{3-8}$cycloalkyl), or =(spiro-(3-8 membered heterocyclyl)), wherein each R$^{34}$ is independently hydrogen, halogen, C$_{1-6}$alkyl, C$_{1-6}$haloalkyl, C$_{3-8}$cycloalkyl, or 3-8 membered heterocyclyl.

(9p) As group (9f), wherein m is 0; bond a is a single bond; and Z is —C(R$^{36}$)$_2$— or —C(=R$^{32}$)—, wherein each R$^{36}$ is independently hydrogen, halogen, C$_{1-6}$alkyl, —C$_{1-6}$alkyl-OH, C$_{1-6}$haloalkyl, or —OH, wherein R$^{32}$ is =O, =C(R$^{34}$)$_2$, =(spiro-C$_{3-8}$cycloalkyl), or =(spiro-(3-8 membered heterocyclyl)), wherein each R$^{34}$ is independently hydrogen, halogen, C$_{1-6}$alkyl, C$_{1-6}$haloalkyl, C$_{3-8}$cycloalkyl, or 3-8 membered heterocyclyl.

(9q) As group (9f), wherein bond a is a single bond; and Z is —N(R$^{35}$)— or —O—.

(9r) R$^3$ is hydrogen, C$_{1-6}$alkyl, aryl, heteroaryl, C$_{3-8}$cycloalkyl, C$_{3-8}$cycloalkenyl, 3-10 membered heterocyclyl, or C$_{3-8}$cycloalkylC$_{1-6}$alkyl, wherein
the C$_{1-6}$alkyl, C$_{3-8}$cycloalkyl, C$_{3-8}$cycloalkenyl, 3-10 membered heterocyclyl, and C$_{3-8}$cycloalkylC$_{1-6}$alkyl, are each optionally substituted by one =R$^{32}$ group and one or two R$^{31}$ groups;
the aryl and heteroaryl groups, are each optionally substituted by one or two R$^{31}$ groups; wherein
each R$^{31}$ is independently halogen, cyano, nitro, C$_{1-6}$alkyl, —C$_{1-6}$alkyl-R$^{33}$, C$_{1-6}$haloalkyl, —OR, —N(R)$_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, —N(R)C(O)N(R)$_2$, wherein R$^{33}$ is —OR, —N(R)$_2$, or —SR; and
R$^{32}$ is oxo, =C(R$^{34}$)$_2$, =(spiro-C$_{3-8}$cycloalkyl), or =(spiro-(3-10 membered heterocyclyl)), wherein each R$^{34}$ is independently hydrogen, halogen, C$_{1-6}$alkyl, or C$_{3-8}$cycloalkyl.

(9s) R$^3$ is aryl, heteroaryl, C$_{3-8}$cycloalkyl, C$_{3-8}$cycloalkenyl, or 3-10 membered heterocyclyl, wherein the C$_{3-8}$cycloalkyl, C$_{3-8}$cycloalkenyl, and 3-10 membered heterocyclyl are each optionally substituted by one =R$^{32}$ group and one, two, three, or four R$^{31}$ groups; and the aryl and heteroaryl are each optionally substituted by one, two, three, or four R$^{31}$ groups.

(9t) R$^3$ is phenyl, cyclopentyl, cyclohexyl, cyclohexenyl, furanyl, tetrahydropyranyl, piperidinyl, imidazolyl, thiazolyl, each optionally substituted by one, two, three, or four R$^{31}$ groups, and wherein the cyclopentyl, cyclohexyl, cyclohexenyl, andy piperidinyl groups are each optionally substituted by one =R$^{32}$ group.

(9u) R$^3$ is phenyl, cyclopentyl, cyclohexyl, cyclohex-1-en-1-yl, cyclohex-3-en-1-yl, furan-2-yl, furan-3-yl, tetrahydropyran-3-yl, tetrahydropyran-4-yl, piperidin-3-yl, piperidin-4-yl, imidazol-2-yl, imidazol-4-yl, thiazol-2-yl, thiazol-4-yl, thiazol-5-yl, each optionally substituted by one or two $R^{31}$ groups, and wherein the cyclopentyl, cyclohexyl, cyclohexenyl, andy piperidinyl groups are each optionally substituted by one $=R^{32}$ group.

(9v) Any one of groups (9a)-(9u), wherein each R is independently hydrogen, $C_{1-6}$alkyl, $C_{1-6}$haloalkyl, aryl, heteroaryl, $C_{3-8}$cycloalkyl, $C_{3-8}$cycloalkenyl, 3-10 membered heterocyclyl, aryl$C_{1-6}$alkyl, heteroaryl$C_{1-6}$alkyl-, $C_{3-8}$cycloalkyl$C_{1-6}$alkyl-, $C_{3-8}$cycloalkenyl$C_{1-6}$alkyl-, or (3-10 membered heterocyclyl)$C_{1-6}$-alkyl-.

(9w) Any one of groups (9a)-(9u), wherein each R is independently hydrogen, $C_{1-6}$alkyl, $C_{1-6}$haloalkyl, phenyl, 5- or 6-membered heteroaryl, $C_{3-8}$cycloalkyl, $C_{3-8}$cycloalkenyl, 3-8 membered heterocyclyl, benzyl, (5- or 6-membered heteroaryl)$C_{1-6}$alkyl-, $C_{3-8}$ cycloalkyl$C_{1-6}$alkyl-, $C_{3-8}$cycloalkenyl$C_{1-6}$alkyl-, or (3-8 membered heterocyclyl) $C_{1-6}$alkyl-.

(9x) Any one of groups (9a)-(9u), wherein each R is independently hydrogen or $C_{1-6}$alkyl.

Particular embodiments of this aspect of the invention include compounds of any one of the formulae (II), (II'), and (IIa)-(IId), each as defined in each of the following rows, wherein each entry is a group number as defined above and a dash "—" indicates that the variable is as defined for formula (II), or (II'), or defined according to any one of the applicable variable definitions (7a)-(9t) [e.g., when $R^C$ is a dash, it can be either as defined for Formula (II), or (II'), or any one of definitions (8a)-(8g)]:

|  | (II) | n & $R^1$ | $R^C$ | $R^3$ |
|---|---|---|---|---|
| (2)-1 | IIb | 7a | 9b | 8c |
| (2)-2 | IIc | 7a | 9b | 8c |
| (2)-3 | IId | 7a | 9b | 8c |
| (2)-4 | IIf | 7a | 9b | 8d |
| (2)-5 | IIg | 7a | 9b | 8d |
| (2)-6 | IIh | 7a | 9b | 8d |
| (2)-7 | IIb | 7a | 9b | 8g |
| (2)-8 | IIc | 7a | 9b | 8g |
| (2)-9 | IId | 7a | 9b | 8g |
| (2)-10 | IIf | 7a | 9e | 8c |
| (2)-11 | IIg | 7a | 9e | 8c |
| (2)-12 | IIh | 7a | 9e | 8c |
| (2)-13 | IIb | 7a | 9e | 8d |
| (2)-14 | IIc | 7a | 9e | 8d |
| (2)-15 | IId | 7a | 9e | 8d |
| (2)-16 | IIf | 7a | 9e | 8g |
| (2)-17 | IIg | 7a | 9e | 8g |
| (2)-18 | IIh | 7a | 9e | 8g |
| (2)-19 | IIb | 7a | 9v | 8c |
| (2)-20 | IIc | 7a | 9v | 8c |
| (2)-21 | IId | 7a | 9v | 8c |
| (2)-22 | IIf | 7a | 9v | 8d |
| (2)-23 | IIg | 7a | 9v | 8d |
| (2)-24 | IIh | 7a | 9v | 8d |
| (2)-25 | IIb | 7a | 9v | 8g |
| (2)-26 | IIc | 7a | 9v | 8g |
| (2)-27 | IId | 7a | 9v | 8g |
| (2)-28 | IIf | 7g | 9b | 8c |
| (2)-29 | IIg | 7g | 9b | 8c |
| (2)-30 | IIh | 7g | 9b | 8c |
| (2)-31 | IIb | 7g | 9b | 8d |
| (2)-32 | IIc | 7g | 9b | 8d |
| (2)-33 | IId | 7g | 9b | 8d |
| (2)-34 | IIf | 7g | 9b | 8g |
| (2)-35 | IIg | 7g | 9b | 8g |
| (2)-36 | IIh | 7g | 9b | 8g |
| (2)-37 | IIb | 7g | 9e | 8c |
| (2)-38 | IIc | 7g | 9e | 8c |
| (2)-39 | IId | 7g | 9e | 8c |
| (2)-40 | IIf | 7g | 9e | 8d |
| (2)-41 | IIg | 7g | 9e | 8d |
| (2)-42 | IIh | 7g | 9e | 8d |
| (2)-43 | IIb | 7g | 9e | 8g |
| (2)-44 | IIc | 7g | 9e | 8g |
| (2)-45 | IId | 7g | 9e | 8g |
| (2)-46 | IIf | 7g | 9v | 8c |
| (2)-47 | IIg | 7g | 9v | 8c |
| (2)-48 | IIh | 7g | 9v | 8c |
| (2)-49 | IIb | 7g | 9v | 8d |
| (2)-50 | IIc | 7g | 9v | 8d |
| (2)-51 | IId | 7g | 9v | 8d |
| (2)-52 | IIf | 7g | 9v | 8g |
| (2)-53 | IIg | 7g | 9v | 8g |
| (2)-54 | IIh | 7g | 9v | 8g |
| (2)-55 | IIb | 7h | 9b | 8c |
| (2)-56 | IIc | 7h | 9b | 8c |
| (2)-57 | IId | 7h | 9b | 8c |
| (2)-58 | IIf | 7h | 9b | 8d |
| (2)-59 | IIg | 7h | 9b | 8d |
| (2)-60 | IIh | 7h | 9b | 8d |
| (2)-61 | IIb | 7h | 9b | 8g |
| (2)-62 | IIc | 7h | 9b | 8g |
| (2)-63 | IId | 7h | 9b | 8g |
| (2)-64 | IIf | 7h | 9e | 8c |
| (2)-65 | IIg | 7h | 9e | 8c |
| (2)-66 | IIh | 7h | 9e | 8c |
| (2)-67 | IIb | 7h | 9e | 8d |
| (2)-68 | IIc | 7h | 9e | 8d |
| (2)-69 | IId | 7h | 9e | 8d |
| (2)-70 | IIf | 7h | 9e | 8g |
| (2)-71 | IIg | 7h | 9e | 8g |
| (2)-72 | IIh | 7h | 9e | 8g |
| (2)-73 | IIb | 7h | 9v | 8c |
| (2)-74 | IIc | 7h | 9v | 8c |
| (2)-75 | IId | 7h | 9v | 8c |
| (2)-76 | IIf | 7h | 9v | 8d |
| (2)-77 | IIg | 7h | 9v | 8d |
| (2)-78 | IIh | 7h | 9v | 8d |
| (2)-79 | IIb | 7h | 9v | 8g |
| (2)-80 | IIc | 7h | 9v | 8g |
| (2)-81 | IId | 7h | 9v | 8g |
| (2)-82 | IIf | 7i | 9b | 8c |
| (2)-83 | IIg | 7i | 9b | 8c |
| (2)-84 | IIh | 7i | 9b | 8c |
| (2)-85 | IIb | 7i | 9b | 8d |
| (2)-86 | IIc | 7i | 9b | 8d |
| (2)-87 | IId | 7i | 9b | 8d |
| (2)-88 | IIf | 7i | 9b | 8g |
| (2)-89 | IIg | 7i | 9b | 8g |
| (2)-90 | IIh | 7i | 9b | 8g |
| (2)-91 | IIb | 7i | 9e | 8c |
| (2)-92 | IIc | 7i | 9e | 8c |
| (2)-93 | IId | 7i | 9e | 8c |
| (2)-94 | IIf | 7i | 9e | 8d |
| (2)-95 | IIg | 7i | 9e | 8d |
| (2)-96 | IIh | 7i | 9e | 8d |
| (2)-97 | IIb | 7i | 9e | 8g |
| (2)-98 | IIc | 7i | 9e | 8g |
| (2)-99 | IId | 7i | 9e | 8g |
| (2)-100 | IIf | 7i | 9v | 8c |
| (2)-101 | IIg | 7i | 9v | 8c |
| (2)-102 | IIh | 7i | 9v | 8c |
| (2)-103 | IIb | 7i | 9v | 8d |
| (2)-104 | IIc | 7i | 9v | 8d |
| (2)-105 | IId | 7i | 9v | 8d |
| (2)-106 | IIf | 7i | 9v | 8g |
| (2)-107 | IIg | 7i | 9v | 8g |
| (2)-108 | IIh | 7i | 9v | 8g |
| (2)-109 | — | — | 9b | 8c |
| (2)-110 | — | — | 9e | 8c |
| (2)-111 | — | — | 9v | 8c |
| (2)-112 | — | — | 9b | 8d |
| (2)-113 | — | — | 9e | 8d |
| (2)-114 | — | — | 9v | 8d |
| (2)-115 | — | — | 9b | 8g |
| (2)-116 | — | — | 9e | 8g |
| (2)-117 | — | — | 9v | 8g |
| (2)-118 | — | 7a | 9b | 8c |
| (2)-119 | — | 7a | 9e | 8c |
| (2)-120 | — | 7a | 9v | 8c |

-continued

| | (II) | n & R$^1$ | R$^C$ | R$^3$ |
|---|---|---|---|---|
| (2)-121 | — | 7a | 9b | 8d |
| (2)-122 | — | 7a | 9e | 8d |
| (2)-123 | — | 7a | 9v | 8d |
| (2)-124 | — | 7a | 9b | 8g |
| (2)-125 | — | 7a | 9e | 8g |
| (2)-126 | — | 7a | 9v | 8g |
| (2)-127 | — | 7g | 9b | 8c |
| (2)-128 | — | 7g | 9e | 8c |
| (2)-129 | — | 7g | 9v | 8c |
| (2)-130 | — | 7g | 9b | 8d |
| (2)-131 | — | 7g | 9e | 8d |
| (2)-132 | — | 7g | 9v | 8d |
| (2)-133 | — | 7g | 9b | 8g |
| (2)-134 | — | 7g | 9e | 8g |
| (2)-135 | — | 7g | 9v | 8g |
| (2)-136 | — | 7h | 9b | 8c |
| (2)-137 | — | 7h | 9e | 8c |
| (2)-138 | — | 7h | 9v | 8c |
| (2)-139 | — | 7h | 9b | 8d |
| (2)-140 | — | 7h | 9e | 8d |
| (2)-141 | — | 7h | 9v | 8d |
| (2)-142 | — | 7h | 9b | 8g |
| (2)-143 | — | 7h | 9e | 8g |
| (2)-144 | — | 7h | 9v | 8g |
| (2)-145 | — | 7i | 9b | 8c |
| (2)-146 | — | 7i | 9e | 8c |
| (2)-147 | — | 7i | 9v | 8c |
| (2)-148 | — | 7i | 9b | 8d |
| (2)-149 | — | 7i | 9e | 8d |
| (2)-150 | — | 7i | 9v | 8d |
| (2)-151 | — | 7i | 9b | 8g |
| (2)-152 | — | 7i | 9e | 8g |
| (2)-153 | — | 7i | 9v | 8g |
| (2)-154 | — | 7a | — | 8c |
| (2)-155 | — | 7a | — | 8d |
| (2)-156 | — | 7a | — | 8g |
| (2)-157 | — | 7g | — | 8c |
| (2)-158 | — | 7g | — | 8d |
| (2)-159 | — | 7g | — | 8g |
| (2)-160 | — | 7h | — | 8c |
| (2)-161 | — | 7h | — | 8d |
| (2)-162 | — | 7h | — | 8g |
| (2)-163 | — | 7i | — | 8c |
| (2)-164 | — | 7i | — | 8d |
| (2)-165 | — | 7i | — | 8g |
| (2)-166 | — | 7a | 9b | — |
| (2)-167 | — | 7a | 9e | — |
| (2)-168 | — | 7a | 9b | — |
| (2)-169 | — | 7g | 9e | — |
| (2)-170 | — | 7g | 9v | — |
| (2)-171 | — | 7g | 9b | — |
| (2)-172 | — | 7h | 9e | — |
| (2)-173 | — | 7h | 9v | — |
| (2)-174 | — | 7h | 9b | — |
| (2)-175 | — | 7i | 9e | — |
| (2)-176 | — | 7i | 9v | — |
| (2)-177 | — | 7i | 9b | — |

In another aspect, the present disclosure provides compounds that are

| No. | Structure | Name |
|---|---|---|
| 1254 | 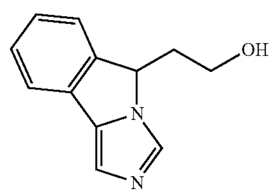 [SMILES: OCCC1c2ccccc2-c2cncn21] | 2-(5H-imidazo[5,1-a]isoindol-5-yl)ethanol |
| 1256 | 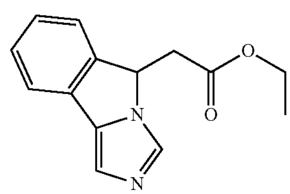 [SMILES: CCOC(=O)CC1c2ccccc2-c2cncn21] | ethyl 2-(5H-imidazo[5,1-a]isoindol-5-yl)acetate |
| 1258 | 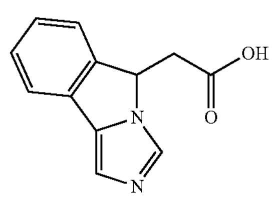 [SMILES: O=C(O)CC1c2ccccc2-c2cncn21] | 2-(5H-imidazo[5,1-a]isoindol-5-yl)acetic acid |
| 1259 | 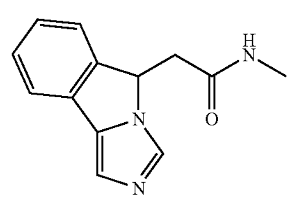 [SMILES: CNC(=O)CC1c2ccccc2-c2cncn21] | 2-(5H-imidazo[5,1-a]isoindol-5-yl)-N-methylacetamide |

| No. | Structure | Name |
|---|---|---|
| 1273 | 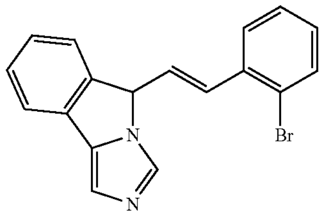 [SMILES: Brc1ccccc1/C=C/C1c2ccccc2-c2cncn21] | (E)-5-(2-bromostyryl)-5H-imidazo[5,1-a]isoindole |
| 1286 | 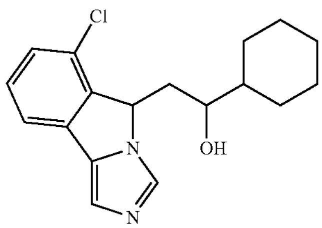 [SMILES: OC(CC1c2c(Cl)cccc2-c2cncn21)C1CCCCC1] | 2-(6-chloro-5H-imidazo[5,1-a]isoindol-5-yl)-1-cyclohexylethanol |
| 1287 | 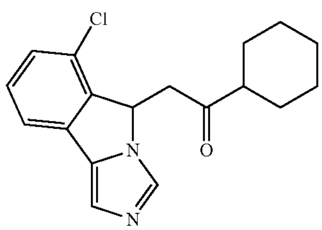 [SMILES: O=C(CC1c2c(Cl)cccc2-c2cncn21)C1CCCCC1] | 2-(6-chloro-5H-imidazo[5,1-a]isoindol-5-yl)-1-cyclohexylethanone |
| 1288 | 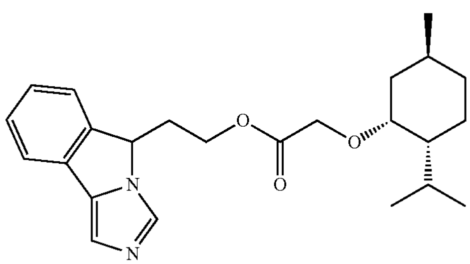 [SMILES: CC(C)[C@H]1CC[C@H](C)C[C@H]1OCC(=O)OCCC1c2ccccc2-c2cncn21] | 2-(5H-imidazo[5,1-a]isoindol-5-yl)ethyl 2-(((1R,2R,5S)-2-isopropyl-5-methylcyclohexyl)oxy)acetate |
| 1300 | 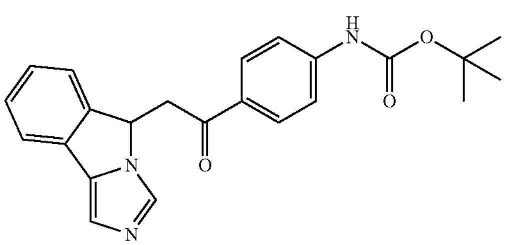 [SMILES: CC(C)(C)OC(=O)Nc1ccc(C(=O)CC2c3ccccc3-c3cncn32)cc1] | tert-butyl (4-(2-(5H-imidazo[5,1-a]isoindol-5-yl)acetyl)phenyl)carbamate |
| 1301 | 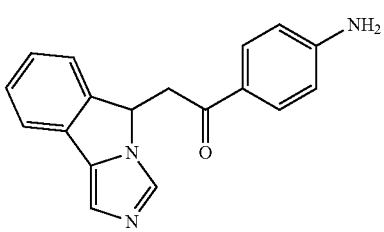 [SMILES: Nc1ccc(C(=O)CC2c3ccccc3-c3cncn32)cc1] | 1-(4-aminophenyl)-2-(5H-imidazo[5,1-a]isoindol-5-yl)ethanone |

| No. | Structure | Name |
|---|---|---|
| 1302 | 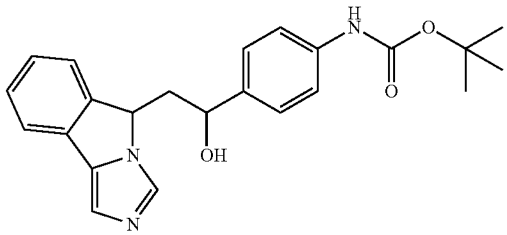 [SMILES: CC(C)(C)OC(=O)Nc1ccc(C(O)CC2c3ccccc3-c3cncn32)cc1] | tert-butyl (4-(1-hydroxy-2-(5H-imidazo[5,1-a]isoindol-5-yl)ethyl)phenyl)carbamate |
| 1303 | 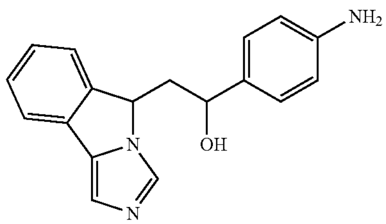 [SMILES: Nc1ccc(C(O)CC2c3ccccc3-c3cncn32)cc1] | 1-(4-aminophenyl)-2-(5H-imidazo[5,1-a]isoindol-5-yl)ethanol |
| 1304 | 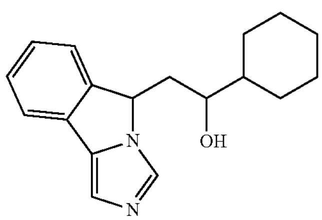 [SMILES: OC(CC1c2ccccc2-c2cncn21)C1CCCCC1] | 1-cyclohexyl-2-(5H-imidazo[5,1-a]isoindol-5-yl)ethanol |
| 1306 | 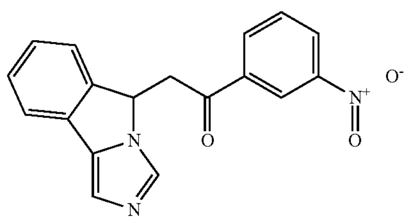 | 2-(5H-imidazo[5,1-a]isoindol-5-yl)-1-(3-nitrophenyl)ethanone |
| 1307 | 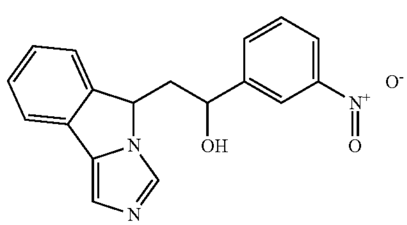 | 2-(5H-imidazo[5,1-a]isoindol-5-yl)-1-(3-nitrophenyl)ethanol |
| 1326 | 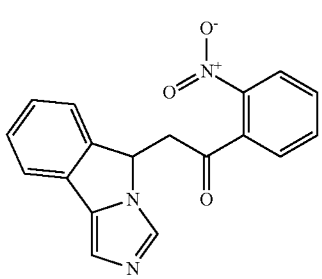 [SMILES: O=C(CC1c2ccccc2-c2cncn21)c1ccccc1[N+](=O)[O-]] | 2-(5H-imidazo[5,1-a]isoindol-5-yl)-1-(2-nitrophenyl)ethanone |

| No. | Structure | Name |
|---|---|---|
| 1327 | 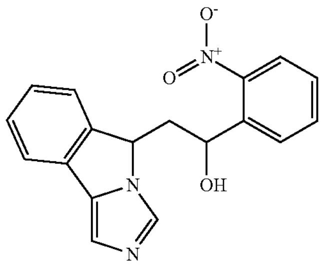 [SMILES: O=[N+]([O-])c1ccccc1C(O)CC1c2ccccc2-c2cncn21] | 2-(5H-imidazo[5,1-a]isoindol-5-yl)-1-(2-nitrophenyl)ethanol |
| 1328 | 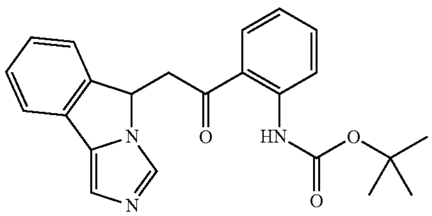 [SMILES: CC(C)(C)OC(=O)Nc1ccccc1C(=O)CC1c2ccccc2-c2cncn21] | tert-butyl (2-(2-(5H-imidazo[5,1-a]isoindol-5-yl)acetyl)phenyl)carbamate |
| 1329 | 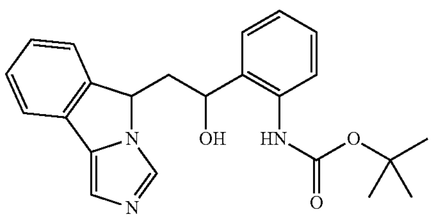 [SMILES: CC(C)(C)OC(=O)Nc1ccccc1C(O)CC1c2ccccc2-c2cncn21] | tert-butyl (2-(1-hydroxy-2-(5H-imidazo[5,1-a]isoindol-5-yl)ethyl)phenyl)carbamate |
| 1330 | 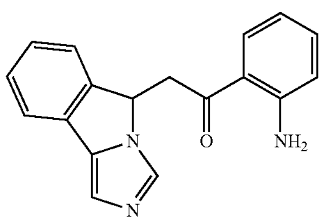 [SMILES: Nc1ccccc1C(=O)CC1c2ccccc2-c2cncn21] | 1-(2-aminophenyl)-2-(5H-imidazo[5,1-a]isoindol-5-yl)ethanone |
| 1331 | 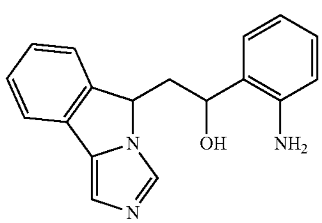 [SMILES: Nc1ccccc1C(O)CC1c2ccccc2-c2cncn21] | 1-(2-aminophenyl)-2-(5H-imidazo[5,1-a]isoindol-5-yl)ethanol |
| 1334 | 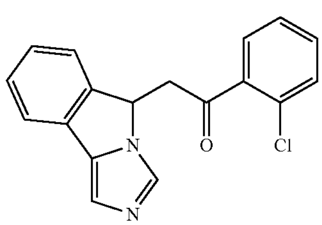 [SMILES: O=C(CC1c2ccccc2-c2cncn21)c1ccccc1Cl] | 1-(2-chlorophenyl)-2-(5H-imidazo[5,1-a]isoindol-5-yl)ethanone |
| 1335 | 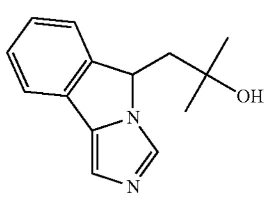 [SMILES: CC(C)(O)CC1c2ccccc2-c2cncn21] | 1-(5H-imidazo[5,1-a]isoindol-5-yl)-2-methylpropan-2-ol |

-continued

| No. | Structure | Name |
|---|---|---|
| 1336 | 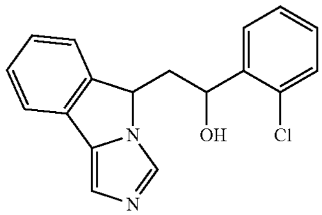 [SMILES: OC(CC1c2ccccc2-c2cncn21)c1ccccc1Cl] | 1-(2-chlorophenyl)-2-(5H-imidazo[5,1-a]isoindol-5-yl)ethanol |
| 1343 | 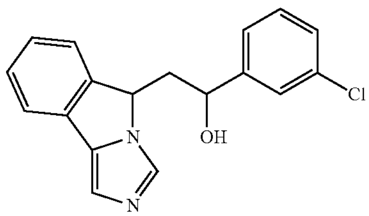 [SMILES: OC(CC1c2ccccc2-c2cncn21)c1cccc(Cl)c1] | 1-(3-chlorophenyl)-2-(5H-imidazo[5,1-a]isoindol-5-yl)ethanol |
| 1348 | 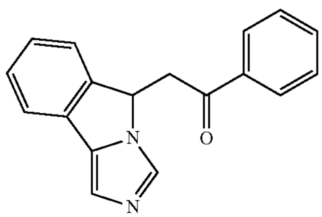 [SMILES: O=C(CC1c2ccccc2-c2cncn21)c1ccccc1] | 2-(5H-imidazo[5,1-a]isoindol-5-yl)-1-phenylethanone |
| 1349 | 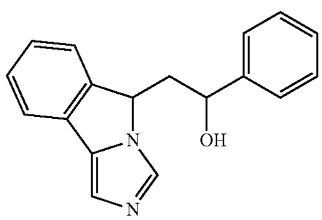 [SMILES: OC(CC1c2ccccc2-c2cncn21)c1ccccc1] | 2-(5H-imidazo[5,1-a]isoindol-5-yl)-1-phenylethanol |
| 1352 | 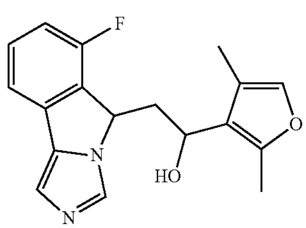 [SMILES: Cc1coc(C)c1C(O)CC1c2c(F)cccc2-c2cncn21] | 1-(2,4-dimethylfuran-3-yl)-2-(6-fluoro-5H-imidazo[5,1-a]isoindol-5-yl)ethanol; |
| 1353 | 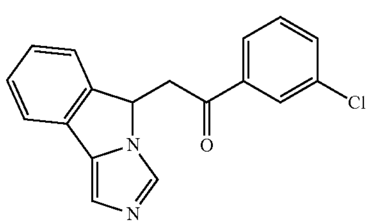 [SMILES: O=C(CC1c2ccccc2-c2cncn21)c1cccc(Cl)c1] | 1-(3-chlorophenyl)-2-(5H-imidazo[5,1-a]isoindol-5-yl)ethanone |
| 1356 | 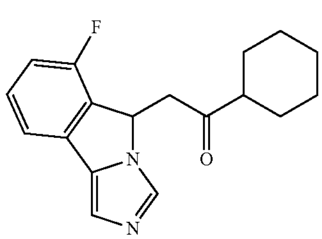 [SMILES: O=C(CC1c2c(F)cccc2-c2cncn21)C1CCCCC1] | 1-cyclohexyl-2-(6-fluoro-5H-imidazo[5,1-a]isoindol-5-yl)ethanone |

-continued

| No. | Structure | Name |
|---|---|---|
| 1357 | 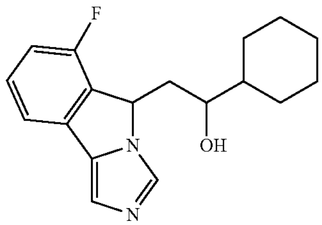 [SMILES: OC(CC1c2c(F)cccc2-c2cncn21)C1CCCCC1] | 1-cyclohexyl-2-(6-fluoro-5H-imidazo[5,1-a]isoindol-5-yl)ethanol |
| 1358 | 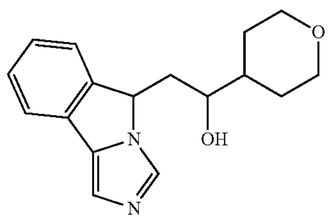 [SMILES: OC(CC1c2ccccc2-c2cncn21)C1CCOCC1] | 2-(5H-imidazo[5,1-a]isoindol-5-yl)-1-(tetrahydro-2H-pyran-4-yl)ethanol |
| 1359 | 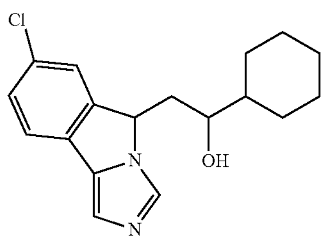 [SMILES: OC(CC1c2cc(Cl)ccc2-c2cncn21)C1CCCCC1] | 2-(7-chloro-5H-imidazo[5,1-a]isoindol-5-yl)-1-cyclohexylethanol |
| 1360 | 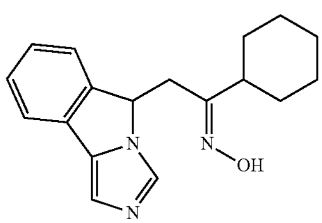 [SMILES: O/N=C(/CC1c2ccccc2-c2cncn21)C1CCCCC1] | (Z)-1-cyclohexyl-2-(5H-imidazo[5,1-a]isoindol-5-yl)ethanone oxime |
| 1362 | 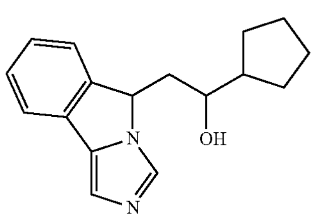 [SMILES: OC(CC1c2ccccc2-c2cncn21)C1CCCC1] | 1-cyclopentyl-2-(5H-imidazo[5,1-a]isoindol-5-yl)ethanol |
| 1363 | 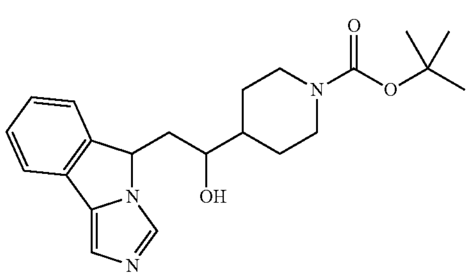 [SMILES: CC(C)(C)OC(=O)N1CCC(C(O)CC2c3ccccc3-c3cncn32)CC1] | tert-butyl 4-(1-hydroxy-2-(5H-imidazo[5,1-a]isoindol-5-yl)ethyl)piperidine-1-carboxylate |

-continued

| No. | Structure | Name |
|---|---|---|
| 1364 | 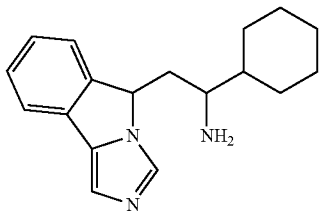 [SMILES: NC(CC1c2ccccc2-c2cncn21)C1CCCCC1] | 1-cyclohexyl-2-(5H-imidazo[5,1-a]isoindol-5-yl)ethanamine |
| 1367 | 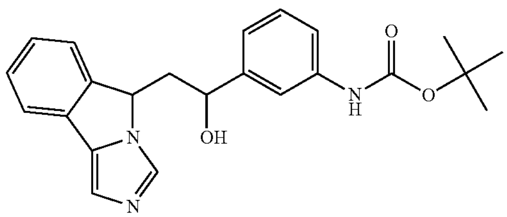 [SMILES: CC(C)(C)OC(=O)Nc1cccc(C(O)CC2c3ccccc3-c3cncn32)c1] | tert-butyl (3-(1-hydroxy-2-(5H-imidazo[5,1-a]isoindol-5-yl)ethyl)phenyl)carbamate |
| 1369 | 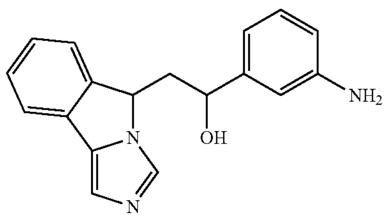 [SMILES: Nc1cccc(C(O)CC2c3ccccc3-c3cncn32)c1] | 1-(3-aminophenyl)-2-(5H-imidazo[5,1-a]isoindol-5-yl)ethanol |
| 1370 | 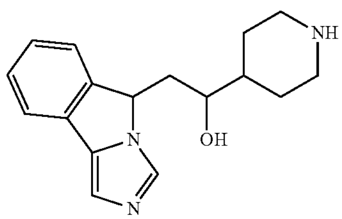 [SMILES: OC(CC1c2ccccc2-c2cncn21)C1CCNCC1] | 2-(5H-imidazo[5,1-a]isoindol-5-yl)-1-(piperidin-4-yl)ethanol |
| 1371 | 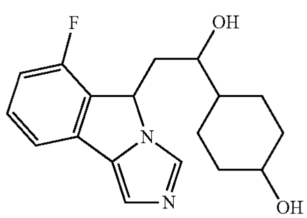 [SMILES: OC1CCC(C(O)CC2c3c(F)cccc3-c3cncn32)CC1] | 4-(2-(6-fluoro-5H-imidazo[5,1-a]isoindol-5-yl)-1-hydroxyethyl)cyclohexanol; |
| 1372 | 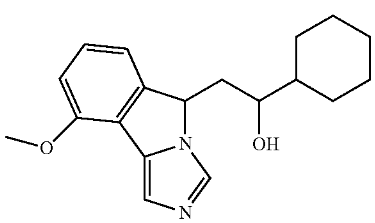 [SMILES: COc1cccc2c1-c1cncn1C2CC(O)C1CCCCC1] | 1-cyclohexyl-2-(9-methoxy-5H-imidazo[5,1-a]isoindol-5-yl)ethanol |
| 1373 | 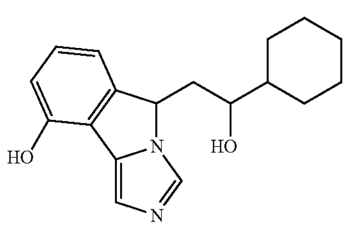 [SMILES: Oc1cccc2c1-c1cncn1C2CC(O)C1CCCCC1] | 5-(2-cyclohexyl-2-hydroxyethyl)-5H-imidazo[5,1-a]isoindol-9-ol |

| No. | Structure | Name |
|---|---|---|
| 1374 | 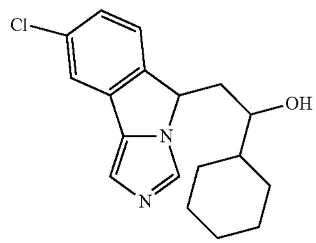 [SMILES: OC(CC1c2ccc(Cl)cc2-c2cncn21)C1CCCCC1] | 2-(8-chloro-5H-imidazo[5,1-a]isoindol-5-yl)-1-cyclohexylethanol; |
| 1375 | 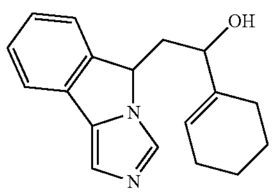 [SMILES: OC(CC1c2ccccc2-c2cncn21)C1=CCCCC1] | 1-(cyclohex-1-en-1-yl)-2-(5H-imidazo[5,1-a]isoindol-5-yl)ethanol; |
| 1376 | 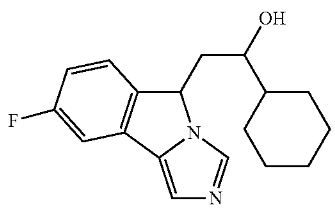 [SMILES: OC(CC1c2ccc(F)cc2-c2cncn21)C1CCCCC1] | 1-cyclohexyl-2-(8-fluoro-5H-imidazo[5,1-a]isoindol-5-yl)ethanol; |
| 1378 | 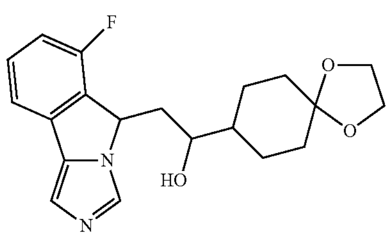 [SMILES: OC(CC1c2c(F)cccc2-c2cncn21)C1CCC2(CC1)OCCO2] | 2-(6-fluoro-5H-imidazo[5,1-a]isoindol-5-yl)-1-(1,4-dioxaspiro[4.5]decan-8-yl)ethanol; |
| 1379 | 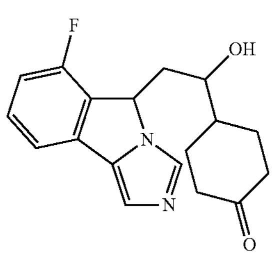 [SMILES: O=C1CCC(C(O)CC2c3c(F)cccc3-c3cncn32)CC1] | 4-(2-(6-fluoro-5H-imidazo[5,1-a]isoindol-5-yl)-1-hydroxyethyl)cyclohexanone; |
| 1381 | 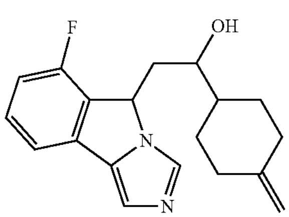 [SMILES: C=C1CCC(C(O)CC2c3c(F)cccc3-c3cncn32)CC1] | 2-(6-fluoro-5H-imidazo[5,1-a]isoindol-5-yl)-1-(4-methylenecyclohexyl)ethanol; |
| 1382 | 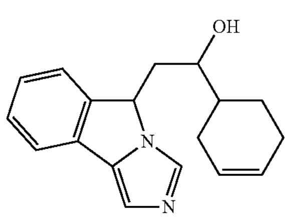 [SMILES: OC(CC1c2ccccc2-c2cncn21)C1CC=CCC1] | 1-(cyclohex-3-en-1-yl)-2-(5H-imidazo[5,1-a]isoindol-5-yl)ethanol; |

-continued

| No. | Structure | Name |
|---|---|---|
| 1383 | 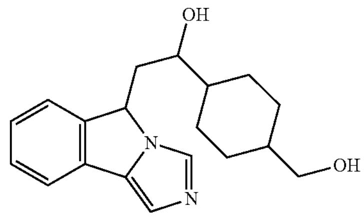 [SMILES: OCC1CCC(C(O)CC2c3ccccc3-c3cncn32)CC1] | 1-(4-(hydroxymethyl)cyclohexyl)-2-(5H-imidazo[5,1-a]isoindol-5-yl)ethanol; |
| 1384 | 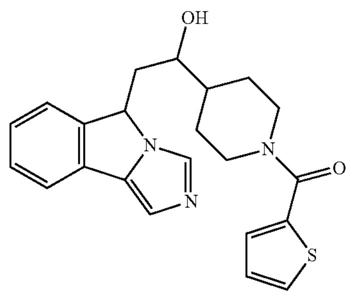 [SMILES: O=C(c1cccs1)N1CCC(C(O)CC2c3ccccc3-c3cncn32)CC1] | (4-(1-hydroxy-2-(5H-imidazo[5,1-a]isoindol-5-yl)ethyl)piperidin-1-yl)(thiophen-2-yl)methanone; |
| 1385 | 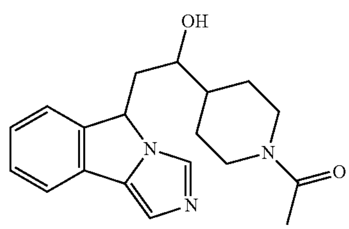 [SMILES: CC(=O)N1CCC(C(O)CC2c3ccccc3-c3cncn32)CC1] | 1-(4-(1-hydroxy-2-(5H-imidazo[5,1-a]isoindol-5-yl)ethyl)piperidin-1-yl)ethanone; |
| 1386 | 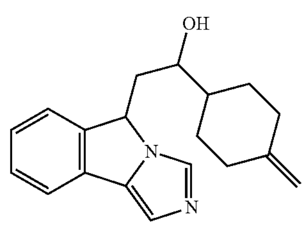 [SMILES: C=C1CCC(C(O)CC2c3ccccc3-c3cncn32)CC1] | 2-(5H-imidazo[5,1-a]isoindol-5-yl)-1-(4-methylenecyclohexyl)ethanol; |
| 1387 | 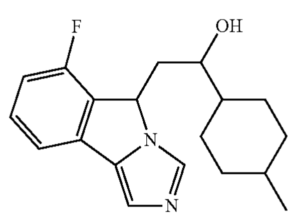 [SMILES: CC1CCC(C(O)CC2c3c(F)cccc3-c3cncn32)CC1] | 2-(6-fluoro-5H-imidazo[5,1-a]isoindol-5-yl)-1-(4-methylcyclohexyl)ethanol; |
| 1389 | 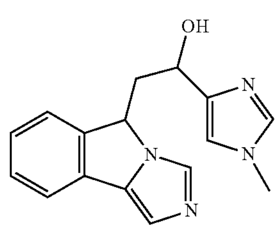 [SMILES: Cn1cnc(C(O)CC2c3ccccc3-c3cncn32)c1] | 2-(5H-imidazo[5,1-a]isoindol-5-yl)-1-(1-methyl-1H-imidazol-4-yl)ethanol; |

-continued

| No. | Structure | Name |
|---|---|---|
| 1390 | 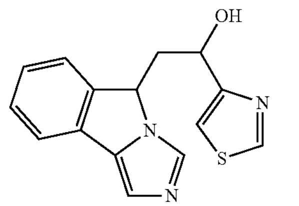 [SMILES: OC(CC1c2ccccc2-c2cncn21)c1cscn1] | 2-(5H-imidazo[5,1-a]isoindol-5-yl)-1-(thiazol-4-yl)ethanol; |
| 1391 | 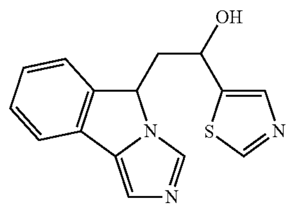 [SMILES: OC(CC1c2ccccc2-c2cncn21)c1cncs1] | 2-(5H-imidazo[5,1-a]isoindol-5-yl)-1-(thiazol-5-yl)ethanol; |
| 1392 | 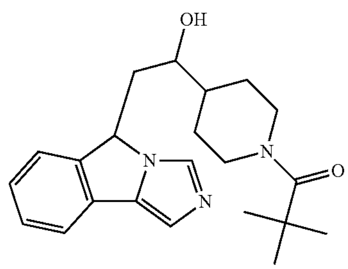 [SMILES: CC(C)(C)C(=O)N1CCC(C(O)CC2c3ccccc3-c3cncn32)CC1] | 1-(4-(1-hydroxy-2-(5H-imidazo[5,1-a]isoindol-5-yl)ethyl)piperidin-1-yl)-2,2-dimethylpropan-1-one; |
| 1393 | 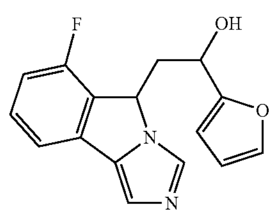 [SMILES: OC(CC1c2c(F)cccc2-c2cncn21)c1ccco1] | 2-(6-fluoro-5H-imidazo[5,1-a]isoindol-5-yl)-1-(furan-2-yl)ethanol; |
| 1394 | 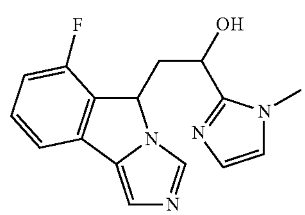 [SMILES: Cn1ccnc1C(O)CC1c2c(F)cccc2-c2cncn21] | 2-(6-fluoro-5H-imidazo[5,1-a]isoindol-5-yl)-1-(1-methyl-1H-imidazol-2-yl)ethanol; |
| 1396 | 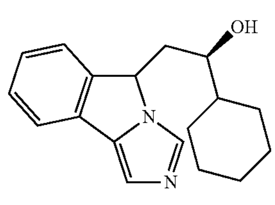 [SMILES: O[C@H](CC1c2ccccc2-c2cncn21)C1CCCCC1] | (1S)-1-cyclohexyl-2-(5H-imidazo[5,1-a]isoindol-5-yl)ethanol; |
| 1397 | 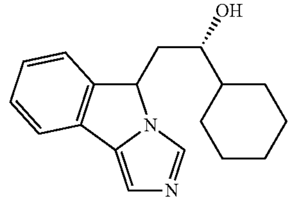 [SMILES: O[C@@H](CC1c2ccccc2-c2cncn21)C1CCCCC1] | (1R)-1-cyclohexyl-2-(5H-imidazo[5,1-a]isoindol-5-yl)ethanol; |

-continued

| No. | Structure | Name |
|---|---|---|
| 1398 | 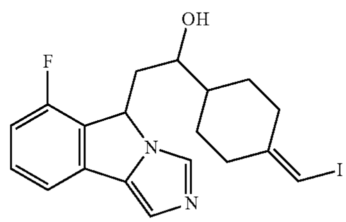 [SMILES: OC(CC1c2c(F)cccc2-c2cncn21)C1CCC(=CI)CC1] | 2-(6-fluoro-5H-imidazo[5,1-a]isoindol-5-yl)-1-(4-(iodomethylene)cyclohexyl)ethanol; |
| 1400 | 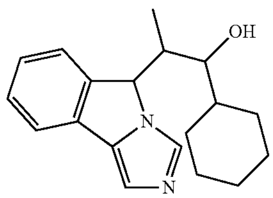 [SMILES: CC(C(O)C1CCCCC1)C1c2ccccc2-c2cncn21] | 1-cyclohexyl-2-(5H-imidazo[5,1-a]isoindol-5-yl)propan-1-ol; |
| 1402 | 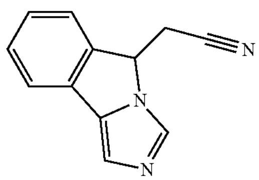 [SMILES: N#CCC1c2ccccc2-c2cncn21] | 2-(5H-imidazo[5,1-a]isoindol-5-yl)acetonitrile; |
| 1403 | 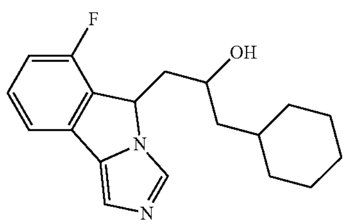 [SMILES: OC(CC1CCCCC1)CC1c2c(F)cccc2-c2cncn21] | 1-cyclohexyl-3-(6-fluoro-5H-imidazo[5,1-a]isoindol-5-yl)propan-2-ol; |
| 1404 | 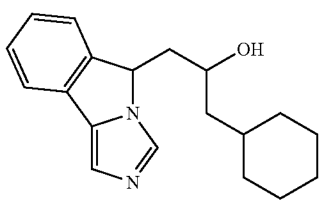 [SMILES: OC(CC1CCCCC1)CC1c2ccccc2-c2cncn21] | 1-cyclohexyl-3-(5H-imidazo[5,1-a]isoindol-5-yl)propan-2-ol; |
| 1405 | 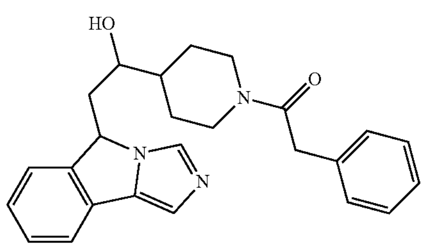 [SMILES: O=C(Cc1ccccc1)N1CCC(C(O)CC2c3ccccc3-c3cncn32)CC1] | 1-(4-(1-hydroxy-2-(5H-imidazo[5,1-a]isoindol-5-yl)ethyl)piperidin-1-yl)-2-phenylethanone; |
| 1406 | 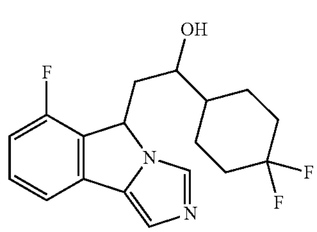 [SMILES: OC(CC1c2c(F)cccc2-c2cncn21)C1CCC(F)(F)CC1] | 1-(4,4-difluorocyclohexyl)-2-(6-fluoro-5H-imidazo[5,1-a]isoindol-5-yl)ethanol; |

-continued

| No. | Structure | Name |
|---|---|---|
| 1407 | 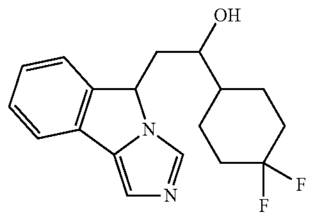 [SMILES: OC(CC1c2ccccc2-c2cncn21)C1CCC(F)(F)CC1] | 1-(4,4-difluorocyclohexyl)-2-(5H-imidazo[5,1-a]isoindol-5-yl)ethanol; |
| 1409 | 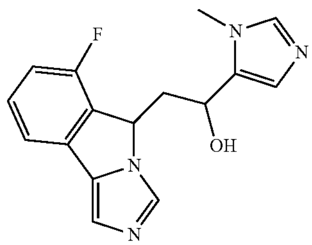 [SMILES: Cn1cncc1C(O)CC1c2c(F)cccc2-c2cncn21] | 2-(6-fluoro-5H-imidazo[5,1-a]isoindol-5-yl)-1-(1-methyl-1H-imidazol-5-yl)ethanol; |
| 1410 | 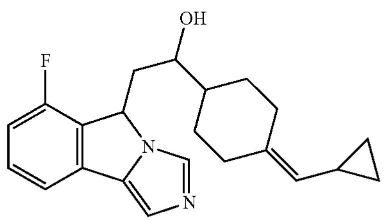 [SMILES: OC(CC1c2c(F)cccc2-c2cncn21)C1CCC(=CC2CC2)CC1] | 1-(4-(cyclopropylmethylene)cyclohexyl)-2-(6-fluoro-5H-imidazo[5,1-a]isoindol-5-yl)ethanol; |
| 1411 | 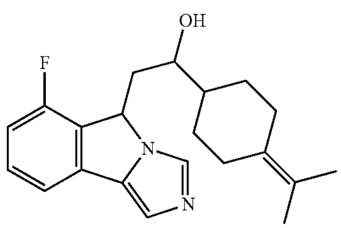 [SMILES: CC(C)=C1CCC(C(O)CC2c3c(F)cccc3-c3cncn32)CC1] | 2-(6-fluoro-5H-imidazo[5,1-a]isoindol-5-yl)-1-(4-(propan-2-ylidene)cyclohexyl)ethanol; |
| 1412 | 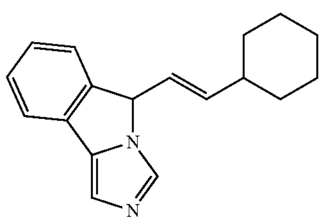 [SMILES: C(=C\C1c2ccccc2-c2cncn21)/C1CCCCC1] | (E)-5-(2-cyclohexylvinyl)-5H-imidazo[5,1-a]isoindole; |
| 1413 | 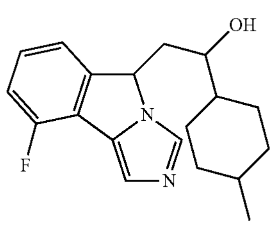 [SMILES: CC1CCC(C(O)CC2c3cccc(F)c3-c3cncn32)CC1] | 2-(9-fluoro-5H-imidazo[5,1-a]isoindol-5-yl)-1-(4-methylcyclohexyl)ethanol; |
| 1414 | 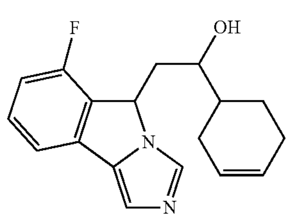 [SMILES: OC(CC1c2c(F)cccc2-c2cncn21)C1CC=CCC1] | 1-(cyclohex-3-en-1-yl)-2-(6-fluoro-5H-imidazo[5,1-a]isoindol-5-yl)ethanol; |

-continued

| No. | Structure | Name |
|---|---|---|
| 1415 | 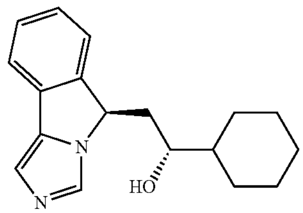 [SMILES: O[C@H](C[C@@H]1c2ccccc2-c2cncn21)C1CCCCC1] | (R)-1-cyclohexyl-2-((R)-5H-imidazo[5,1-a]isoindol-5-yl)ethanol |
| 1416 | 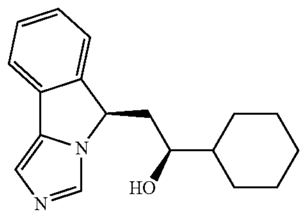 [SMILES: O[C@@H](C[C@@H]1c2ccccc2-c2cncn21)C1CCCCC1] | (S)-1-cyclohexyl-2-((R)-5H-imidazo[5,1-a]isoindol-5-yl)ethanol |
| 1417 | 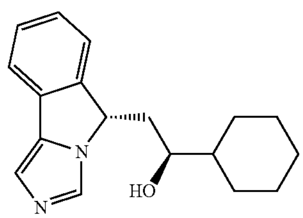 [SMILES: O[C@@H](C[C@H]1c2ccccc2-c2cncn21)C1CCCCC1] | (S)-1-cyclohexyl-2-((S)-5H-imidazo[5,1-a]isoindol-5-yl)ethanol |
| 1418 | 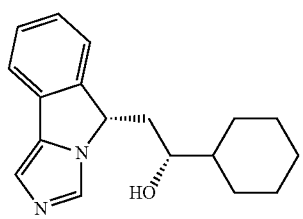 [SMILES: O[C@H](C[C@H]1c2ccccc2-c2cncn21)C1CCCCC1] | (R)-1-cyclohexyl-2-((S)-5H-imidazo[5,1-a]isoindol-5-yl)ethanol |
| 1419 | 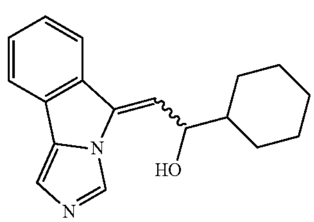 [SMILES: OC(C=c1c2ccccc2c2cncn12)C1CCCCC1] | 1-cyclohexyl-2-(5H-imidazo[5,1-a]isoindol-5-ylidene)ethanol |
| 1420 | 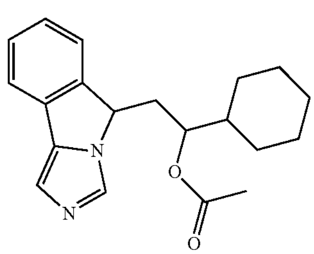 [SMILES: CC(=O)OC(CC1c2ccccc2-c2cncn21)C1CCCCC1] | 1-cyclohexyl-2-(5H-imidazo[5,1-a]isoindol-5-yl)ethyl acetate |
| 1421 | 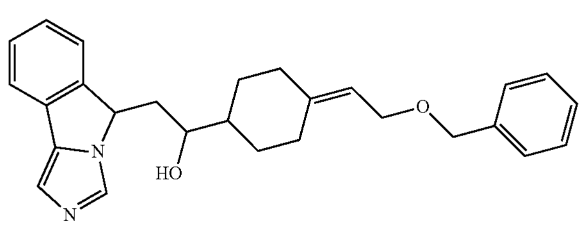 [SMILES: OC(CC1c2ccccc2-c2cncn21)C1CCC(=CCOCc2ccccc2)CC1] | 1-(4-(2-(benzyloxy)ethylidene)cyclohexyl)-2-(5H-imidazo[5,1-a]isoindol-5-yl)ethanol |

| No. | Structure | Name |
| --- | --- | --- |
| 1422 | 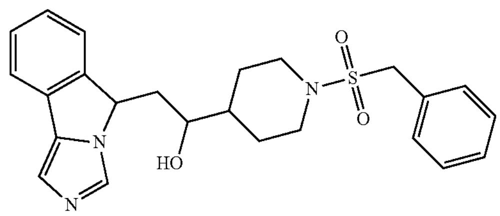 [SMILES: O=S(=O)(Cc1ccccc1)N1CCC(C(O)CC2c3ccccc3-c3cncn32)CC1] | 1-(1-(benzylsulfonyl)piperidin-4-yl)-2-(5H-imidazo[5,1-a]isoindol-5-yl)ethanol |
| 1423 | 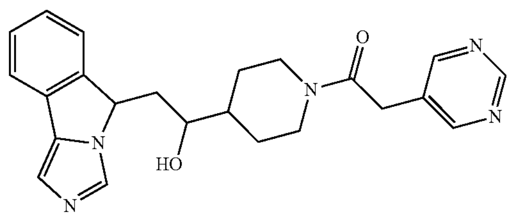 [SMILES: O=C(Cc1cncnc1)N1CCC(C(O)CC2c3ccccc3-c3cncn32)CC1] | 1-(4-(1-hydroxy-2-(5H-imidazo[5,1-a]isoindol-5-yl)ethyl)piperidin-1-yl)-2-(pyrimidin-5-yl)ethanone |
| 1424 | 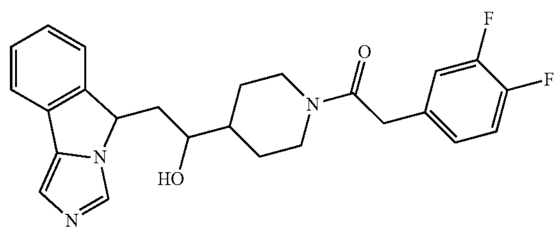 [SMILES: O=C(Cc1ccc(F)c(F)c1)N1CCC(C(O)CC2c3ccccc3-c3cncn32)CC1] | 2-(3,4-difluorophenyl)-1-(4-(1-hydroxy-2-(5H-imidazo[5,1-a]isoindol-5-yl)ethyl)piperidin-1-yl)ethanone |
| 1425 | 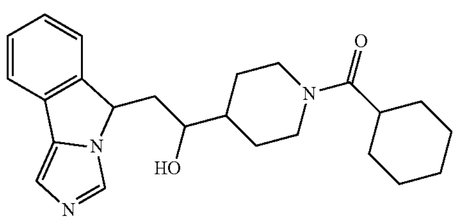 [SMILES: O=C(C1CCCCC1)N1CCC(C(O)CC2c3ccccc3-c3cncn32)CC1] | cyclohexyl(4-(1-hydroxy-2-(5H-imidazo[5,1-a]isoindol-5-yl)ethyl)piperidin-1-yl)methanone |
| 1426 | 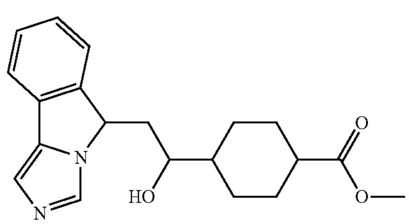 [SMILES: COC(=O)C1CCC(C(O)CC2c3ccccc3-c3cncn32)CC1] | methyl 4-(1-hydroxy-2-(5H-imidazo[5,1-a]isoindol-5-yl)ethyl)cyclohexanecarboxylate |
| 1427 | 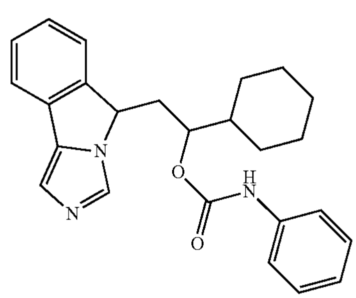 [SMILES: O=C(Nc1ccccc1)OC(CC1c2ccccc2-c2cncn21)C1CCCCC1] | 1-cyclohexyl-2-(5H-imidazo[5,1-a]isoindol-5-yl)ethyl phenylcarbamate |

-continued

| No. | Structure | Name |
|---|---|---|
| 1428 | 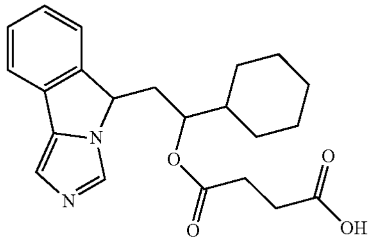 [SMILES: O=C(O)CCC(=O)OC(CC1c2ccccc2-c2cncn21)C1CCCCC1] | 4-(1-cyclohexyl-2-(5H-imidazo[5,1-a]isoindol-5-yl)ethoxy)-4-oxobutanoic acid |
| 1429 | 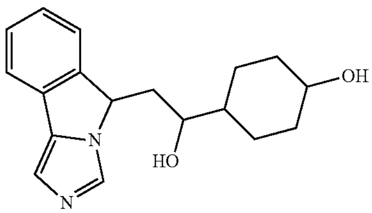 [SMILES: OC1CCC(C(O)CC2c3ccccc3-c3cncn32)CC1] | 4-(1-hydroxy-2-(5H-imidazo[5,1-a]isoindol-5-yl)ethyl)cyclohexanol |
| 1431 | 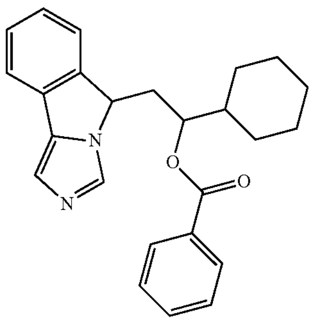 [SMILES: O=C(OC(CC1c2ccccc2-c2cncn21)C1CCCCC1)c1ccccc1] | 1-cyclohexyl-2-(5H-imidazo[5,1-a]isoindol-5-yl)ethyl benzoate |
| 1432 | 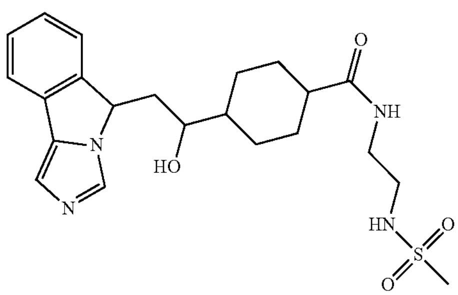 [SMILES: CS(=O)(=O)NCCNC(=O)C1CCC(C(O)CC2c3ccccc3-c3cncn32)CC1] | 4-(1-hydroxy-2-(5H-imidazo[5,1-a]isoindol-5-yl)ethyl)-N-(2-(methylsulfonamido)ethyl)cyclohexanecarboxamide |
| 1433 | 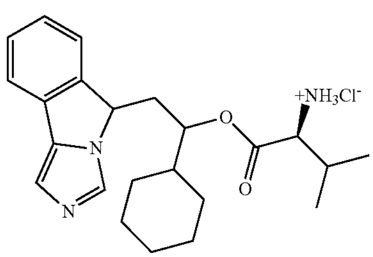 | (2S)-1-(1-cyclohexyl-2-(5H-imidazo[5,1-a]isoindol-5-yl)ethoxy)-3-methyl-1-oxobutan-2-aminium chloride |
| 1434 | 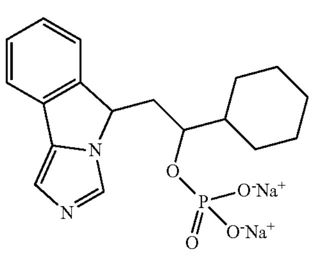 | sodium 1-cyclohexyl-2-(5H-imidazo[5,1-a]isoindol-5-yl)ethyl phosphate |

-continued

| No. | Structure | Name |
|---|---|---|
| 1436 | 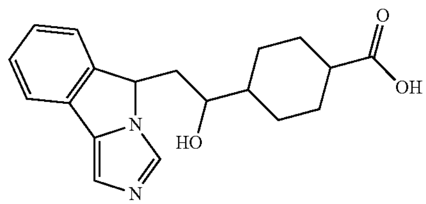 [SMILES: O=C(O)C1CCC(C(O)CC2c3ccccc3-c3cncn32)CC1] | 4-(1-hydroxy-2-(5H-imidazo[5,1-a]isoindol-5-yl)ethyl)cyclohexanecarboxylic acid |
| 1437 | 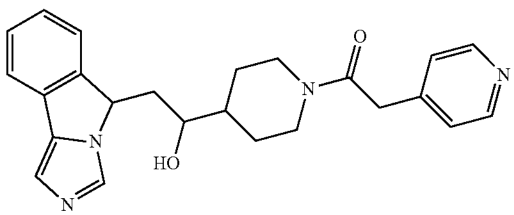 [SMILES: O=C(Cc1ccncc1)N1CCC(C(O)CC2c3ccccc3-c3cncn32)CC1] | 1-(4-(1-hydroxy-2-(5H-imidazo[5,1-a]isoindol-5-yl)ethyl)piperidin-1-yl)-2-(pyridin-4-yl)ethanone |
| 1438 | 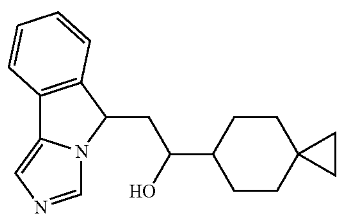 [SMILES: OC(CC1c2ccccc2-c2cncn21)C1CCC2(CC1)CC2] | 2-(5H-imidazo[5,1-a]isoindol-5-yl)-1-(spiro[2.5]octan-6-yl)ethanol |
| 1439 | 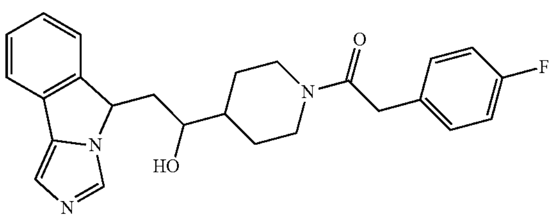 | 2-(4-fluorophenyl)-1-(4-(1-hydroxy-2-(5H-imidazo[5,1-a]isoindol-5-yl)ethyl)piperidin-1-yl)ethanone |
| 1440 | 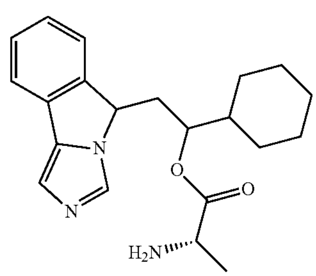 [SMILES: C[C@H](N)C(=O)OC(CC1c2ccccc2-c2cncn21)C1CCCCC1] | (2S)-1-cyclohexyl-2-(5H-imidazo[5,1-a]isoindol-5-yl)ethyl 2-aminopropanoate |
| 1441 | 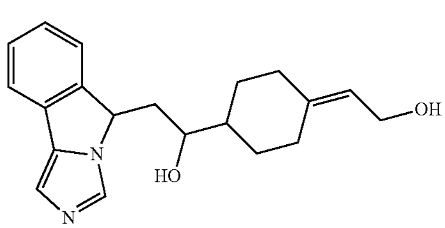 [SMILES: OCC=C1CCC(C(O)CC2c3ccccc3-c3cncn32)CC1] | 1-(4-(2-hydroxyethylidene)cyclohexyl)-2-(5H-imidazo[5,1-a]isoindol-5-yl)ethanol |

| No. | Structure | Name |
|---|---|---|
| 1442 | 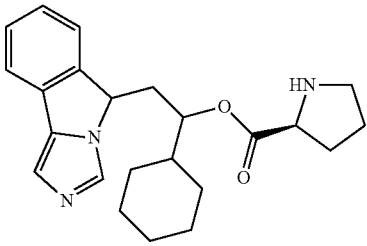 [SMILES: O=C(OC(CC1c2ccccc2-c2cncn21)C1CCCCC1)[C@@H]1CCCN1] | (2S)-1-cyclohexyl-2-(5H-imidazo[5,1-a]isoindol-5-yl)ethyl pyrrolidine-2-carboxylate |
| 1443 | 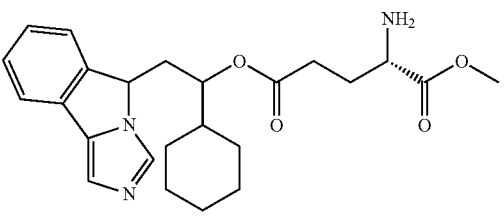 [SMILES: COC(=O)[C@@H](N)CCC(=O)OC(CC1c2ccccc2-c2cncn21)C1CCCCC1] | (2S)-5-(1-cyclohexyl-2-(5H-imidazo[5,1-a]isoindol-5-yl)ethyl) 1-methyl 2-aminopentanedioate |
| 1447 | 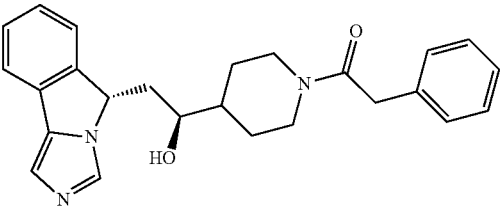 [SMILES: O=C(Cc1ccccc1)N1CCC([C@@H](O)C[C@H]2c3ccccc3-c3cncn32)CC1] | 1-(4-((S)-1-hydroxy-2-((S)-5H-imidazo[5,1-a]isoindol-5-yl)ethyl)piperidin-1-yl)-2-phenylethanone |
| 1448 | 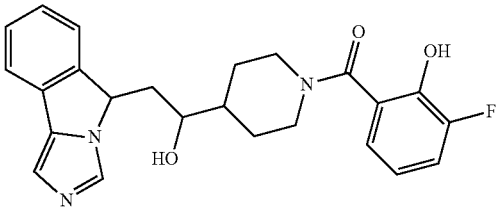 [SMILES: O=C(c1cccc(F)c1O)N1CCC(C(O)CC2c3ccccc3-c3cncn32)CC1] | (3-fluoro-2-hydroxyphenyl)(4-(1-hydroxy-2-(5H-imidazo[5,1-a]isoindol-5-yl)ethyl)piperidin-1-yl)methanone |
| 1449 | 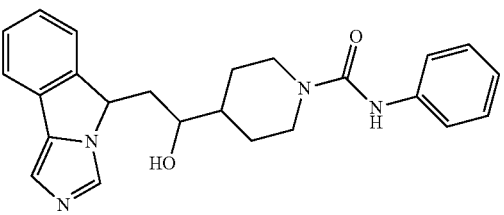 | 4-(1-hydroxy-2-(5H-imidazo[5,1-a]isoindol-5-yl)ethyl)-N-phenylpiperidine-1-carboxamide |
| 1450 | 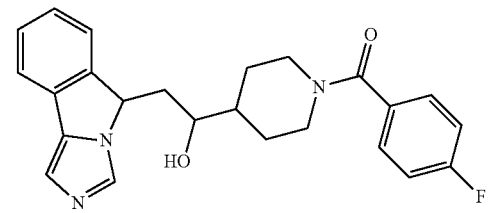 [SMILES: O=C(c1ccc(F)cc1)N1CCC(C(O)CC2c3ccccc3-c3cncn32)CC1] | (4-fluorophenyl)(4-(1-hydroxy-2-(5H-imidazo[5,1-a]isoindol-5-yl)ethyl)piperidin-1-yl)methanone |
| 1451 | 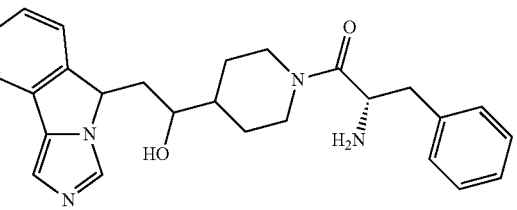 | (2S)-2-amino-1-(4-(1-hydroxy-2-(5H-imidazo[5,1-a]isoindol-5-yl)ethyl)piperidin-1-yl)-3-phenylpropan-1-one |

-continued

| No. | Structure | Name |
|---|---|---|
| 1454 | 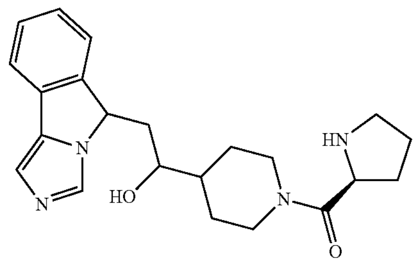 [SMILES: O=C([C@@H]1CCCN1)N1CCC(C(O)CC2c3ccccc3-c3cncn32)CC1] | (4-(1-hydroxy-2-(5H-imidazo[5,1-a]isoindol-5-yl)ethyl)piperidin-1-yl)((S)-pyrrolidin-2-yl)methanone |
| 1455 | 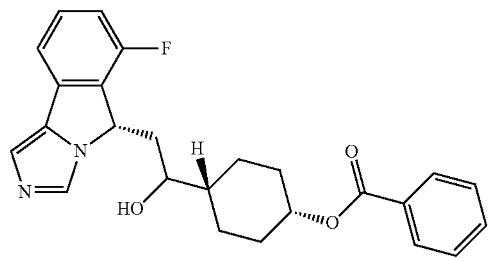 [SMILES: O=C(O[C@H]1CC[C@@H](C(O)C[C@H]2c3c(F)cccc3-c3cncn32)CC1)c1ccccc1] | (1R,4s)-4-(2-((S)-6-fluoro-5H-imidazo[5,1-a]isoindol-5-yl)-1-hydroxyethyl)cyclohexyl benzoate |
| 1456 | 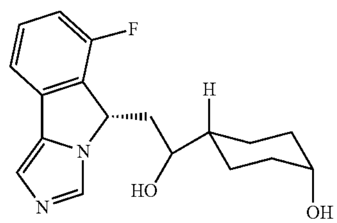 [SMILES: OC1CCC(C(O)C[C@H]2c3c(F)cccc3-c3cncn32)CC1] | (1R,4s)-4-(2-((S)-6-fluoro-5H-imidazo[5,1-a]isoindol-5-yl)-1-hydroxyethyl)cyclohexanol |
| 1458 | 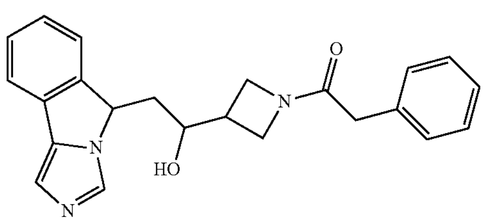 [SMILES: O=C(Cc1ccccc1)N1CC(C(O)CC2c3ccccc3-c3cncn32)C1] | 1-(3-(1-hydroxy-2-(5H-imidazo[5,1-a]isoindol-5-yl)ethyl)azetidin-1-yl)-2-phenylethanone |
| 1459 | 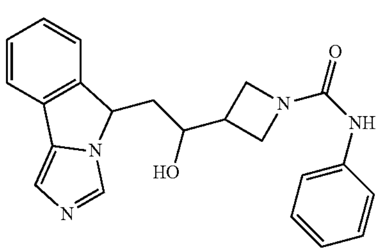 [SMILES: O=C(Nc1ccccc1)N1CC(C(O)CC2c3ccccc3-c3cncn32)C1] | 3-(1-hydroxy-2-(5H-imidazo[5,1-a]isoindol-5-yl)ethyl)-N-phenylazetidine-1-carboxamide |
| 1460 | 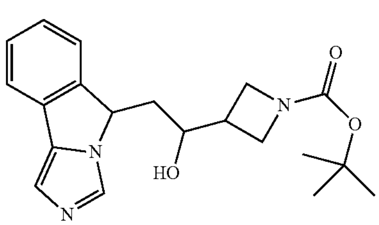 [SMILES: CC(C)(C)OC(=O)N1CC(C(O)CC2c3ccccc3-c3cncn32)C1] | tert-butyl 3-(1-hydroxy-2-(5H-imidazo[5,1-a]isoindol-5-yl)ethyl)azetidine-1-carboxylate |

-continued

| No. | Structure | Name |
|---|---|---|
| 1461 | 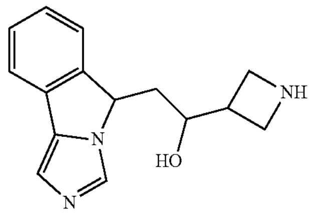 [SMILES: OC(CC1c2ccccc2-c2cncn21)C1CNC1] | 1-(azetidin-3-yl)-2-(5H-imidazo[5,1-a]isoindol-5-yl)ethanol |
| 1469 | 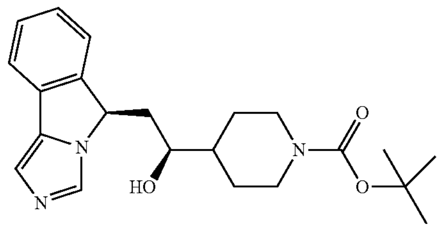 [SMILES: CC(C)(C)OC(=O)N1CCC([C@@H](O)C[C@@H]2c3ccccc3-c3cncn32)CC1] | tert-butyl 4-((S)-1-hydroxy-2-((R)-5H-imidazo[5,1-a]isoindol-5-yl)ethyl)piperidine-1-carboxylate |
| 1470 | 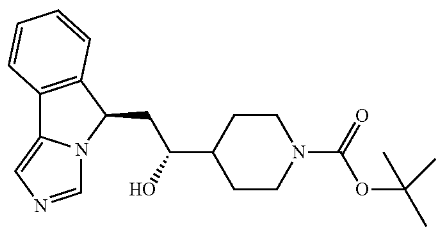 [SMILES: CC(C)(C)OC(=O)N1CCC([C@H](O)C[C@@H]2c3ccccc3-c3cncn32)CC1] | tert-butyl 4-((R)-1-hydroxy-2-((R)-5H-imidazo[5,1-a]isoindol-5-yl)ethyl)piperidine-1-carboxylate |
| 1471 | 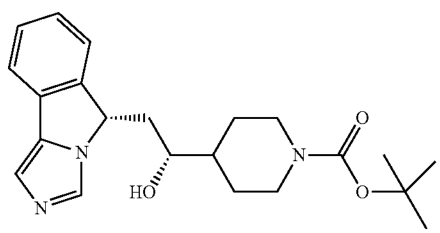 [SMILES: CC(C)(C)OC(=O)N1CCC([C@H](O)C[C@H]2c3ccccc3-c3cncn32)CC1] | tert-butyl 4-((R)-1-hydroxy-2-((S)-5H-imidazo[5,1-a]isoindol-5-yl)ethyl)piperidine-1-carboxylate |
| 1472 | 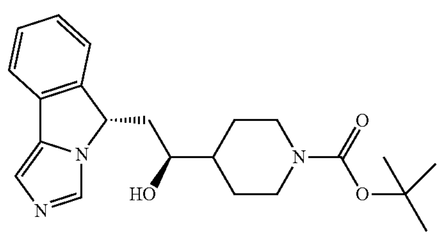 [SMILES: CC(C)(C)OC(=O)N1CCC([C@@H](O)C[C@H]2c3ccccc3-c3cncn32)CC1] | tert-butyl 4-((S)-1-hydroxy-2-((S)-5H-imidazo[5,1-a]isoindol-5-yl)ethyl)piperidine-1-carboxylate |
| 1473 | 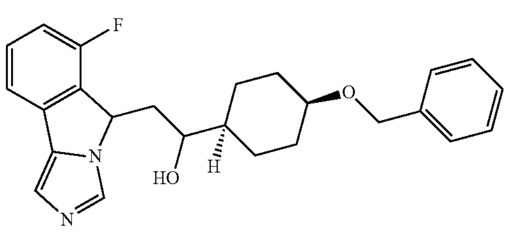 [SMILES: OC(CC1c2c(F)cccc2-c2cncn21)[C@H]1CC[C@@H](OCc2ccccc2)CC1] | 1-((1s,4s)-4-(benzyloxy)cyclohexyl)-2-(6-fluoro-5H-imidazo[5,1-a]isoindol-5-yl)ethanol |
| 1474 | 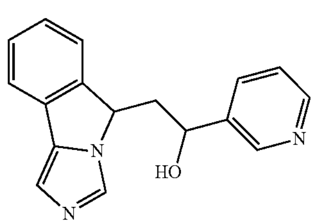 [SMILES: OC(CC1c2ccccc2-c2cncn21)c1cccnc1] | 2-(5H-imidazo[5,1-a]isoindol-5-yl)-1-(pyridin-3-yl)ethanol |

-continued

| No. | Structure | Name |
|---|---|---|
| 1475 | 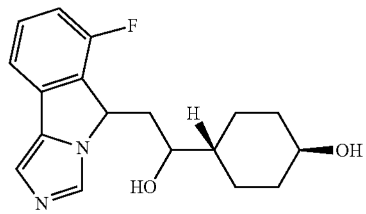 [SMILES: OC(CC1c2c(F)cccc2-c2cncn21)[C@H]1CC[C@H](O)CC1] | (1r,4r)-4-(2-(6-fluoro-5H-imidazo[5,1-a]isoindol-5-yl)-1-hydroxyethyl)cyclohexanol |
| 1476 | 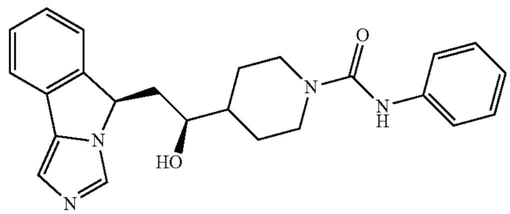 [SMILES: O=C(Nc1ccccc1)N1CCC([C@@H](O)C[C@@H]2c3ccccc3-c3cncn32)CC1] | 4-((S)-1-hydroxy-2-((R)-5H-imidazo[5,1-a]isoindol-5-yl)ethyl)-N-phenylpiperidine-1-carboxamide |
| 1477 | 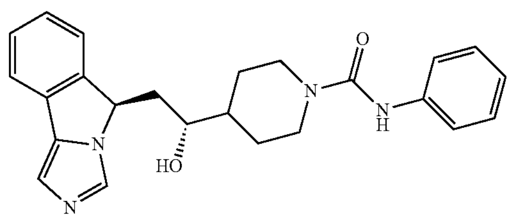 [SMILES: O=C(Nc1ccccc1)N1CCC([C@H](O)C[C@@H]2c3ccccc3-c3cncn32)CC1] | 4-((R)-1-hydroxy-2-((R)-5H-imidazo[5,1-a]isoindol-5-yl)ethyl)-N-phenylpiperidine-1-carboxamide |
| 1478 | 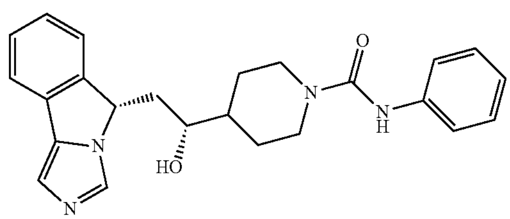 [SMILES: O=C(Nc1ccccc1)N1CCC([C@H](O)C[C@H]2c3ccccc3-c3cncn32)CC1] | 4-((R)-1-hydroxy-2-((S)-5H-imidazo[5,1-a]isoindol-5-yl)ethyl)-N-phenylpiperidine-1-carboxamide |
| 1479 | 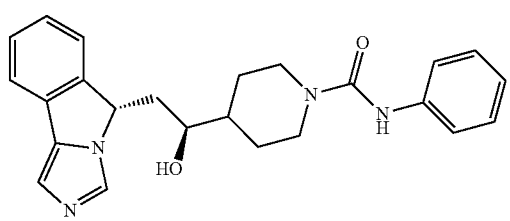 [SMILES: O=C(Nc1ccccc1)N1CCC([C@@H](O)C[C@H]2c3ccccc3-c3cncn32)CC1] | 4-((S)-1-hydroxy-2-((S)-5H-imidazo[5,1-a]isoindol-5-yl)ethyl)-N-phenylpiperidine-1-carboxamide |
| 1480 | 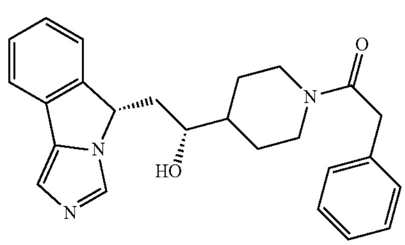 [SMILES: O=C(Cc1ccccc1)N1CCC([C@H](O)C[C@H]2c3ccccc3-c3cncn32)CC1] | 1-(4-((R)-1-hydroxy-2-((S)-5H-imidazo[5,1-a]isoindol-5-yl)ethyl)piperidin-1-yl)-2-phenylethanone |
| 1482 | 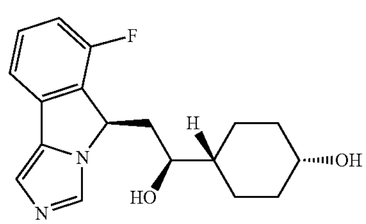 [SMILES: O[C@@H](C[C@@H]1c2c(F)cccc2-c2cncn21)[C@H]1CC[C@@H](O)CC1] | (1R,4s)-4-((S)-2-((R)-6-fluoro-5H-imidazo[5,1-a]isoindol-5-yl)-1-hydroxyethyl)cyclohexanol |

| No. | Structure | Name |
| --- | --- | --- |
| 1483 | 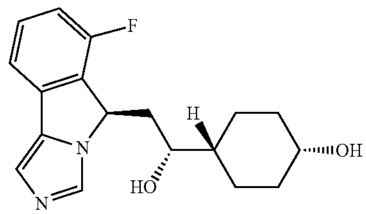 [SMILES: O[C@H](C[C@@H]1c2c(F)cccc2-c2cncn21)[C@H]1CC[C@@H](O)CC1] | (1S,4s)-4-((R)-2-((R)-6-fluoro-5H-imidazo[5,1-a]isoindol-5-yl)-1-hydroxyethyl)cyclohexanol |
| 1484 | 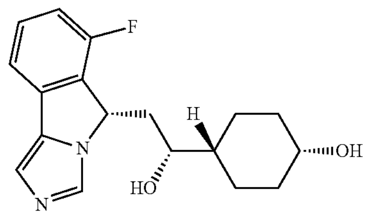 [SMILES: O[C@H](C[C@H]1c2c(F)cccc2-c2cncn21)[C@H]1CC[C@@H](O)CC1] | (1S,4s)-4-((R)-2-((S)-6-fluoro-5H-imidazo[5,1-a]isoindol-5-yl)-1-hydroxyethyl)cyclohexanol |
| 1485 | 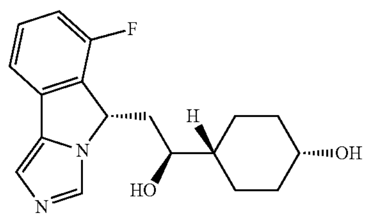 [SMILES: O[C@@H](C[C@H]1c2c(F)cccc2-c2cncn21)[C@H]1CC[C@@H](O)CC1] | (1R,4s)-4-((S)-2-((S)-6-fluoro-5H-imidazo[5,1-a]isoindol-5-yl)-1-hydroxyethyl)cyclohexanol |
| 1486 | 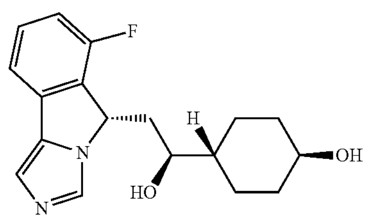 [SMILES: O[C@@H](C[C@H]1c2c(F)cccc2-c2cncn21)[C@H]1CC[C@H](O)CC1] | (1S,4r)-4-((S)-2-((S)-6-fluoro-5H-imidazo[5,1-a]isoindol-5-yl)-1-hydroxyethyl)cyclohexanol |
| 1487 | 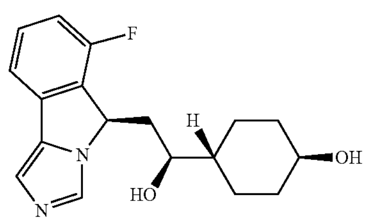 [SMILES: O[C@@H](C[C@@H]1c2c(F)cccc2-c2cncn21)[C@H]1CC[C@H](O)CC1] | (1S,4r)-4-((S)-2-((R)-6-fluoro-5H-imidazo[5,1-a]isoindol-5-yl)-1-hydroxyethyl)cyclohexanol |
| 1488 | 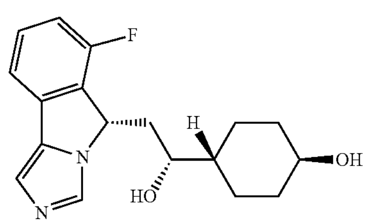 [SMILES: O[C@H](C[C@H]1c2c(F)cccc2-c2cncn21)[C@H]1CC[C@H](O)CC1] | (1R,4r)-4-((R)-2-((S)-6-fluoro-5H-imidazo[5,1-a]isoindol-5-yl)-1-hydroxyethyl)cyclohexanol |
| 1489 | 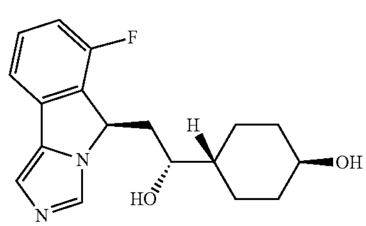 [SMILES: O[C@H](C[C@@H]1c2c(F)cccc2-c2cncn21)[C@H]1CC[C@H](O)CC1] | (1R,4r)-4-((R)-2-((R)-6-fluoro-5H-imidazo[5,1-a]isoindol-5-yl)-1-hydroxyethyl)cyclohexanol |

| No. | Structure | Name |
|---|---|---|
| 1490 | 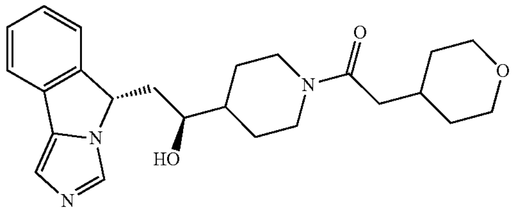 [SMILES: O=C(CC1CCOCC1)N1CCC([C@@H](O)C[C@H]2c3ccccc3-c3cncn32)CC1] | 1-(4-((S)-1-hydroxy-2-((S)-5H-imidazo[5,1-a]isoindol-5-yl)ethyl)piperidin-1-yl)-2-(tetrahydro-2H-pyran-4-yl)ethanone |
| 1491 | 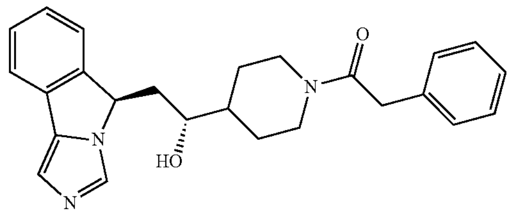 [SMILES: O=C(Cc1ccccc1)N1CCC([C@H](O)C[C@@H]2c3ccccc3-c3cncn32)CC1] | 1-(4-((R)-1-hydroxy-2-((R)-5H-imidazo[5,1-a]isoindol-5-yl)ethyl)piperidin-1-yl)-2-phenylethanone |
| 1492 | 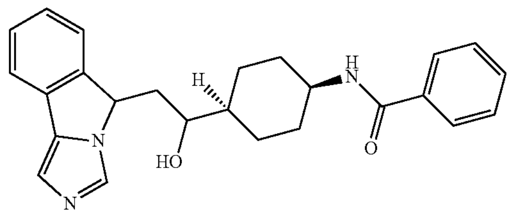 [SMILES: O=C(N[C@H]1CC[C@@H](C(O)CC2c3ccccc3-c3cncn32)CC1)c1ccccc1] | N-((1s,4s)-4-(1-hydroxy-2-(5H-imidazo[5,1-a]isoindol-5-yl)ethyl)cyclohexyl)benzamide |
| 1493 | 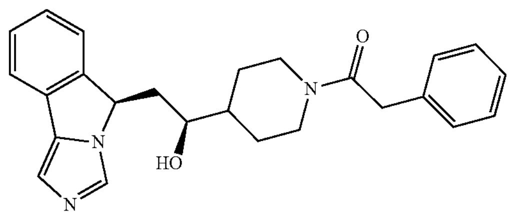 [SMILES: O=C(Cc1ccccc1)N1CCC([C@@H](O)C[C@@H]2c3ccccc3-c3cncn32)CC1] | 1-(4-((S)-1-hydroxy-2-((R)-5H-imidazo[5,1-a]isoindol-5-yl)ethyl)piperidin-1-yl)-2-phenylethanone |
| 1494 | 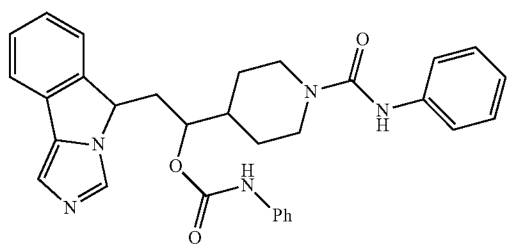 [SMILES: O=C(Nc1ccccc1)OC(CC1c2ccccc2-c2cncn21)C1CCN(C(=O)Nc2ccccc2)CC1] | 2-(5H-imidazo[5,1-a]isoindol-5-yl)-1-(1-(phenylcarbamoyl)piperidin-4-yl)ethyl phenylcarbamate |
| 1495 | 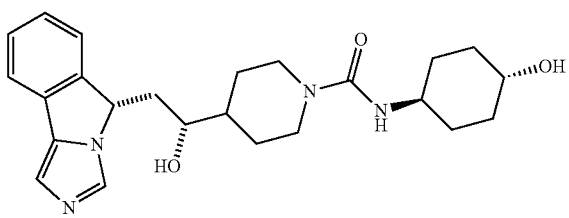 [SMILES: O=C(N[C@H]1CC[C@H](O)CC1)N1CCC([C@H](O)C[C@H]2c3ccccc3-c3cncn32)CC1] | 4-((R)-1-hydroxy-2-((S)-5H-imidazo[5,1-a]isoindol-5-yl)ethyl)-N-((1r,4R)-4-hydroxycyclohexyl)piperidine-1-carboxamide |
| 1496 | 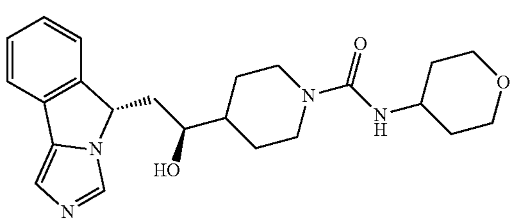 [SMILES: O=C(NC1CCOCC1)N1CCC([C@@H](O)C[C@H]2c3ccccc3-c3cncn32)CC1] | 4-((S)-1-hydroxy-2-((S)-5H-imidazo[5,1-a]isoindol-5-yl)ethyl)-N-(tetrahydro-2H-pyran-4-yl)piperidine-1-carboxamide |

-continued

| No. | Structure | Name |
|---|---|---|
| 1497 | 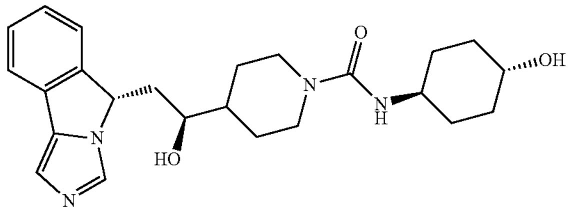 [SMILES: O=C(N[C@H]1CC[C@H](O)CC1)N1CCC([C@@H](O)C[C@H]2c3ccccc3-c3cncn32)CC1] | 4-((S)-1-hydroxy-2-((S)-5H-imidazo[5,1-a]isoindol-5-yl)ethyl)-N-((1r,4S)-4-hydroxycyclohexyl)piperidine-1-carboxamide |
| 1498 | 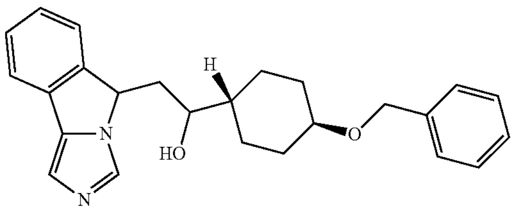 [SMILES: OC(CC1c2ccccc2-c2cncn21)[C@H]1CC[C@H](OCc2ccccc2)CC1] | 1-((1r,4r)-(benzyloxy)cyclohexyl)-2-(5H-imidazo[5,1-a]isoindol-5-yl)ethanol |
| 1499 | 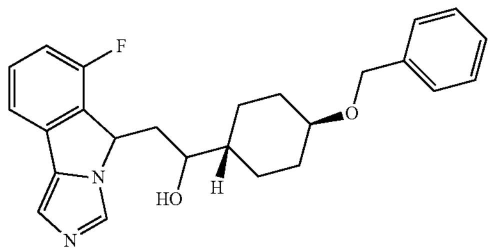 [SMILES: OC(CC1c2c(F)cccc2-c2cncn21)[C@H]1CC[C@H](OCc2ccccc2)CC1] | 1-((1r,4r)-4-(benzyloxy)cyclohexyl)-2-(6-fluoro-5H-imidazo[5,1-a]isoindol-5-yl)ethanol |
| 1500 | 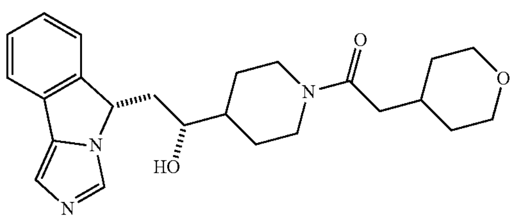 [SMILES: O=C(CC1CCOCC1)N1CCC([C@H](O)C[C@H]2c3ccccc3-c3cncn32)CC1] | 1-(4-((R)-1-hydroxy-2-((S)-5H-imidazo[5,1-a]isoindol-5-yl)ethyl)piperidin-1-yl)-2-(tetrahydro-2H-pyran-4-yl)ethanone |
| 1501 | 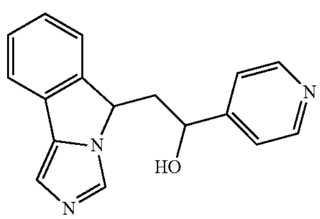 [SMILES: OC(CC1c2ccccc2-c2cncn21)c1ccncc1] | 2-(5H-imidazo[5,1-a]isoindol-5-yl)-1-(pyridin-4-yl)ethanol |
| 1502 | 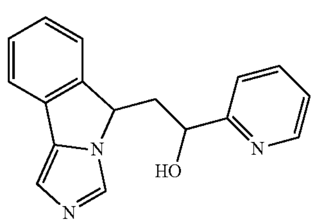 [SMILES: OC(CC1c2ccccc2-c2cncn21)c1ccccn1] | 2-(5H-imidazo[5,1-a]isoindol-5-yl)-1-(pyridin-2-yl)ethanol |
| 1503 | 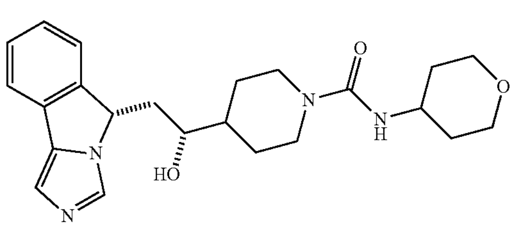 [SMILES: O=C(NC1CCOCC1)N1CCC([C@H](O)C[C@H]2c3ccccc3-c3cncn32)CC1] | 4-((R)-1-hydroxy-2-((S)-5H-imidazo[5,1-a]isoindol-5-yl)ethyl)-N-(tetrahydro-2H-pyran-4-yl)piperidine-1-carboxamide |

| No. | Name |
|---|---|
| 1504 | N-cyclohexyl-4-((R)-1-hydroxy-2-((S)-5H-imidazo[5,1-a]isoindol-5-yl)ethyl)piperidine-1-carboxamide |
| 1505 | N-((1r,4r)-4-(1-hydroxy-2-(5H-imidazo[5,1-a]isoindol-5-yl)ethyl)cyclohexyl)benzamide |
| 1507 | N-cyclopentyl-4-((R)-1-hydroxy-2-((S)-5H-imidazo[5,1-a]isoindol-5-yl)ethyl)piperidine-1-carboxamide |
| 1508 | 2-(6-fluoro-5H-imidazo[5,1-a]isoindol-5-yl)-1-(4-(trifluoromethyl)cyclohexyl)ethanol |
| 1509 | 2-(5H-imidazo[5,1-a]isoindol-5-yl)-1-(4-(trifluoromethyl)cyclohexyl)ethanol |
| 1511 | 2-(4-fluorophenyl)-1-(4-((R)-1-hydroxy-2-((S)-5H-imidazo[5,1-a]isoindol-5-yl)ethyl)piperidin-1-yl)ethanone |
| 1512 | 4-((R)-1-hydroxy-2-((S)-5H-imidazo[5,1-a]isoindol-5-yl)ethyl)-N-(4-(trifluoromethyl)phenyl)piperidine-1-carboxamide |

|  No. | Structure | Name |
| --- | --- | --- |
| 1513 | 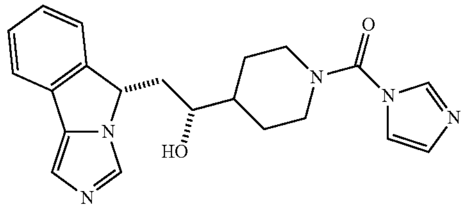 [SMILES: O=C(N1CCC([C@H](O)C[C@H]2c3ccccc3-c3cncn32)CC1)n1ccnc1] | (4-((R)-1-hydroxy-2-((S)-5H-imidazo[5,1-a]isoindol-5-yl)ethyl)piperidin-1-yl)(1H-imidazol-1-yl)methanone |
|  |  | 1-(5H-imidazo[5,1-a]isoindol-5-yl)-3-methylbutan-2-ol |
|  |  | 2-(5H-imidazo[5,1-a]isoindol-5-yl)-1-(tetrahydro-2H-pyran-3-yl)ethanol |
|  |  | 2-(5H-imidazo[5,1-a]isoindol-5-yl)-1-(piperidin-3-yl)ethanol |
|  |  | 1-cyclohexyl-2-((R)-5H-imidazo[5,1-a]isoindol-5-yl)ethanol |
|  |  | 1-cyclohexyl-2-((S)-5H-imidazo[5,1-a]isoindol-5-yl)ethanol |
|  |  | 1-cyclohexyl-3-(5H-imidazo[5,1-a]isoindol-5-yl)propan-1-ol |

| No. | Structure | Name |
|---|---|---|
| | | 1-cyclohexyl-2-(9-fluoro-5H-imidazo[5,1-a]isoindol-5-yl)ethanol |
| | | N-(4-(l-hydroxy-2-(5H-imidazo[5,1-a]isoindol-5-yl)ethyl)phenyl)-2-(tetrahydro-2H-pyran-4-yl)acetamide |
| | | 2-(5H-imidazo[5,1-a]isoindol-5-yl)-1-(1H-imidazol-2-yl)ethanol |
| | | 2-(5H-imidazo[5,1-a]isoindol-5-yl)-1-(1H-imidazol-4-yl)ethanol |
| | | 2-(6-fluoro-5H-imidazo[5,1-a]isoindol-5-yl)-1-(thiazol-2-yl)ethanol |
| | | (5S)-5-(2-cyclohexyl-2-hydroxyethyl)-5H-imidazo[5,1-a]isoindol-6-ol |
| | | 1-(2-aminocyclohexyl)-2-(5H-imidazo[5,1-a]isoindol-5-yl)ethanol |

| No. | Structure | Name |
|---|---|---|
| | | N-(1-cyclohexyl-2-(5H-imidazo[5,1-a]isoindol-5-yl)ethyl)acetamide |
| | | N-(2-(1-hydroxy-2-(5H-imidazo[5,1-a]isoindol-5-yl)ethyl)cyclohexyl)acetamide |
| | | 1-cyclohexyl-2-(5H-imidazo[5,1-a]isoindol-5-yl)-N-methylethanamine |
| | | 2-((1-cyclohexyl-2-((S)-5H-imidazo[5,1-a]isoindol-5-yl)ethyl)amino)ethanesulfonamide |
| | | 2-(6-fluoro-5H-imidazo[5,1-a]isoindol-5-yl)-1-(1-methylpiperidin-4-yl)ethanol |
| | | 1-(4-aminocyclohexyl)-2-(5H-imidazo[5,1-a]isoindol-5-yl)ethanol |

| No. | Structure | Name |
|---|---|---|
| | | N-(4-(1-hydroxy-2-(5H-imidazo[5,1-a]isoindol-5-yl)ethyl)cyclohexyl)acetamide |
| | | 1-(4-(aminomethyl)cyclohexyl)-2-(5H-imidazo[5,1-a]isoindol-5-yl)ethanol |
| | | 4-(1-hydroxy-2-(5H-imidazo[5,1-a]isoindol-5-yl)ethyl)cyclohexanecarboxamide |
| | | 1-(3-aminocyclohexyl)-2-(5H-imidazo[5,1-a]isoindol-5-yl)ethanol |
| | | 2-(5H-imidazo[5,1-a]isoindol-5-yl)-1-((1r,4r)-4-(pyridin-2-ylmethoxy)cyclohexyl)ethanol |
| | | 2-(5H-imidazo[5,1-a]isoindol-5-yl)-1-((1r,4r)-4-(pyridin-3-ylmethoxy)cyclohexyl)ethanol |

| No. | Structure | Name |
|---|---|---|
| | | 2-(5H-imidazo[5,1-a]isoindol-5-yl)-1-((1r,4r)-4-(pyridin-4-ylmethoxy)cyclohexyl)ethanol |
| | | 1-((1r,4r)-4-((2-aminopyridin-4-yl)methoxy)cyclohexyl)-2-(5H-imidazo[5,1-a]isoindol-5-yl)ethanol |
| | | 2-(5H-imidazo[5,1-a]isoindol-5-yl)-1-((1r,4r)-4-(pyrazin-2-ylmethoxy)cyclohexyl)ethanol |
| | | 2-(5H-imidazo[5,1-a]isoindol-5-yl)-1-((1r,4r)-4-(pyrimidin-5-ylmethoxy)cyclohexyl)ethanol |
| | | 1-((1r,4r)-4-((6-aminopyridin-2-yl)methoxy)cyclohexyl)-2-(5H-imidazo[5,1-a]isoindol-5-yl)ethanol |
| | | 1-((1r,4r)-4-((6-aminopyridin-3-yl)methoxy)cyclohexyl)-2-(5H-imidazo[5,1-a]isoindol-5-yl)ethanol |

| No. | Structure | Name |
|---|---|---|
| | | 1-((1r,4r)-4-((3-aminopyridin-2-yl)methoxy)cyclohexyl)-2-(5H-imidazo[5,1-a]isoindol-5-yl)ethanol |
| | | 1-((1r,4r)-4-((2-aminopyrimidin-5-yl)methoxy)cyclohexyl)-2-(5H-imidazo[5,1-a]isoindol-5-yl)ethanol |
| | | 1-((1r,4r)-4-((4-aminopyrimidin-5-yl)methoxy)cyclohexyl)-2-(5H-imidazo[5,1-a]isoindol-5-yl)ethanol |
| | | 1-((1r,4r)-4-((5-aminopyridin-2-yl)methoxy)cyclohexyl)-2-(5H-imidazo[5,1-a]isoindol-5-yl)ethanol |
| | | 4-((((1r,4r)-4-(1-hydroxy-2-(5H-imidazo[5,1-a]isoindol-5-yl)ethyl)cyclohexyl)oxy)methyl)-N,N-dimethylbenzamide |

| No. | Structure | Name |
|---|---|---|
| | | 3-((((1r,4r)-4-(1-hydroxy-2-(5H-imidazo[5,1-a]isoindol-5-yl)ethyl)cyclohexyl)oxy)methyl)-N,N-dimethylbenzamide |
| | | 2-((((1r,4r)-4-(1-hydroxy-2-(5H-imidazo[5,1-a]isoindol-5-yl)ethyl)cyclohexyl)oxy)methyl)-N,N-dimethylbenzamide |
| | | 4-((((1r,4r)-4-(1-hydroxy-2-(5H-imidazo[5,1-a]isoindol-5-yl)ethyl)cyclohexyl)oxy)methyl)benzenesulfonamide |
| | | 3-((((1r,4r)-4-(1-hydroxy-2-(5H-imidazo[5,1-a]isoindol-5-yl)ethyl)cyclohexyl)oxy)methyl)benzenesulfonamide |
| | | 2-((((1r,4r)-4-(1-hydroxy-2-(5H-imidazo[5,1-a]isoindol-5-yl)ethyl)cyclohexyl)oxy)methyl)benzenesulfonamide |

| No. | Structure | Name |
|---|---|---|
| | | 4-((((1r,4r)-4-(1-hydroxy-2-(5H-imidazo[5,1-a]isoindol-5-yl)ethyl)cyclohexyl)oxy)methyl)benzamide |
| | | 3-((((1r,4r)-4-(1-hydroxy-2-(5H-imidazo[5,1-a]isoindol-5-yl)ethyl)cyclohexyl)oxy)methyl)benzamide |
| | | 2-((((1r,4r)-4-(1-hydroxy-2-(5H-imidazo[5,1-a]isoindol-5-yl)ethyl)cyclohexyl)oxy)methyl)benzamide |
| | | methyl 4-((((1r,4r)-4-(1-hydroxy-2-(5H-imidazo[5,1-a]isoindol-5-yl)ethyl)cyclohexyl)oxy)methyl)benzoate |
| | | methyl 3-((((1r,4r)-4-(1-hydroxy-2-(5H-imidazo[5,1-a]isoindol-5-yl)ethyl)cyclohexyl)oxy)methyl)benzoate |

| No. | Structure | Name |
|---|---|---|
| | | methyl 2-((((1r,4r)-4-(1-hydroxy-2-(5H-imidazo[5,1-a]isoindol-5-yl)ethyl)cyclohexyl)oxy)methyl)benzoate |
| | | 2-(5H-imidazo[5,1-a]isoindol-5-yl)-1-((1r,4r)-4-methoxycyclohexyl)ethanol |
| | | 1-((1r,4r)-4-ethoxycyclohexyl)-2-(5H-imidazo[5,1-a]isoindol-5-yl)ethanol |
| | | 2-(5H-imidazo[5,1-a]isoindol-5-yl)-1-((1r,4r)-4-isopropoxycyclohexyl)ethanol |
| | | 1-((1r,4r)-4-(cyclopropylmethoxy)cyclohexyl)-2-(5H-imidazo[5,1-a]isoindol-5-yl)ethanol |
| | | 1-((1r,4r)-4-(cyclopentylmethoxy)cyclohexyl)-2-(5H-imidazo[5,1-a]isoindol-5-yl)ethanol |

| No. | Structure | Name |
|---|---|---|
| | | 2-(5H-imidazo[5,1-a]isoindol-5-yl)-1-((1r,4r)-4-(thiophen-2-ylmethoxy)cyclohexyl)ethanol |
| | | 1-((1r,4r)-4-((1H-indol-3-yl)oxy)cyclohexyl)-2-(5H-imidazo[5,1-a]isoindol-5-yl)ethanol |
| | | 1-((1r,4r)-4-((1H-indol-5-yl)oxy)cyclohexyl)-2-(5H-imidazo[5,1-a]isoindol-5-yl)ethanol |
| | | 2-(5H-imidazo[5,1-a]isoindol-5-yl)-1-(4-(((tetrahydro-2H-pyran-4-yl)methoxy)cyclohexyl)ethanol |
| | | 4-(((4-(1-hydroxy-2-(5H-imidazo[5,1-a]isoindol-5-yl)ethyl)cyclohexyl)oxy)methyl)benzenesulfonamide |
| | | 2-(5H-imidazo[5,1-a]isoindol-5-yl)-1-(4-(oxazol-2-ylmethoxy)cyclohexyl)ethanol |

| No. | Structure | Name |
| --- | --- | --- |
| | | 2-(5H-imidazo[5,1-a]isoindol-5-yl)-1-(4-(thiazol-2-ylmethoxy)cyclohexyl)ethanol |
| | | 2-(5H-imidazo[5,1-a]isoindol-5-yl)-1-(1-(1-imino-2-phenylethyl)piperidin-4-yl)ethanol |
| | | 4-(1-hydroxy-2-(5H-imidazo[5,1-a]isoindol-5-yl)ethyl)-N-phenylpiperidine-1-carboximidamide |
| | | 4-(1-hydroxy-2-(5H-imidazo[5,1-a]isoindol-5-yl)ethyl)-N-(pyridin-4-yl)piperidine-1-carboximidamide |
| | | 4-(1-hydroxy-2-(5H-imidazo[5,1-a]isoindol-5-yl)ethyl)-N-(tetrahydro-2H-pyran-4-yl)piperidine-1-carboximidamide |
| | | N-(4-cyanophenyl)-4-(1-hydroxy-2-(5H-imidazo[5,1-a]isoindol-5-yl)ethyl)piperidine-1-carboxamide |
| | | N-(tert-butyl)-4-(1-hydroxy-2-(5H-imidazo[5,1-a]isoindol-5-yl)ethyl)piperidine-1-carboxamide |

| No. | Structure | Name |
|---|---|---|
| | | N-(tert-butyl)-4-(1-hydroxy-2-(5H-imidazo[5,1-a]isoindol-5-yl)ethyl)piperidine-1-sulfonamide |
| | | 1-(4-(1-hydroxy-2-(5H-imidazo[5,1-a]isoindol-5-yl)ethyl)piperidin-1-yl)-2-(3-hydroxyphenyl)ethanone |
| | | 2-(1-(azetidine-1-carbonyl)piperidin-4-yl)-2-hydroxy-1-(4-(1-hydroxy-2-(5H-imidazo[5,1-a]isoindol-5-yl)ethyl)piperidin-1-yl)ethanone |
| | | 2-cyclopentyl-1-(4-(1-hydroxy-2-(5H-imidazo[5,1-a]isoindol-5-yl)ethyl)piperidin-1-yl)ethanone |
| | | 1-(4-(1-hydroxy-2-(5H-imidazo[5,1-a]isoindol-5-yl)ethyl)piperidin-1-yl)-2-(2-methylthiazol-5-yl)ethanone |
| | | N-cyclohexyl-N-hydroxy-4-(1-hydroxy-2-(5H-imidazo[5,1-a]isoindol-5-yl)ethyl)piperidine-1-carboxamide |

| No. | Structure | Name |
|---|---|---|
| | | N-(4-(2-(4-(1-hydroxy-2-(5H-imidazo[5,1-a]isoindol-5-yl)ethyl)piperidin-1-yl)-2-oxoethyl)phenyl)methanesulfonamide |
| | | N-cyclopropyl-N-hydroxy-4-(1-hydroxy-2-(5H-imidazo[5,1-a]isoindol-5-yl)ethyl)piperidine-1-carboxamide |
| | | 3,3-difluoro-1-(4-(1-hydroxy-2-(5H-imidazo[5,1-a]isoindol-5-yl)ethyl)piperidin-1-yl)butan-1-one |
| | | 1-(4-(1-hydroxy-2-(5H-imidazo[5,1-a]isoindol-5-yl)ethyl)piperidin-1-yl)-2-(p-tolyl)ethanone |
| | | 1-(1-(4-aminopyrimidin-2-yl)piperidin-4-yl)-2-(5H-imidazo[5,1-a]isoindol-5-yl)ethanol |
| | | 1-(1-(2-aminopyrimidin-4-yl)piperidin-4-yl)-2-(5H-imidazo[5,1-a]isoindol-5-yl)ethanol |
| | | N-cyclopropyl-4-(1-hydroxy-2-(5H-imidazo[5,1-a]isoindol-5-yl)ethyl)piperidine-1-carboxamide |

| No. | Structure | Name |
|---|---|---|
| | | 2-cyclopropyl-1-(4-(1-hydroxy-2-(5H-imidazo[5,1-a]isoindol-5-yl)ethyl)piperidin-1-yl)ethanone |
| | | 2-(4-(1-hydroxy-2-(5H-imidazo[5,1-a]isoindol-5-yl)ethyl)cyclohexylidene)acetonitrile |
| | | 4-(1-hydroxy-2-(5H-imidazo[5,1-a]isoindol-5-yl)ethyl)-N-(4-(trifluoromethyl)thiazol-2-yl)piperidine-1-carboxamide |
| | | 4-(2-(4-(1-hydroxy-2-(5H-imidazo[5,1-a]isoindol-5-yl)ethyl)piperidin-1-yl)-2-oxoethyl)benzamide |
| | | 1-(4-(1-hydroxy-2-(5H-imidazo[5,1-a]isoindol-5-yl)ethyl)piperidin-1-yl)-2-(4-(methylsulfonyl)phenyl)ethanone |
| | | 4-(1-hydroxy-2-(5H-imidazo[5,1-a]isoindol-5-yl)ethyl)-N-((1r,4r)-4-methylcyclohexyl)piperidine-1-carboxamide |

-continued

| No. | Structure | Name |
|---|---|---|
| | | 1-(4-(1-hydroxy-2-(5H-imidazo[5,1-a]isoindol-5-yl)ethyl)piperidin-1-yl)-3,3-dimethylbutan-1-one |
| | | 4-(2-(4-(1-hydroxy-2-(5H-imidazo[5,1-a]isoindol-5-yl)ethyl)piperidin-1-yl)-2-oxoethyl)benzenesulfonamide |
| | | N-(tert-butyl)-4-(2-(4-(1-hydroxy-2-(5H-imidazo[5,1-a]isoindol-5-yl)ethyl)piperidin-1-yl)-2-oxoethyl)benzenesulfonamide |
| | | 4-(2-(4-(1-hydroxy-2-(5H-imidazo[5,1-a]isoindol-5-yl)ethyl)piperidin-1-yl)-2-oxoethyl)benzoic acid |
| | | 1-(4-(difluoromethylene)cyclohexyl)-2-(5H-imidazo[5,1-a]isoindol-5-yl)ethanol |
| | | 2-(5H-imidazo[5,1-a]isoindol-5-yl)-1-(4-(2,2,2-trifluoroethylidene)cyclohexyl)ethanol |

| No. | Structure | Name |
|---|---|---|
| | | N-benzyl-4-(2-(6-fluoro-5H-imidazo[5,1-a]isoindol-5-yl)-1-hydroxyethyl)cyclohexanecarboxamide |
| | | 4-(2-(6-fluoro-5H-imidazo[5,1-a]isoindol-5-yl)-1-hydroxyethyl)-N-phenylcyclohexanecarboxamide |
| | | N-(4-(2-(6-fluoro-5H-imidazo[5,1-a]isoindol-5-yl)-1-hydroxyethyl)cyclohexyl)benzamide |
| | | 1-(4-(2-(6-fluoro-5H-imidazo[5,1-a]isoindol-5-yl)-1-hydroxyethyl)cyclohexyl)-3-phenylurea |
| | | N-(4-(2-(6-fluoro-5H-imidazo[5,1-a]isoindol-5-yl)-1-hydroxyethyl)cyclohexyl)-2-phenylacetamide | and pharmaceutically acceptable salts thereof.

In another aspect, the present disclosure provides compounds and pharmaceutical compositions comprising the compounds according to any one of the preceding aspects of the invention or any embodiment thereof, together with a pharmaceutically acceptable excipient, diluent, or carrier.

In another aspect, the invention provides methods for treating indoleamine 2,3-dioxygenase (IDO) mediated immunosuppression in a subject in need thereof, comprising administering an effective indoleamine 2,3-dioxygenase inhibiting amount of a compound or a pharmaceutical composition according to any of the preceding aspects of the invention or any embodiment thereof.

In one embodiment, the immunosuppression is associated with an infectious disease, or cancer.

In another embodiment, the immunosuppression is associated with an infectious disease and the infectious disease is a viral infection selected from the group consisting of: hepatitis C virus (HCV), human papilloma virus (HPV), cytomegalovirus (CMV), Epstein-Barr virus (EBV), poliovirus, varicella zoster virus, coxsackie virus, human immunodeficiency virus (HIV).

In another embodiment, the immunosuppression is immunosupression associated with HIV-1 infection.

In another embodiment, the immunosuppression is associated with a cancer.

In an embodiment, the immunosuppression is tumor-specific immunosuppression associated with cancer.

In another embodiment, the immunosuppression is associated with a cancer, wherein the cancer is colon, pancreas, breast, prostate, lung, brain, ovary, cervix, testes, renal, head, or neck cancer, or lymphoma, leukemia, or melanoma.

In another aspect, the invention provides the use of compounds described by any one of the preceding aspects (and any embodiment thereof), as defined above, for the preparation of a medicament for the treatment of medical conditions that benefit from the inhibition of enzymatic activity of indoleamine-2,3-dioxygenase. Medical conditions contemplated in this aspect include all the conditions described herein.

In another aspect, the invention provides a use of compounds described by any one of the preceding aspects (and any embodiment thereof), as defined above, for the preparation of a medicament to stimulate T cell proliferation or to reverse an immunologic state of anergy or immunosuppression.

In one embodiment, the anergy or immunosuppression is caused by expression of the enzyme indoleamine-2,3-dioxygenase.

In another aspect, the invention provides the use of compounds described by any one of the preceding aspects (and any embodiment thereof), as defined above, for the preparation of a medicament for the treatment of immunosuppression associated with cancer, infectious diseases, or viral infections.

In one embodiment, the invention provides the use of compounds described in to any one of the preceding aspects (and any embodiment thereof), as defined above, for the preparation of a medicament for the treatment of tumor-specific immunosuppression associated with cancer. Preferably, the cancer is cancer of the colon, pancreas, breast, prostate, lung, brain, ovary, cervix, testes, renal, or head and neck, lymphoma, leukemia, melanoma, and the like.

In another embodiment, the invention provides the use of compounds described in any of the preceding aspects (and any embodiment thereof), as defined above, and embodiments thereof as defined above, for the preparation of a medicament for the treatment of infectious diseases where the infectious disease is a viral infection. Preferably, the viral infection is selected from the group consisting of: influenza, hepatitis C virus (HCV), human papilloma virus (HPV), cytomegalovirus (CMV), Epstein-Barr virus (EBV), varicella zoster virus, poliovirus, coxsackie virus, and human immunodeficiency virus (HIV). More preferably, the viral infection is human immunodeficiency virus (HIV).

Definitions

Terms used herein may be preceded and/or followed by a single dash, "-", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl, arylalkyl-, and -alkylaryl indicate the same functionality.

Further, certain terms herein may be used as both monovalent and divalent linking radicals as would be familiar to those skilled in the art, and by their presentation linking between two other moieties. For example, an alkyl group can be both a monovalent radical or divalent radical; in the latter case, it would be apparent to one skilled in the art that an additional hydrogen atom is removed from a monovalent alkyl radical to provide a suitable divalent moiety.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, —CH$_2$CH(CH$_2$CH$_3$)CH$_2$—.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The term "arylalkyl," "-alkylaryl," and "arylalkyl-" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

"Cycloalkenyl" as used herein refers to a monocyclic or a bicyclic cycloalkenyl ring system. Monocyclic ring systems are cyclic hydrocarbon groups containing from 3 to 8 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or a fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic cycloalkenyls include, but are not limited to, norbornenyl and bicyclo[2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heteroarylalkyl" and "-alkylheteroaryl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, pyridin-4-ylmethyl, pyrimidin-5-ylmethyl, 2-(pyrimidin-2-yl)propyl, thien-2-ylmethyl, and thien-3-ylmethyl.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "hydroxy" as used herein, means an —OH group.

The term "nitro" as used herein, means a —NO₂ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "spiro" as used herein refers to a cyclic moiety formed by the substituted atom and two available substitutable postions on that same atom. For example, moiety such as

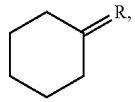

where R is a spiro-cycloalkyll= group includes compounds such as

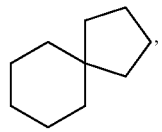

where the spiro-cyclopentyl group is the R group attached to the parent cyclohexyl ring by two single bonds. Similarly, where R is a spiro-heterocyclyl group, such compounds include

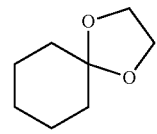

where the spiro-1,3-dioxolanyl ring is the R group attached to the parent cyclohexyl ring by two single bonds.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound includes the administration of a compound described herein to an individual or patient, such as a human, having IDO, as well as, for example, introducing a compound into a sample containing a cellular or purified preparation containing the IDO enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; or (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or (ii) eliciting the referenced biological effect (e.g., IDO modulation or tryptophan degradation inhibition).

Manifestation of amelioration of a disease condition with underlying IDO-mediated immunosuppression may require the concomitant or sequential administration of additional therapeutic agents, such as antineoplastic agents in the case of cancer, or antiretroviral agents in the case of viral diseases. For example, administration of IDO inhibitors for the treatment of cancer does not always produce a direct antitumor effect when used as a single agent. However, when combined with chemotherapeutic drugs (antineoplastic) the antitumor effect observed is higher than the sum of effects of each agent alone.

As used herein, the terms "catalytic pocket", "catalytic site", "active site" collectively and indistinctly refer to a region of the enzyme that contains amino acid residues responsible for the substrate binding (charge, hydrophobicity, steric hindrance) and catalytic amino acid residues which act as proton donors or acceptors or are responsible for binding a cofactor and participate in the catalysis of a chemical reaction.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, $HOOC-(CH_2)_n-COOH$ where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Methods of Use

The compounds and pharmaceutical compositions described herein can modulate activity of the enzyme indoleamine-2,3-dioxygenase (IDO). The term "modulate" is meant to refer to an ability to decrease activity of an enzyme or receptor. Accordingly, compounds described herein can be used in methods of modulating IDO by contacting the enzyme with any one or more of the compounds or compositions described herein. In some embodiments, the compounds described herein can act as inhibitors of IDO. In further embodiments, the compounds described herein can be used to modulate activity of IDO in cell or in an individual in need of modulation of the enzyme by administering a modulating (e.g., inhibiting) amount of a compound described herein.

Further provided are methods of inhibiting the degradation of tryptophan and preventing the production of N-formylkynurenine in a system containing cells expressing IDO such as a tissue, living organism, or cell culture. In some embodiments methods of altering (e.g., increasing) extracellular tryptophan levels in a mammal comprise administering an effective amount of a compound or pharmaceutical composition provided herein. Methods of measuring tryptophan levels and tryptophan degradation are routine in the art.

Further provided are methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, infectious diseases (e.g., viral infection), viral replication, etc.

Further provided are methods for treating tumor-specific immunosuppression associated with cancer in a patient by administering to the patient an effective amount of a compound or composition recited herein. Example tumor-specific immunosuppression associated with cancers treatable by the methods herein include immunosuppression associated with cancer of the colon, pancreas, breast, prostate, lung, brain, ovary, cervix, testes, renal, head and neck, lymphoma, leukemia, melanoma, and the like.

For example, a patient undergoing or having completed a course of chemotherapy and/or radiation therapy for the treatment of a disease state, such as a cancer, can benefit from administering to the patient a therapeutically effective amount of a compound or composition recited herein for inhibiting immunosuppression resulting from the disease state and/or treatment thereof.

Further provided are methods for treating immunosupression associated with an infectious disease, e.g., HIV-1 infection, in a patient by administering to the patient an effective amount of a compound or composition recited herein.

For example, IDO-mediated immunosuppression associated with viral infection, is associated with a viral infection selected from the group consisting of: influenza, hepatitis C virus (HCV), human papilloma virus (HPV), cytomegalovirus (CMV), Epstein-Barr virus (EBV), poliovirus, varicella zoster virus, coxsackie virus, human immunodeficiency virus (HIV).

Further provided are methods of treating diseases associated with activity or expression, including abnormal activity and/or overexpression, of IDO in an individual (e.g., patient) by administering to the individual in need of such treatment a therapeutically effective amount or dose of a compound described herein or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity.

Examples of IDO-associated diseases include cancer, viral infection such as HIV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, inflammatory bowel disease, psoriasis and systemic lupus erythematosusor. Example cancers treatable by the methods herein include cancer of the colon, pancreas, breast, prostate, lung, brain, ovary, cervix, testes, renal, head and neck, lymphoma, leukemia, melanoma, and the like.

Combination Therapy

One or more additional pharmaceutical agents for treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with the compounds and pharmaceutical compositions described herein for treatment of IDO-associated diseases, disorders or conditions (as noted above) or for enhancing the effectiveness of the treatment of a disease state or condition, such as cancer. The agents can be combined with the present compounds in a single dosage form, or the agents can be administered simultaneously or sequentially as separate dosage forms.

Therapeutic agents that constitute the standard of care for a particular cancer type or infectious disease are expected to benefit when combined with IDO inhibitors of the present invention. For example, for the case of tumors, is it preferable that the tumor is sensitive to the cytotoxic effects of the chemotherapeutic agent in order to stimulate the release of antigens that will eventually mediate an immune response that will be enhanced by addition of IDO inhibitors to the combination treatment. A person of skill in the art will know how to select such chemotherapeutic agent based on the clinical characteristics and known sensitivity of each tumor to different antineoplastic agents.

Suitable antiviral agents contemplated for use in combination with the compounds described herein can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2, 4(1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylenemelamine, triethylenethiophosphoramine, busulfan, carmustine, lomustine, streptozocin, dacarbazine, and temozolomide.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol™), docetaxel, mithramycin, deoxyco-formycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-β, etc.).

Other anti-cancer agents also include those that block immune cell migration such as antagonists to chemokine receptors, including CCR2, CCR4 and CCR6.

Other anti-cancer agents also include those that augment the immune system such as adjuvants or adoptive T cell transfer.

Anti-cancer vaccines include dendritic cells, synthetic peptides, DNA vaccines and recombinant viruses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as antiviral agents, vaccines, antibodies, immune enhancers, immune suppressants, anti-inflammatory agents and the like.

Labeled Compounds and Assay Methods

Another aspect relates to fluorescent dye, spin label, heavy metal or radio-labeled derivatives of the compounds described herein that would be useful not only in imaging but also in assays, both in vitro and in vivo, for localizing and quantitating the IDO enzyme in tissue samples, including human, and for identifying IDO enzyme ligands by inhibition binding of a labeled compound. Accordingly, further provided are IDO enzyme assays that contain such labeled compounds.

Further provided are isotopically-labeled compounds of the compounds described herein. An "isotopically" or "radio-labeled" compound is a compound described herein where one or more atoms are replaced or substituted by an atom having an atomic mass or mass number different from the atomic mass or mass number typically found in nature (i.e., naturally occurring). Suitable radionuclides that may be include but are not limited to 2H (also written as D for deuterium), 3H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro IDO enzyme labeling and competition assays, compounds that incorporate $^{3}$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br Or $^{77}$Br will generally be most useful.

It is understood that a "radio-labeled" or "labeled compound" is a compound that has incorporated at least one radionuclide. In some embodiments the radionuclide is selected from the group consisting of $^{3}$H, $^{14}$C, $^{125}$I, $^{35}$S and $^{82}$Br.

Synthetic methods for incorporating radio-isotopes into organic compounds are applicable to compounds described herein and are well known in the art.

A radio-labeled compound described herein can be used in a screening assay to identify/evaluate compounds. In general terms, a newly synthesized or identified compound (i.e., test compound) can be evaluated for its ability to reduce binding of the radio-labeled compound described herein to the IDO enzyme. Accordingly, the ability of a test compound to compete with the radio-labeled compound for binding to the IDO enzyme directly correlates to its binding affinity.

Kits

Also included are pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound described herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The following examples are offered for illustrative purposes, and are not intended to limit the disclosure in any manner. Those of skill in the art will readily recognize a variety of noncritical parameters which can be changed or modified to yield essentially the same results. The example compounds below were found to be inhibitors of IDO according to one or more of the assays described herein.

EXAMPLES

All reagents and solvents were purchased from commercial sources. All commercial reagents and solvents were used as received without further purification. The reactions were monitored using analytical thin layer chromatography (TLC) with 0.25 mm EM Science silica gel plates (60F-254). The developed TLC plates were visualized by short wave UV light (254 nm) or immersion in potassium permanganate solution followed by heating on a hot plate. Flash chromatography was performed with Selecto Scientific silica gel, 32-63 µm particle sizes. All reactions were performed in flame or oven-dried glassware under a nitrogen atmosphere. All reactions were stirred magnetically at ambient temperature unless otherwise indicated. $^{1}$H NMR spectra were obtained with a Bruker DRX400, Varian VXR400 or VXR300. $^{1}$H NMR spectra were reported in parts per million ($\delta$) relative to TMS (0.0), DMSO-$d_6$ (2.50) or CD$_3$OD (4.80) as an internal reference. All $^{1}$H NMR spectra were taken in CDCl$_3$ unless otherwise indicated. The following starting materials were prepared according to their literature procedures: (E)-ethyl 3-(2-iodophenyl)acrylate (Synth. Comm. 2007, 37, 2989-2994), 2-chloro-6-iodobenzaldehyde (J. Agric. Food Chem. 2008, 56, 5247-5253), 2-iodo-3-methoxybenzaldehyde (Chem.-Eur. J., 2004, 10, 5233-5242), dimethyl (2-(cyclohex-1-en-1-yl)-2-oxoethyl)phosphonate (Phosphorus, Sulfur Silicon Relat. Elem., 1999, 155, 67-80), dimethyl (2-cyclohexyl-2-oxo)ethylphosphonate (Patent: U.S. Pat. No. 5,807,892 A1, 1998), ethyl 1,4-dioxaspiro[4.5]decane-8-carboxylate (Patent: US2008/306084 A1, 2008), (trans)-ethyl 4-((tert-butyldimethylsilyl)oxy)cyclohexanecarboxylate (Patent: US2006/25383 A1, 2006), ethyl spiro[2.5]octane-6-carboxylate (Bioorg. Med. Chem. Lett. 2008, 18, 5280-5284), ethyl 4-(cyclopropylmethylene)cyclohexanecarboxylate (Patent: U.S. Pat. No. 4,584,013 A1, 1986), The aforementioned compounds are assigned compound identification numbers 86-91 and 113-115 respectively for future reference in this patent. (4.80) as an internal reference. All spectra are recorded in CDCl$_3$ unless otherwise indicated.

A variety of methods used in this patent to synthesize intermediate A are outlined below in Scheme 1. Palladium-catalyzed Suzuki cross-coupling of 4-iodo-1-trityl-1H-imidazole with phenylboronic acids gives rise to 2-(1-trityl-1H- imidazol-4-yl)benzaldehydes. The resulting 2-(1-trityl-1H-imidazol-4-yl)benzaldehydes are affected by aldol condensations or Horner-Wadsworth reactions to afford intermediate A. Alternatively, the synthesis of intermediate A can be achieved by allowing 2-iodobenzaldehydes to react with substituted methyl ketones in the presence of a base to afford 3-(2-iodophenyl)prop-2-en-1-ones. Negishi cross-coupling of the resulting 3-(2-iodophenyl)prop-2-en-1-ones with 4-iodo-1-trityl-1H-imidazole, also leads to intermediate A. Subjecting intermediate A to trityl deprotection conditions gives rise to 2-(5H-imidazo[5,1-a]isoindol-5-yl)ethanone B, which may be reduced to 2-(5H-imidazo[5,1-a]isoindol-5-yl)ethanol C (Scheme 2).

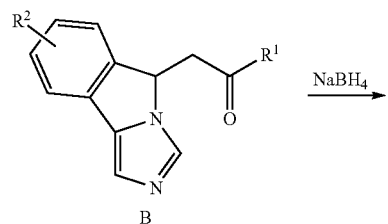

Scheme 1. Synthesis of (E)-3-(2-(1-trityl-1H-imidazol-4-yl)phenyl)prop-2-en-1-ones (Intermediate A)

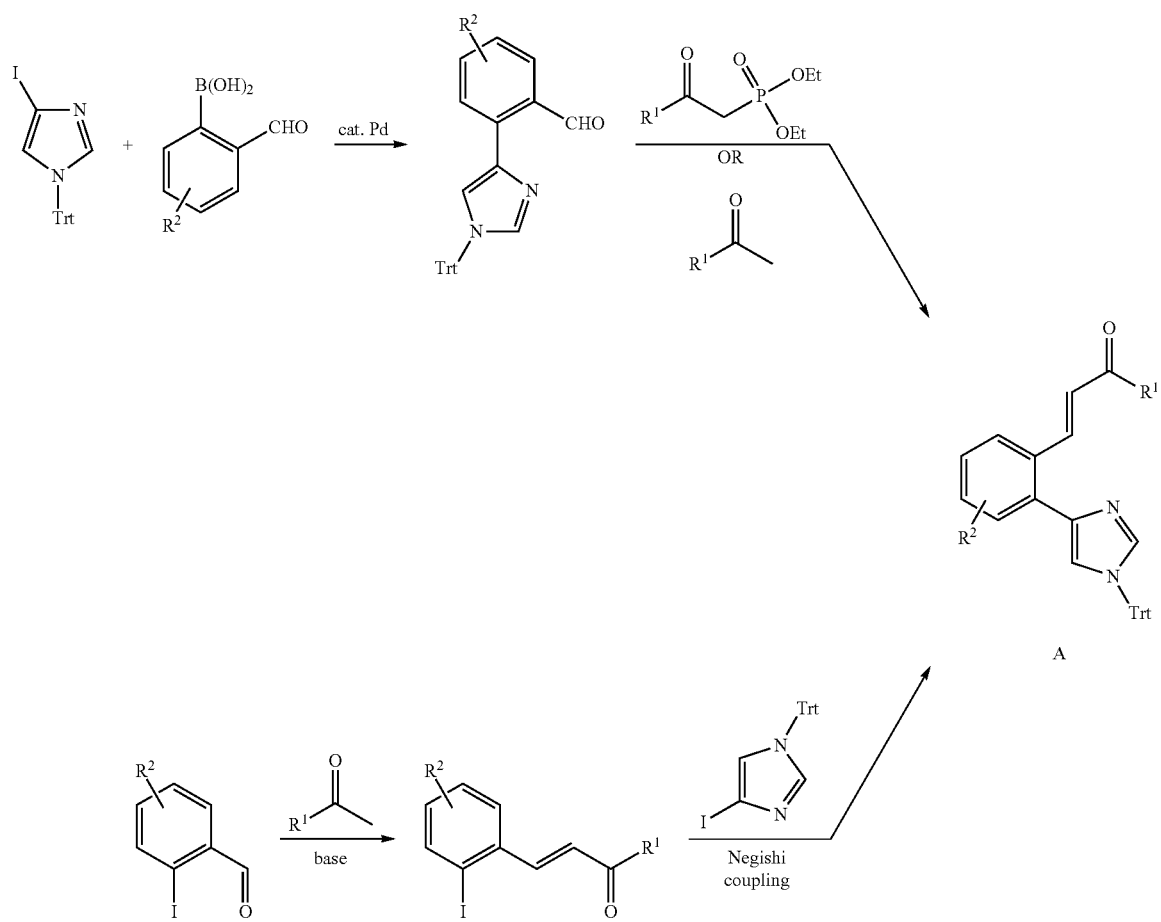

Scheme 2. Synthesis of 2-(5H-imidazo[5,1-a]isoindol-5-yl)ethanones and Their Corresponding 2-(5H-imidazo[5,1-a]isoindol-5-yl)ethanols

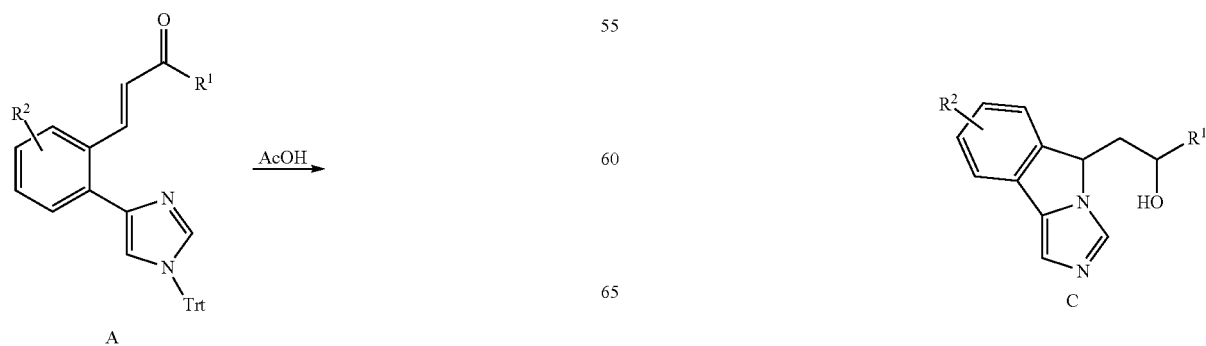

Example 1

General Procedure for the Synthesis of 3-(2-Iodophenyl)prop-2-en-1-ones by Aldol Condensation

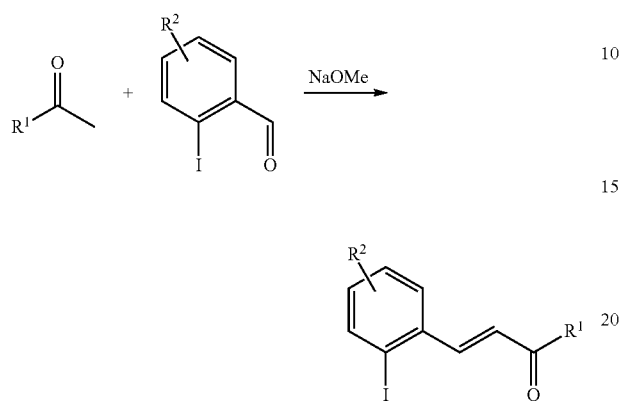

To a solution of the appropriate commercially available benzaldehyde or 87 (4.31 mmol) in anhydrous MeOH (15 mL) at rt was added NaOMe (4.31 mmol, 0.5 M in MeOH) and the yellow solution was allowed to stir for 5 min. The appropriate ketone (4.31 mmol) was added dropwise as a solution in MeOH (3 mL). After stirring overnight, the solvent was removed under reduced pressure and the crude was diluted with satd. NH$_4$Cl (20 mL). The aqueous layer was extracted with CH$_2$Cl$_2$ (3×20 mL) and the combined organic extracts were dried (MgSO$_4$) and the solvent distilled off under reduced pressure to afford a crude residue. The crude product was purified by silica flash chromatography to afford the following compounds.

Example 2

General Procedure for the Synthesis of 2-(5H-imidazo[5,1-a]isoindol-5-yl)ethanones by Palladium-Catalyzed Negishi Cross-Coupling of Aryl Iodides 1 and 2 with 4-Iodo-1-Trityl-1H-imidazole

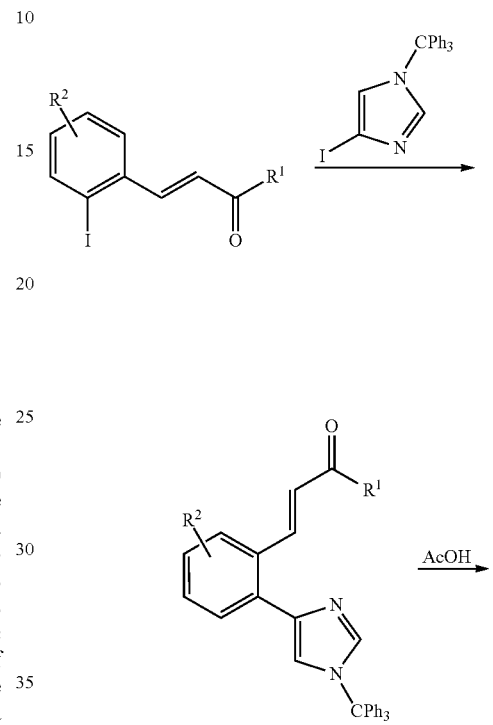

| # | Compound | Name | Yield (%) |
|---|----------|------|-----------|
| 1 | (structure with Cl, I, cyclohexyl) | (E)-3-(2-chloro-6-iodophenyl)-1-cyclohexylprop-2-en-1-one | 63 |

$^1$H NMR 1.22-1.45 (m, 5H), 1.70-174 (m, 1H), 1.79-1.85 (m, 2H), 1.93-1.99 (m, 2H), 2.61-2.65 (m, 1H), 6.67 (d, 1H, J = 16 Hz), 6.93 (t, 1H, J = 8 Hz), 7.42 (d, 1H, J = 8 Hz), 7.48 (d, 1H, J = 16 Hz), 7.82 (d, 1H, J = 8 Hz)

| # | Compound | Name | Yield (%) |
|---|----------|------|-----------|
| 2 | (structure with O$_2$N, I) | (E)-3-(2-iodophenyl)-1-(3-nitrophenyl)prop-2-en-1-one | 53 |

$^1$H NMR 7.10-7.16 (m, 1H), 7.34 (d, 1H, J = 15.6 Hz), 7.41-7.46 (m, 1H), 7.71-7.76 (m, 2H), 7.94-7.97 (m, 1H), 8.05 (d, 1H, J = 15.6 Hz), 8.34-8.48 (m, 2H), 8.81 (s, 1H)

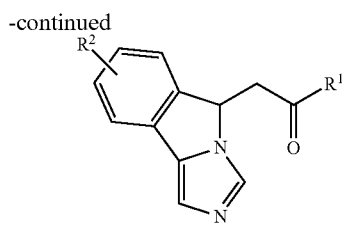

To a stirred solution of 4-iodo-1-trityl-1H-imidazole (218 mg, 0.5 mmol) in anhydrous THF (4 mL) at rt was added EtMgBr (1.0 M in THF, 0.5 mmol, 0.5 mL) dropwise, under an atmosphere of $N_2$. The resulting solution was allowed to stir for 90 min and anhydrous $ZnCl_2$ (0.5 mmol, 68.2 mg) was added. The resulting white suspension was allowed to stir for 90 min and a solution of the appropriate aryl iodide 1, 2 or 86 (0.5 mmol) in THF (1 mL) was added followed by the immediate addition of $Pd(PPh_3)_4$ (56 mg, 0.05 mmol). The reaction mixture was allowed to stir at 70° C. for 12 h under an atmosphere of $N_2$. After cooling to room temperature, the solution was diluted with $CH_2Cl_2$ (20 mL) and the organic layer was washed with an EDTA (aq) buffer (pH=9) (2×5 mL) and brine. The organic layer was dried ($Na_2SO_4$) and concentrated under reduced pressure. The crude residue was used in next step without further purification. To a solution of the crude imidazole from the previous step was added acetic acid (1.0 mL) and MeOH (4.0 mL). The solution was stirred at 90° C. for 3 h. The reaction mixture was allowed to cool to room temperature and the pH was adjusted to ~10 with satd. $K_2CO_3$ (acq). The aqueous phase was extracted with EtOAc (3×20 mL). The combined organic layers were washed with water, brine and dried. The solvent was removed in vacuo to afford the crude residue, which was purified by flash column chromatography on silica gel to afford the following compounds.

| # | Compound | Name | Yield (%) |
|---|---|---|---|
| 1287 | | 2-(6-chloro-5H-imidazo[5,1-a]isoindol-5-yl)-1-cyclohexylethanone | 25 |
| | $^1$H NMR 1.18-1.36 (m, 5H), 1.68-1.88 (m, 5H), 2.37-2.40 (m, 1H), 2.64 (dd, 1H, J = 20.0 Hz, 10.0 Hz), 3.79 (dd, 1H, J = 16.0 Hz, 4.0 Hz), 5.70 (d, 1H, J = 8.0 Hz), 7.17-7.20 (m, 2H), 7.32 (t, 1H, J = 8.0 Hz), 7.43 (d, 1H, J = 8.0 Hz), 7.61 (s, 1H) | | |
| 1256 | | ethyl 2-(5H-imidazo[5,1-a]isoindol-5-yl)acetate | 23 |
| | $^1$H NMR 1.31 (t, 3H, J = 7.5 Hz), 2.67 (dd, 1H, J = 20.0 Hz, 12.0 Hz), 3.07 (dd, 1H, J = 20.0 Hz, 4.0 Hz), 4.25 (q, 2H, J = 6.0 Hz), 5.53 (dd, 1H, J = 12.0 Hz, 4.0 Hz), 7.16 (s, 1H), 7.21-7.37 (m, 3H), 7.51 (d, 1H, J = 6.0 Hz), 7.75 (s, 1H | | |
| 1306 | | 2-(5H-imidazo[5,1-a]isoindol-5-yl)-1-(3-nitrophenyl)ethanone | 15 |
| | $^1$H NMR 3.49 (dd, 1H, J = 18.6 Hz, 9.6 Hz), 3.80 (dd, 2H, J = 18.3 Hz, 3.3 Hz), 5.84 (dd, 1H, J = 3 Hz, 9.3 Hz), 7.26-7.32 (m, 1H), 7.38-7.49 (m, 2H), 7.55-7.59 (m, 1H), 7.70-7.76 (m, 2H), 8.32 (d, 1H, J = 6 Hz), 8.46-8.50 (m, 1H), 8.78 (s, 1H) | | |

Example 3

Suzuki Cross-Coupling of 4-Iodo-1-trityl-1H-imidazole with Phenylboronic Acids

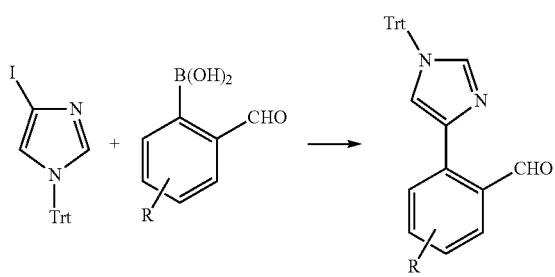

A suspension of 4-iodo-1-trytyl-1H-imidazole (6.88 mmol), the appropriate 2-formyl boronic acid derivative (10.31 mmol) and $K_3PO_4$ (20.63 mmol) in N,N-dimethylformamide (30 mL) and water (6 mL) was purged with nitrogen for 5 minutes, followed by the addition of $Pd(PPh_3)_4$ and the mixture was purged with nitrogen for another 5 minutes. The reaction mixture was stirred at 90° C. for 16 h under an atmosphere of $N_2$. The solution was allowed to cool and was filtered through a plug of celite. The mixture was diluted with water (50 mL) and EtOAc (25 mL). The organic layer was collected and the aqueous layer was extracted with EtOAc (2×25 mL). The combined organic extracts were washed with water (2×25 mL), brine and dried ($Na_2SO_4$). The solution was filtered and the solvent was removed under reduced pressure to afford the crude product which was purified by flash column chromatography on silica gel to provide the following compounds.

| # | Compound | Name | Yield (%) |
|---|----------|------|-----------|
| 3 | | 2-(1-trityl-1H-imidazol-4-yl)benzaldehyde | 52 |

$^1$H NMR 7.03 (s, 1H), 7.18-7.20 (m, 6H), 7.36-7.39 (m, 10H), 7.53-7.58 (m, 3H), 7.64 (d, 1H, J = 7.78 Hz), 7.93 (d, 1H, J = 7.87 Hz)

| # | Compound | Name | Yield (%) |
|---|----------|------|-----------|
| 4 | | 2-fluoro-6-(1-trityl-1H-imidazol-4-yl)benzaldehyde | 46 |

$^1$H NMR 7.02-7.07 (m, 1H), 7.10 (d, 1H, J = 1.6 Hz), 7.16-7.18 (m, 6H), 7.36-7.39 (m, 9H), 7.46-7.52 (m, 2H), 7.57 (s, 1H), 10.27 (s, 1H)

| # | Compound | Name | Yield (%) |
|---|----------|------|-----------|
| 5 | | 5-chloro-2-(1-trityl-1H-imidazol-4-yl)benzaldehyde | 48 |

$^1$H NMR 7.04 (d, 1H, J = 1.2 Hz), 7.10-7.19 (m, 5H), 7.32-7.38 (m, 12H), 7.58 (dd, 1H, J = 2.4, 8.4 Hz), 7.57-7.59 (m, 2H), 7.89 (d, 1H, J = 2.0 Hz), 10.34 (s, 1H)

| # | Compound | Name | Yield (%) |
|---|----------|------|-----------|
| 6 | | 4-chloro-2-(1-trityl-1H-imidazol-4-yl)benzaldehyde | 55 |

$^1$H NMR 7.08-7.38 (m, 18H), 7.60 (s, 1H), 7.88 (d, 1H, J = 8.4 Hz), 10.41 (s, 1H)

| # | Compound | Name | Yield (%) |
|---|---|---|---|
| 7 | | 4-fluoro-2-(1-trityl-1H-imidazol-4-yl)benzaldehyde | 89 |

$^1$H NMR (MeOH-d$_4$) 7.16-7.27 (m, 6H), 7.29-7.47 (m, 3H), 7.60-7.70 (m, 9H), 7.85-7.90 (m, 2H), 10.26 (s, 1H).

Example 4

3-Methoxy-2-(1-trityl-1H-imidazol-4-yl)benzaldehyde

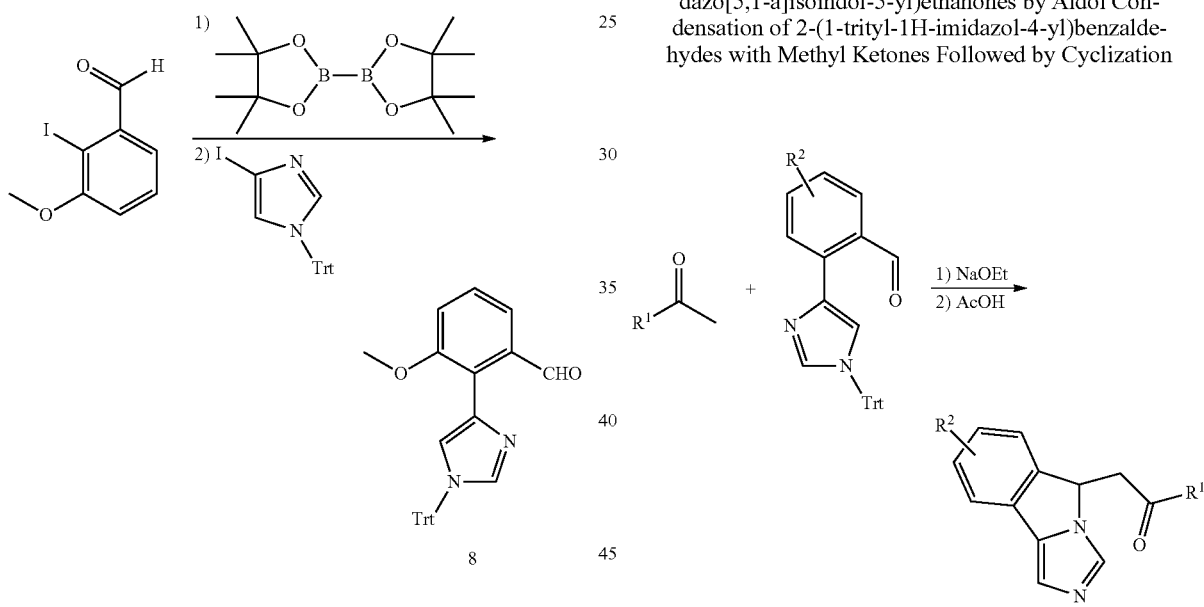

8

A suspension of 88 (667 mg, 2.55 mmol), bis(pinacolato)diboron (711 mg, 2.88 mmol), KOAc (749 mg, 7.64 mmol), Pd(OAc)$_2$ (17 mg, 76 μmol) in DMF (10 mL) was stirred at 80° C. for 16 h. The mixture was filtered through a plug of Celite and the filtrate poured into water. The aqueous layer was extracted with EtOAc (2×30 mL). The combined organic extracts were washed with water (2×10 mL), brine, dried and concentrated. The crude product was used without further purification. A suspension of 4-iodo-1-trityl-1H-imidazole (400 mg, 0.917 mmol), 3-methoxy-2-(4,4,5,5-tetramethyl-1,3,2-dioxaborolan-2-yl)benzaldehyde (288 mg, 1.10 mmol), K$_2$CO$_3$ (444 mg, 3.21 mmol), Pd(dppf)Cl$_2$.CH$_2$Cl$_2$ complex (150 mg, 0.18 mmol) in DMSO (10 mL) was heated at 80° C. for 20 h. The solution was filtered through Celite and the filtrate poured into water. The aqueous layer was extracted with ethyl acetate (2×20 mL). The combined organic layers were washed with water (2×10 mL), brine, dried, and concentrated. The crude was purified by flash column chromatography to afford 8 as a white solid (78 mg, 19%). $^1$H NMR: 3.75 (s, 3H), 7.08 (d, 1H, J=8.0 Hz), 7.20-7.25 (m, 7H), 7.30-7.36 (m, 10H), 7.52 (s, 1H), 7.55 (d, 1H, J=4.0 Hz), 10.31 (s, 1H).

Example 5

General Procedure for the Synthesis of 2-(5H-imidazo[5,1-a]isoindol-5-yl)ethanones by Aldol Condensation of 2-(1-trityl-1H-imidazol-4-yl)benzaldehydes with Methyl Ketones Followed by Cyclization To a solution of the appropriate aldehyde 3-8 (0.97 mmol) and ketone (0.97 mmol) in anhydrous THF (5 mL) at rt was added NaOEt (1.25 mmol, 21 wt % solution in EtOH) and the yellow solution was allowed to stir 3 h at rt. The solvent was distilled off and the crude was diluted with saturated NH$_4$Cl (10 mL) and the aqueous layer was extracted with dichloromethane (3×20 mL). The combined organic extracts were washed with brine, dried over Na$_2$SO$_4$ and the solvent evaporated under reduced pressure to afford the crude product. To the crude imidazole from the previous step was added acetic acid (1.0 mL) and MeOH (4.0 mL). The solution was stirred at 90° C. for 3-10 h. The reaction mixture was allowed to cool to room temperature and the pH was adjusted to ~10 with satd. K$_2$CO$_3$ (aq). The aqueous phase was extracted with EtOAc (3×20 mL). The combined organic layers were washed with water, brine, and dried. The solvent was removed in vacuo to afford the crude residue, which was purified by flash column chromatography on silica gel to afford the following compounds.

| # | Compound | Name | Yield (%) |
|---|---|---|---|
| 1326 | | 2-(5H-imidazo[5,1-a]isoindol-5-yl)-1-(2-nitrophenyl)ethanone | 16 |

$^1$H NMR 3.19 (dd, 1H, J = 20.0 Hz, 8.0 Hz), 3.65 (dd, 1H, J = 20.0 Hz, 4.0 Hz), 5.81 (dd, 1H, J = 8.0 Hz, 4.0 Hz), 7.19 (s, 1H), 7.22-7.28 (m, 1H), 7.36 (m, 3H), 7.54 (d, 1H, J = 8.0 Hz), 7.61-7.65 (m, 1H), 7.70-7.74 (m, 1H), 7.85 (s, 1H), 8.16 (d, 1H, J = 8.0 Hz).

| # | Compound | Name | Yield (%) |
|---|---|---|---|
| 1328 | | tert-butyl (2-(2-(5H-imidazo[5,1-a]isoindol-5-yl)acetyl)phenyl)carbamate | 44 |

$^1$H NMR 1.50 (s, 9H), 3.47 (dd, 1H, J = 18.0 Hz, 9.6 Hz), 3.77 (dd, 1H, 18.0 Hz, 3.3 Hz), 5.77-5.81 (m, 1H), 6.98 (t, 1H, J = 8.0 Hz), 7.19 (s, 1H), 7.28 (d, 1H, J = 7.6 Hz), 7.37 (d, 1H, J = 8.0 Hz), 7.41 (d, 1H, J = 8.0 Hz), 7.52-7.56 (m, 2H), 7.72 (d, 1H, J = 8.0 Hz), 7.77 (s, 1H), 8.54 (d, 1H, J = 8.4 Hz)

| # | Compound | Name | Yield (%) |
|---|---|---|---|
| 1300 | | tert-butyl (4-(2-(5H-imidazo[5,1-a]isoindol-5-yl)acetyl)phenyl)carbamate | 39 |

$^1$H NMR 1.52 (s, 9H), 3.39 (dd, 1H, J = 18.6 Hz, 9.6 Hz), 3.68 (dd, 1H, J = 18.3 Hz, 3.3 Hz), 5.83 (dd, 1H, J = 3 Hz, 9.3 Hz), 6.88 (s, 1H), 7.14-7.58 (m, 7H), 7.75 (s, 1H), 7.92 (d, 2H, J = 9 Hz)

| # | Compound | Name | Yield (%) |
|---|---|---|---|
| 1348 | | 2-(5H-imidazo[5,1-a]isoindol-5-yl)-1-phenylethanone | 45 |

$^1$H NMR 3.44 (dd, 1H, J = 20.0 Hz, 8.0 Hz), 3.72 (dd, 1H, J = 20.0 Hz, 4.0 Hz), 5.83 (d, 1H, J = 8.0 Hz), 7.18 (s, 1H), 7.25-7.29 (m, 1H), 7.40 (t, 2H, J = 10 Hz), 7.47 (t, 2H, J = 8.0 Hz), 7.57 (d, 1H, J = 8.0 Hz), 7.61 (t, 1H, J = 6.0 Hz), 7.74 (s, 1H), 7.97 (d, 2H, J = 8 Hz)

| # | Compound | Name | Yield (%) |
|---|---|---|---|
| 9 | | tert-butyl 4-(2-(5H-imidazo[5,1-a]isoindol-5-yl)acetyl)piperidine-1-carboxylate | 19 |

$^1$H NMR 1.44 (s, 9H), 1.50-1.82 (m, 4H), 2.72-2.76 (m, 2H), 2.90 (dd, 1H, J = 18.5 Hz, 9.4 Hz), 3.21 (dd, 1H, J = 18.57 Hz, 3.6 Hz), 5.63 (dd, 1H, J = 9.6 Hz, 3.6 Hz), 7.16 (s, 1H), 7.23 (m, 2H), 7.35-7.39 (m, 1H), 7.53 (d, 1H, J = 7.5 Hz), 7.59 (s, 1H)

-continued

| # | Compound | Name | Yield (%) |
|---|---|---|---|
| 10 | | 2-(6-fluoro-5H-imidazo[5,1-a]isoindol-5-yl)-1-(1,4-dioxaspiro[4.5]decan-8-yl)ethanone | 18 |
| | $^1$H NMR (MeOH-d$_4$) 1.50-1.90 (m, 6H), 2.35-2.60 (m, 2H), 2.98 (dd, 1H, J = 18.9 Hz, 10.2 Hz), 3.61 (dd, 1H, J = 18.9 Hz, 2.7 Hz), 5.78-5.82 (m, 1H), 7.01-7.07 (m, 1H), 7.16 (s, 1H), 7.42-7.45 (m, 2H), 7.66 (s, 1H) | | |
| 11 | | 2-(8-chloro-5H-imidazo[5,1-a]isoindol-5-yl)-1-cyclohexylethanone | 21 |
| | $^1$H NMR (MeOH-d$_4$) 1.10-1.90 (m, 10H), 2.42-2.48 (m, 1H), 2.99 (dd, 1H, J = 18.9 Hz, 9 Hz), 3.40 (dd, 1H, J = 18.9 Hz, 3.6 Hz), 5.58-5.62 (m, 1H), 6.95-7.08 (m, 1H), 7.16-7.88 (m, 4H) | | |
| 12 | | 2-(7-chloro-5H-imidazo[5,1-a]isoindol-5-yl)-1-cyclohexylethanone | 43 |
| | $^1$H NMR 1.19-1.46 (m, 5H), 1.68-1.70 (m, 1H), 1.78-1.91 (m, 5H), 2.35-2.43 (m, 1H), 2.91 (dd, 1H, J = 10.0, 20.0 Hz), 3.18 (dd, 1H, J = 4.0, 20.0 Hz), 5.611 (dd, 1H, J = 4.0, 8.0 Hz), 7.15 (s, 1H), 7.28 (s, 1H), 7.35 (d, 1H, J = 8.0 Hz), 7.45 (d, 1H, J = 8.0 Hz), 7.60 (s, 1H) | | |
| 13 | | 1-cyclohexyl-2-(6-fluoro-5H-imidazo[5,1-a]isoindol-5-yl)ethanone | 50 |
| | $^1$H NMR 1.20-1.48 (m, 5H), 1.66-1.69 (m, 1H) 1.78-1.92 (m, 5H), 2.36-2.44 (m, 1H), 2.79 (dd, J = 12.0, 20.0 Hz), 3.50 (dd, 1H, J = 4.0, 20.0 Hz), 5.77 (d, 1H, J = 8.0 Hz), 6.94 (t, 1H, J = 8.0 Hz), 7.18 (s, 1H), 7.31-7.37 (m, 2H), 7.62 (s, 1H) | | |
| 14 | | 1-cyclohexyl-2-(9-methoxy-5H-imidazo[5,1-a]isoindol-5-yl)ethanone | 41 |
| | $^1$H NMR 1.32-1.42 (m, 2H), 1.66-1.69 (m, 1H), 1.78-1.90 (m, 4H), 2.35-2.38 (m, 1H), 2.88 (dd, 1H, J = 18.4 Hz, 10 Hz), 3.17 (dd, 1H, J = 13.8 Hz, 3.2 Hz), 3.96 (s, 3H), 5.60-5.64 (m, 1H), 6.88 (d, 2H, J = 8 Hz), 7.15 (s, 1H), 7.21 (t, 1H, J = 8 Hz), 7.59 (s, 1H), | | |

-continued

| # | Compound | Name | Yield (%) |
|---|---|---|---|
| 15 | | 2-(5H-imidazo[5,1-a]isoindol-5-yl)-1-(tetrahydro-2H-pyran-4-yl)ethanone | 61 |

¹H NMR 1.75-1.84 (m, 4H), 2.58-2.62 (m, 1H), 2.90 (dd, 1H, J = 18.4 Hz, 9.6 Hz), 3.21 (dd, 1H, J = 18.4 Hz, 3.6 Hz), 3.38-3.45 (m, 2H), 3.99-4.01 (m, 2H), 5.65 (dd, 1H, J = 9.6 Hz, 3.6 Hz), 7.17 (s, 1H), 7.22-7.30 (m, 2H), 7.38 (dt, 1H, J = 7.2 Hz, 0.8 Hz), 7.54 (d, 1H, J = 7.6 Hz), 7.61 (s, 1H)

| 16 | | 1-cyclohexyl-2-(8-fluoro-5H-imidazo[5,1-a]isoindol-5-yl)ethanone | 58 |

¹H NMR a

| 17 | | tert-butyl (3-(2-(5H-imidazo[5,1-a]isoindol-5-yl)acetyl)phenyl)carbamate | 80 |

¹H NMR a

| 18 | | 1-cyclopentyl-2-(5H-imidazo[5,1-a]isoindol-5-yl)ethanone | 11 |

¹H NMR a

| 1334 | | 1-(2-chlorophenyl-2-(5H-imidazo[5,1-a]isoindol-5-yl)ethanone | 15 |

¹H NMR 3.30-3.50 (m, 1H), 3.65-3.85 (m, 1H), 5.50-5.70 (m, 1H), 7.17 (s, 1H), 7.20-7.60 (m, 8H), 7.75 (s, 1H)

| # | Compound | Name | Yield (%) |
|---|----------|------|-----------|
| 1353 | 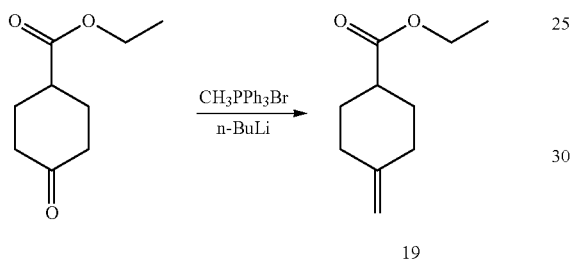 | 1-(3-chlorophenyl-2-(5H-imidazo[5,1-a]isoindol-5-yl)ethanone | 20 |

¹H NMR 3.30-3.50 (m, 1H), 3.60-3.75 (m, 1H), 5.75-5.85 (m, 1H), 7.15 (s, H), 7.20-7.60 (m, 6H), 7.69 (s, 1H), 7.82 (d, 1H, J = 10.4 Hz), 7.93 (t, 1H, J = 2.4 Hz)

a The compound was not characterized and was used as such for the next synthetic step

Example 6

Ethyl 4-methylenecyclohexanecarboxylate

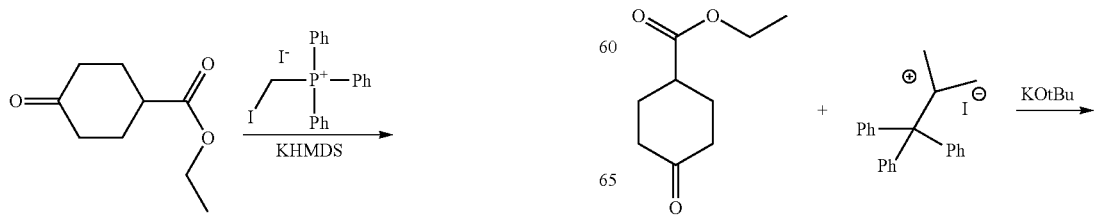

19

To a suspension of methyltriphenylphosphonium bromide (1.57 g, 4.41 mmol) in THF (9 mL) at −10° C. was added n-BuLi (2.5 M in hexanes, 1.65 mL, 4.11 mmol) dropwise and the solution was allowed to stir for 1 h. Ethyl 4-oxocyclohexanecarboxylate (0.47 mL, 2.94 mmol) was added and the reaction was allowed to warm to room temperature over 3 h. Acetone (3 mL) was added and the solvent was removed under reduced pressure. The residue was suspended in dichloromethane and ethyl ether (1:1), filtered and concentrated. The crude was purified by flash column chromatography to afford 19 as clear oil (419 mg, 85%). ¹H NMR: 1.25 (t, 3H), 1.50-1.70 (m, 2H), 1.90-2.16 (m, 4H), 2.30-2.50 (m, 3H), 4.12 (q, 2H), 4.65 (s, 2H).

Example 7

Ethyl 4-(iodomethylene)cyclohexanecarboxylate

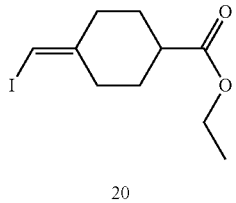

20

To a suspension of iodomethyltriphenylphosphonium iodide (1.95 g, 3.67 mmol) in THF (10 mL) at −23° C. was slowly added a solution of potassium hexamethyldisilazane (20% in toluene, 7.34 mL, 3.67 mmol) and the resulting solution was allowed to stir for 15 min. Ethyl 4-oxocyclohexanecarboxylate (500 mg, 2.94 mmol) was added. The cold bath was removed and the solution was allowed to stir at room temperature for 2 days. The reaction mixture was diluted with water (20 mL) and extracted with ether (3×20 mL). The combined organic layers were dried over anhydrous MgSO₄ and concentrated to obtain the crude product. The crude residue was purified by column chromatography to obtain 20 as light pink oil (207 mg, 24%). ¹H NMR: 1.21-1.52 (m, 2H), 1.93-2.13 (m, 4H), 2.30-2.50 (m, 4H), 2.49-2.70 (m, 4H), 4.12 (q, 2H), 4.60 (s, 1H)

Example 8

Ethyl 4-(propan-2-ylidene)cyclohexanecarboxylate

-continued

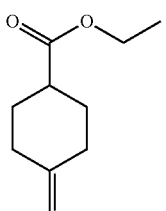

21

To a suspension of isopropyltriphenylphosphonium iodide (3.81 g, 8.81 mmol) in anhydrous THF (20 mL) at 0° C. was added a solution of t-BuOK (1.19 g, 10.58 mmol) in THF (15 mL). The reaction mixture was allowed to warm to rt and stirred for 1 h. The resulting mixture was cooled to 0° C., 4-Oxo-cyclohexanecarboxylic acid ethyl ester (1.0 g, 5.88 mmol) was added over a period of 5 min. The solution was allowed to slowly warm to rt and stirred for 2 h. The solution was stirred at 50° C. overnight. The solvent was distilled off under reduced pressure and the crude was partitioned between $CH_2Cl_2$ (50 mL) and satd. $NH_4Cl$ (30 mL). The organic layer was collected and the aqueous layer was extracted with $CH_2Cl_2$ (2×30 mL). The organic layer was washed with brine, dried ($Na_2SO_4$) and concentrated under reduced pressured to obtain the crude product. The crude was purified by column chromatography on silica gel to afford 21 as a clear oil (280 mg, 24%). $^1$H NMR: 1.24 (t, 3H, J=6.0 Hz), 1.43-1.50 (m, 2H), 1.63 (s, 6H), 1.74-1.83 (m, 2H), 1.92-1.98 (m, 2H), 2.39-2.47 (m, 1H), 2.58-2.69 (m, 2H).

Example 9

Ethyl 4-(cyclopropylmethylene)cyclohexanecarboxylate

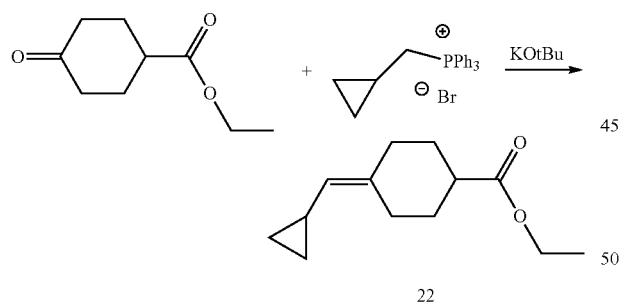

22

To a suspension of cyclopropylmethyltriphenylphosphonium iodide (3.5 g, 8.81 mmol) in anhydrous THF (20 mL) at 0° C. was added a solution of t-BuOK (1.19 g, 10.58 mmol) in THF (15 mL). The reaction mixture was allowed to warm to rt and stirred for 1 h. The resulting mixture was cooled to 0° C., 4-Oxo-cyclohexanecarboxylic acid ethyl ester (1.0 g, 5.88 mmol) was added over a period of 5 min. The solution was allowed to slowly warm to rt and stirred for 2 h. The solution was stirred at 50° C. overnight. The solvent was distilled off under reduced pressure and the crude was partitioned between $CH_2Cl_2$ (50 mL) and satd. $NH_4Cl$ (30 mL). The organic layer was collected and the aqueous layer was extracted with $CH_2Cl_2$ (2×30 mL). The organic layer was washed with brine, dried ($Na_2SO_4$) and concentrated under reduced pressured to obtain the crude product. The crude was purified by column chromatography on silica gel to afford 22 as colorless oil (800 mg, 65%). $^1$H NMR: $CDCl_3$ 0.22-0.26 (m, 2H), 0.62-0.68 (m, 2H), 1.22 (t, 3H, J=7.2 Hz), 1.39-1.47 (m, 3H), 1.75-2.04 (m, 4H), 2.14-2.20 (m, 1H), 2.37-2.46 (m, 1H), 2.67-2.75 (m, 1H), 4.10 (q, 2H, J=7.2 Hz), 4.49 (d, 1H, J=9.3 Hz).

Example 10

Ethyl 4-(trityloxy)cyclohexanecarboxylate

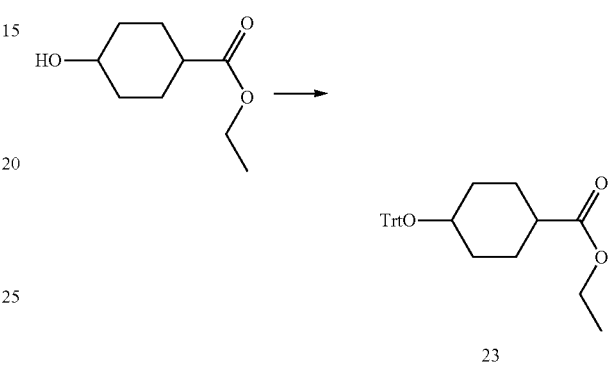

23

To a solution of triphenylmethyl chloride (0.97 g, 3.48 mmol) in dichloromethane (10 mL) was added DBU (0.61 mL, 4.06 mmol) and ethyl 4-hydroxycyclohexanecarboxylate (500 mg, 2.90 mmol) and the mixture was refluxed for 24 h. The reaction mixture cooled and cold water (40 mL) was added. The organic layer was collected and the aqueous layer was extracted with dichloromethane (2×30 ml). The combined organic layers were dried ($Na_2SO_4$) and concentrated under reduced pressure. The crude was purified by flash column chromatography to afford 23 as colorless oil (714 mg, 59%). $^1$HNMR: (mixture of cis and trans isomers (1:1.4)) 1.06 (t, 2H, J=12.4 Hz), 1.16-1.26 (m, 14H), 1.32-1.35 (m, 2H), 1.54-1.58 (m, 2H), 1.76-1.79 (m, 3H), 1.95-2.04 (m, 2H), 2.11-2.22 (m, 2H), 3.35-3.41 (m, 1.4H), 3.72-3.76 (m, 1H), 4.04 (q, 2.8H, J=7.2 Hz), 4.14 (q, 2H, J=6.8 Hz), 7.22-7.27 (m, 24H, merged with $CHCl_3$), 7.49-7.51 (m, 13H).

Example 11

Methyl cis-4-aminocyclohexanecarboxylate hydrochloride

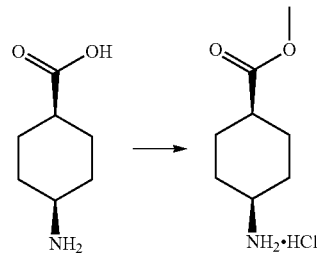

115

A solution of cis-4-aminocyclohexanecarboxylic acid (1.04 g, 7.26 mmol) in 10 mL of methanol was cooled to 0° C.

and thionyl chloride (1.58 mL, 21.79 mmol) was added. The reaction mixture was warmed to RT and stirred for 18 h. The reaction solution was concentrated, and the residue was washed with ethyl ether to obtain 115 as colorless crystals (1.3 g, 92%). $^1$H NMR (CD$_3$OD): 1.73-1.77 (m, 4H), 1.92-1.96 (m, 2H), 2.16-2.73 (m, 2H), 2.70-2.73 (m, 1H), 3.19-3.24 (m, 1H), 3.74 (s, 3H).

Example 12

Methyl cis-4-benzamidocyclohexanecarboxylate

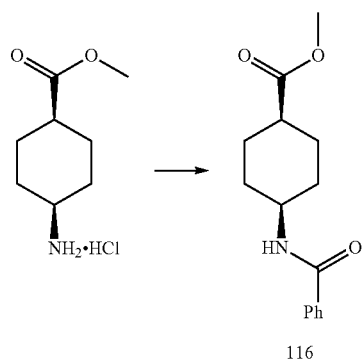

To a suspension of methyl cis-4-aminocyclohexanecarboxylate hydrochloride (0.63 g, 3.26 mmol) in CH$_2$Cl$_2$ (10 mL) at 0° C. was added diisopropylethylamine (1.71 mL, 9.79 mmol) and the suspension was stirred for 10 minutes. Benzoyl chloride (0.45 mL, 3.92 mmol) was added dropwise and the clear solution was allowed to warm to rt and stirred overnight. The reaction was diluted with water (15 mL) and CH$_2$Cl$_2$ (15 mL), the organic layer was collected and the aqueous layer was extracted with CH$_2$Cl$_2$ (2×25 mL). The combined organic extracts were dried over Na$_2$SO$_4$ and concentrated under reduce pressure to afford 116 as a clear gel (850 mg, 100%). $^1$H NMR: 1.70-1.73 (m, 2H), 1.76-1.90 (m, 4H), 1.95-2.06 (m, 2H), 2.55-2.61 (m, 1H), 3.72 (s, 3H), 4.14-4.20 (m, 1H), 6.14 (d, 1H, J=6.0 Hz), 7.43-7.47 (m, 2H), 7.49-7.51 (m, 1H), 7.76-7.78 (m, 2H).

Example 13

Methyl trans-4-aminocyclohexanecarboxylate hydrochloride

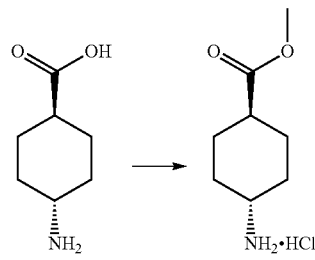

A solution of trans-4-aminocyclohexanecarboxylic acid (1.24 g, 8.66 mmol) in 12 mL of methanol was cooled to 0° C.

and thionyl chloride (1.89 mL, 25.98 mmol) was added. The reaction mixture was warmed to RT and stirred for 18 h. The reaction solution was concentrated, and the residue was washed with ethyl ether to obtain 117 as colorless crystals (1.61 g, 95%). $^1$H NMR (CD$_3$OD): 1.43-1.61 (m, 4H), 2.11-2.15 (m, 4H), 2.39 (dt, 1H, J=2.8, 11.8 Hz), 3.12 (dt, 1H, J=3.2, 8.0 Hz), 3.70 (s, 3H).

Example 14

Methyl trans-4-benzamidocyclohexanecarboxylate

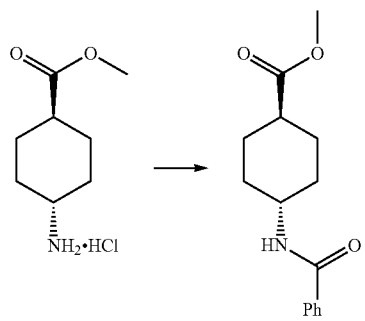

To a suspension of methyl trans-4-aminocyclohexanecarboxylate hydrochloride, 9.79 mmol) and the suspension was stirred for 10 minutes. Benzoyl chloride (0.45 mL, 3.92 mmol) was added dropwise and the clear solution was allowed to warm to rt and stirred overnight. The reaction was diluted with water (15 mL) and CH$_2$Cl$_2$ (15 mL), the organic layer was separated and the aqueous layer was extracted with CH$_2$Cl$_2$ (2×25 mL). The combined organic extract was dried over Na$_2$SO$_4$ and concentrated under reduce pressure to afford 118 as a white solid (200 mg, 24%). $^1$H NMR (CD$_3$OD): 1.46 (q, 2H, J=11.5 Hz), 1.60 (q, 2H, J=12.0 Hz), 2.09 (d, 4H, J=11.2 Hz), 2.37 (t, 1H, J=12.0 Hz), 3.71 (s, 3H), 3.90 (t, 1H, J=11.4 Hz), 7.46-7.57 (m, 3H), 7.83 (d, 2H, J=7.1 Hz).

Example 15

1-tert-butyl 3-methyl azetidine-1,3-dicarboxylate

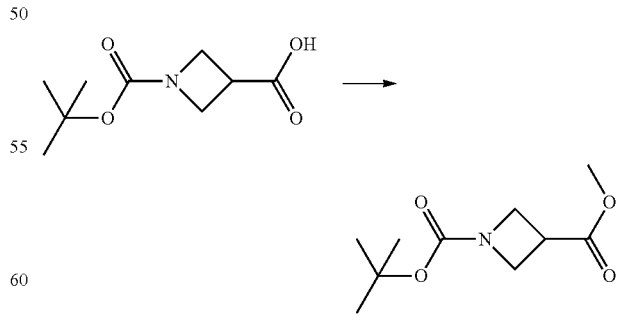

1-(t-butoxycarbonyl)azetidine-3-carboxylic acid (2.03 g, 10.09 mmol) was dissolved in MeOH (10 ml) and DCM (10 mL) and then cooled to 0° C. A 2M solution of trimethylsilyldiazomethane in ether (7.57 ml, 15.1 mmol) was then added drop-wise over 5 minutes. The solution was stirred for 10 minutes at 0° C. and then warmed to room temperature over 30 minutes. The solution was concentrated under reduced pressure to remove volatiles to afford crude 119, which was used directly in the next step without further purification. $^1$H NMR: 1.44 (s, 9H), 3.35 (m, 1H), 3.75 (s, 3H), 4.10 (d, 4H, J=7.6 Hz).

Example 16

Methyl cis-4-hydroxycyclohexanecarboxylate

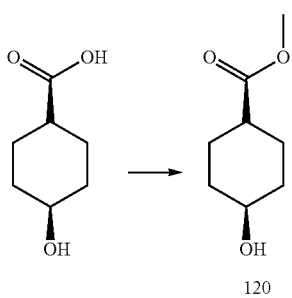

120

To a solution of cis-4-hydroxycyclohexanecarboxylic acid (5.0 g, 34.7 mmol) in dry MeOH (40 mL) at RT, was added concentrated $H_2SO_4$ (0.2 mL, 3.47 mmol) and the solution was stirred at 65° C. for 16 h. The solvent was distilled off and the crude was dissolved in EtOAc (40 mL) and the solution was washed with sat'd $NaHCO_3$ solution (25 mL). The organic layer was separated and the aqueous layer was extracted with EtOAc (2×20 mL). The combined organic extracts were dried over $Na_2SO_4$ and concentrated under reduced pressure to afford 120 (4.90 g, 89%). $^1$H NMR: 1.62-2.01 (m, 8H), 2.34-2.38 (m, 1H), 3.64 (s, 3H), 3.82-3.88 (m, 1H).

Example 17

Methyl cis-4-(benzyloxy)cyclohexanecarboxylate

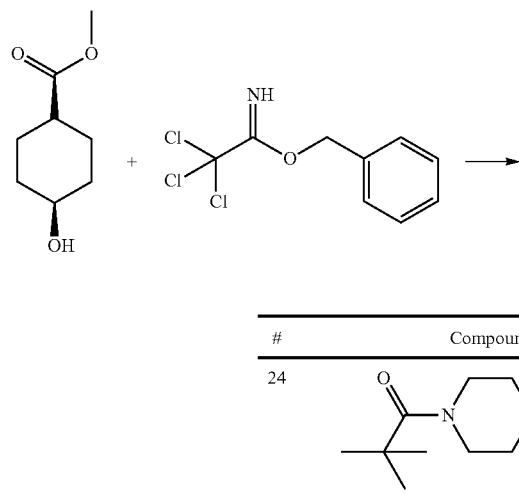

121

To a solution of methyl cis-4-hydroxycyclohexanecarboxylate (4.80 g, 30.3 mmol) in hexane/CHCl3 2:1 (60 mL) was added benzyl trichloroacetimidate (9.19 g, 36.4 mmol) and trifluoromethanesulfonic acid (683 mg, 4.55 mmol) at 23° C. The reaction mixture was stirred for 18 h and diluted with EtOAc (300 mL). The mixture was washed with saturated aqueous NaHCO3, water and brine. The organic layer was dried over anhydrous Na2SO4 and concentrated under reduced pressure. The crude reside was purified by column chromatography on silica gel to afford 121 (4.60 g, 18.5 mmol). $^1$H NMR: 1.55-1.98 (m, 8H), 2.36-2.41 (s, 1H), 3.56-3.66 (, 1H), 3.67 (s, 3H), 4.51 (s, 2H), 7.28-7.35 (m, 5H).

Example 18

General Procedure for the Reaction of Methyl Piperidine-4-carboxylate hydrochloride with Acid Chlorides

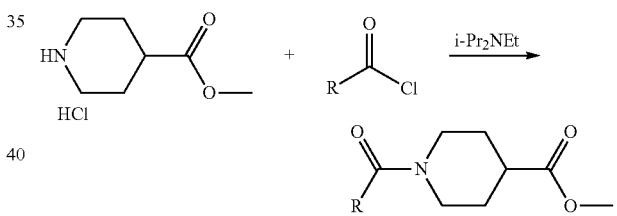

To a suspension of methyl piperidine-4-carboxylate hydrochloride (5.6 mmol) in $CH_2Cl_2$ (20 mL) at 0° C. was added diisopropylethyl amine (16.7 mmol) and the suspension was stirred for 10 minutes. Appropriate acid chloride (8.4 mmol) was added dropwise and the solution was allowed to warm to rt and stirred overnight. The reaction was diluted with water (15 mL) and $CH_2Cl_2$ (15 mL). The organic layer was collected and the aqueous layer was extracted with $CH_2Cl_2$ (2×20 mL). The combined organic extracts were dried ($Na_2SO_4$) and concentrated under reduce pressure to afford the following compounds.

| # | Compound | Name | Yield (%) |
|---|---|---|---|
| 24 |  | methyl 1-pivaloylpiperidine-4-carboxylate | 77 |

$^1$H NMR 1.21 (s, 9H) 1.65-1.53 (m, 2H), 1.87-1.92 (m, 2H), 2.48-2.52 (m, 1H), 2.89-2.93 (m, 2H), 3.63 (s, 3H), 4.18-4.22 (m, 1H), 4.24-4.27 (m, 1H)

| # | Compound | Name | Yield (%) |
|---|---|---|---|
| 25 | | methyl 1-(thiophene-2-carbonyl)piperidine-4-carboxylate | 91 |

¹H NMR 1.69-1.79 (m, 2H), 1.89-1.95 (m, 2H), 2.56-2.63 (m, 1H), 3.12 (t, 2H, J = 12.0 Hz), 3.68 (s, 3H), 4.28-4.31 (m, 2H), 7.0-7.02 (m, 1H), 7.24-7.26 (m, 1H), 7.40-7.42 (m, 1H)

| # | Compound | Name | Yield (%) |
|---|---|---|---|
| 26 | | methyl 1-(2-phenylacetyl)piperidine-4-carboxylate | 44 |

¹H NMR 1.30-1.95 (m, 4H), 2.35-2.55 (m, 1H), 2.70-2.85 (m, 1H), 2.95-3.10 (m, 1H), 3.62 (s, 3H), 3.70 (s, 2H), 3.70-3.85 (m, 1H), 4.30-4.40 (m, 1H), 7.15-7.35 (m, 5H)

Example 19

Methyl 2-bromo-3-fluorobenzoate

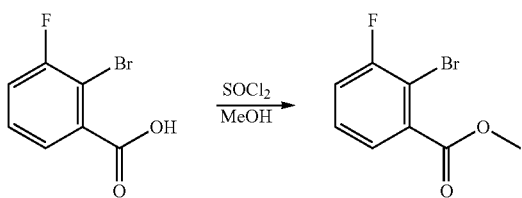

To a suspension of 2-bromo-3-fluorobenzoic acid (300 mg, 1.37 mmol) in methanol (10 mL) at rt, was added SOCl₂ (0.11 mL, 1.51 mmol) and the mixture was stirred at rt for 18 h. The solvent was distilled off under reduced pressure. The crude was basified by adding saturated aqueous NaHCO₃ solution and the aqueous layer was extracted with EtOAc (3×25 mL). The combined organic layers were dried over Na₂SO₄, filtered and concentrated. The obtained crude product was used in the next step without further purification.

Example 20

Methyl 3-fluoro-2-(1-trityl-1H-imidazol-4-yl)benzoate

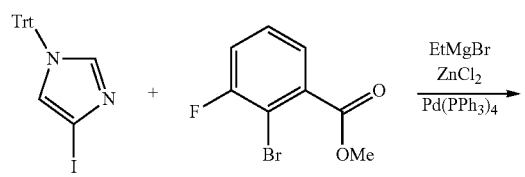

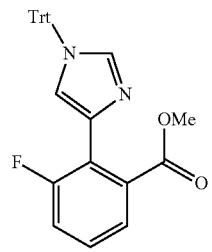

To a stirred solution of 4-iodo-1-trityl-1H-imidazole (436 mg, 1.0 mmol) in anhydrous THF (6 mL) was added EtMgBr (3.0 M in THF, 1.20 mmol, 0.40 mL) under an atmosphere of N₂. The resulting solution was allowed to stir for 90 min and ZnCl₂ (0.5 M in THF, 2.40 mL, 1.20 mmol) was added. The resulting white suspension was allowed to stir for 90 min and a solution of methyl 2-bromo-3-fluorobenzoate (280 mg, 1.20 mmol) in THF (1 mL) was added followed by the immediate addition of Pd(PPh₃)₄ (58 mg, 0.05 mmol). The reaction mixture was allowed to stir at 90° C. for 18 h under an atmosphere of N₂. After cooling to room temperature, the solution was diluted with CH₂Cl₂ (20 mL) and the organic layer was washed with an EDTA (aq) buffer (pH=9) (2×5 mL) and brine. The organic layer was dried (Na₂SO₄) and concentrated under reduced pressure. The crude residue was purified by flash column chromatography to afford the desired product as yellow oil (190 mg, 41%). ¹H NMR: 3.93 (s, 3H), 7.12-7.59 (m, 18H), 7.56 (s, 1H), 7.73-7.75 (m, 1H).

Example 21

3-Fluoro-2-(1-trityl-1H-imidazol-4-yl)benzaldehyde

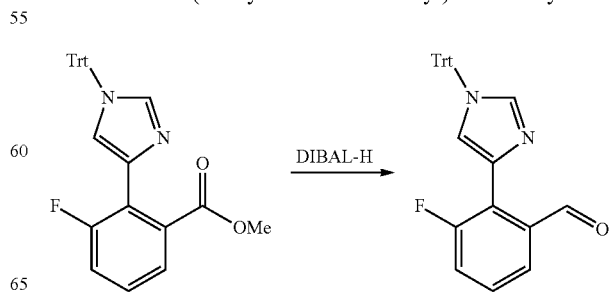

To a solution of methyl 3-fluoro-2-(1-trityl-1H-imidazol-4-yl)benzoate (62 mg, 0.134 mmol) in toluene (4 mL) at −78° C. was added dropwise a solution DIBAH (1 M, 0.161 mL, 0.161 mmol) Stirring was continued at for 10 min. At this temperature, dry methanol was added. The mixture was poured into saturated aqueous NH₄Cl (5 mL), diluted with EtOAc (15 mL), shaken vigorously for 3 min, added brine (5 mL), shaken again, the phases separated and the organic layer dried over Na₂SO₄, filtered, and evaporated to give the desired aldehyde which was used without further purification.

Example 22

General Procedure for the Synthesis of Dimethyl (2-oxo)phosphonates

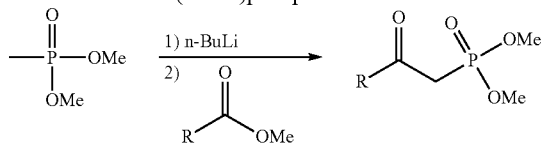

To a stirred solution of dimethyl methylphosphonate (3.14 g, 25.3 mmol) in 20 ml of anhydrous tetrahydrofuran at −78° C. was added dropwise a solution of n-butyl lithium (10.13 mL, 25.3 mmol, 2.5 M in hexanes) under an atmosphere of N₂, and the mixture was stirred for 30 minutes. To this reaction mixture was added dropwise a solution of the appropriate commercially available methyl or ethyl ester or 19-26, 91 or 115-121 (12.7 mmol) as a solution in THF (5 mL). After being stirred for 30 minutes, the reaction mixture was allowed to warm to 0° C., and stirred for 1 h. The solvent was distilled off and the crude was diluted with saturated NH₄Cl (10 mL) and 10 ml of water. The mixture was extracted with ethyl acetate (2×40 mL). The combined ethyl acetate layers were washed with water (1×20 mL), brine (1×20 mL) and dried over anhydrous sodium sulfate. The solution was filtered and concentrated under reduced pressure to afford the crude product. The crude was purified by column chromatography to afford the following compounds.

| # | Compound | Name | Yield (%) |
|---|----------|------|-----------|
| 27 | | dimethyl (2-(2,5-dimethylfuran-3-yl)-2-oxoethyl)phosphonate | 52 |
| | ¹H NMR 2.23 (s, 3H), 2.53 (s, 3H), 3.31 (d, 2H, J = 22.5 Hz), 3.75 (s, 3H), 3.79 (s, 3H), 6.24 (s, 1H) | | |
| 28 | | dimethyl (2-(furan-2-yl)-2-oxoethyl)phosphonate | 63 |
| | ¹H NMR 3.52 (d, 2H, J = 22.6 Hz), 3.75 (s, 3H), 3.78 (s, 3H), 6.56 (d, 1H, J = 1.6 Hz), 7.29 (s, 1H), 7.62 (s, 1H) | | |
| 29 | | dimethyl (2-(1-methyl-1H-imidazol-2-yl)-2-oxoethyl)phosphonate | 45 |
| | ¹H NMR 3.80 (s, 3H), 3.83 (s, 3H), 3.88 (d, 2H, J = 22.2 Hz), 4.01 (s, 3H), 7.07 (s, 1H), 7.18 (s, 1H) | | |
| 30 | | dimethyl (2-oxo-2-(thiazol-4-yl)ethyl)phosphonate | 91 |
| | ¹H NMR 3.76 (s, 3H), 3.79 (s, 3H), 3.90 (d, 2H, J = 22.8 Hz), 8.32 (s, 1H), 8.85 (s, 1H) | | |

-continued

| # | Compound | Name | Yield (%) |
|---|---|---|---|
| 31 | | dimethyl 2-(4,4-difluorocyclohexyl)-2-oxoethylphosphonate | 82 |

¹H NMR 1.72-1.81 (m, 4H), 1.96-1.98 (m, 2H), 2.11-2.13 (m, 2H), 2.68-2.70 (m, 1H), 3.14 (d, 2H, J = 22.4 Hz), 3.79 (d, 6H, J = 11.2 Hz)

| 32 | | dimethyl 2-(4-methylenecyclohexyl)-2-oxoethylphosphonate | 67 |

¹H NMR 1.43-1.53 (m, 2H), 1.95-2.13 (m, 4H), 2.37-2.41 (m, 2H), 2.72-2.78 (m, 1H), 3.18 (d, 2H, J = 22.5 Hz), 3.82 (d, 6H, J = 11.3 Hz), 4.68 (s, 2H)

| 33 | | dimethyl 2-oxo-2-(1,4-dioxaspiro[4.5]decan-8-yl)ethylphosphonate | 72 |

¹H NMR 1.31-1.39 (m, 2H), 1.70-1.85 (m, 5H), 1.85-1.98 (m, 2H), 3.15 (d, 2H, J = 11.2 Hz), 3.77 (d, J = 18 Hz, 6H), 3.92 (m, 4H)

| 34 | | dimethyl 2-(4-methylcyclohexyl)-2-oxoethylphosphonate | 60 |

¹H NMR 0.88-0.90 (m, 3H), 1.20-1.50 (m, 2H), 1.50-1.65 (m, 5H), 1.80-1.95 (m, 2H), 2.62-2.71 (m, 2H), 3.13 (d, J = 22.8 Hz, 2H), 3.73 and 3.80 (two s, 6H)

| 35 | | dimethyl 2-(4-(iodomethylene)cyclohexyl)-2-oxoethylphosphonate | 47 |

¹H NMR 1.20-1.52 (m, 2H), 1.93-2.10 (m, 4H), 2.30-2.36 (m, 1H), 2.49-2.58 (m, 4H), 3.07-3.10 (m, 2H), 3.73-3.76 (m, 6H), 4.60 (s, 1H)

| 36 | | dimethyl (2-oxo-2-(4-(propan-2-ylidene)cyclohexyl)ethyl)phosphonate | 70 |

¹H NMR 1.28-1.42 (m, 2H), 1.63 (s, 6H), 1.72-1.96 (m, 4H), 2.65-2.75 (m, 3H), 3.12 (d, 1H, J = 21.0 Hz), 3.75 (d, 6H, J = 12.0 Hz)

| 37 | | dimethyl (2-(4-(cyclopropylmethylene)cyclohexyl)-2-oxoethyl)phosphonate | 68 |

¹H NMR 0.24 (s, 2H), 0.67 (d, 2H, J = 7.8 Hz), 1.39-1.43 (m, 3H), 1.86-2.07 (m, 4H), 2.17-2.21 (m, 1H), 2.71-2.79 (m, 2H), 3.13 (d, 2H, J = 22.5 Hz), 3.77 (d, 6H, J = 11.2 Hz), 4.50 (d, 1H, J = 9.3 Hz)

-continued

| # | Compound | Name | Yield (%) |
|---|----------|------|-----------|
| 38 | | dimethyl (2-oxo-2-(1-pivaloylpiperidin-4-yl)ethyl)phosphonate | 68 |

$^1$H NMR 1.23 (s, 9H), 1.51 (m, 1H), 1.87 (m, 3H), 2.85 (m, 3H), 3.02 (s, 1H), 3.14 (s, 1H), 3.75 (d, 6H, J = 11.2 Hz), 4.34 (m, 1H), 4.37 (m, 1H)

| # | Compound | Name | Yield (%) |
|---|----------|------|-----------|
| 39 | | dimethyl (2-(1-methyl-1H-imidazol-5-yl)-2-oxoethyl)phosphonate | 36 |

$^1$H NMR 3.35 (d, 2H, J = 22.8 Hz), 3.74 (d, 6H, J = 11.2 Hz), 3.86 (s, 3H), 7.54 (s, 1H), 7.78 (s, 1H)

| # | Compound | Name | Yield (%) |
|---|----------|------|-----------|
| 40 | | dimethyl (2-(1-methyl-1H-imidazol-4-yl)-2-oxoethyl)phosphonate | 29 |

$^1$H NMR 3.66-3.74 (s, 3H merged with d, 2H, J = 22.5 Hz), 3.78 (d, 6H, J = 11.2 Hz), 7.44 (s, 1H), 7.63 (s, 1H)

| # | Compound | Name | Yield (%) |
|---|----------|------|-----------|
| 41 | | dimethyl (2-oxo-2-(thiazol-5-yl)ethyl)phosphonate | 18 |

$^1$H NMR 3.53 (s, 1H), 3.61 (s, 1H), 3.73 (d, 6H, J = 11.2 Hz), 8.52 (s, 1H), 9.04 (s, 1H)

| # | Compound | Name | Yield (%) |
|---|----------|------|-----------|
| 42 | | dimethyl (2-(1-acetylpiperidin-4-yl)-2-oxoethyl)phosphonate | 64 |

$^1$H NMR 1.44-1.69 (m, 2H), 1.83-1.89 (m, 2H), 2.07 (s, 3H), 2.66-2.73 (m, 1H), 2.79-2.85 (m, 1H), 3.03-3.22 (m, 3H), 3.72-3.83 (m, 1H overlapping with d, 6H, J = 11.2 Hz), 4.53 (d, 1H, J = 13.4 Hz)

| # | Compound | Name | Yield (%) |
|---|----------|------|-----------|
| 43 | | dimethyl (2-oxo-2-(1-(thiophene-2-carbonyl)piperidin-4-yl)ethyl)phosphonate | 59 |

$^1$H NMR 1.63 (m, 2H), 1.95 (m, 2H), 2.89 (s, 1H), 3.07 (m, 2H), 3.10 (s, 1H), 3.18 (s, 1H), 3.77 (d, 6H, J = 11.2 Hz), 4.38 (m, 2H), 7.02 (dd, 1H, J = 5.0 Hz, 3.7 Hz), 7.25 (dd, 1H, J = 3.7 Hz, 1.1 Hz), 7.42 (dd, 1H, J = 5.1 Hz, 1.2 Hz)

| # | Compound | Name | Yield (%) |
|---|----------|------|-----------|
| 44 | | dimethyl 2-oxo-2-(1-(2-phenylacetyl)piperidin-4-yl)ethylphosphonate | 39 |

$^1$H NMR 1.20-1.90 (m, 4H), 1.67 (d, 1H, J = 10.2 Hz), 1.84 (d, 1H, J = 9.6 Hz), 2.55-2.75 (m, 2H), 2.90-3.15 (m, 2H), 3.65 (s, 2H), 3.70 (d, 6H, J = 11.2 Hz), 3.90 (d, 1H, J = 10.2 Hz), 4.48 (d, 1H, J = 9.9 Hz), 7.10-7.30 (m, 5H)

-continued

| # | Compound | Name | Yield (%) |
|---|---|---|---|
| 45 | | dimethyl 3-cyclohexyl-2-oxopropylphosphonate | 70 |

$^1$H NMR 0.60-1.15 (m, 5H), 1.35-1.71 (m, 5H), 2.28 (d, 2H, J = 8.8 Hz), 2.83 (s, 1H), 2.91 (s, 1H), 3.55 (s, 3H), 3.59 (s, 1H)

| 46 | | dimethyl (2-oxo-2-(4-(trityloxy)cyclohexyl)ethyl)phosphonate | 79 |

$^1$H NMR (mixture of cis and trans isomers) 1.08-1.36 (m, 5H), 1.59-1.91 (m, 3H), 2.41-2.52 (m, 1H), 3.03 and 3.13 (two d, 2H, J = 20.0 Hz), 3.35-3.79 (m, 1H), 3.73-3.79 (m, 6H), 7.22-7.29 (m, 9H), 7.49-7.51 (m, 6H)

| 122 | | (trans)-methyl 4-(2-(dimethoxyphosphoryl)acetyl)cyclohexanecarboxylate | 70 |

$^1$H NMR 1.31-1.53 (m, 4H), 2.00-2.20 (m, 4H), 2.23-2.31 (m, 1H), 2.53-2.61 (m, 1H), 3.13 (d, 2H, J = 22.6 Hz), 3.67 (s, 3H), 3.79 (d, 6H, J = 11.2 Hz)

| 124 | | dimethyl (2-oxo-2-(4-(propan-2-ylidene)cyclohexyl)ethyl)phosphonate | 70 |

$^1$H NMR 1.28-1.42 (m, 2H), 1.63 (s, 6H), 1.72-1.96 (m, 4H), 2.65-2.75 (m, 3H), 3.12 (d, 1H, J = 21.0 Hz), 3.75 (d, 6H, J = 12.0 Hz)

| 125 | | dimethyl (2-oxo-2-(spiro[2.5]octan-6-yl)ethyl)phosphonate | 77 |

$^1$H NMR 0.13-0.27 (m, 4H), 0.91-0.95 (m, 2H), 1.40-2.06 (m, 6H), 2.52-2.58 (m, 1H), 3.11 (d, 2H, J = 24.0 Hz), 3.75 (d, 6H, J = 12.0 Hz)

| 126 | | dimethyl (2-((trans)-4-((tert-butyldimethylsilyl)oxy)cyclohexyl)-2-oxoethyl)phosphonate | 96 |

$^1$H NMR 0.11 (s, 6H), 0.82 (s, 9H), 1.19-1.32 (m, 4H), 1.85-1.88 (m, 4H), 2.41-2.47 (m, 1H), 3.08 (d, 2H, J = 24.0 Hz), 3.72 (s, 3H), 3.74 (s, 3H)

| # | Compound | Name | Yield (%) |
|---|---|---|---|
| 127 | | dimethyl (2-((trans)-4-(benzyloxy)cyclohexyl)-2-oxoethyl)phosphonate | 16 |

¹H NMR 1.13-1.41 (m, 4H), 1.93-2.02 (m, 2H), 2.12-2.15 (m, 2H), 2.51-2.56 (m, 1H), 3.11 (d, 2H, J = 24 Hz), 3.27-3.32 (m, 1H), 3.75 (d, 6H, J = 12 Hz ), 7.22-7.32 (m, 5H)

| 128 | | dimethyl (2-(cis-4-benzamidocyclohexyl)-2-oxoethyl)phosphonate | 83 |

¹H NMR 1.76-1.85 (m, 8H), 2.78-2.79 (m, 1H), 3.18 (d, 2H, J = 22.8 Hz), 3.82 (d, 6H, J = 11.2 Hz), 4.21-4.25 (m, 1H), 7.40-7.52 (m, 3H), 7.76-7.78 (m, 2H)

| 129 | | dimethyl (2-(trans-4-benzamidocyclohexyl)-2-oxoethyl)phosphonate | 54 |

¹H NMR 1.29 (dq, 2H, J = 3.1, 12.1 Hz), 1.54 (dq, 2H, J = 3.0, 11.5 Hz), 2.04 (d, 2H, J = 12.9 Hz), 2.12 (dd, 2H, J = 3.0, 12.6 Hz), 2.60 (tt, 1H, J = 3.4, 12.0 Hz), 3.15 (d, 2H, J = 22.6 Hz), 3.79 (d, 6H, J = 11.2 Hz), 3.93-3.99 (m, 1H), 5.98 (d, 1H, J = 7.7 Hz), 7.41-7.45 (m, 2H), 7.48-7.52 (m, 2H), 7.74 (d, 2H, J = 7.1 Hz)

| 130 | | dimethyl (2-oxo-2-(4-(2-(trityloxy)ethylidene)cyclohexyl)ethyl)phosphonite | 42 |

¹H NMR 1.26-1.60 (m, 2H), 1.35-1.37 (m, 1H), 1.80-2.30 (m, 3H), 2.25-2.40 (m, 2H), 2.70-2.76 (m, 1H), 3.05 (d, J = 27 Hz, 2H), 3.57-3.61 (m, 2H), 3.71-3.75 (d, J = 12 Hz, 2H), 7.19-7.32 (m, 9H), 7.44-7.51 (m, 6H)

| 131 | | tert-butyl 3-(2-(dimethoxyphosphoryl)acetyl)azetidine-1-carboxylate | 99 |

¹H NMR 1.43 (s, 9H), 3.11 (d, J = 24 Hz, 2H), 3.68-3.82 (m, 7H), 3.81-4.12 (m, 4H)

| # | Compound | Name | Yield (%) |
|---|---|---|---|
| 132 | 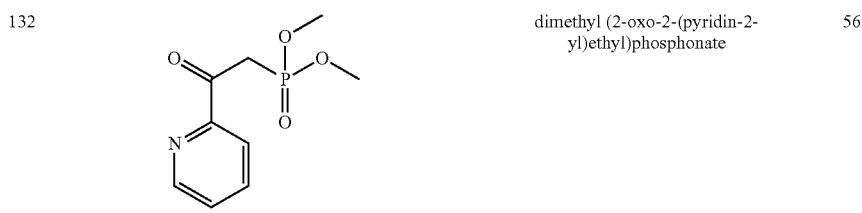 | dimethyl (2-oxo-2-(pyridin-2-yl)ethyl)phosphonate | 56 |
$^1$H NMR 3.69-3.77 (m, 6H), 3.96-4.04 (m, 2H), 7.45-7.48 (m, 1H), 7.80-7.85 (m, 1H), 8.03-8.09 (m, 1H), 8.66-8.69 (m, 1H)
| 133 | 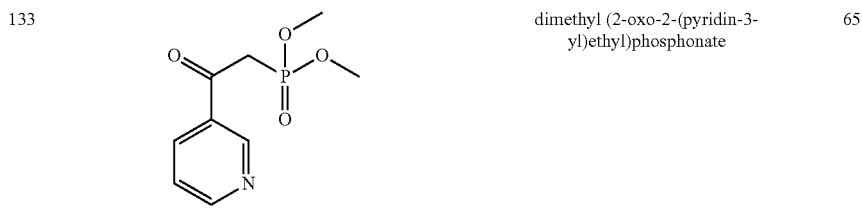 | dimethyl (2-oxo-2-(pyridin-3-yl)ethyl)phosphonate | 65 |
|---|---|---|---|
$^1$H NMR 3.60-3.80 (m, 8H), 7.41-7.45 (m, 1H), 8.26-8.29 (m, 1H), 8.78-8.79 (m, 1H), 9.18 (m, 1H)
| 134 | 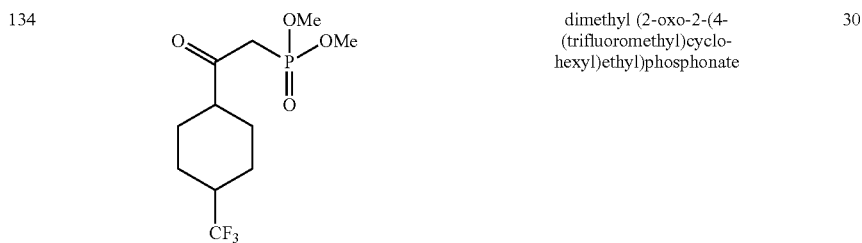 | dimethyl (2-oxo-2-(4-(trifluoromethyl)cyclohexyl)ethyl)phosphonate | 30 |
|---|---|---|---|
$^1$H NMR 1.55-1.64 (m, 4H), 1.75-1.77 (m, 2H), 204-2.16 (m, 3H), 2.83-2.84 (m, 1H), 3.14 (d, J = 22.4 Hz, 2H), 3.78 (d, J = 11.2 Hz, 6H)
| 135 | 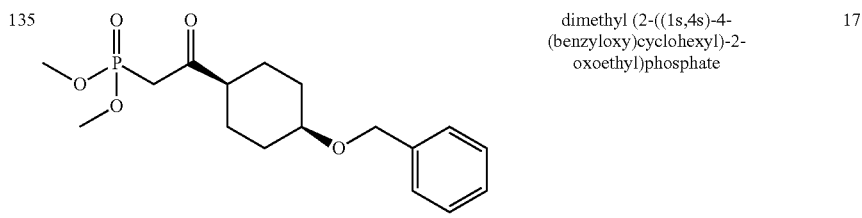 | dimethyl (2-((1s,4s)-4-(benzyloxy)cyclohexyl)-2-oxoethyl)phosphate | 17 |
|---|---|---|---|
$^1$H NMR 1.47-1.55 (m, 2H), 1.66-1.71 (m, 2H), 1.78-1.85 (m, 2H), 1.95-1.99 (m, 2H), 2.58-2.62 (m, 1H), 3.14 (d, 2H, J = 22.4 Hz), 3.60-3.63 (m, 1H), 3.78 (d, 6H, J = 11.2 Hz), 4.48 (s, 2H), 7.24-7.33 (m, 5H)

Example 23

General Procedure for the Synthesis of 2-(5H-imidazo[5,1-a]isoindol-5-yl)ethanones by Horner-Wadsworth-Emmons Reaction Followed by Cyclization

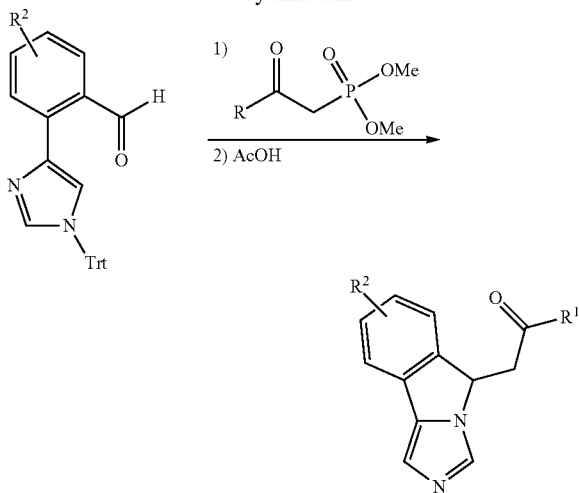

To a suspension of 95% NaH (17.4 mg, 0.7 mmol) in THF (3 mL) at 0° C. was added the appropriate phosphonate reagent 27-46, 89, 90 or 122-135 (0.75 mmol) as a solution in THF (2 mL) and the mixture was stirred for 40 min. The appropriate 2-(1-trityl-1H-imidazol-4-yl)benzaldehyde was added as a solution in THF (3 mL) drop wise over a period of 3 min. The reaction was allowed to warm to RT and stirred overnight. The solvent was removed under reduced pressure and the crude was diluted with saturated NH$_4$Cl (10 mL) and water (10 mL). The aqueous layer was extracted with CH$_2$Cl$_2$ (2×20 mL) and the combined organic fractions were washed with brine (15 mL), dried over Na$_2$SO$_4$ and concentrated under reduced pressure to afford the crude product. To the crude residue was added AcOH (1 mL) and MeOH (3 mL) and the solution was stirred at 90° C. for 2 h. After cooling to rt, the solvent was distilled off and the crude was stirred in a mixture of sat'd K$_2$CO$_3$ (5 mL) and EtOAc (5 mL). The organic layer was separated and the aqueous layer was extracted with EtOAc (2×10 mL). The combined organic layers were washed with water, brine and dried (Na$_2$SO$_4$) and the solvent evaporated under reduced pressure. The crude residue was purified by flash column chromatography on silica gel to afford the following compounds.

| # | Compound | Name | Yield (%) |
|---|---|---|---|
| 47 | | 1-(cyclohex-1-en-1-yl)-2-(5H-imidazo[5,1-a]isoindol-5-yl)ethanone | 54 |

$^1$H NMR 1.64-1.68 (m, 4H), 2.23-2.33 (m, 4H), 3.12 (dd, 1H, J = 9.8, 17.8 Hz), 3.36 (dd, 1H, J = 3.2, 18.0 Hz), 5.72 (dd, 1H, J = 3.6, 7.6 Hz), 6.86-6.88 (m, 1H), 7.17 (s, 1H), 7.32 (d, 1H, J = 7.6 Hz), 7.38 (t, 1H, J = 7.4 Hz), 7.55 (d, 1H, J = 7.2 Hz), 7.65 (s 1H)

| 48 | | 1-(2,5-dimethylfuran-3-yl)-2-(6-fluoro-5H-imidazo[5,1-a]isoindol-5-yl)ethanone | 93 |

$^1$H NMR 2.22 (s, 3H), 2.60 (s, 3H), 2.97 (dd, 1H, J = 10.8, 18.4 Hz), 3.72 (d, 1H, J = 18.2 Hz), 5.86 (d, 1H, J = 10.7 Hz), 6.11 (s, 1H), 6.93 (t, 1H, J = 8.5 Hz), 7.16 (s, 1H), 7.30-7.37 (m, 2H). 7.74 (s, 1H)

| 49 | | 2-(6-fluoro-5H-imidazo[5,1-a]isoindol-5-yl)-1-(furan-2-yl)ethanone | 65 |

$^1$H NMR 3.16 (dd, 1H, J = 10.5, 18.4 Hz), 3.85 (d, 1H, J = 18.4 Hz), 5.86 (d, 1H, J = 10.5 Hz), 6.54 (s, 1H), 6.92 (t, 1H, J = 8.9 Hz), 7.14 (s, 1H), 7.24-7.35 (m, 3H), 7.57 (s, 1H), 7.74 (s, 1H)

| # | Compound | Name | Yield (%) |
|---|---|---|---|
| 50 | | 2-(6-fluoro-5H-imidazo[5,1-a]isoindol-5-yl)-1-(1-methyl-1H-imidazol-2-yl)ethanone | 39 |

¹H NMR 3.56 (dd, 1H, J = 12.0, 20.0 Hz), 4.07 (s, 3H), 4.13 (d, 1H, J = 20.0 Hz), 5.86 (d, 1H, J = 12.0 Hz), 6.92 (t, 1H, J = 8.0 Hz), 7.09 (d, 1H, J = 8.0 Hz), 7.15 (s, 1H), 7.31-7.34 (m, 3H), 7.71 (s, 1H)

| 51 | | 2-(5H-imidazo[5,1-a]isoindol-5-yl)-1-(thiazol-4-yl)ethanone | 58 |

¹H NMR 3.62 (dd, 1H, J = 9.7, 18.8 Hz), 3.92 (dd, 1H, J = 3.0, 18.9 Hz), 5.79 (d, 1H, 9.5 Hz), 7.18 (s, 1H), 7.26-7.28 (m, 1H overlap with CHCl3), 7.36-7.40 (m, 2H), 7.55 (d, 1H, J = 7.4 Hz), 7.75 (s, 1H), 8.38 (s, 1H), 8.82 (s, 1H)

| 52 | | 1-(4,4-difluorocyclohexyl)-2-(6-fluoro-5H-imidazo[5,1-a]isoindol-5-yl)ethanone | 81 |

¹H NMR 1.65-1.82 (m, 4H), 1.90-2.01 (m, 2H), 2.11-2.16 (m, 2H), 2.44-2.48 (m, 1H), 2.79 (dd, 1H, J = 10.4 Hz, 18.4 Hz), 3.52 (dd, 1H, J = 2 Hz, 18.4 Hz), 5.72 (d, 1H, J = 10.4 Hz), 6.92 (t, 1H, J = 8.8 Hz), 7.15 (s, 1H), 7.28-7.35 (m, 2H), 7.58 (s, 1H)

| 53 | | 1-(4,4-difluorocyclohexyl)-2-(5H-imidazo[5,1-a]isoindol-5-yl)ethanone | 96 |

¹H NMR 1.73-1.80 (m, 4H), 1.91-1.95 (m, 2H), 2.10-2.14 (m, 2H), 2.41-2.47 (m, 1H), 2.90 (dd, 1H, J = 9.4 Hz, 18.8 Hz), 3.21 (dd, 1H, J = 3.6 Hz, 18.4 Hz), 5.60 (dd, 1H, J = 3.4 Hz, 9.4 Hz), 7.13 (s, 1H), 7.22-7.28 (m, 2H), 7.36 (t, 1H, J = 7.2 Hz), 7.51 (d, 1H, J = 7.6 Hz), 7.57 (s, 1H)

| 54 | | 2-(5H-imidazo[5,1-a]isoindol-5-yl)-1-(4-methylenecyclohexyl)ethanone | |

¹H NMR 1.30-1.50 (m, 2H), 1.80-2.05 (m, 3H), 2.20-2.32 (m, 2H), 2.40-2.50 (m, 1H), 2.58-2.67 (m, 1H), 2.78-2.88 (m, 1H), 3.16-3.17 (m, 1H), 5.50-5.54 (m, 1H), 7.13-7.17 (m, 1H), 7.20-7.30 (m, 2H), 7.43-7.45 (m, 1H), 7.52 (s, 1H)

| # | Compound | Name | Yield (%) |
|---|---|---|---|
| 55 | | 2-(6-fluoro-5H-imidazo[5,1-a]isoindol-5-yl)-1-(4-methylenecyclohexyl)ethanone | 64 |

$^1$H NMR 1.30-1.60 (m, 2H), 1.90-2.10 (m, 3H), 2.32-2.35 (m, 2H), 2.50-2.60 (m, 1H), 2.60-2.72 (m, 1H), 2.76-2.84 (m, 1H), 3.52 (d, J = 18.4 Hz, 1H), 4.63 (s, 2H), 5.73 (d, J = 10.4 Hz, 1H), 6.91-6.96 (m, 1H), 7.20-7.30 (m, 2H), 7.43-7.45 (m, 1H), 7.52 (s, 1H)

| # | Compound | Name | Yield (%) |
|---|---|---|---|
| 56 | | 2-(6-fluoro-5H-imidazo[5,1-a]isoindol-5-yl)-1-(1,4-dioxaspiro[4.5]decan-8-yl)ethanone | 84 |

$^1$H NMR (CD$_3$OD) 1.48-1.91 (m, 6H), 2.35-2.65 (m, 2H), 3.58-3.65 (m, 1H), 3.91 (s, 4H), 5.79-5.82 (m, 1H), 7.01-7.07 (m, 1H), 7.16 (m, 1H), 7.42-7.45 (m, 2H), 7.70 (s, 1H)

| # | Compound | Name | Yield (%) |
|---|---|---|---|
| 57 | | 2-(6-fluoro-5H-imidazo[5,1-a]isoindol-5-yl)-1-(4-methylcyclohexyl)ethanone | 87 |

$^1$H NMR 0.80-0.95 (m, 3H), 1.24-1.40 (m, 2H), 1.40-1.68 (m, 5H), 1.70-2.00 (m, 2H), 2.40-2.55 (m, 1H), 2.72-2.84 (m, 1H), 3.48 (d, J = 18.4 Hz, 1H), 5.75 (d, J = 10.4 Hz, 1H), 6.89-6.95 (m, 1H), 7.15 (s, 1H), 7.26-7.38 (m, 2H), 7.62 (s, 1H)

| # | Compound | Name | Yield (%) |
|---|---|---|---|
| 58 | | 2-(6-fluoro-5H-imidazo[5,1-a]isoindol-5-yl)-1-(4-(iodomethylene)cyclohexyl)ethanone | 46 |

$^1$H NMR (CD$_3$OD) 1.20-1.52 (m, 2H), 1.80-2.20 (m, 4H), 2.30-2.36 (m, 1H), 2.45-2.80 (m, 3H), 2.90-3.02 (m, 1H), 3.59-3.64 (m, 1H), 4.63 (s, 1H), 5.75-5.80 (m, 1H), 7.02-7.08 (m, 1H), 7.15 (s, 1H), 7.42-7.47 (m, 2H), 7.65 (s, 1H).

| # | Compound | Name | Yield (%) |
|---|---|---|---|
| 59 | | 2-(9-fluoro-5H-imidazo[5,1-a]isoindol-5-yl)-1-(4-methylcyclohexyl)ethanone | 55 |

$^1$H NMR (CD$_3$OD) 0.80-0.95 (m, 3H), 1.24-1.40 (m, 2H), 1.40-1.68 (m, 5H), 1.70-2.00 (m, 2H), 2.40-2.55 (m, 1H), 2.72-2.84 (m, 1H), 3.48 (d, J = 18.4 Hz, 1H), 5.49-5.59 (m, 1H), 7.10-7.18 (m, 2H), 7.60-8.00 (m, 1H)

-continued

| # | Compound | Name | Yield (%) |
|---|----------|------|-----------|
| 60 | | 2-(6-fluoro-5H-imidazo[5,1-a]isoindol-5-yl)-1-(4-(propan-2-ylidene)cyclohexyl)ethanone | 36 |

¹H NMR 1.30-1.52 (m, 2H), 1.64 (s, 6H), 1.70-1.81 (m, 2H), 1.85-1.98 (m, 2H), 2.52-2.62 (m, 1H), 2.68-2.74 (m, 2H), 2.80 (dd, 1H, J = 18.5 Hz, 10.6 Hz), 3.50 (dd, 1H, J = 18.5 Hz, 2.2 Hz), 5.75 (d, 1H, J = 9.27 Hz), 6.90-6.96 (m, 1H), 7.17 (s, 1H), 7.32-7.36 (m, 2H), 7.59 (s, 1H)

| # | Compound | Name | Yield (%) |
|---|----------|------|-----------|
| 61 | | 1-(4-(cyclopropylmethylene)cyclohexyl)-2-(6-fluoro-5H-imidazo[5,1-a]isoindol-5-yl)ethanone | 49 |

¹H NMR 0.24 (s, 2H), 0.67 (d, 2H, J = 7.8 Hz), 1.43-1.49 (m, 3H), 1.82-2.15 (m, 3H), 2.12-2.28 (m, 1H), 2.50-2.62 (m, 1H), 2.75-2.85 (m, 2H), 3.52 (d, 1H, J = 18.6 Hz), 4.52 (d, 1H, J = 9.3 Hz), 5.75 (d, 1H J = 10.2 Hz), 6.89-6.95 (m, 1H), 7.16 (s, 1H), 7.25-7.36 (m, 3H), 7.59 (s, 1H)

| # | Compound | Name | Yield (%) |
|---|----------|------|-----------|
| 62 | | 1-(4-(2-(5H-imidazo[5,1-a]isoindol-5-yl)acetyl)piperidin-1-yl)-2,2-dimethylpropan-1-one | 42 |

¹H NMR 1.26 (s, 9H), 1.60 (m, 2H), 1.88 (m, 2H), 2.61 (m, 1H), 2.84 (m, 2H), 2.89 (dd, 1H, J = 9.39 Hz, 18.6 Hz), 3.22 (dd, 1H, J = 3.6 Hz, 18.3 Hz), 4.41 (m, 2H), 5.62 (dd, 1H, J = 3.54 Hz, 9.45 Hz), 7.16 (s, 1H), 7.24 (m, 2H), 7.37 (m, 1H), 7.53 (d, 1H, J = 7.56 Hz), 7.59 (s, 1H)

| # | Compound | Name | Yield (%) |
|---|----------|------|-----------|
| 63 | | 2-(6-fluoro-5H-imidazo[5,1-a]isoindol-5-yl)-1-(1-methyl-1H-imidazol-5-yl)ethanone | 62 |

¹H NMR 3.13-3.20 (m, 1H), 3.85-3.89 (m, 1H), 4.0 (s, 3H), 5.79 and 5.89 (two d, 1H, J = 10.4 Hz), 6.96 (t, 1H, J = 8.8 Hz), 7.20 (s, 1H), 7.33-7.38 (m, 2H), 7.62 (s, 1H), 7.74 and 7.81 (two s, 3H)

| # | Compound | Name | Yield (%) |
|---|---|---|---|
| 64 | | 2-(5H-imidazo[5,1-a]isoindol-5-yl)-1-(1-methyl-1H-imidazol-4-yl)ethanone | 24 |

¹H NMR 3.42 (d, 1H, J = 9.9 Hz), 3.48 (d, 1H, J = 8.7 Hz), 3.75 (s, 3H), 5.75 (dd, 1H, J = 3.4 Hz, 9.8 Hz), 7.26-7.19 (m, 1H), 7.14 (s, 1H), 7.35 (m, 2H), 7.41 (d, 1H, J = 1.0 Hz), 7.52 (dd, 1H, J = 1.2 Hz, 7.35 Hz), 7.71 (s, 1H), 7.67 (d, 1H, J = 1.2 Hz),

| 65 | | 2-(5H-imidazo[5,1-a]isoindol-5-yl)-1-(thiazol-5-yl)ethanone | 30 |

¹H NMR 3.40 (dd, 1H, J = 9.6 Hz, 18.4 Hz), 3.71 (dd, 1H, J = 3.2 Hz, 18.0 Hz), 5.80 (dd, 1H, J = 2.8 Hz, 9.2 Hz), 7.21 (s, 1H), 7.29 (d, 1H, J = 7.2 Hz), 7.36-7.41 (m, 2H), 7.57 (d, 1H, J = 8.0 Hz), 8.41 (s, 1H), 7.73 (s, 1H), 9.0 (s, 1H),

| 66 | | 1-(1-acetylpiperidin-4-yl)-2-(5H-imidazo[5,1-a]isoindol-5-yl)ethanone | 74 |

¹H NMR 1.57 (m, 2H), 1.90 (m, 2H), 2.09 (s, 3H), 2.60 (m, 2H), 2.91 (m, 1H), 3.07-3.26 (m, 2H), 3.82 (m, 1H), 4.58 (m, 1H), 5.62 (m, 1H), 7.16 (s, 1H) 7.29 (m, 2H), 7.37 (m, 1H), 7.53 (d, 1H, J = 10.4 Hz), 7.58 (d, 1H, J = 4.8 Hz)

| 67 | | 2-(5H-imidazo[5,1-a]isoindol-5-yl)-1-(1-thiophene-2-carbonyl)piperidin-4-yl)ethanone | |

¹H NMR a

| 68 | | 1-(4-(2-(5H-imidazo[5,1-a]isoindol-5-yl)acetyl)piperidin-1-yl)-2-phenylethanone | 49 |

¹H NMR 1.20-1.90 (m, 4H), 2.40-3.33 (m, 5H), 3.73 (s, 2H), 3.89 (d, 1H, J = 13.5 Hz), 4.59 (d, 1H, J = 13.5 Hz), 5.50-5.70 (m, 1H), 7.15-7.45 (m, 9H), 7.53 (d, 1H, J = 7.5 Hz), 7.68 (d, 1H, J = 7.8 Hz)

-continued

| # | Compound | Name | Yield (%) |
|---|---|---|---|
| 69 | | 1-cyclohexyl-3-(5H-imidazo[5,1-a]isoindol-5-yl)propan-2-one | 82 |

¹H NMR 0.85-1.35 (m, 5H), 1.55-1.175 (m, 5H), 1.80-1.95 (m, 1H), 2.25-2.38 (m, 2H), 2.70-2.80 (m, 1H), 3.16 (dd, 1H, J = 2.4, 14.8 Hz), 5.50-5.60 (m, 1H), 7.16 (s, 1H), 7.20-7.30 (m, 3H), 7.35 (t, 1H, J = 5.4 Hz), 7.41 (d, 1H, J = 5.4 Hz), 7.73 (s, 1H)

| 70 | | 1-cyclohexyl-3-(6-fluoro-5H-imidazo[5,1-a]isoindol-5-yl)propan-2-one | 78 |

¹H NMR 0.80-1.40 (m, 5H), 1.45-2.00 (m, 6H), 2.32 (t, 2H, J = 9.3 Hz), 2.80-2.60 (m, 1H), 3.46 (d, 1H, J = 18.6 Hz), 5.72 (d, 1H, J = 10.5 Hz), 6.92 (t, 1H, J = 9.3 Hz), 7.18 (s, 1H), 7.25-7.40 (m, 2H), 7.71 (s, 1H)

| 71 | | 2-(6-fluoro-5H-imidazo[5,1-a]isoindol-5-yl)-1-(4-hydroxycyclohexyl)ethanone | 89 |

¹H NMR (mixture of cis and trans isomers) 1.25-1.77 (m, 6H), 1.90-2.06 (m, 3H), 2.34-2.42 (m, 1H), 2.80 (dd, 1H, J = 10.8 Hz, 18.8 Hz), 3.51 (d, 1H, J = 18.8 Hz), 3.60-3.62 and 3.97-4.01 (m, 1H), 5.73-5.76 (m, 1H), 6.93 (t, 1H, J = 8.4 Hz), 7.17 (s, 1H), 7.30-7.37 (m, 2H), 7.59 and 7.62 (two s, 1H)

| 72 | | 1-cyclohexyl-2-(5H-imidazo[5,1-a]isoindol-5-yl)ethanone | 86 |

¹H NMR 1.25 (m, 5H), 1.79 (m, 5H), 2.38 (m, 1H), 2.89 (dd, 1H, J = 18.0 Hz, 9.0 Hz), 3.18 (dd, 1H, J = 18 Hz, 3.0 Hz), 5.63 (m, 1H), 7.16 (s, 1H), 7.21-7.28 (m, 2H), 7.37 (t, 1H, J = 7.5 Hz), 7.53 (d, 1H, J = 6 Hz), 7.60 (s, 1H)

a The compound was not characterized and was used as such for the next synthetic step

| 136 | 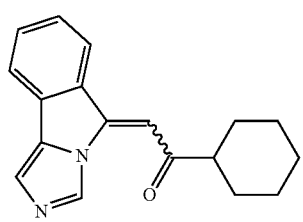 [SMILES: O=C(C=c1c2ccccc2c2cncn12)C1CCCCC1] | 1-cyclohexyl-2-(5H-imidazo[5,1-a]isoindol-5-ylidene)ethanone | 62 |

¹H NMR Indistinguishable mixture of E/Z isomers 1.26-1.48 (m, 8.9H), 1.63-1.94 (m, 13.7H), 2.58-2.62 (m, 0.6H), 3.33-3.38 (m, 1H), 6.40 (s, 0.4H), 6.60 (s, 0.53H), 7.15 (d, 0.8 Hz, J = 6.0 Hz), 7.25-7.28 (m merged with CHCl3, 0.8H), 7.43-7.49 (m, 3H), 7.63-7.67 (m, 2H), 7.74-7.77 (m, 3H), 7.93 (s, 1H), 8.06 (d, 1H, J = 8.0 Hz), 9.25 (s, 0.4H), 9.43 (s, 0.8H)

| # | Compound | Name | Yield (%) |
|---|---|---|---|
| 137 | 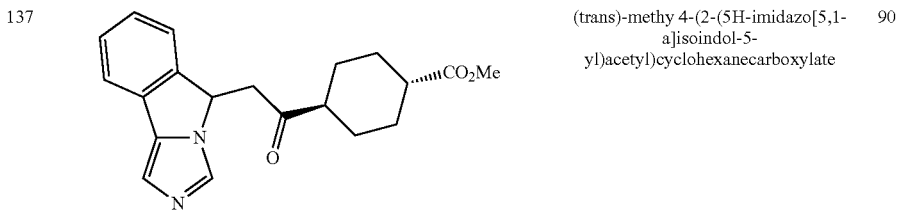 | (trans)-methy 4-(2-(5H-imidazo[5,1-a]isoindol-5-yl)acetyl)cyclohexanecarboxylate | 90 |

$^1$H NMR 1.38-1.49 (m, 4H), 1.95-2.11 (m, 4H), 2.27-2.32 (m, 1H), 2.27-2.42 (m, 1H), 2.91 (dd, J = 9.5, 18.5 Hz, 1H), 3.21 (dd, J = 3.5, 18.5 Hz, 1H), 3.67 (s, 3H), 5.63 (dd, J = 3.3, 9.5 Hz), 7.17 (s, 1H), 7.22-7.29 (m, 2H), 7.38 (t, 1H, J = 7.5 Hz), 7.54 (d, 1H, J = 7.6 Hz), 7.60 (s, 1H)

| # | Compound | Name | Yield (%) |
|---|---|---|---|
| 139 | 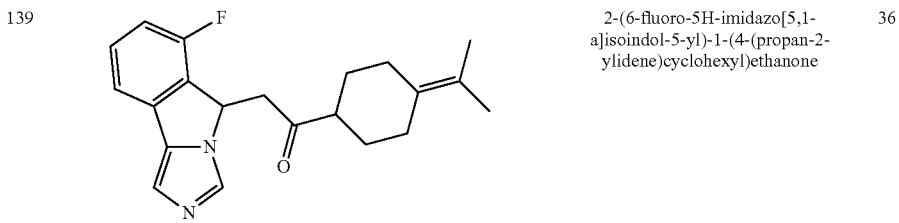 | 2-(6-fluoro-5H-imidazo[5,1-a]isoindol-5-yl)-1-(4-(propan-2-ylidene)cyclohexyl)ethanone | 36 |

$^1$H NMR 1.30-1.52 (m, 2H), 1.64 (s, 6H), 1.70-1.81 (m, 2H), 1.85-1.98 (m, 2H), 2.52-2.62 (m, 1H), 2.68-2.74 (m, 2H), 2.80 (dd, 1H, J = 18.5 Hz, 10.6), 3.50 (dd, 1H, J = 18.5 Hz, 2.2 Hz), 5.75 (d, 1H, J = 9.27 Hz), 6.90-6.96 (m, 1H), 7.17 (s, 1H), 7.32-7.36 (m, 2H), 7.59 (s, 1H)

| # | Compound | Name | Yield (%) |
|---|---|---|---|
| 140 | 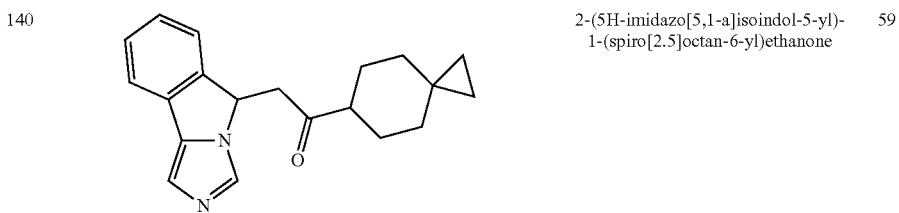 | 2-(5H-imidazo[5,1-a]isoindol-5-yl)-1-(spiro[2.5]octan-6-yl)ethanone | 59 |

$^1$H NMR 0.18-0.30 (m, 4H), 0.90-0.98 (m, 2H), 1.52-1.87 (m, 6H), 2.38-2.53 (m, 1H), 2.91 (dd, 1H, J = 18.4, 9.60 Hz), 3.20 (dd, 1H, J = 18.47, 3.6 Hz), 5.58-5.65 (m, 1H), 7.15 (s, 1H), 7.21-7.27 (m, 2H), 7.36 (t, 1H, J = 7.60 Hz), 7.52 (d, 1H, J = 7.60 Hz), 7.61 (s, 1H)

| # | Compound | Name | Yield (%) |
|---|---|---|---|
| 141 | 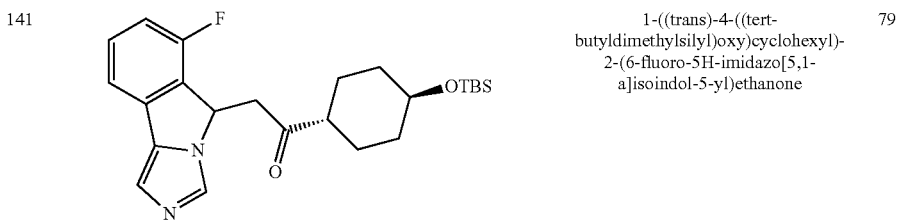 | 1-((trans)-4-((tert-butyldimethylsilyl)oxy)cyclohexyl)-2-(6-fluoro-5H-imidazo[5,1-a]isoindol-5-yl)ethanone | 79 |

$^1$H NMR 0.028 (s, 6H), 0.88 (s, 9H), 11.27-1.96 (m, 8H), 2.32-2.38 (m, 1H), 2.80 (dd, 1H, J = 18.8, 10.6 Hz), 3.48-3.57 (m, 2H), 5.75 (d, J = 9.3 Hz), 6.91-6.95 (m, 1H), 7.17 (s, 1H), 7.23-7.39 (m, 2H), 7.59 and 7.64 (two s, 1H)

| # | Compound | Name | Yield (%) |
|---|---|---|---|
| 142 | | 1-((trans)-4-(benzyloxy)cyclohexyl)-2-(6-fluoro-5H-imidazo[5,1-a]isoindol-5-yl)ethanone | 72 |

¹H NMR 1.15-1.54 (m, 4H), 1.91-2.20 (m, 4H), 2.37-2.43 (m, 1H), 2.80 (dd, 1H, J = 18.5, 10.5 Hz), 3.31-3.36 (m, 1H), 3.51 (d, 1H, J = 18.6 Hz), 4.55 (s, 2H), 5.74 (d, 1H, J = 10.3 Hz), 6.93 (t, 1H, J = 8.0 Hz), 7.17 (s, 1H), 7.29-7.39 (m, 7H), 7.59 and 7.78 (two s, 1H)

| # | Compound | Name | Yield (%) |
|---|---|---|---|
| 143 | | 1-((trans)-4-(benzyloxy)cyclohexyl)-2-(5H-imidazo[5,1-a]isoindol-5-yl)ethanone | 81 |

¹H NMR 1.14-1.50 (m, 4H), 1.92-2.01 (m, 2H), 2.15-2.19 (m, 2H), 2.34-2.43 (m, 1H), 2.90 (dd, 1H, J = 18, 9 Hz), 3.19 (dd, 1H, J = 24, 6 Hz), 3.30-3.37 (m, 1H), 4.49 and 4.55 (two s, 2H), 5.61 (dd, 1H, J = 10.5, 4.5 Hz), 7.16-7.39 (m, 9H), 7.53 (d, 1H, J = 9 Hz), 7.62 (s, 1H)

| # | Compound | Name | Yield (%) |
|---|---|---|---|
| 144 | | N-((cis)-4-(2-(5H-imidazo[5,1-a]isoindol-5-yl)acetyl)cyclohexyl)benzamide | 53 |

¹H NMR 1.25-1.34 (m, 2H), 1.53-1.63 (m, 2H), 1.98-2.08 (m, 2H), 2.20 (t, 2H, J = 11.6 Hz), 2.36 (t, 1H, J = 12.2 Hz), 2.90 (dd, 1H, J = 9.4, 18.6 Hz), 3.25 (dd, 1H, J = 3.2, 18.4 Hz), 3.93-4.00 (m, 1H), 5.63 (dd, 1H, J = 3.2, 9.2 Hz), 6.32 (d, 1H, J = 6.8 Hz), 7.19 (s, 1H), 7.26-7.35 (m, 2H, merged with chloroform), 7.38-7.43 (m, 3H), 7.48 (d, 1H, J = 7.2 Hz), 7.55 (d, 1H, J = 7.6 Hz), 7.71 (s, 1H), 7.76 (d, 2H, J = 7.6 Hz)

| # | Compound | Name | Yield (%) |
|---|---|---|---|
| 145 | | N-((trans)-4-(2-(5H-imidazo[5,1-a]isoindol-5-yl)acetyl)cyclohexyl)benzamide | 69 |

¹H NMR 1.19-1.36 (m, 2H), 1.48-1.65 (m, 2H), 1.93-2.07 (m, 2H), 2.18-2.23 (m, 2H), 2.35 (tt, 1H, J = 3.2, 12.2 Hz), 2.90 (dd, 1H, J = 9.5, 18.4 Hz), 3.22 (dd, 1H, J = 3.6, 18.4 Hz), 3.92-3.99 (m, 1H), 5.62 (dd, 1H, J = 3.4, 9.4 Hz), 6.23 (d, 1H, J = 7.6 Hz), 7.23-7.32 (m, 3H, merged with chloroform), 7.34-7.42 (m, 3H), 7.46-7.50 (m, 1H), 7.54 (d, 1H, J = 7.6 Hz), 7.63 (s, 1H), 7.76 (d, 2H, J = 7.6 Hz)

| # | Compound | Name | Yield (%) |
|---|----------|------|-----------|
| 146 | | 1-(4-(2-hydroxyethylidene)cyclohexyl)-2-(5H-imidazo[5,1-a]isoindol-5-yl)ethanone | 85 |

¹H NMR 1.26-1.50_(m, 2H), 1.70-2.30 (m, 4H), 2.31-2.40 (m, 1H), 2.41-2.75 (m, 2H), 2.76-2.90 (m, 1H), 3.15-3.25 (m, 1H), 4.08-4.13 (m, 1H), 5.25-5.40 (m, 1H), 5.51-5.60 (m, 1H), 7.12 (s, 1H), 7.13-7.40 (m, 2H), 7.48-7.60 (m, 3H)

| # | Compound | Name | Yield (%) |
|---|----------|------|-----------|
| 147 | | tert-butyl 3-(2-(5H-imidazo[5,1-a]isoindol-5-yl)acetyl)azetidine-1-carboxylate | 77 |

¹H NMR 1.38 (s, 9H), 2.85-2.92 (m, 1H), 3.20-3.25 (m, 1H), 3.44-3.48 (m, 1H), 3.65-3.70 (m, 2H), 4.01-4.28 (m, 2H), 5.63-5.66 (m, 1H), 7.16 (s, 1H), 7.21-7.31 (m, 2H), 7.36-7.40 (m, 1H), 7.53-7.55 (m, 1H), 7.66 (s, 1H)

| # | Compound | Name | Yield (%) |
|---|----------|------|-----------|
| 148 | | 2-(5H-imidazo[5,1-a]isoindol-5-yl)-1-(pyridin-2-yl)ethanone | 75 |

¹H NMR 3.60 (dd, J = 10, 19.2 Hz, 1H), 3.91 (dd, J = 3.2, 19.2 Hz, 1H), 5.65 (dd, J = 3.2, 10 Hz, 1H), 7.08 (s, 1H), 7.13-7.17 (m, 1H), 7.25-7.30 (m, 2H), 7.38-7.45 (m, 2H), 7.66 (s, 1H), 7.78-7.80 (m, 1H), 8.05 (d, J = 8 Hz, 1H), 8.51-8.53 (m, 1H)

| # | Compound | Name | Yield (%) |
|---|----------|------|-----------|
| 149 | | 2-(5H-imidazo[5,1-a]isoindol-5-yl)-1-(pyridin-3-yl)ethanone | 89 |

¹H NMR 3.57-3.67 (m, 1H), 3.80-3.95 (m, 1H), 6.01-6.05 (m, 1H), 7.27-7.73 (m, 6H), 8.29-8.36 (m, 1H), 8.61 (s, 1H), 8.86 (d, J = 3 Hz, 1H), 9.18 (s, 1H)

| # | Compound | Name | Yield (%) |
|---|----------|------|-----------|
| 150 | | 2-(5H-imidazo[5,1-a]isoindol-5-yl)-1-(pyridin-4-yl)ethanone | 21 |

¹H NMR 3.42-3.49 (dd, J = 9.2, 18.8 Hz, 1H), 3.76 (dd, J = 3.6, 18.8 Hz, 1H), 5.83 (dd, J = 3.2, 9.2 Hz, 1H), 7.20 (s, 1H), 7.28-7.32 (m, 1H), 7.38-7.45 (m, 2H), 7.58-7.60 (m, 1H), 7.74-7.75 (m, 2H), 7.81 (s, 1H), 8.84-8.86 (m, 2H)

-continued

| # | Compound | Name | Yield (%) |
|---|---|---|---|
| 151 | | 2-(5H-imidazo[5,1-a]isoindol-5-yl)-1-(4-(trifluoromethyl)cyclohexyl)ethanone | 50 |
| | ¹H NMR 1.55-1.81 (m, 5H), 2.08-2.29 (m, 4H), 2.58-2.62 (m, 1H), 2.94 (dd, J = 9, 18 Hz, 1H), 3.22 (dd, J = 6, 18 Hz, 1H), 5.68 (dd, J = 6, 9 Hz, 1H), 7.18-7.57 (m, 5H), 7.81 and 7.83 (two s, 1H) | | |
| 152 | | 2-(6-fluoro-5H-imidazo[5,1-a]isoindol-5-yl)-1-(4-(trifluoromethyl)cyclohexyl)ethanone | 53 |
| | ¹H NMR 1.51-1.83 (m, 6H), 1.95-2.21 (m, 3H), 2.58-2.62 (m, 1H), 2.79 (dd, J = 9, 18 Hz, 1H), 3.46-3.55 (m, 1H), 5.73-5.79 (m, 1H), 6.89-6.98 (m, 1H), 7.20-7.38 (m, 4H), 7.71 (s, 1H) | | |
| 153 | | 1-((cis)-4-(benzyloxy)cyclohexyl)-2-(6-fluoro-5H-imidazo[5,1-a]isoindol-5-yl)ethanone | 77 |
| | ¹H NMR 1.67-2.04 (m, 8H), 2.39-2.45 (m, 1H), 2.79 (dd, 1H, J = 18.6, 10.6 Hz), 3.50 (dd, 1H, J = 16.4, 2.4 Hz), 3.60-3.65 (m, 1H), 4.49 and 4.55 (two s, 1H), 5.76 (d, 1H, J = 8.8 Hz), 6.91-6.95 (m, 1H), 7.17 (s, 1H), 7.26-7.35 (m, 7H), 7.63 (s, 1H) | | |

Example 24

1-(Cyclohex-3-enyl)-2-(6-fluoro-5H-imidazo[5,1-a]isoindol-5-yl)ethanone

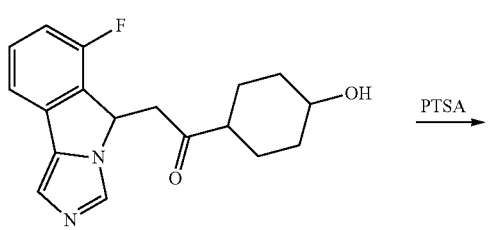

71

-continued

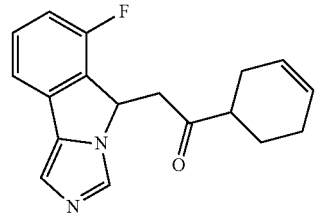 [SMILES: OC(CC1c2c(F)cccc2-c2cncn21)C1CC=CCC1]

155

71 (270 mg, 0.86 mmol) was dissolved in benzene (7 mL) and p-toluenesulfonic acid (444 mg, 2.58 mmol) was added. The reaction mixture was heated at 100° C. for 48 h and concentrated. The residue was basified with aqueous potassium carbonate solution (5 mL). The aqueous solution was extracted with ethyl acetate (2×20 mL). The combined organic layers were washed with water, brine, dried over $Na_2SO_4$, filtered and concentrated. The residue was purified by flash column chromatography to afford the title compound 155 as yellow gel (218 mg, 86%). $^1$H NMR: 1.35-1.71 (m, 1H), 1.88-2.40 (m, 5H), 2.62-2.67 (m, 1H), 2.74-2.87 (m, 1H), 3.47-3.58 (m, 1H), 5.66-5.75 (m, 3H), 6.91 (t, 1H, J=8.9 Hz), 7.15 (s, 1H), 7.26-7.35 (m, 2H), 7.62 (d, 1H, J=9.8 Hz).

Example 25

General Procedure for the Reduction of 2-(5H-imidazo[5,1-a]isoindol-5-yl)ethanones to 2-(5H-imidazo[5,1-a]isoindol-5-yl)ethanols

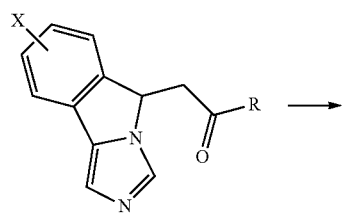

→

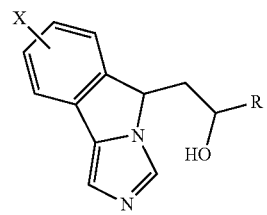

To a solution of the appropriate ketone (9-18, 47-72, 136-153, 155, 1256, 1287, 1300, 1306, 1326, 1328, 1334, 1348 or 1353) (0.25 mmol) in MeOH (2 mL) at 0° C., was added $NaBH_4$ (0.75 mmol) and the solution was allowed to stir for 1 h. The solvent was removed under reduced pressure and 2M HCl (2 mL) was added to the crude. The solution was allowed to stir for 10 min and was made basic by satd. $K_2CO_3$ solution. The aqueous layer was extracted with $CH_2Cl_2$ (3×5 mL). The combined organic layers were washed with brine, dried (MgSO4) and concentrated under reduced pressure to afford the crude residue. The crude was purified by column chromatography using 1-10% MeOH:DCM gradient to afford the following compounds.

| # | Compound | Name | Yield (%) |
|---|----------|------|-----------|
| 1286 | 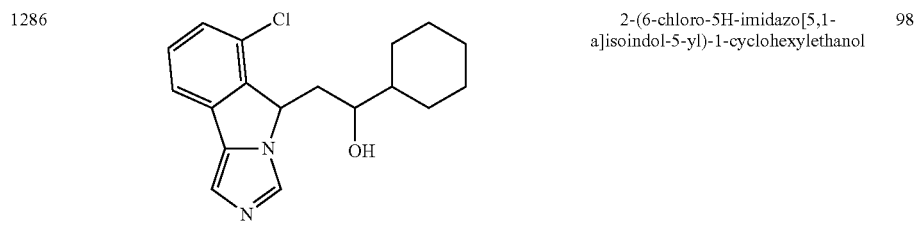 | 2-(6-chloro-5H-imidazo[5,1-a]isoindol-5-yl)-1-cyclohexylethanol | 98 |

$^1$H NMR (a mixture of diastereomers) 0.96-1.35 (m, 6H), 1.60-1.86 (m, 5H), 2.10 (m, 1H), 2.52-2.69 (m, 1H), 3.58-3.69 (m, 1H), 5.31 and 5.59 (two dd, 1H, J = 6.0 Hz, 2.80 Hz, $J_2$ = 10.4 Hz, 2.80 Hz), 7.16-7.19 (m, 2H), 7.28 (m, 1H), 7.41 (t, 1H, J = 5.4 Hz), 7.82 and 7.94 (two s, 1H)

| 1304 | 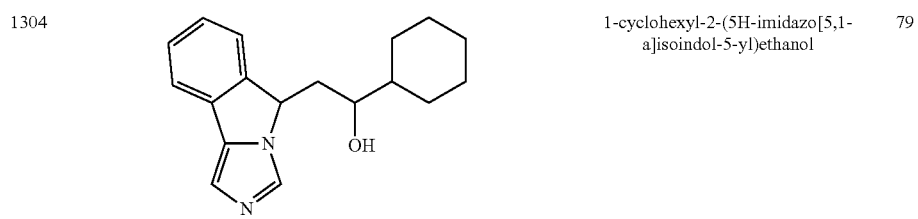 | 1-cyclohexyl-2-(5H-imidazo[5,1-a]isoindol-5-yl)ethanol | 79 |

$^1$H NMR (a mixture of diastereomers) 1.10-1.37 (m, 6H), 1.66-1.80 (m, 5H), 2.05 (m, 2H), 2.15 (m, 1H), 3.72 (m, 1H), 5.36 and 5.46 (two m, 1H), 7.16 (s, 1H), 7.25 (m, 1H), 7.34 (m, 1H), 7.43 (d, 1H, J = 7.6 Hz), 7.54 (d, 1H, J = 7.6 Hz), 7.80 (s, 1H)

| # | Compound | Name | Yield (%) |
|---|----------|------|-----------|
| 1327 | | 2-(5H-imidazo[5,1-a]isoindol-5-yl)-1-(2-nitrophenyl)ethanol | 73 |

$^1$H NMR (a mixture of diastereomers) 2.29 (m, 1H), 2.61 (m, 1H), 5.44 (m, 1H), 5.71 (dd, 1H, J = 9.0 Hz, 4.5 Hz), 7.08 (s, 1H), 7.27 (m, 2H), 7.34 (m, 1H), 7.45-7.53 (m, 3H), 7.68 (m, 1H), 7.95 (m, 2H)

| # | Compound | Name | Yield (%) |
|---|----------|------|-----------|
| 1307 | | 2-(5H-imidazo[5,1-a]isoindol-5-yl)-1-(3-nitrophenyl)ethanol | 39 |

$^1$H NMR (a mixture of diastereomers) 2.32-2.40 (m, 1H), 2.48-2.58 (m, 1H), 5.06-5.11 (m, 1H), 5.41 and 5.61 (two m, 1H), 7.09 (s, 1H), 7.30-7.43 (m, 2H), 7.48-7.57 (m, 3H), 7.64-7.72 (m, 2H), 8.12-8.19 (m, 2H)

| # | Compound | Name | Yield (%) |
|---|----------|------|-----------|
| 1329 | | tert-butyl (2-(1-hydroxy-2-(5H-imidazo[5,1-a]isoindol-5-yl)ethyl)phenyl)carbamate | 50 |

$^1$H NMR (a mixture of diastereomers) 1.50 and 1.55 (two s, 9H), 2.50 and 2.78 (two m, 2H), 5.02 and 5.07 (two m, 1H), 5.19 and 5.56 (two m, 1H), 6.93-7.02 (m, 2H), 7.12 (d, 1H, J = 8.0 Hz), 7.24 (m, 2H), 7.36 (m, 2H), 7.49 (d, 1H, J = 7.6 Hz), 7.71 (br s, 1H), 7.80 and 7.85 (two s, 1H, J = 8.0 Hz), 8.12 and 8.45 (two s, 1H)

| # | Compound | Name | Yield (%) |
|---|----------|------|-----------|
| 1302 | | tert-butyl (4-(1-hydroxy-2-(5H-imidazo[5,1-a]isoindol-5-yl)ethyl)phenyl)carbamate | 81 |

$^1$H NMR (a mixture of diastereomers) 1.50 (s, 9H), 2.28-2.41 (m, 2H), 4.98-5.03 (m, 1H), 5.25 and 5.55 (two m, 1H), 6.55 and 6.61 (two s, 1H), 7.12-7.54 (m, 7H), 7.66 and 7.78 (two s, 1H)

| # | Compound | Name | Yield (%) |
|---|----------|------|-----------|
| 1367 | | tert-butyl (3-(1-hydroxy-2-(5H-imidazo[5,1-a]isoindol-5-yl)ethyl)phenyl)carbamate | 52 |

$^1$H NMR (a mixture of diastereomers) (MeOH-d$_4$) 1.51 (s, 9H), 2.33-2.57 (m, 2H), 4.93-4.96 (m, 1H), 5.36 and 5.49 (two m, 1H), 7.00-7.06 (m, 2H), 7.19-7.40 (m, 4H), 7.48 (s, 1H), 7.53-7.57 (m, 2H), 7.72 (s, 1H)

| # | Compound | Name | Yield (%) |
|---|---|---|---|
| 1349 | | 2-(5H-imidazo[5,1-a]isoindol-5-yl)-1-phenylethanol | 73 |

¹H NMR (a mixture of diastereomers) 2.30 (m, 1H), 2.41 (m, 1H), 5.08 (m, 1H), 5.31 (m, 1H), 7.08 (m, 1H), 7.20-7.51 (m, 9H), 7.63 (s, 1H).

| 1363 | | tert-butyl 4-(1-hydroxy-2-(5H-imidazo[5,1-a]isoindol-5-yl)ethyl)piperidine-1-carboxylate | 83 |

¹H NMR (a mixture of diastereomers) 1.26 (m, 2H), 1.44 (s, 9H), 1.47-1.59 (m, 2H), 1.76 (m, 1H), 206-2.11 (m, 1H), 2.14-2.20 (m, 1H), 2.64 (m, 2H), 3.73 and 3.80 (two m, 1H), 4.16 (m, 2H), 5.37 and 5.51 (two m, 1H), 7.16 (s, 1H), 7.22 (m, 1H), 7.32-7.41 (m, 2H), 7.54 (d, 1H, J = 4.0 Hz), 7.79 and 7.81 (two s, 1H)

| 1357 | | 1-cyclohexyl-2-(6-fluoro-5H-imidazo[5,1-a]isoindol-5-yl)ethanol | 96 |

¹H NMR (a mixture of diastereomers) 0.98-1.39 (m, 6H), 1.65-1.79 (m, 5H), 2.03-2.07 (m, 1H) 2.34-2.50 (m, 2H), 3.54-3.73 (m, 1H), 5.46 and 5.67 (two dd, 1H, $J_1$ = , 3.0, 8.0 Hz, $J_2$ = 3.0, 10.4 Hz), 6.93 (t, 1H, J = 8.0 Hz), 7.17 (d, 1H, J = 7.17 Hz), 7.30-7.37 (m, 2H), 7.82, 7.88 (two s, 1H)

| 1359 | | 2-(7-chloro-5H-imidazo[5,1-a]isoindol-5-yl)-1-cyclohexylethanol | 98 |

¹H NMR (a mixture of diastereomers) 1.00-1.28 (m, 5H), 1.37-1.40 (m, 1H), 1.66-2.01 (m, 5H), 1.91-2.0 (m, 1H) 2.12-2.23 (m, 1H), 3.71-3.75 (m, 1H), 7.15 (s, 1H), 7.33 (d, 1H, J = 8.0 Hz), 7.45 (d, 1H, J = 8.0 Hz), 7.79, 7.82 (two s, 1H)

-continued

| # | Compound | Name | Yield (%) |
|---|---|---|---|
| 1362 | | 1-cyclopentyl-2-(5H-imidazo[5,1-a]isoindol-5-yl)ethanol | 91 |
| | $^1$H NMR (a mixture of diastereomers) 1.11-1.41 (m, 2H), 1.55-1.70 (m, 4H), 1.83-2.17 (m, 4H), 3.74-3.79 (m, 1H), 5.38, 5.49 (one t and one d, 1H, J = 6.0 Hz, J$_2$ = 6.0 Hz), 7.18 (s, 1H), 7.25 (d merged with CHCl$_3$, 1H), 7.38 (t, 1H, J = 7.2 Hz), 7.46 (d, 1H, J = 7.6 Hz), 7.55 (d, 1H, J = 7.6 Hz), 7.84 (s, 1H) | | |
| 1375 | | 1-(cyclohex-1-en-1-yl)-2-(5H-imidazo[5,1-a]isoindol-5-yl)ethanol | 92 |
| | $^1$H NMR (a mixture of diastereomers) 1.47-1.68 (m, 3H), 1.73-1.82 (m, 1H), 1.93-2.14 (m, 4H), 2.18-2.22 (m, 1H), 2.33-2.40 (m, 2H), 4.36 (t, 1H, J = 7.0 Hz), 5.26, 5.44 (one t and one dd, 1H, J$_1$ = 6.0 Hz, J$_2$ = 10.0 Hz), 5.71, 5.72 (two s, 1H), 7.15, 7.18 (two, s, 1H), 7.2-7.26 (m, 1H), 7.34, 7.38 (two d, 1H, J$_1$ = 6.8 Hz, J$_2$ = 7.27 Hz), 7.43 (d, 1H, J = 7.6 Hz), 7.54 (d, 1H, J = 7.6 Hz), 7.81, 7.86 (two s, 1H) | | |
| 1343 | | 1-(3-chlorophenyl)-2-(5H-imidazo[5,1-a]isoindol-5-yl)ethanol | 59 |
| | $^1$H NMR (a mixture of diastereomers) 2.18-2.52 (m, 2H), 5.25-5.40 (m, 1H), 5.46-5.60 (m, 1H), 7.07 (s, 1H), 7.15-7.55 (m, 7H), 7.69 (d, 1H, J = 8.0 Hz), 7.79 (s, 1H) | | |
| 1336 | | 1-(2-chlorophenyl)-2-(5H-imidazo[5,1-a]isoindol-5-yl)ethanol | 45 |
| | $^1$H NMR (a mixture of diastereomers) 2.20-2.50 (m, 2H), 5.0-5.08 (m, 1H), 5.26-5.38 (m, 1H), 7.05 (s, 1H), 7.20-7.45 (m, 7H), 7.45 (d, 1H, J = 7.6 Hz), 7.52 (d, 1H, J = 7.6 Hz) 7.68 (s, 1H) | | |
| 1374 | | 2-(8-chloro-5H-imidazo[5,1-a]isoindol-5-yl)-1-cyclohexylethanol | 41 |
| | $^1$H NMR (a mixture of diastereomers) (MeOH-d$_4$) 1.00-2.30 (m, 13H), 3.60-3.70 (m, 1H), 5.35 and 5.50 (two m, 1H), 6.95-7.08 (m, 1H), 7.16-7.88 (m, 4H) | | |

| # | Compound | Name | Yield (%) |
|---|---|---|---|
| 1376 | | 1-cyclohexyl-2-(8-fluoro-5H-imidazo[5,1-a]isoindol-5-yl)ethanol | 15 |

¹H NMR (a mixture of diastereomers) (MeOH-$d_4$) 1.00-2.30 (m, 13H), 3.50-3.57 (m, 1H), 5.35 and 5.50 (m, 1H), 7.18-7.50 (m, 3H), 7.60-7.65 (m, 1H), 7.92 and 7.98 (two s, 1H)

| # | Compound | Name | Yield (%) |
|---|---|---|---|
| 1378 | | 2-(6-fluoro-5H-imidazo[5,1-a]isoindol-5-yl)-1-(1,4-dioxaspiro[4.5]decan-8-yl)ethanol | 90 |

¹H NMR (a mixture of diastereomers) (MeOH-$d_4$) 1.31-1.52 (m, 5H), 1.60-1.63 (m, 1H), 1.71-1.78 (m, 3H), 1.86-2.07 (m, 1H), 2.43-2.48 (m, 1H), 3.48-3.64 (m, 1H), 3.90 (s, 4H) 5.57 and 5.69 (two m, 1H), 7.00-7.06 (m, 1H), 7.18 (d, 1H, J = 11.6 Hz), 7.41-7.44 (m, 2H), 7.94-8.00 (m, 2H)

| # | Compound | Name | Yield (%) |
|---|---|---|---|
| 1358 | | 2-(5H-imidazo[5,1-a]isoindol-5-yl)-1-(tetrahydro-2H-pyran-4-yl)ethanol | 92 |

¹H NMR (a mixture of diastereomers) 1.39-1.51 (m, 2H), 1.59-1.65 (m, 1H), 1.71-1.75 (m, 1H), 2.11-2.17 (m, 1H), 3.32-3.39 (m, 3H), 3.69-3.73 (m, 1H), 3.96-4.05 (m, 3H), 5.39 and 5.49 (two m, 1H), 7.17 (s, 1H), 7.23-7.28 (m, 1H), 7.33-7.44 (m, 2H), 7.55 (d, 1H, J = 8 Hz), 7.84 (s, 1H)

| # | Compound | Name | Yield (%) |
|---|---|---|---|
| 1372 | | 1-cyclohexyl-2-(9-methoxy-5H-imidazo[5,1-a]isoindol-5-yl)ethanol | 83 |

¹H NMR (a mixture of diastereomers) (CD$_3$OD) 1.05-1.11 (m, 1H), 1.13-1.33 (m, 4H), 1.58-1.81 (m, 5H), 2.01-2.08 (m, 1H), 3.57 and 3.67 (two m, 1H), 3.95 (s, 3H), 5.40 and 5.47 (two m, 1H), 6.81 and 6.83 (two d, 1H, J = 8 Hz), 6.90 and 6.97 (two d, 1H, J = 7.6 Hz), 7.04 and 7.05 (two s, 1H), 7.12-7.17 (m, 1H), 7.92 and 7.99 (two s, 1H).

| # | Compound | Name | Yield (%) |
|---|---|---|---|
| 1352 | 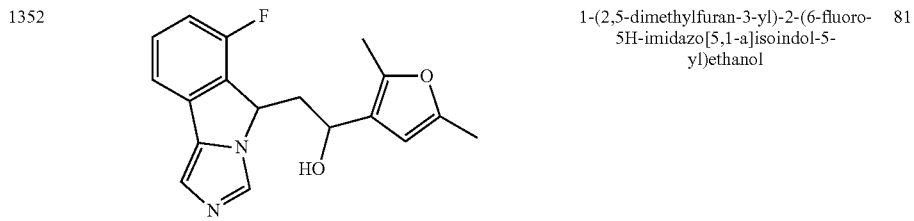 | 1-(2,5-dimethylfuran-3-yl)-2-(6-fluoro-5H-imidazo[5,1-a]isoindol-5-yl)ethanol | 81 |

¹H NMR (a mixture of diastereomers) 1.89-1.96, 2.37-2.45, 2.53-2.59, 2.77-2.83 (four m, 2H), 2.11, 2.17 (s, 3H), 2.20, 2.22 (two s, 3H), 4.79-4.88 (m, 1H), 5.36-5.68, 5.63-5.64 (two m, 1H), 5.94, 5.97 (two s, 1H), 6.87-6.97 (m, 1H), 7.15, 7.21 (two s, 1H), 7.32-7.38 (m, 2H), 7.74, 7.88 (two s, 1H)

| 1393 | 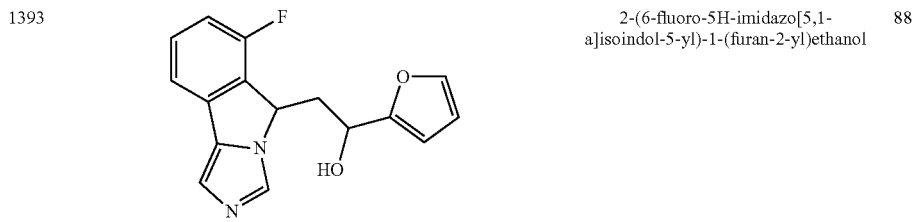 | 2-(6-fluoro-5H-imidazo[5,1-a]isoindol-5-yl)-1-(furan-2-yl)ethanol | 88 |

¹H NMR (a mixture of diastereomers) 1.99-2.06, 2.36-2.43 (two m, 1H), 2.77-2.80, 2.92-2.98 (two m, 1H), 3.72 (d, 1H, J = 11.0 Hz), 5.02-5.08 (m, 1H), 5.39-5.40, 5.67-5.69 (two m, 1H), 6.27 (t, 1H, J = 6.4 Hz), 6.31 (s, 1H), 6.93 (s, 1H, J = 9.2 Hz), 7.08 (d, 1H, J = 12.2 Hz), 7.26-7.36 (m, 2H), 7.77, 7.86 (two s, 1H)

| 1394 | 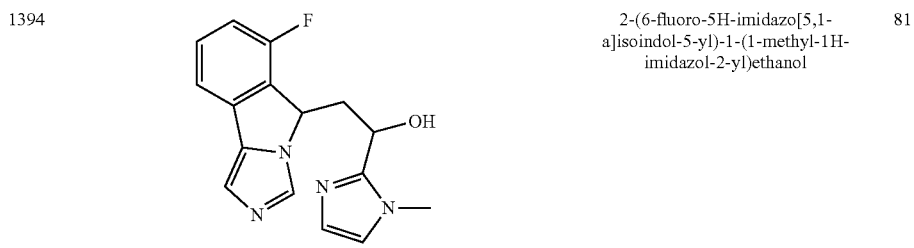 | 2-(6-fluoro-5H-imidazo[5,1-a]isoindol-5-yl)-1-(1-methyl-1H-imidazol-2-yl)ethanol | 81 |

¹H NMR (a mixture of diastereomers) 2.43-2.51, 2.81-2.85, 2.99-3.15 (three m, 2H), 3.69 (s, 3H), 5.00-5.08 (m, 1H), 5.38-5.40, 5.67-5.69 (two m, 1H), 6.77 (s, 1H), 6.79 (s, 1H), 6.91 (t, 1H, J = 8.9 Hz), 7.07 (s, 1H), 7.28-7.33 (m, 2H), 7.79 (s, 1H)

| 1390 | 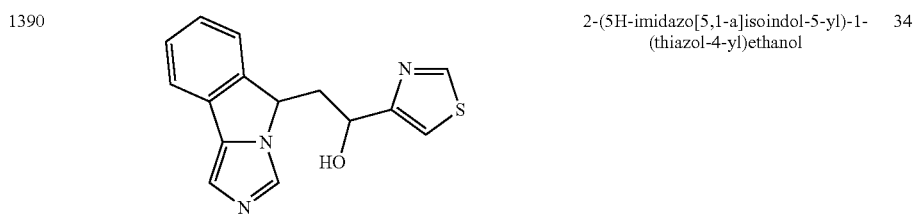 | 2-(5H-imidazo[5,1-a]isoindol-5-yl)-1-(thiazol-4-yl)ethanol | 34 |

¹H NMR (a mixture of diastereomers) 2.14-2.21, 2.49-2.58, 2.68-2.82 (m, 2H), 5.23-5.53 (m, 2H), 7.11 (s, 1H), 7.21 (s, 1H), 7.25-7.28 (m, 1H, overlap with CHCl3), 7.37 (t, 1H, J = 7.5 Hz), 7.47-7.54 (m, 2H), 7.74 (s, 1H), 8.79 (s, 1H)

-continued

| # | Compound | Name | Yield (%) |
|---|---|---|---|
| 1407 | | 1-(4,4-difluorocyclohexyl)-2-(5H-imidazo[5,1-a]isoindol-5-yl)ethanol | 61 |

¹H NMR (a mixture of diastereomers) 1.26-1.36 (m, 3H), 1.63-1.97 (m, 5H), 2.02-2.08 (m, 3H), 3.69-3.72 (m, 1H), 5.02 and 5.12 (two d, 1H, J = 6.0 Hz), 5.34-5.53 and 5.41-5.43 (two m, 1H), 7.10 and 7.12 (two s, 1H), 7.25 (t, 1H, J = 7.4 Hz), 7.36 (t, 1H, J = 7.4 Hz), 7.54-7.58 (m, 2H), 7.91 and 7.93 (two s, 1H

| 1406 | | 1-(4,4-difluorocyclohexyl)-2-(6-fluoro-5H-imidazo[5,1-a]isoindol-5-yl)ethanol | 78 |

¹H NMR (a mixture of diastereomers) (DMSO-$d_6$): 1.21-1.29 (m, 3H), 1.56-1.72 (m, 4H) 1.88-1.96 (m, 3H), 2.28 and 2.32 (two t, 1H, J = 5 Hz), 3.41-3.44 and 3.62-3.65 (two m, 1H), 4.73 and 5.17 (two d, 1H, J = 8.2 Hz), 5.56-5.59 and 5.61-5.64 (two m, 1H), 7.03-7.17 (m, 2H), 7.39-7.44 (m, 2H), 7.91 and 7.95 (two s, 1H)

| 1414 | | 1-(cyclohex-3-enyl)-2-(6-fluoro-5H-imidazo[5,1-a]isoindol-5-yl)ethanol | 74 |

¹H NMR (a mixture of diastereomers) 1.21-1.42 (m, 2H), 1.62-1.83 (m, 4H), 1.93-2.15 (m, 7H), 2.30-2.44 (m, 1H), 2.6 (brs, 1H), 3.67-3.72 (m, 1H), 3.77-3.82 (m, 1H), 5.49 (q, 1H, J = 5.3 Hz), 5.64-5.70 (m, 3H), 6.92-6.96 (m, 2H), 7.16-7.19 (m, 2H), 7.31-7.38 (m, 3H), 7.77-7.79 (m, 1H), 7.88 (d, 1H, J = 3.6 Hz), 7.91 (s, 1H)

| 1386 | | 2-(5H-imidazo[5,1-a]isoindol-5-yl)-1-(4-methylenecyclohexyl)ethanol | 70 |

¹H NMR (a mixture of diastereomers) 1.11-1.20 (m, 2H), 1.49-1.55 (m, 1H), 1.74-1.78 (m, 1H), 1.90-2.10 (m, 4H), 2.16-2.23 (m, 1H), 2.31-2.38 (m, 2H), 3.74-3.77 and 3.80-3.85 (two m, 1H), 4.62 (d, 2H, J = 0.8 Hz), 5.37 and 5.48 (t and dd, 1H, J = 6 Hz and J = 3 Hz, 10.4 Hz), 7.18 (s, 1H), 7.23 (dd, 1H, J = 1.2 Hz, 7.6 Hz), 7.37 (t, 1H, J = 7.6 Hz), 7.43 (d, 1H, J = 7.6 Hz), 7.55 (d, 1H, J = 7.6 Hz), 7.77 and 7.79 (two s, 1H)

| # | Compound | Name | Yield (%) |
|---|---|---|---|
| 1381 | | 2-(6-fluoro-5H-imidazo[5,1-a]isoindol-5-yl)-1-(1,4-dioxaspiro[4.5]decan-8-yl)ethanol | 90 |

$^1$H NMR (a mixture of diastereomers) (CD$_3$OD) 1.20-2.00 (m, 2H), 1.38-1.60 (m, 1H), 1.70-1.80 (m, 1H), 1.87-2.09 (m, 6H), 3.30-3.34 and 3.53-3.78 (two m, 1H), 5.56-5.58 and 5.69-5.71 (two m, 1H), 7.00-7.04 (m, 1H), 7.42 and 7.62 (m and s, 2H), 7.93 and 8.00 (two s, 1H)

| # | Compound | Name | Yield (%) |
|---|---|---|---|
| 1387 | | 2-(6-fluoro-5H-imidazo[5,1-a]isoindol-5-yl)-1-(4-methylcyclohexyl)ethanol | 68 |

$^1$H NMR (a mixture of diastereomers) 0.81-0.95 (m, 3H), 1.20-1.83 (m, 10H), 1.85-2.03 (m, 1H), 2.35-2.52 (m, 1H), 3.45-3.80 (m, 1H), 5.50-5.60 and 5.65-5.71 (two m, 1H), 6.98-7.06 (m, 1H), 7.14 and 7.18 (two s, 1H), 7.30-7.42 (m, 2H), 7.93 and 7.98 (two s, 1H)

| # | Compound | Name | Yield (%) |
|---|---|---|---|
| 1398 | | 2-(6-fluoro-5H-imidazo[5,1-a]isoindol-5-yl)-1-(4-(iodomethylene)cyclohexyl)ethanol | 77 |

$^1$H NMR (a mixture of diastereomers) 0.92-1.45 (m, 2H), 1.54-1.76 (m, 2H), 1.80-2.11 (m, 3H), 2.33-3.10 (m, 4H), 3.59-3.90 (m, 1H), 4.60 (s, 1H), 5.45-5.81 (m, 1H), 6.91-6.95 (m, 1H), 7.16 (s, 1H), 7.26-7.31 (m, 2H), 7.81-7.83 (m, 1H)

| # | Compound | Name | Yield (%) |
|---|---|---|---|
| 1413 | | 2-(9-fluoro-5H-imidazo[5,1-a]isoindol-5-yl)-1-(4-methylcyclohexyl)ethanol | 35 |

$^1$H NMR (a mixture of diastereomers) (CD$_3$OD) 0.75-0.96 (m, 3H), 1.00-1.25 (m, 1H), 1.28-1.74 (m, 9H), 2.01-2.14 (m, 2H), 3.67-3.80 (m, 1H), 5.49-5.59 (m, 1H), 7.10-7.18 (m, 2H), 7.60-8.00 (m, 1H)

| # | Compound | Name | Yield (%) |
|---|---|---|---|
| 1411 | | 2-(6-fluoro-5H-imidazo[5,1-a]isoindol-5-yl)-1-(4-(propan-2-ylidene)cyclohexyl)ethanol | 77 |

$^1$H NMR (a mixture of diastereomers) 1.01-1.06 (m, 2H), 1.46-1.57 (m, 2H), 1.63 (s, 6H), 1.68-1.75 (m, 2H), 1.82-1.96 (two m, 1H), 2.03-2.11 (m, 1H), 2.32-2.39 (two m, 1H), 2.45-2.51 and 2.66-2.75 (two m, 2H), 3.65-3.75 (m, 1H), 5.44-5.65 (two m, 1H), 6.91 (t, 1H, J = 8.7 Hz), 7.16 and 7.17 (two s, 1H), 7.28-7.36 (m, 2H), 7.80 and 7.87 (two s, 1H)

| # | Compound | Name | Yield (%) |
|---|---|---|---|
| 1410 | | 1-(4-(cyclopropylmethylene)cyclohexyl)-2-(6-fluoro-5H-imidazo[5,1-a]isoindol-5-yl)ethanol | 75 |

$^1$H NMR (a mixture of diastereomers) 0.24 (s, 2H), 0.65 (d, 2H, J = 7.4 Hz), 1.12-1.20 (m, 2H), 1.44-1.54 (m, 2H), 1.71-2.03 (m, 6H), 2.34-2.54 (two m, 1H), 2.72-2.84 (m, 1H), 3.63-3.80 (m, 1H), 4.48 (d, 1H, J = 9.0 Hz), 5.43-5.67 (two m, 1H), 6.81-6.94 (m, 1H), 7.15 (s, 1H), 7.15-7.30 (m, 3H), 7.80 and 7.88 (two s, 1H)

| # | Compound | Name | Yield (%) |
|---|---|---|---|
| 1392 | | 1-(4-(1-hydroxy-2-(5H-imidazo[5,1-a]isoindol-5-yl)ethyl)piperidin-1-yl)-2,2-dimethylpropan-1-one | 77 |

$^1$H NMR (a mixture of diastereomers) 1.24 (s, 9H), 1.28 (m, 2H), 1.60 (m, 2H), 2.13-1.86 (m, 3H), 2.70 (m, 2H), 3.78 (m, 1H), 4.46 (m, 2H), 5.53 and 5.38 (two m, 1H), 7.12 (s, 1H), 7.21 (m, 1H), 7.33 (m, 1H), 7.42 (d, 1H, J = 7.5 Hz), 7.52 (d, 1H, J = 7.5 Hz), 7.81 and 7.79 (two s, 1H),

| # | Compound | Name | Yield (%) |
|---|---|---|---|
| 1409 | | 2-(6-fluoro-5H-imidazo[5,1-a]isoindol-5-yl)-1-(1-methyl-1H-imidazol-5-yl)ethanol | 44 |

$^1$H NMR (a mixture of diastereomers) 1.92-2.42 (three m, 1H), 2.72-3.10 (three m, 1H), 3.72 (s, 3H), 4.90-5.10 (three m, 1H), 5.42-5.76 (three m, 1H), 6.77-6.92 (m, 2H), 7.07 and 7.13 (two s, 1H), 7.25-7.37 (m, 3H), 7.82, 7.88 and 7.94 (three s, 1H)

| # | Compound | Name | Yield (%) |
| --- | --- | --- | --- |
| 1389 | | 2-(5H-imidazo[5,1-a]isoindol-5-yl)-1-(1-methyl-1H-imidazol-4-yl)ethanol | 94 |

$^1$H NMR (a mixture of diastereomers) 2.01, 2.51, 2.67 (three m, 2H), 3.61 (s, 3H), 5.09 and 5.00 (two m, 1H), 5.53 and 5.33 (two m, 1H), 6.75 and 6.70 (two s, 1H), 7.11 (s, 1H), 7.25-7.16 (m, 2H), 7.32 (m, 1H), 7.37 (s, 1H), 7.49 (t, 1H, J = 7.80 Hz), 7.88 and 7.67 (two s, 1H),

| # | Compound | Name | Yield (%) |
| --- | --- | --- | --- |
| 1391 | | 2-(5H-imidazo[5,1-a]isoindol-5-yl)-1-(thiazol-5-yl)ethanol | 75 |

$^1$H NMR (a mixture of diastereomers) 1.84, 2.03, 2.45, 2.51, 2.66, (five m, 2H), 5.29 5.41, 5.55 (three m, 2H), 7.06-7.28 (m, 2H), 7.37 (t, 1H, J = 7.5 Hz), 7.41 (d, 1H, J = 7.5 Hz), 7.52 (d, 1H, J = 7.5 Hz), 7.71, 7.73 (two s, 1H), 7.83 (s, 1H), 8.70, 8.71 (two s, 1H),

| # | Compound | Name | Yield (%) |
| --- | --- | --- | --- |
| 1385 | | 1-(4-(1-hydroxy-2-(5H-imidazo[5,1-a]isoindol-5-yl)ethyl)piperidin-1-yl)ethanone | 93 |

$^1$H NMR (a mixture of diastereomers) 1.28 (m, 2H), 1.62 (m, 2H), 1.83 (m, 1H), 2.04 and 2.06 (two s, 3H), 2.19 (m, 1H), 2.47 (t, 1H, J = 12.4 Hz), 3.00 (t, 1H, J = 13.1 Hz), 3.74 (m, 1H), 3.84 (t, 1H, J = 15.5 Hz), 4.68 (d, 1H, J = 14.6 Hz), 5.37 and 5.51 (two m, 1H), 7.15 (s, 1H), 7.23 (m, 1H), 7.39 (m, 2H), 7.54 (d, 1H, J = 7.5 Hz), 7.80 (s, 1H)

| # | Compound | Name | Yield (%) |
| --- | --- | --- | --- |
| 1384 | | (4-(1-hydroxy-2-(5H-imidazo[5,1-a]isoindol-5-yl)ethyl)piperidin-1-yl)(thiophen-2-yl)methanone | 72 |

$^1$H NMR (a mixture of diastereomers) 1.39 (m, 2H), 1.66 (m, 2H), 2.07 (m, 1H), 2.17 (m, 1H), 2.89 (m, 2H), 3.76 (m, 1H), 5.37 and 5.51 (m, 1H), 7.01 (t, 1H, J = 4.3 Hz), 7.16 (s, 1H), 7.24 (m, 2H), 7.31-7.40 (m, 3H), 7.54 (d, 1H, J = 7.6 Hz), 7.81 (s, 1H)

| # | Compound | Name | Yield (%) |
| --- | --- | --- | --- |
| 1405 | | 1-(4-(1-hydroxy-2-(5H-imidazo[5,1-a]isoindol-5-yl)ethyl)piperidin-1-yl)-2-phenylethanone | 68 |

$^1$H NMR (a mixture of diastereomers) 1.00-2.25 (m, 6H), 2.47 (t, 1H, J = 9.8 Hz), 2.47 (t, 1H, J = 9.8 Hz), 2.89 (t, 1H, J = 12.0 Hz), 3.70 (m, 3H), 3.90 (t, 1H, J = 12.6 Hz), 3.90 (t, 1H, J = 12.3 Hz), 5.25-5.50 (m, 1H), 7.10-7.30 (m, 9H), 7.36 (t, 1H, J = 9.6 Hz), 7.53 (d, 1H, J = 7.8 Hz)

| # | Compound | Name | Yield (%) |
|---|---|---|---|
| 1404 | | 1-cyclohexyl-3-(5H-imidazo[5,1-a]isoindol-5-yl)propan-2-ol | 85 |
| | $^1$H NMR (a mixture of diastereomers) 0.80-1-85 (m, 14H), 2.00-2.20 (m, 1H), 4.20-4.50 (m, 1H), 5.30-5.60 (m, 1H), 7.14 (s, 1H), 7.20-7.39 (m, 2H), 7.43 (d, 1H, J = 7.2 Hz), 7.43 (d, 1H, J = 7.2 Hz), 7.91 (s, 1H) | | |
| 1403 | | 1-cyclohexyl-3-(6-fluoro-5H-imidazo[5,1-a]isoindol-5-yl)propan-2-ol | 55 |
| | $^1$H NMR (a mixture of diastereomers) 0.55-1.75 (m, 13H), 2.00-2.50 (m, 2H), 3.75-4.10 (m, 1H), 5.30-5.75 (m, 1H), 6.85-7.00 (m, 1H), 7.10-7.25 (m, 2H), 7.25-7.40 (m, 2H), 7.93 (s, 1H) | | |
| 1419 | | 1-cyclohexyl-2-(5H-imidazo[5,1-a]isoindol-5-ylidene)ethanol | 72 |
| | $^1$H NMR mixture of E/Z isomers: 1.15-1.30 (m, 10H), 1.66-1.83 (m, 10H), 2.00-2.12 (m, 2H), 4.56 (t, 1H, J = 6.4 Hz), 4.66 (d, 1H, J = 7.4 Hz), 6.02 (d, 1H, J = 8.3 Hz), 6.76 (s, 1H), 7.07 (s, 1H), 7.33-7.48 (m, 4H), 7.56 (d, 2H, J = 7.8 Hz), 7.82 (s, 1H), 7.98 (d, 1H, J = 7.9 Hz), 8.04 (s, 1H), 8.42 (s, 1H). | | |
| 1426 | | (trans)-methyl 4-((1R)-1-hydroxy-2-(5H-imidazo[5,1-a]isoindol-5-yl)ethyl)cyclohexanecarboxylate | 87 |
| | $^1$H NMR (a mixture of diastereomers) 1.05-1.20 (m, 2H), 1.42 (qt, J = 12.7, 4.0 Hz, 3H), 1.63-1.82 (m, 1H), 1.92-2.10 (m, 4H), 2.11-2.31 (m, 2H), 3.65 (s, 3H), 3.72-3.83 (m, 1H), 5.36 (t, J = 6.2 Hz, 0.7H), 5.52 (dd, J = 10.8, 3.1 Hz, 0.3H), 7.14 (s, 1H), 7.23 (t, J = 7.4 Hz, 1H), 7.31-7.40 (m, 1H), 7.42 (d, J = 7.7 Hz, 1H), 7.53 (d, J = 7.6 Hz, 1H), 7.83 (s, 1H) | | |

-continued

| # | Compound | Name | Yield (%) |
|---|---|---|---|
| 1438 | | 2-(5H-imidazo[5,1-a]isoindol-5-yl)-1-(spiro[2.5]octan-6-yl)ethanol | 46 |

$^1$H NMR (a mixture of diastereomers) 0.14-0.28 (m, 4H), 0.89 (t, 2H, J = 12.0 Hz), 1.19-2.938 (m, 9H), 2.81 (br s, 1H), 3.80-3.82 (m, 1H), 5.36-5.39 and 5.50-5.53 (two m, 1H), 7.16 (s, 1H), 7.21-7.25 (m, 1H), 7.33 (t, 1H, J = 7.6 Hz), 7.44 (d, 1H, J = 7.6 Hz), 7.53 (d, 1H, J = 7.6 Hz), 7.80 and 7.81 (two s, 1H)

| # | Compound | Name | Yield (%) |
|---|---|---|---|
| 1475 | | (trans)-4-(2-(6-fluoro-5H-imidazo[5,1-a]isoindol-5-yl)-1-hydroxyethyl)cyclohexanol | 92 |

$^1$H NMR (a mixture of diastereomers) 1.07-2.52 (m, 11H), 3.48-3.68 (two m, 2H), 5.45 (t, 1H, J = 6.0 Hz), 5.65 (dd, 1H, J = 9.0, 3.0 Hz), 6.89-6.96 (m, 1H), 7.16 (s, 1H), 7.29-7.38 (m, 2H), 7.80 and 7.88 (two s, 1H)

| # | Compound | Name | Yield (%) |
|---|---|---|---|
| 1499 | | (1R)-1-((trans)-4-(benzyloxy)cyclohexyl)-2-(6-fluoro-5H-imidazo[5,1-a]isoindol-5-yl)ethanol | 65 |

$^1$H NMR (a mixture of diastereomers) 1.04-1.33 (m, 5H), 1.71-2.32 (m, 5H), 2.75-2.51 (two m, 1H), 3.24-3.29 (m, 1H), 3.65-3.69 (m, 1H), 4.54 (s, 2H), 5.43 (t, 1H, J = 4.7 Hz, isomer), 5.65 (dd, 1H, J = 10.4, 2.4 Hz, isomer), 6.92 (t, 1H, J = 8.8 Hz), 7.14 (s, 1H), 7.26-7.33 (m, 7H), 7.79 and 7.88 (two s, 1H)

| # | Compound | Name | Yield (%) |
|---|---|---|---|
| 1498 | | (1R)-1-((trans)-4-(benzyloxy)cyclohexyl)-2-(5H-imidazo[5,1-a]isoindol-5-yl)ethanol | 78 |

$^1$H NMR (a mixture of diastereomers) 1.15-2.20 (m, 11H), 3.22-3.31 (m, 1H), 3.65-3.75 (m, 1H), 4.48 and 4.54 (two s, 2H), 5.35 (t, 1H, J = 8.0 Hz, isomer), 5.48 (dd, 1H, J = 16.0, 4.0 Hz, isomer), 7.15-7.55 (m, 10H), 7.77 and 7.79 and 7.81 (three s, 1H)

-continued

| # | Compound | Name | Yield (%) |
|---|---|---|---|
| 1492 | | N-((cis)-4-(1-hydroxy-2-(5H-imidazo[5,1-a]isoindol-5-yl)ethyl)cyclohexyl)benzamide | 63 |

¹H NMR (a mixture of diastereomers) (CD₃OD) 1.27-1.46 (m, 5H), 1.79 (d, 1H, J = 12.0 Hz), 2.04-2.22 (m, 5H), 3.78-3.88 (m, 2H), 5.47-5.49 and 5.53-5.54 (two m, 1H), 7.16 and 7.19 (two s, 1H), 7.35 (t, 1H, J = 7.4 Hz), 7.42-7.49 (m, 3H), 7.53 (d, 1H, J = 7.2 Hz), 7.59 (d, 1H, J = 7.6 Hz), 7.64 (d, 1H, J = 7.6 Hz), 7.82 (d, 2H, J = 7.6 Hz), 7.97 and 8.01 (two s, 1H)

| # | Compound | Name | Yield (%) |
|---|---|---|---|
| 1505 | | N-((trans)-4-(1-hydroxy-2-(5H-imidazo[5,1-a]isoindol-5-yl)ethyl)cyclohexyl)benzamide | 57 |

¹H NMR (a mixture of diastereomers) 1.14-1.45 (m, 4H), 1.74 (d, 1H, J = 10.6 Hz), 1.97 (d, 1H, J = 10.6 Hz), 2.09-2.20 (m, 4H), 3.71-3.82 (m, 1H), 3.85-3.95 (m, 1H), 5.3-5.40 and 5.48-5.59 (two m, 1H), 6.03 (d, 1H, J = 7.6 Hz), 7.17 (s, 1H), 7.21-7.30 (m, 1H, merged with chloroform), 7.31-7.51 (m, 5H), 7.55 (d, 1H, J = 7.4 Hz), 7.74 (d, 2H, J = 7.6 Hz), 7.83 (s, 1H)

| # | Compound | Name | Yield (%) |
|---|---|---|---|
| 1441 | | 1-(4-(2-hydroxyethylidene)cyclohexyl)-2-(5H-imidazo[5,1-a]isoindol-5-yl)ethanol | 59 |

¹H NMR (a mixture of diastereomers) 1.00-1.30 (m, 2H), 1.40-1.60 (m, 1H), 1.62-1.81 (m, 2H), 1.82-2.13 (m, 3H), 2.60-2.75 (m, 1H), 3.60-3.75 (m, 1H), 3.90-4.10 (m, 2H), 5.25-5.31 (m, 1H), 5.33-5.48 (m, 1H), 7.13 (s, 1H), 7.20-7.43 (m, 2H), 7.46-7.60 (m, 2H), 7.97 (s, 1H)

| # | Compound | Name | Yield (%) |
|---|---|---|---|
| 1460 | | tert-buty 3-(1-hydroxy-2-(5H-imidazo[5,1-a]isoindol-5-yl)ethyl)azetidine-1-carboxylate | 43 |

¹H NMR (a mixture of diastereomers) 1.42 (s, 9H), 1.92-2.23 (m, 2H), 2.50-2.63 (m, 1H), 3.61-3.80 (m, 2H), 3.90-4.02 (m, 3H), 4.20-4.58 (br, 1H), 5.33-5.41 and 5.52-5.58 (two m, 1H), 7.13 (s, 1H), 7.21-7.28 (m, 1.58H), 7.30-7.39 (m, 1.33H), 7.41-7.48 (m, 0.8H), 7.58 (d, J = 14.3 Hz, 1H), 7.93 and 7.99 (two s, 1H)

-continued

| # | Compound | Name | Yield (%) |
|---|---|---|---|
| 1502 | | 2-(5H-imidazo[5,1-a]isoindol-5-yl)-1-(pyridin-2-yl)ethanol | 82 |

¹H NMR (a mixture of diastereomers) 2.25-2.33 (m, 2H), 5.06-5.07 (m, 1H), 5.09 (br s, 1H), 5.35-5.38 and 5.46-5.49 (two m, 1H), 7.02 (s, 1H), 7.13-7.24 (m, 4H), 7.44-7.48 (m 2H), 7.57-7.62 (m, 2H), 8.46-8.47 (m, 1H)

| 1474 | | 2-(5H-imidazo[5,1-a]isoindol-5-yl)-1-(pyridin-3-yl)ethanol | 69 |

¹H NMR (a mixture of diastereomers) 1.75-2.43 (m, 2H), 5.07-5.12 (m, 1H), 5.38-5.40 and 5.56-5.58 (two m, 2H), 6.98 and 7.11 (two s, 1H), 7.19-7.33 (m, 3H), 7.43-7.49 (m, 2H), 7.43-7.79 (m, 2H), 8.3-8.51 (m, 2H)

| 1501 | | 2-(5H-imidazo[5,1-a]isoindol-5-yl)-1-(pyridin-4-yl)ethanol | 30 |

¹H NMR (a mixture of diastereomers) 1.98-2.32 (m, 2H), 3.59 (br, 1H), 5.03-5.06 (m, 1H), 5.42-5.45 and 5.56-5.58 (two m, 1H), 7.20-7.23 (m, 1H), 7.24-7.25 (m, 4H), 7.34 (t, J = 7.0 Hz, 1H), 7.41 (d, J = 7.2 Hz, 1H), 7.49 (d, J = 7.6 Hz, 1H), 8.44-8.46 (m, 2H)

| 1509 | | 2-(5H-imidazo[5,1-a]isoindol-5-yl)-1-(4-(trifluoromethyl)cyclohexyl)ethanol | 69 |

¹H NMR (a mixture of diastereomers) 1.53-2.22 (m, 12H), 3.92-3.98 (m, 1H), 4.12 (br s, 1H), 5.39-5.43 and 5.50-5.60 (two m, 1H), 7.14 (s, 1H), 7.23-7.54 (m, 5H), 7.94 (s, 1H)

| 1508 | | 2-(6-fluoro-5H-imidazo[5,1-a]isoindol-5-yl)-1-(4-(trifluoromethyl)cyclohexyl)ethanol | 61 |

¹H NMR (a mixture of diastereomers) 1.40-1.70 (m, 7H), 1.70-1.90 (m, 2H), 1.91-2.04 (m, 1H), 2.09-2.28 (m, 1H), 2.38-2.48 (m, 1H), 3.80-3.98 (br, 2H), 5.43-5.71 (two m, 1H), 6.91-6.94 (m, 1H), 7.14 (s, 1H), 7.29-7.38 (m, 2H), 7.93 and 7.97 (two s, 1H)

| # | Compound | Name | Yield (%) |
|---|---|---|---|
| 1473 | 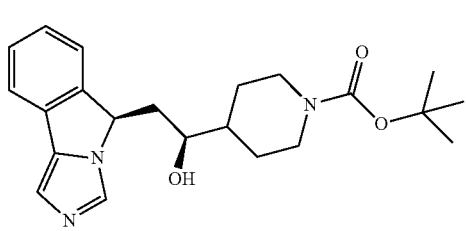 | 1-((cis)-4-(benzyloxy)cyclohexyl)-2-(6-fluoro-5H-imidazo[5,1-a]isoindol-5-yl)ethanol | 87 |

$^1$H NMR (a mixture of diastereomers) 1.39-2.42 (m, 12 H), 3.39-3.78 (m, 2H), 4.47 and 4.48 (two s, 2H), 5.44 (t, 1H, J = 5.1 Hz), 5.67 (dd, 1H, J = 10.2, 2.8 Hz), 6.88-6.94 (m, 1H), 7.25-7.36 (m, 8H), 7.80, 7.82, 7.88 and 7.90 (four s, 1H).

Example 26

Preparation of 1469-1472

1469

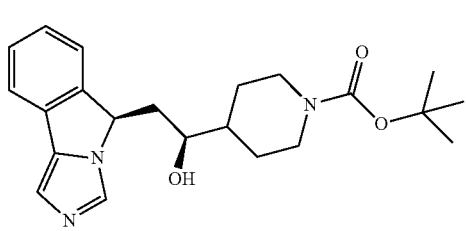

1470

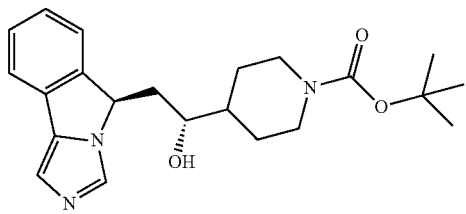

1471

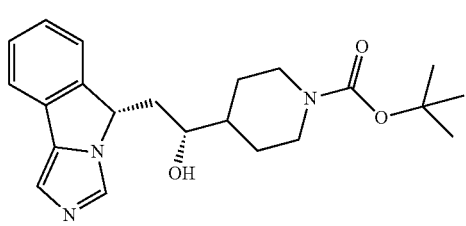

1472

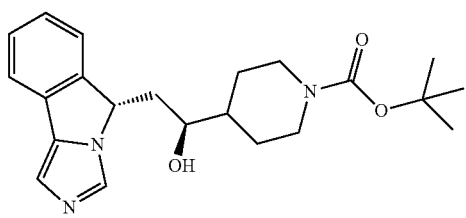

The pure diastereomers were obtained from the racemic mixture of 1363 using preparative chiral supercritical fluid chromatography (SFC) technique, using a AD-H column (Regis Technologies, Inc.) in methanol:$CO_2$ (24:76).

Example 27

General Procedure for the Removal of Boc Protecting Group

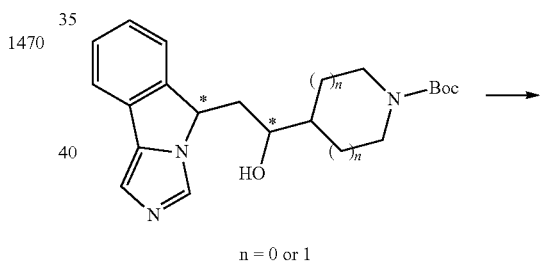

n = 0 or 1

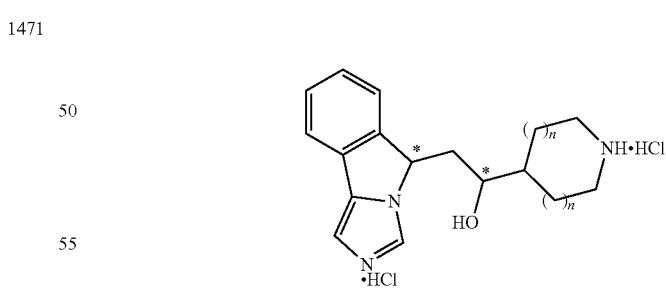

n = 0 or 1

To a solution of the appropriate Boc protected amine 1363, 1469, 1470, 1471, 1472 or 1460 (1.13 mmol) in dichloromethane (10 mL) was added trifluoroacetic acid (33.8 mmol). The resulting solution was stirred at RT for 2 h and concentrated. The crude was dissolved in methanol (4 mL) and hydrogen chloride (4M in dioxane) (3.39 mmol) was added. The mixture was concentrated and dried under high vacuum to give the desired product as a dihydrochloride salt which was directly used in the next step without further purification.

Example 28

General Procedure for the Synthesis of 1423, 1424, 1425, 1437, 1439, 1448, 1450, 1458, 1480, 1481, 1490, 1493, 1500 and 1511 Using HATU Coupling

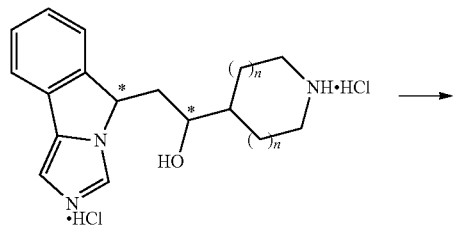

n = 0 or 1

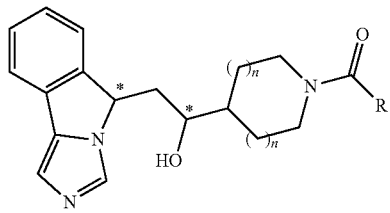

n = 0 or 1

To a vial containing appropriate amine salt obtained from Example 27 (0.25 mmol) in DMF (4 mL) was added the corresponding carboxylic acid (0.26 mmol), DIPEA (1.5 mmol) and HATU (0.28 mmol). The reaction mixture was stirred at rt for 18 h and poured into water (10 mL) and the aqueous layer was extracted with dichloromethane (2×20 mL). The combined organic layers were washed with water (2×10 mL), dried over Na$_2$SO$_4$, and concentrated. The crude product was purified by flash column chromatography to afford 1423, 1424, 1425, 1437, 1439, 1448, 1450, 1458, 1480, 1481, 1490, 1493 or 1500.

Example 29

General Procedure for the Synthesis of 1449, 1459, 1476, 1477, 1478 and 1479

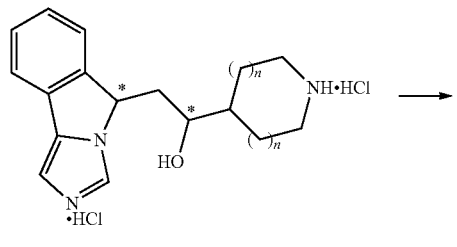

n = 0 or 1

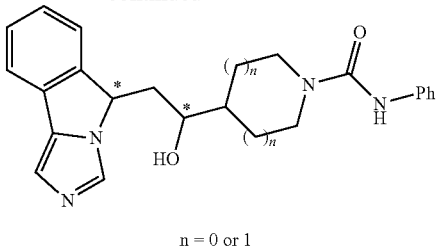

n = 0 or 1

To a vial containing appropriate amine salt obtained from Example 19 (0.25 mmol) in dichloromethane (4 mL) was added DIPEA (1.0 mmol) and phenylisocyanate (0.25 mmol). The reaction mixture was stirred at rt for 30 min and concentrated. The residue was dissolved in dichloromethane (30 mL) and washed with water (3×10 mL). The organic layer was dried over Na$_2$SO$_4$ and concentrated. The crude product was purified by flash column chromatography to afford ureas 1449, 1459, 1476, 1477, 1478 and 1479.

Example 30

General Procedure for the Synthesis of 1495, 1496, 1497, 1503, 1504, 1507, 1512

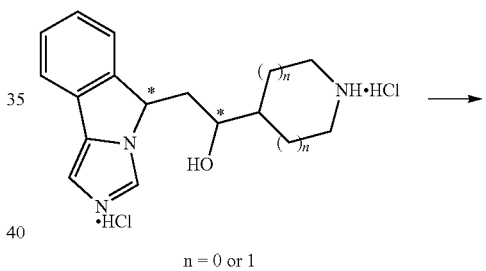

n = 0 or 1

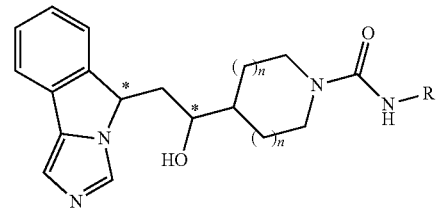

n = 0 or 1

To a solution of appropriate amine (0.3 mmol) in CH$_2$Cl$_2$ (3 mL) was added carbonyldiimidazole (0.35 mmol) and ethyl diisopropylamine (2.0 mmol) at 0° C. under an atmosphere of N$_2$ and the mixture was stirred for 1 h. The appropriate amine salt obtained from Example 19 (0.25 mmol) was added and the mixture was allowed to stir overnight. The solution was partitioned with water in a separatory funnel and the organic layer was collected. The aqueous layer was extracted with dichloromethane (3×10 mL) and the combined organic fractioned were dried (Na$_2$SO$_4$). The crude was purified by flash column chromatography to afford 1495, 1496, 1497, 1503, 1504 or 1507.

| # | Compound | Name | Yield (%) |
|---|---|---|---|
| 1423 | | 1-(4-(1-hydroxy-2-(5H-imidazo[5,1-a]isoindol-5-yl)ethyl)piperidin-1-yl)-2-(pyrimidin-5-yl)ethanone | 76 |

$^1$H NMR (a mixture of diastereomers) 1.30-1.41 (m, 3H), 1.63-1.72 (m, 2H), 1.87-2.22 (m, 2H), 2.56 (t, 1H, J = 12.4 Hz), 3.01-3.15 (m, 2H), 3.67 (d, 1H, J = 6.0 Hz), 3.83-3.85 (m, 1H), 3.96 (t, 1H, J = 14.6 Hz), 4.66 (t, 1H, J = 14.6 Hz), 5.44-5.46 and 5.62-5.65 (two m, 1H), 7.17 and 7.19 (two s, 1H), 7.26-7.30 (m, 1H, merged with chloroform), 7.39 (t, 1H, J = 7.4 Hz), 7.46 (d, 1H, J = 7.6 Hz), 7.56 (d, 1H, J = 7.2 Hz), 8.14 (d, 1H, J = 13.2 Hz), 8.63 (d, 2H, J = 4.4 Hz), 9.08-9.10 (m, 1H)

| # | Compound | Name | Yield (%) |
|---|---|---|---|
| 1424 | | 2-(3,4-difluorophenyl)-1-(4-(1-hydroxy-2-(5H-imidazo[5,1-a]isoindol-5-yl)ethyl)piperidin-1-yl)ethanone | 71 |

$^1$H NMR (a mixture of diastereomers) 1.16-1.33 (m, 2H), 1.61-1.64 (m, 3H), 1.84-1.92 (m, 1H), 2.09-2.15 (m, 1H), 2.53 (t, 1H, J = 12.8 Hz), 2.98 (t, 1H, J = 12.8 Hz), 3.67 (d, 2H, J = 4.0 Hz), 3.76-3.78 (m, 1H), 3.90 (t, 1H, J = 13.6 Hz), 4.19 (br s, 1H), 4.70 (t, 1H, J = 13.6 Hz), 5.32-5.36 and 5.49-5.53 (two m, 1H), 6.94 (s, 1H), 7.06-7.13 (m, 2H), 7.14 (s, 1H), 7.24-7.30 (m, 1H), 7.34-7.42 (m, 2H), 7.56 (d, 1H, J = 6.8 Hz), 7.81-7.85 (m, 1H)

| # | Compound | Name | Yield (%) |
|---|---|---|---|
| 1425 | | cyclohexyl(4-(1-hydroxy-2-(5H-imidazo[5,1-a]isoindol-5-yl)ethyl)piperidin-1-yl)methanone | 44 |

$^1$H NMR (a mixture of diastereomers) 1.20-1.34 (m, 6H), 1.49-1.77 (m, 10H), 1.87-1.97 (m, 1H), 2.03-2.08 (m, 1H), 2.16-2.20 (m, 1H), 2.46 (t, 2H, J = 12.0 Hz), 3.76-3.79 (m, 1H), 3.97 (t, 1H, J = 16.2 Hz), 4.70 (t, 1H, J = 14.2 Hz), 5.38-5.41 and 5.51-5.56 (two m, 1H), 7.15 (s, 1H), 7.23-7.27 (m, 1H, merged with chloroform), 7.37 (t, 1H, J = 7.8 Hz), 7.44 (d, 1H, J = 7.6 Hz), 7.54 (d, 1H, J = 7.6 Hz), 7.79 and 7.82 (two s, 1H)

| # | Compound | Name | Yield (%) |
|---|---|---|---|
| 1437 | | 1-(4-(1-hydroxy-2-(5H-imidazo[5,1-a]isoindol-5-yl)ethyl)piperidin-1-yl)-2-(140yridine-4-yl)ethanone | 49 |

$^1$H NMR (a mixture of diastereomers) 1.08-1.16 (m, 1H), 1.23-1.33 (m, 1H), 1.57-1.65 (m, 2H), 1.86 (t, 1H, J = 14.0 Hz), 1.99-2.17 (m, 2H), 2.52 (dt, 1H, J = 2.4, 12.8 Hz), 2.97 (dt, 1H, J = 4.0, 12.8 Hz), 3.70 (d, 2H, J = 7.2 Hz), 3.70-3.76 (m, 1H, merged with doublet at 3.70), 3.83 (t, 1H, J = 13.8 Hz), 4.30 (br s, 1H), 4.69 (t, 1H, J = 14.0 Hz), 5.32-5.36 and 5.51-5.53 (two m, 1H), 7.10 and 7.12 (two s, 1H), 7.16-7.25 (m, 3H), 7.35-7.41 (m, 2H), 7.54 (d, 1H, J = 7.6 Hz), 7.76 (d, 1H, J = 4.4 Hz), 8.49-8.52 (m, 2H)

| # | Compound | Name | Yield (%) |
|---|----------|------|-----------|
| 1439 | | 2-(4-fluorophenyl)-1-(4-(1-hydroxy-2-(5H-imidazo[5,1-a]isoindol-5-yl)ethyl)piperidin-1-yl)ethanone | 80 |

¹H NMR (a mixture of diastereomers) 1.08-1.13 (m, 1H), 1.23-1.30 (m, 1H), 1.54-1.63 (m, 2H), 1.78 and 1.86 (two d, 1H, J = 13.0 Hz), 1.99-2.12 (m, 2H), 2.49 (dt, 1H, J = 2.4, 12.8 Hz), 2.93 (dt, 1H, J = 3.0, 12.8 Hz), 3.66 (d, 2H, J = 4.4 Hz), 3.71-3.73 (m, 2H, merged with broad singlet of OH), 3.90 (t, 1H, J = 15.2 Hz), 4.68 (t, 1H, J = 13.6 Hz), 5.30-5.37 and 5.47-5.50 (two m, 1H), 6.94-7.00 (m, 2H), 7.13 (s, 1H), 7.15-7.20 (m, 2H), 7.22-7.31 (m, 1H, merged with chloroform), 7.35-7.41 (m, 2H), 7.54 (d, 1H, J = 7.6 Hz), 7.84 (d, 1H, J = 5.2 Hz)

| # | Compound | Name | Yield (%) |
|---|----------|------|-----------|
| 1448 | | (3-fluoro-2-hydroxyphenyl)(4-(1-hydroxy-2-(5H-imidazo[5,1-a]isoindol-5-yl)ethyl)piperidin-1-yl)methanone | 26 |

¹H NMR 1.35-1.47 (m, 2H), 1.66-1.70 (m, 2H), 1.86-2.15 (m, 7H), 2.89 (m, 1H), 4.31 (br s, 1H), 5.43-5.47 and 5.53-5.59 (two m, 1H), 6.78-6.84 (m, 1H), 6.99 (d, 1H, J = 7.6 Hz), 7.11 (t, 1H, J = 9.4 Hz), 7.19 (s, 1H), 7.33 (d, 1H, J = 7.2 Hz), 7.37-7.47 (m, 2H), 7.58 (d, 1H, J = 7.2 Hz), 8.03 and 8.13 (two s, 1H)

| # | Compound | Name | Yield (%) |
|---|----------|------|-----------|
| 1449 | | 4-(1-hydroxy-2-(5H-imidazo[5,1-a]isoindol-5-yl)ethyl)-N-phenylpiperidine-1-carboxamide | 62 |

¹H NMR (CD₃OD) 1.33-1.43 (m, 2H), 1.59-1.71 (m, 2H), 1.92-1.95 (m, 1H), 2.10-2.22 (m, 2H), 2.87 (t, 2H, J = 11.8 Hz), 3.79-3.83 (m, 1H), 4.25 (t, 2H, J = 15.2 Hz), 5.48 and 5.52-5.55 (t, J = 6.0 Hz, and m, 1H), 7.03 (t, 1H, J = 7.4 Hz), 7.16 and 7.19 (two s, 1H), 7.28 (t, 2H, J = 8.0 Hz), 7.33-7.37 (m, 3H), 7.43 (t, 1H, J = 7.4 Hz), 7.62 (dd, 2H, J = 7.6, 21.6 Hz), 7.94 and 7.97 (two s, 1H), 8.01 (s, 1H)

| # | Compound | Name | Yield (%) |
|---|----------|------|-----------|
| 1450 | | (4-fluorophenyl)(4-(1-hydroxy-2-(5H-imidazo[5,1-a]isoindol-5-yl)ethyl)piperidin-1-yl)methanone | 29 |

¹H NMR 1.29-1.37 (m, 3H), 1.57-1.87 (m, 3H), 2.18-2.36 (m, 2H), 3.73-3.86 (m, 4H), 4.74 (br s, 1H), 5.44-5.49 and 5.58-5.63 (two m, 1H), 7.08 (t, 2H, J = 7.2 Hz), 7.23 (s, 1H), 7.31-7.48 (m, 5H), 7.59 (d, 1H, J = 7.2 Hz), 8.20 and 8.27 (two s, 1H)

| # | Compound | Name | Yield (%) |
|---|----------|------|-----------|
| 1458 | | 1-(3-(1-hydroxy-2-(5H-imidazo[5,1-a]isoindol-5-yl)ethyl)azetidin-1-yl)-2-phenylethanone | 55 |

¹H NMR (a mixture of diastereomers) 1.79-2.13 (m, 2H), 2.44-2.48 (m, 1H), 3.33-3.42 (m, 2H), 3.67-3.93 (m, 2H), 3.97-4.04 (m, 2H), 4.12-4.19 (m, 1H), 5.23-5.31 and 5.34-5.42 (two m, 1H), 7.08-7.37 (m, 9H), 7.46-7.48 (m, 1H), 7.93 and 8.07 (two d, 1H, J = 7.6 Hz)

| # | Compound | Name | Yield (%) |
|---|---|---|---|
| 1459 | | 3-(1-hydroxy-2-(5H-imidazo[5,1-a]isoindol-5-yl)ethyl)-N-phenylazetidine-1-carboxamide | 19 |

¹H NMR (a mixture of diastereomers) 1.95-2.20 (m, 2H), 2.64-2.68 (m, 1H), 3.76-3.81 (m, 1H), 3.98-4.10 (m, 4H), 5.43-5.46 and 5.51-5.57 (two m, 1H), 6.97-7.14 (m, 1H), 7.22 and 7.24 (two s, 1H), 7.26-7.38 (m, 3.3H), 7.40-7.42 (m, 3H), 7.57-7.62 (m, 1.7H), 7.99 and 8.00 (two s, 1H)

| # | Compound | Name | Yield (%) |
|---|---|---|---|
| 1476 | | 4-((S)-1-hydroxy-2-((R)-5H-imidazo[5,1-a]isoindol-5-yl)ethyl)-N-phenylpiperidine-1-carboxamide | 67 |

¹H NMR 1.32-1.41 (m, 2H), 1.51-1.57 (m, 1H), 1.61 (d, 1H, J = 12.4 Hz), 1.83 (d, 1H, J = 12.4 Hz), 2.00-2.14 (m, 2H), 2.78 (t, 2H, J = 12.0 Hz), 3.74-3.76 (m, 1H), 4.15-4.18 (m, 2H), 4.42 (br s, 1H), 5.32 (t, 1H, J = 6.0 Hz), 6.98 (t, 1H, J = 7.4 Hz), 7.15 (d, 2H, J = 14.4 Hz), 7.20-7.25 (m, 3H), 7.35-7.37 (m, 3H), 7.40 (d, 1H, J = 7.6 Hz), 7.52 (d, 1H, J = 7.6 Hz), 7.86 (s, 1H)

| # | Compound | Name | Yield (%) |
|---|---|---|---|
| 1477 | | 4-((R)-1-hydroxy-2-((R)-5H-imidazo[5,1-a]isoindol-5-yl)ethyl)-N-phenylpiperidine-1-carboxamide | 78 |

¹H NMR 1.15-1.61 (m, 6H), 1.86 (d, 1H, J = 12.8 Hz), 2.17-2.22 (t, J = 11.2 Hz), 2.66-2.75 (m, 2H), 3.68-3.76 (m, 1H), 4.04-4.08 (m, 2H), 4.60 (br, 2H), 5.47 (d, 1H, J = 8.8 Hz), 6.86-6.90 (t, 1H, J = 11.2 Hz), 6.94 (s, 1H), 7.09-7.31 (m, 7H), 7.45 (d, 1H, J = 7.2 Hz), 8.24 (s, 1H)

| # | Compound | Name | Yield (%) |
|---|---|---|---|
| 1478 | | 4-((R)-1-hydroxy-2-((S)-5H-imidazo[5,1-a]isoindol-5-yl)ethyl)-N-phenylpiperidine-1-carboxamide | 74 |

¹H NMR 1.32-1.61 (m, 4H), 1.81 (d, 1H, J = 12.5 Hz), 2.01-2.15 (m, 2H), 2.77 (t, 2H, J = 12.4 Hz), 3.68-3.73 (m, 1H), 4.08-4.14 (m, 2H), 5.31 (t, 1H, J = 4.0 Hz), 6.92 (s, 1H), 6.97 (t, 1H, J = 6.0 Hz), 7.12 (s, 1H), 7.21-7.38 (m, 6H), 7.51 (d, 1H, J = 7.4 Hz), 7.87 (s, 1H)

| # | Compound | Name | Yield (%) |
|---|---|---|---|
| 1479 | | 4-((S)-1-hydroxy-2-((S)-5H-imidazo[5,1-a]isoindol-5-yl)ethyl)-N-phenylpiperidine-1-carboxamide | 78 |

¹H NMR 1.15-1.61 (m, 6H), 1.86 (d, 1H, J = 12.8 Hz), 2.17-2.22 (t, 1H, J = 11.2 Hz), 2.66-2.75 (m, 2H), 3.68-3.76 (m, 1H), 4.04-4.08 (m, 2H), 4.60 (br, 2H), 5.47 (d, 1H, J = 8.8 Hz), 6.86-6.90 (t, 1H, J = 11.2 Hz), 6.94 (s, 1H), 7.09-7.31 (m, 7H), 7.45 (d, 1H, J = 7.2 Hz), 8.24 (s, 1H)

| # | Compound | Name | Yield (%) |
|---|---|---|---|
| 1480 | | 1-(4-((R)-1-hydroxy-2-((S)-5H-imidazo[5,1-a]isoindol-5-yl)ethyl)piperidin-1-yl)-2-phenylethanone | 82 |

$^1$H NMR 1.0-2.14 (m, 8H), 2.46 (t, 1H, J = 12 Hz), 2.91 (t, 1H, J = 12 Hz), 3.65-3.72 (m, 3H), 3.91 (t, 1H, J = 16 Hz), 4.71 (t, 1H, J = 12 Hz), 7.15-7.56 (m, 9H), 7.55 (d, 1H, J = 7.51 Hz), 7.91 (d, 1H, J = 7.7 Hz)

| 1481 | | 1-(4-((S)-1-hydroxy-((S)-5H-imidazo[5,1-a]isoindol-5-yl)ethyl)piperidin-1-yl)-2-phenylethanone | 85 |

$^1$H NMR 1.04-1.27 (m, 2H), 1.51-1.67 (m, 3H), 1.81-1.89 (m, 1H), 2.19-2.55 (m, 1H), 2.46-2.52 (m, 1H), 2.90 (t, 1H, J = 12.8 Hz), 3.66-3.74 (m, 3H), 3.90 (t, 1H, J = 16.0 Hz), 4.62-4.70 (m, 1H), 5.23 (br s, 1H), 5.49 (dd, 1H, J = 2.2, 10.2 Hz), 7.12 (s, 1H), 7.18-7.37 (m, 8H), 7.53 (d, 1H, J = 7.5 Hz), 7.92 (d, 1H, J = 3.0 Hz)

| 1490 | | 1-(4-((S)-1-hydroxy-2-((S)-5H-imidazo[5,1-a]isoindol-5-yl)ethyl)piperidin-1-yl)-2-(tetrahydro-2H-pyran-4-yl)ethanone | 77 |

$^1$H NMR (CD$_3$OD) δ 1.06-1.46 (m, 4H), 1.56-1.73 (m, 3H), 1.82-2.08 (m, 3H), 2.32 (t, J = 6.4 Hz, 2H), 2.39 (dd, J = 18.4, 7.2 Hz, 1H), 2.54 (t, J = 13.0 Hz, 1H), 3.03 (t, J = 12.9 Hz, 1H), 3.40 (t, J = 11.7 Hz, 2H), 3.48-3.59 (m, 1H), 3.90 (d, J = 11.5 Hz, 2H), 3.94-4.06 (m, 1H), 4.57 (t, J = 14.8 Hz, 1H), 5.71 (d, J = 6.5 Hz, 1H), 7.41-7.52 (m, 2H), 7.55 (d, J = 7.3 Hz, 1H), 7.73 (d, J = 7.1 Hz, 1H), 7.90 (s, 1H), 8.57 (s, 1H)

| 1493 | | 1-(4-((S)-1-hydroxy-2-((R)-5H-imidazo[5,1-a]isoindol-5-yl)ethyl)piperidin-1-yl)-2-phenylethanone | 63 |

$^1$H NMR 0.49-1.21 (m, 4H), 1.44-1.56 (m, 1H), 1.96-2.05 (m, 2H), 2.38-2.47 (m, 1H), 2.80-2.86 (m, 1H), 3.58-3.64 (m, 2H), 3.83 (t, J = 13.2 Hz, 1H), 4.62 (t, J = 13.2 Hz, 1H), 5.25-5.30 (m, 1H), 7.13-7.24 (m, 7H), 7.29-7.34 (m, 2H), 7.48 (d, J = 7.6 Hz, 1H), 7.94 (br s, 1H)

| 1495 | | 4-((R)-1-hydroxy-2-((S)-5H-imidazo[5,1-a]isoindol-5-yl)ethyl)-N-((trans)-4-hydroxycyclohexyl)piperidine-1-carboxamide | 56 |

$^1$H NMR (CD$_3$OD) 1.21-1.43 (m, 7H), 1.48-1.66 (m, 2H), 1.81-2.01 (m, 5H), 2.14 (ddd, 2H, J = 4.4, 8.4, 10.4 Hz), 2.71 (t, 2H, J = 11.7 Hz), 3.49-3.55 (m, 2H), 3.74-3.79 (m, 1H), 4.08 (t, 1H, J = 13.6 Hz), 5.46 (t, 1H, J = 6.2 Hz), 7.16 (s, 1H), 7.34 (t, 1H, J = 7.5 Hz), 7.43 (t, 1H, J = 7.3 Hz), 7.57 (d, 1H, J = 7.6 Hz), 7.64 (d, 1H, J = 7.6 Hz), 8.00 (s, 1H)

| # | Compound | Name | Yield (%) |
|---|---|---|---|
| 1496 | | 4-((S)-1-hydroxy-2-((S)-5H-imidazo[5,1-a]isoindol-5-yl)ethyl)-N-(tetrahydro-2H-pyran-4-yl)piperidine-1-carboxamide | 84 |

¹H NMR 1.16-1.74 (m, 6H), 1.78-2.00 (m, 2H), 2.18-2.37 (m, 1H), 2.70 (t, J = 12.7 Hz, 2H), 3.33-3.51 (m, 2H), 3.71-4.13 (m, 5H), 4.76 (d, J = 7.4 Hz, 1H), 5.54 (dd merged with br s, J = 10.6, 2.3 Hz, 3H), 7.13 (s, 1H), 7.20-7.38 (m, 3H), 7.51 (d, J = 7.5 Hz, 1H), 7.90 (s, 1H)

| 1497 | | 4-((S)-1-hydroxy-2-((S)-5H-imidazo[5,1-a]isoindol-5-yl)ethyl)-N-((trans)-4-hydroxycyclohexyl)piperidine-1-carboxamide | 65 |

¹H NMR 1.08-1.44 (m, 6H), 1.57 (t, J = 12.5 Hz, 2H), 1.67-1.80 (m, 1H), 1.90 (dd, J = 24.8, 9.8 Hz, 4H), 2.29 (ddd, J = 14.3, 11.0, 3.1 Hz, 1H), 2.69 (t, J = 12.8 Hz, 2H), 3.35 (s, 1H), 3.49 (d, J = 4.4 Hz, 2H), 3.63-3.77 (m, 1H), 3.95-4.19 (m, 2H), 5.50 (dd, J = 9.7, 3.0 Hz, 1H), 6.05 (d, J = 7.8 Hz, 1H), 7.15 (s, 1H), 7.31 (td, J = 7.5, 1.0 Hz, 1H), 7.39 (t, J = 7.4 Hz, 1H), 7.46 (d, J = 7.2 Hz, 1H), 7.60 (d, J = 7.5 Hz, 1H), 7.91 (d, J = 8.5 Hz, 1H)

| 1500 | | 1-(4-((R)-1-hydroxy-2-((S)-5H-imidazo[5,1-a]isoindol-5-yl)ethyl)piperidin-1-yl)-2-(tetrahydro-2H-pyran-4-yl)ethanone | 46 |

¹H NMR 1.19-1.42 (m, 4H), 1.54-1.67 (m, 4H), 1.86-1.90 (m, 1H), 2.08-2.25 (m, 4H), 2.43-2.51 (m, 1H), 2.92-3.01 (m, 1H), 3.39 (t, 2H, J = 11.8 Hz), 3.72-3.76 (m, 1H), 3.90-3.99 (m, 3H), 4.70 (m, 1H, J = 9.75 Hz), 5.35-5.40 (m, 1H), 7.13 (s, 1H), 7.24-7.27 (m, 1H), 7.35-7.43 (m, 2H), 7.54 (d, 1H, J = 7.4 Hz), 7.80 (s, 1H)

| 1503 | | 4-((R)-1-hydroxy-2-((S)-5H-imidazo[5,1-a]isoindol-5-yl)ethyl)-N-(tetrahydro-2H-pyran-4-yl)piperidine-1-carboxamide | 77 |

¹H NMR 1.29-1.33 (m, 1H), 1.41-1.47 (m, 2H), 1.51-1.61 (m, 1H), 1.62 (d, 1H, J = 12.7 Hz), 1.83 (d, 1H, J = 12.4 Hz), 1.91 (d, 2H, J = 12.4 Hz), 2.07-2.26 (m, 2H), 2.73 (t, 2H, J = 12.2 Hz), 3.46 (t, 2H, J = 10.8 Hz), 3.73-3.78 (m, 1H), 3.81-3.89 (m, 1H), 3.93-4.05 (m, 4H), 4.40 (d, 1H, J = 7.5 Hz), 4.61 (br s, 2H), 5.41 (t, 1H, J = 5.9 Hz), 7.18 (s, 1H), 7.24-7.30 (m, 1H, merged with chloroform), 7.39 (t, 1H, J = 7.5 Hz), 7.44 (d, 1H, J = 7.6 Hz), 7.56 (d, 1H, J = 7.6 Hz), 7.92 (s, 1H)

| 1504 | | N-cyclohexyl-4-((R)-1-hydroxy-2-((S)-5H-imidazo[5,1-a]isoindol-5-yl)ethyl)piperidine-1-carboxamide | 77 |

¹H NMR 0.97-1.23 (m, 3H), 1.26-1.36 (m, 4H), 1.48-1.70 (m, 5H), 1.82 (d, J = 13.1 Hz, 1H), 1.93 (d, J = 10.3 Hz, 2H), 2.07 (ddd, J = 14.3, 6.8, 2.7 Hz, 1H), 2.14-2.27 (m, 1H), 2.70 (td, J = 12.8, 2.5 Hz, 2H), 3.57-3.65 (m, 1H), 3.71-3.81 (m, 1H), 3.97 (t, J = 13.2 Hz, 2H), 4.31 (d, J = 7.6 Hz, 1H), 5.39 (t, J = 6.0 Hz, 1H), 7.16 (s, 1H), 7.24 (dd, J = 7.6, 1.0 Hz, 1H), 7.37 (t, J = 7.4 Hz, 1H), 7.43 (d, J = 7.6 Hz, 1H), 7.55 (d, J = 7.6 Hz, 1H), 7.80 (s, 1H)

| # | Compound | Name | Yield (%) |
|---|---|---|---|
| 1507 | | N-cyclopentyl-4-((R)-1-hydroxy-2-((S)-5-imidazo[5,1-a]isoindol-5-yl)ethyl)piperidine-1-carboxamide | 87 |

¹H NMR

| 1511 | | 1-(4-((R)-1-hydroxy-2-((S)-5H-imidazo[5,1-a]isoindol-5-yl)ethyl)piperidin-1-yl)-2-(4-(trifluoromethyl)phenyl)ethanone | 69 |

¹H NMR 1.03-1.26 (m, 2H), 1.28-1.39 (m, 2H), 1.56 (q, J = 13.9, 13.1 Hz, 2H), 1.75 (d, J = 13.0 Hz, 1H), 1.91-2.10 (m, 2H), 2.45 (t, J = 13.4 Hz, 1H), 2.90 (t, J = 13.0 Hz, 1H), 3.68 (d, J = 6.5 Hz, 2H), 3.83 (t, J = 13.9 Hz, 1H), 4.59 (t, J = 11.5 Hz, 1H), 4.94 (br s, 1H), 5.35 (q, J = 6.6 Hz, 1H), 7.06 (d, J = 7.6 Hz, 1H), 7.21-7.40 (m, 5H), 7.42-7.56 (m, 3H), 8.16 (d, J = 17.3 Hz, 1H).

| 1512 | | 4-((R)-1-hydroxy-2-((S)-5H-imidazo[5,1-a]isoindol-5-yl)ethyl)-N-(4-(trifluoromethyl)phenyl)piperidine-1-carboxamide | 78 |

¹H NMR 1.15-1.16 (m, 6H), 1.86 (d, 1H, J = 12.8 Hz), 2.17-2.22 (t, 1H, J = 11.2 Hz), 2.66-2.75 (m, 2H), 3.68-3.76 (m, 1H), 4.04-4.08 (m, 2H), 4.60 (br, 2H), 5.47 (d, 1H, J = 8.8 Hz), 6.86-6.90 (t, 1H, J = 11.2 Hz), 6.94 (s, 1H), 7.09-7.31 (m, 7H), 7.45 (d, 1H, J = 7.2 Hz), 8.24 (s, 1H)

| 1513 | | (4-((R)-1-hydroxy-2-((S)-5H-imidazo[5,1-a]isoindol-5-yl)ethyl)piperidin-1-yl)(1H-imidazol-1-yl)methanone | 50 |

¹H NMR 1.44-1.54 (m, 2H), 1.65-1.68 (m, 1H), 1.73 (d, 1H, J = 12.8 Hz), 1.98 (d, 1H, J = 13.0 Hz), 2.05-2.14 (m, 1H), 2.18-2.25 (m, 1H), 2.99 (t, 2H, J = 12.0 Hz), 3.82-3.87 (m, 1H), 4.16 (t, 2H, J = 10.7 Hz), 4.80 (br s, 1H), 5.41 (t, 1H, J = 5.9 Hz), 7.07 (s, 1H), 7.14 (s, 1H), 7.18 (s, 1H), 7.24-7.28 (m, 1H, merged with chloroform), 7.38 (t, 1H, J = 7.5 Hz), 7.43 (d, 1H, J = 7.6 Hz), 7.55 (d, 1H, J = 7.6 Hz), 7.84 (s, 1H), 7.86 (s, 1H).

Example 31

1-(1-(benzylsulfonyl)piperidin-4-yl)-2-(5H-imidazo[5,1-a]isoindol-5-yl)ethanol

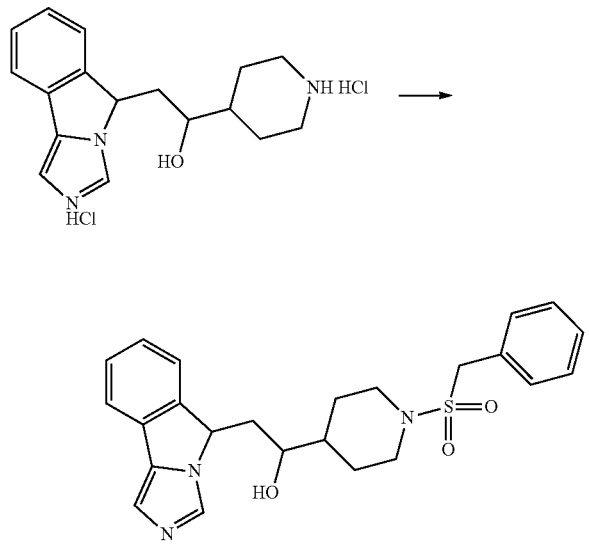

1442

To a vial 2-(5H-imidazo[5,1-a]isoindol-5-yl)-1-(piperidin-4-yl)ethanol dihydrochloride (0.12 g, 0.34 mmol) in CH$_2$Cl$_2$ (3 mL) was added ethyl diisopropylamine (0.35 mL, 2.0 mmol) and benzyl sulfonyl chloride (67 mg, 0.35 mmol). The reaction mixture was stirred at RT for 18 h and concentrated. The residue was dissolved in dichloromethane (30 mL) and washed with water (3×10 ml). The organic layer was dried over Na$_2$SO$_4$ and concentrated. The crude product was purified by flash column chromatography to afford 1442 as white solid (85 mg, 58%). $^1$H NMR (a mixture of diastereomers) 1.21-1.29 (m, 2H), 1.34-1.36 (m, 1H), 1.57-1.60 (m, 1H), 1.79-1.90 (m, 2H), 2.03-2.10 (m, 1H), 2.52-2.66 (m, 2H), 3.55-3.63 (m, 2H), 3.67-3.71 (m, 1H), 4.38 (s, 2H), 5.03 and 5.14 (two d, 1H, J=6.0 Hz, OH), 5.39 (t, 1H, J=6.8 Hz), 7.13 and 7.16 (two s, 1H), 7.29 (t, 1H, J=7.2 Hz), 7.37-7.42 (m, 6H), 7.60 (dd, 2H, J=7.8, 14.2 Hz), 7.92 and 7.95 (two s, 1H).

Example 32

2-(5H-imidazo[5,1-a]isoindol-5-yl)acetic acid

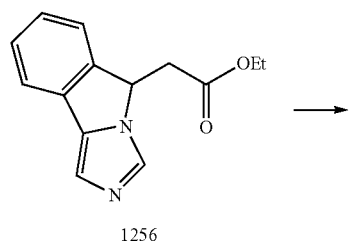

1256

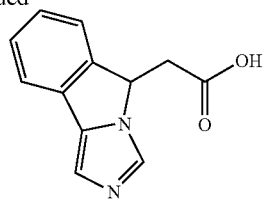

1258

To a solution of 1256 (0.41 mmol) in tetrahydrofuran (2 mL) at rt was added LiOH.H$_2$O (0.45 mmol) and water (0.5 mL) the solution was stirred overnight. The solvent was distilled off and the crude was dissolved in methanol (1.5 mL) followed by the addition of ethyl acetate (2.5 mL), the precipitated white solid was filtered, washed with ethylacetate and dried under reduced pressure to afford 1258 (68 mg, 75%). $^1$H NMR: 2.10 (dd, 1H, J=18.0 Hz, 9.0 Hz), 2.66 (dd, 1H, J=15.0 Hz, 3.0 Hz), 5.43-5.47 (m, 1H), 7.05 (s, 1H), 7.20 (t, 1H, J=9.0 Hz), 7.32 (t, 1H, J=9.0 Hz), 7.50-7.54 (m, 2H), 7.90 (s, 1H).

Example 33

2-(5H-imidazo[5,1-a]isoindol-5-yl)ethanol

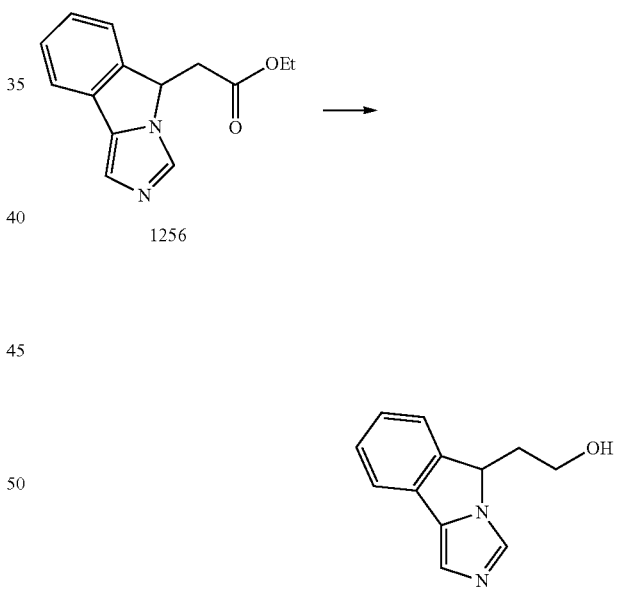

To a solution of 1256 (3.51 mmol) in a 1:2 mixture of THF:EtOH (24 mL) at rt, was added NaBH$_4$ (12.28 mmol) and LiCl (12.28 mmol). After stirring overnight, the solvents were distilled off and the crude was diluted with satd. NH$_4$Cl (20 mL). The aqueous layer was extracted with CH$_2$Cl$_2$ (3×40 mL). The combined organic extracts were dried over MgSO$_4$ and the solvent distilled off under reduced pressure to afford a crude residue. The crude product was purified by silica flash chromatography to afford 1254 (638 mg, 91%). $^1$H NMR: 2.04-2.08 (m, 1H), 2.36-2.40 (m, 1H), 3.84 (t, 2H, J=6.3 Hz), 5.37-5.41 (m, 1H), 7.17 (s, 1H), 7.25-7.28 (m, 1H), 7.35 (d, 1H, J=6.90 Hz), 7.38 (d, 1H, J=7.2 Hz), 7.54 (d, 1H, J=7.5 Hz), 7.76 (s, 1H).

Example 34

2-(5H-imidazo[5,1-a]isoindol-5-yl)-N-methylacetamide

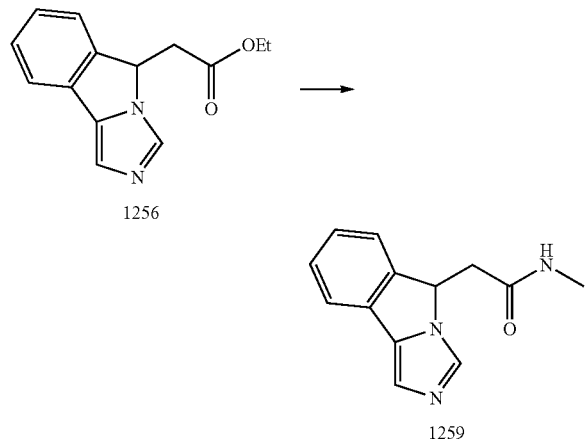

To a solution of 1256 (0.124 mmol) in tetrahydrofuran (1.5 mL) at rt, was added the methylamine solution (1.24 mmol, 0.62 mL, 2M in THF) and the solution was stirred at 60° C. overnight. After cooling to rt the solvent was distilled off under reduced pressure and the crude was purified by column chromatography to afford 1259 (21 mg, 75%). $^1$H NMR: 2.43 (dd, 1H, J=20.0 Hz, 12.8 Hz), 2.91 (d, 3H, J=4.8 Hz), 2.94 (dd, 1H, J=20.0 Hz, 6.0 Hz) 5.69 (dd, 1H, J=12.8 Hz, 5.60 Hz), 5.81 (br s, 1H), 7.13 (s, 1H), 7.22-7.26 (m, 1H), 7.33 (d, 1H, J=8.4 Hz), 7.38 (d, 1H, J=7.2 Hz), 7.53 (d, 1H, J=7.80 Hz), 7.67 (s, 1H).

Example 35

2-(SH-imidazo[5,1-a]isoindol-5-yl)acetaldehyde

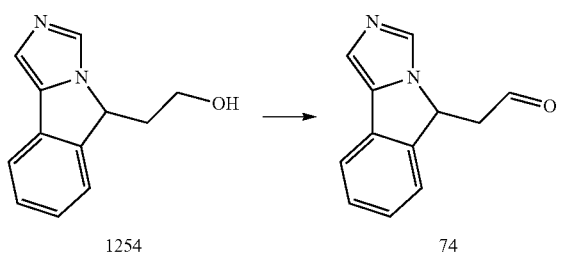 [SMILES: OCCC1c2ccccc2-c2cncn21 ; O=CCC1c2ccccc2-c2cncn21]

To a solution of 1254 (0.5 mmol) in dichloromethane (5 mL) at 0° C. was added pyridinium chlorochromate (0.6 mmol) and the solution was allowed to warm to rt. After stirring for 4 h, the solvent was distilled off under reduced pressure and the crude was purified by column chromatography to afford 74 (63 mg, 64%). $^1$H NMR: 2.99 (dd, 1H, J=7.5 Hz, 6.0 Hz), 3.28 (dd, 1H, J=12.0 Hz), 5.61-5.65 (m, 1H), 7.18 (s, 1H), 7.26-7.30 (m, 1H), 7.32 (d, 1H, J=6.0 Hz), 7.39 (t, 1H, J=6.0 Hz), 7.55 (d, 1H, J=6.0 Hz), 7.68 (s, 1H), 9.80 (s, 1H).

Example 36

(E)-5-(2-bromostyryl)-5H-imidazo[5,1-a]isoindole

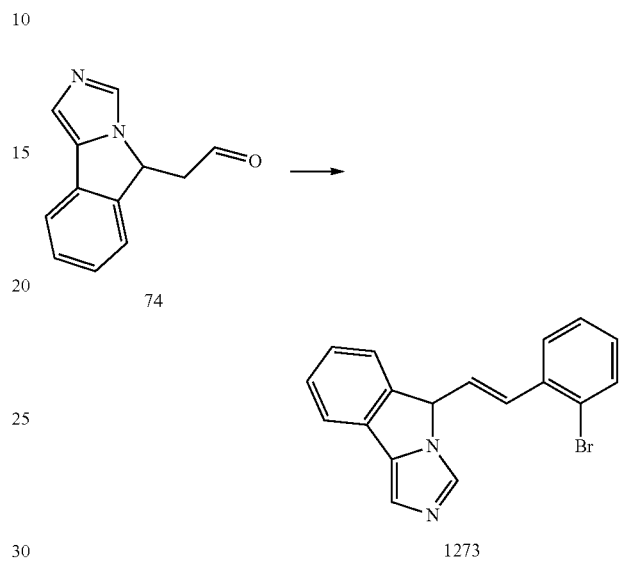

To a solution of 74 (1.21 mmol) in tetrahydrofuran (4 mL) at −20° C. was added iPrMgCl.LiCl (1.21 mmol, 1.3 M in THF) dropwise. After stirring for 1 h at −20° C., 2-(5H-imidazo[5,1-a]isoindol-5-yl)acetaldehyde was added as a solution in tetrahydrofuran (2 mL) and the reaction was allowed to warm to −10° C. After stirring for 2 h at −10° C. the reaction was quenched by adding sat'd NH$_4$Cl solution (2 mL) and water (2 mL). The aqueous layer was extracted with EtOAc (3×15 mL). The combined organic extract was dried over Na$_2$SO$_4$ and concentrated under reduced pressure to afford the crude reside. Chromatographic purification of the crude using EtOAc:MeOH (98:2) afforded 1273 (42 mg, 21%). $^1$H NMR 5.77 (d, 1H, J=6.0 Hz), 6.26 (dd, 1H, J=15.0 Hz, Hz, 6.0 Hz), 6.97 (d, 1H, J=15.0 Hz), 7.13-7.17 (m, 2H), 7.26-7.33 (m, 2H), 7.47-7.65 (m, 5H).

Example 37

2-(5H-imidazo[5,1-a]isoindol-5-yl)ethyl 2-(((1R,2R,5S)-2-isopropyl-5-methylcyclohexyl)oxy)acetate

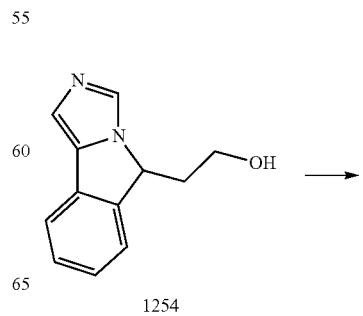

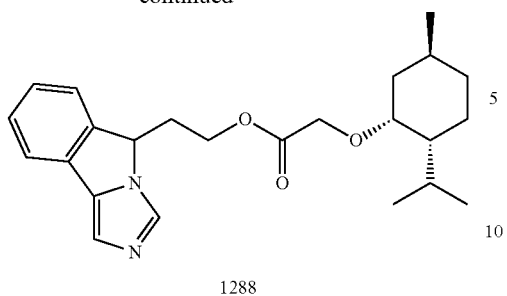

1288

To a solution of 1254 (110 mg, 0.55 mmol) in CH$_2$Cl$_2$ at 0° C. was added diisopropylethylamine (110 mg, 0.824 mmol). The mixture was allowed to stir for 5 min and 2-(((1S,2S,5R)-2-isopropyl-5-methylcyclohexyl)oxy)acetyl chloride (129 mg, 0.55 mmol) was added. The solution was allowed to warm to rt and stirred for 4 h. The reaction mixture was diluted with water (10 mL) and the organic layer was collected. The aqueous layer was extracted with CH$_2$Cl$_2$ (3×15 mL). The combined organic extract was dried (MgSO$_4$) and concentrated under reduced pressure to afford the crude product. The crude residue was purified by flash chromatography to afford 1288 (200 mg, 92%). $^1$H NMR: 0.77 (d, 3H, J=3.0 Hz), 0.75-1.25 (m, 7H) 1.23-1.31 (m, 2H), 1.54-1.72 (m, 3H), 1.98-2.03 (m, 1H), 2.20-2.28 (m, 2H), 2.50-2.54 (m, 1H), 3.09-3.14 (m, 1H), 3.97-4.15 (m, 2H), 4.27 (t, 2H, J=4.5 Hz), 5.26-5.31 (m, 1H), 7.19 (s, 1H), 7.26-7.30 (m, 1H), 7.35 (d, 1H, J=6.0 Hz), 7.39 (d, 1H, J=6.0 Hz), 7.55 (d, 1H, J=6.0 Hz), 7.75 (s, 1H).

Example 38

1-Cyclohexyl-2-(5H-imidazo[5,1-a]isoindol-5-yl)ethanamine and (E)-5-(2-Cyclohexylvinyl)-5H-imidazo[5,1-a]isoindole

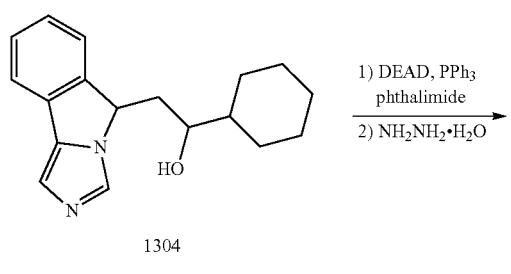

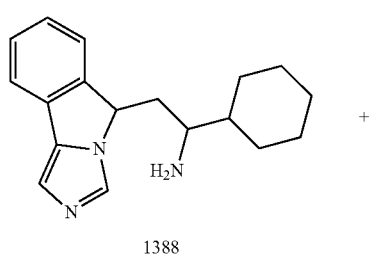

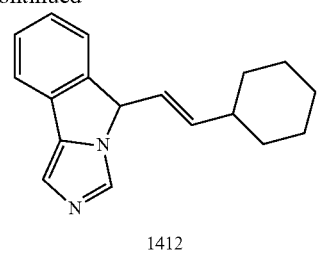

1412

To a solution of triphenylphosphine (255 mg, 0.97 mmol) in THF (10 mL) at 0° C. was added phthalimide (143 mg, 0.97 mmol) and 1304 (250 mg, 0.885 mmol) followed by the dropwise addition of DEAD (0.44 mL, 0.97 mmol). The reaction mixture was allowed to warm to room temperature and stirred overnight. The solvent was distilled off under reduced pressure, diluted with CH$_2$Cl$_2$ (30 mL) and washed successively with 10% aq NaOH (2×15 mL), water and brine. The organic layer was dried (Na$_2$SO$_4$) and the solvent was evaporated under reduced pressure to afford an off-white solid. The solid was dissolved in EtOH (5 mL) and hydrazine monohydrate (0.09 mL, 1.77 mmol) was added. The mixture was heated at 80° C. overnight. The solution was cooled to rt and the solvent was distilled off under reduced pressure. The crude was diluted with CH$_2$Cl$_2$ (20 mL) and the organic phase was washed with water (10 mL). The organic layer was dried (Na$_2$SO$_4$) and the solvent was evaporated under reduced pressure to afford a crude residue that was purified by column chromatography to afford 1388 as a white solid (50 mg, 14%) and an eliminated side product 1412 (30 mg). 1388 $^1$H NMR: 0.97-1.24 (m, 7H), 1.62-1.71 (m, 6H), 2.0 (m, 1H), 2.89 (m, 1H), 5.34 (dd, 1H, J=8.4 Hz, 15.6 Hz), 5.38 and 5.49 (two m, 1H), 7.15 (s, 1H), 7.24 (m, 1H), 7.31-7.52 (m, 3H), 7.77 and 7.81 (two s, 1H). 1412 $^1$H NMR: 1.11-1.28 (m, 5H), 1.55-1.75 (m, 5H), 2.01-2.11 (m, 1H), 5.47 (d, 1H, J=8.0 Hz), 6.01 (dd, 1H, J=6.8 Hz, 15.0 Hz), 7.18 (s, 1H), 7.26 (m, 2H), 7.36 (m, 1H), 7.52 (d, 1H, J=7.6 Hz), 7.64 (s, 1H).

Example 39

4-(2-(6-fluoro-5H-imidazo[5,1-a]isoindol-5-yl)-1-hydroxyethyl)cyclohexanone

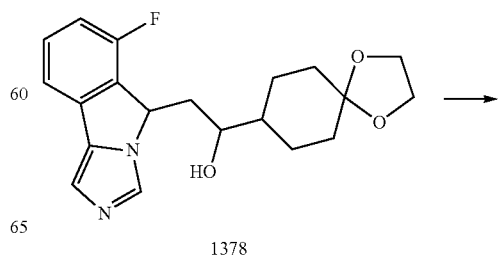

1378

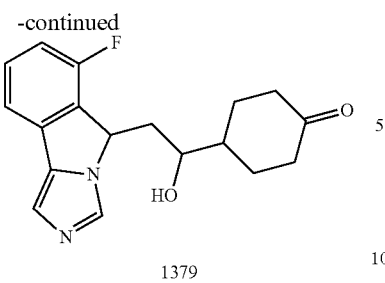

1379

To a solution of 1378 (186 mg, 0.52 mmol) in THF (5 mL) was added 2M HCl (5 mL) and the solution was stirred at room temperature overnight. The solvent was removed in vacuo and remaining solution basified with 2M aqueous NaOH (6 mL) to pH>8.0. The aqueous solution was extracted with dichloromethane (2×50 mL) and the combined organic layers were dried ($Na_2SO_4$) and concentrated in vacuo to give 1379 as a white solid (155 mg, 95%).

$^1$H NMR: ($CD_3OD$) 1.23-2.51 (m, 11H), 3.53-3.77 (m, 2H), 5.60-5.75 (m, 1H), 7.03-7.08 (m, 1H), 7.26-7.27 (m, 1H), 7.43-7.44 (m, 1H), 8.13 and 8.21 (two s, 1H).

Example 40

1-(4-(Hydroxymethyl)cyclohexyl)-2-(5H-imidazo[5,1-a]isoindol-5-yl)etanol (1383)

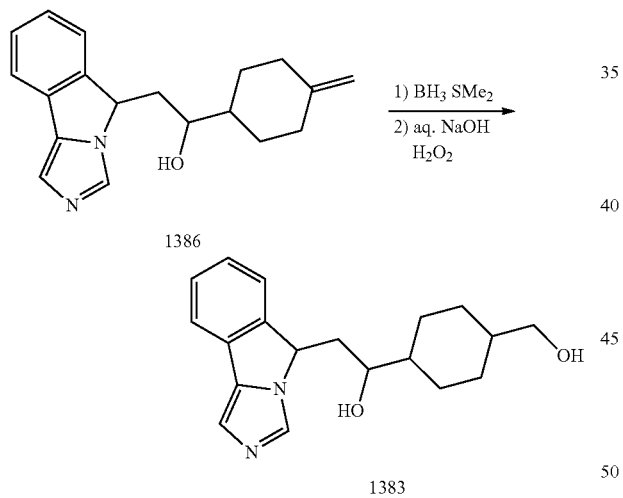

To a solution of 1386 (121 mg, 0.41 mmol) in dry THF (10 mL) at 0° C. was added $BH_3 \cdot SMe_2$ (0.05 mL, 0.53 mmol). The reaction mixture was allowed to warm to room temperature and stirred overnight under an atmosphere of $N_2$. The solution was diluted with water (10 mL) and cooled to 0° C. 3M NaOH (0.55 mL, 1.64 mmol) and 30% (w/w) hydrogen peroxide solution (0.19 mL, 1.64 mmol) were added sequentially. The reaction mixture was allowed to stir overnight at room temperatura. The aqueous layer was extracted with $CH_2Cl_2$ (3×40 mL). The combined organic layers were ($Na_2SO_4$) and concentrated under reduced pressure. The crude residue was purified by flash column chromatography to afford 1383 as a white solid (45 mg, 35%). $^1$H NMR MeOH-$d_4$: 1.20-1.78 (m, 11H), 2.02-2.22 (m, 2H), 3.46-3.51 (m, 2H), 3.78-3.88 (m, 2H), 5.38-5.44 (m, 1H), 7.12 and 7.14 (two s, 1H), 7.27-7.46 (m, 2H), 7.52-7.61 (m, 2H), 7.92 and 7.95 (two s, 1H).

Example 41

1-(5H-imidazo[5,1-a]isoindol-5-yl)-2-methylpropan-2-ol

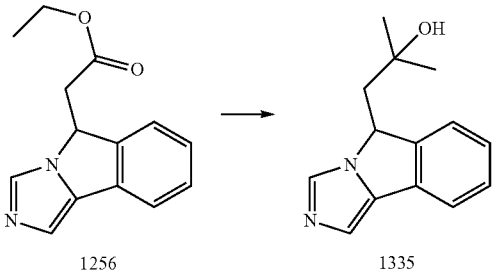 [SMILES: CCOC(=O)CC1c2ccccc2-c2cncn21 ; CC(C)(O)CC1c2ccccc2-c2cncn21]

To a stirred solution of 1256 (48 mg, 0.20 mmol) in THF at 0° C. was added MeMgBr 1.0 M in THF (0.4 mL,) dropwise. The resulting solution was allowed to stir at rt for 2 h. The reaction was quenched by the careful addition of methanol to the reaction mixture. The crude mixture was concentrated, absorbed in silica gel and purified by column chromatography to afford 1335 (24 mg, 52%). $^1$H NMR 1.43 (s, 3H), 1.49 (s, 3H), 2.05-2.30 (m, 2H), 5.30-5.35 (m, 1H), 7.14 (s, 1H), 7.20-7.40 (m, 3H), 7.52 (d, 1H, J=9.6 Hz), 8.02 (s, 1H).

Example 42

4-(2-(6-Fluoro-5H-imidazo[5,1-a]isoindol-5-yl)-1-hydroxyethyl)cyclohexanol

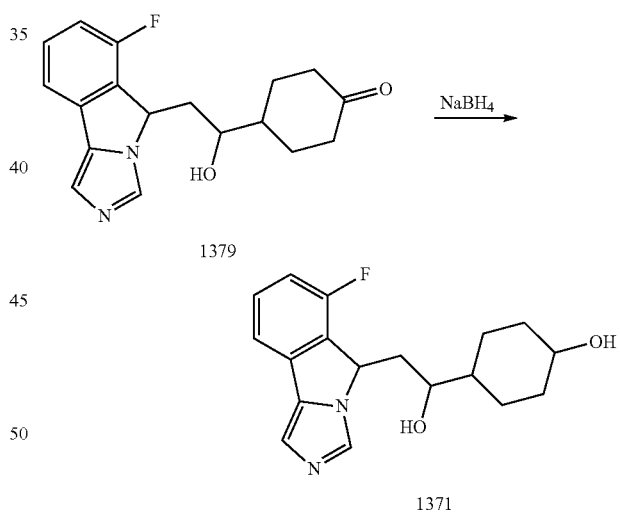

To a mixture of 1379 (38 mg, 0.12 mmol) in anhydrous MeOH at 0° C., was added $NaBH_4$ (0.36 mmol) and the solution was allowed to stir for 2 h at rt. The solvent was distilled off under reduced pressure and the residue was partitioned between $CH_2Cl_2$ (15 mL) and satd. $NH_4Cl$ (5 mL). The organic layer was collected and the aqueous layer was extracted with $CH_2Cl_2$ (2×10 mL). The combined organic extract was washed with brine, dried ($Na_2SO_4$) and the solvent evaporated. The crude was purified by column chromatography (25% MeOH in EtOAc) to afford 1371 (29 mg, 76%). $^1$H NMR MeOH-$d_4$ (mixture of diastereomers): 1.00-1.40 (m, 5H), 1.40-2.10 (m, 5H), 2.37-2.47 (m, 1H), 3.39-3.57 (m, 2H), 5.54 and 5.72 (two m, 1H), 6.98-7.06 (m, 1H), 7.15-7.18 (m, 1H), 7.37-7.42 (m, 2H), 7.93-7.99 (m, 1H).

Example 43

1-cyclohexyl-2-(5H-imidazo[5,1-a]isoindol-5-yl)ethanone oxime

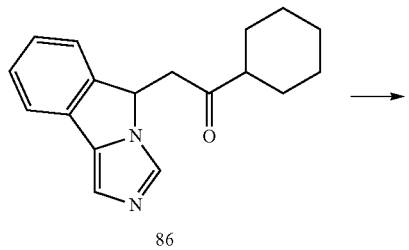

86

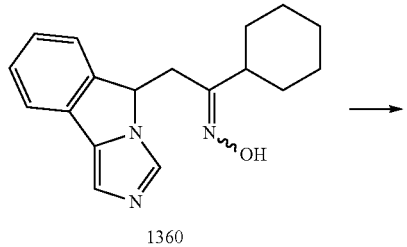

1360

To a solution of 86 (160 mg, 0.57 mmol) in EtOH (3 mL) at rt was added 50% aq NH$_2$OH (1.71 mmol) and the solution was stirred at 50° C. overnight. After cooling to rt, the solvent was removed under reduced pressure and the crude was purified by flash column chromatography to afford 1360 (120 mg, 71%). $^1$H NMR 0.99-1.15 (m, 5H), 1.45-1.72 (m, 6 H), 2.43 and 2.58 (two m, 1H), 2.70 and 2.91 (m, 1H), 4.69 (m, 1H), 7.23-7.29 (m, 3H), 7.40 and 7.46 (two m, 1H), 7.53 and 7.58 (two m, 1H), 7.75 and 7.76 (two s, 1H), 10.34 and 10.41 (two s, 1H).

Example 44

1-cyclohexyl-2-(5H-imidazo[5,1-a]isoindol-5-yl)ethanamine

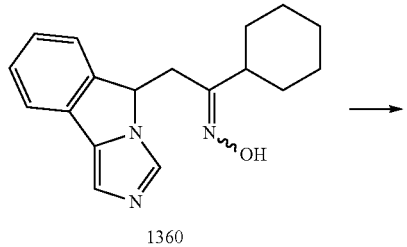

1360

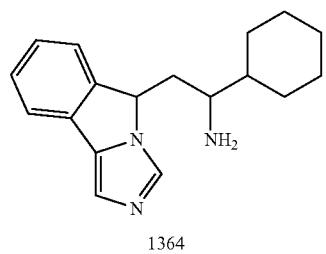

1364

To a solution of 1360 (100 mg, 0.34 mmol) in 1:1 EtOH/AcOH (4 mL) was added zinc powder (67 mg, 1.0 mmol) and the mixture was stirred overnight at it. The solvent was removed under reduced pressure and the mixture was suspended in 1:1 MeOH/DCM (10 mL) and filtered. The filtrate was collected and concentrated under reduced pressure. The crude was purified by ion-exchange chromatography using water and NH$_4$OH as the eluent to afford 1364 (25 mg, 26%). $^1$H NMR (mixture of diastereomers) 0.89-1.75 (m, 11H), 2.24 and 2.42 (two m, 1H), 2.62 (m, 1H), 4.52 (m, 1H), 7.09 (t, 1H, J=9.2 Hz), 7.29 (m, 2H), 7.38 (m, 1H), 7.47 (m, 1H), 7.60 (d, 1H, J=9.2 Hz).

Example 45

General Procedure for the Removal the BOC Protecting Group from Substituted Anilines and Amines

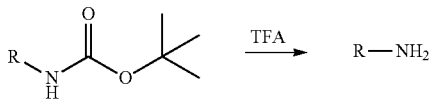

To a solution of 17, 1300, 1328 or 1363 (66.0 µmol) in dichloromethane (2 mL) was added trifluoroacetic acid (0.2 mL, 2.66 mmol) and the mixture was stirred at it for 2 h. The solvents were distilled off under reduced pressure and the solution was basified with satd. NaHCO$_3$. The aqueous layer was extracted with EtOAc (3×15 mL). The combined organic layers were washed with water, brine and dried (Na$_2$SO$_4$). The solution as filtered and the solvent removed under reduced pressure. The crude residue was purified by column chromatography to afford the following compounds.

| # | Compound | Name | Yield (%) |
|---|---|---|---|
| 1330 | | 1-(2-aminophenyl)-2-(5H-imidazo[5,1-a]isoindol-5-yl)ethanone | 76 |

$^1$H NMR 3.40 (dd, 1H, J = 18.0 Hz, 9.6 Hz), 3.70 (dd, 1H, J = 18.0 Hz, 3.3 Hz), 5.81 (dd, 1H, J = 6.3 Hz, J = 3.3 Hz), 6.43 (br s, 2H), 6.60 (t, 1H, J = 7.5 Hz), 6.68 (d, 1H, J = 8.4 Hz), 7.18 (s, 1H), 7.29 (m, 2H), 7.36 (d, 2H, J = 7.8 Hz), 7.55 (d, 2H, J = 7.5 Hz), 7.74 (s, 1H)

-continued

| # | Compound | Name | Yield (%) |
|---|---|---|---|
| 1370 | | 2-(5H-imidazo[5,1-a]isoindol-5-yl)-1-(piperidin-4-yl)ethanol | 15 |

¹H NMR (Mixture of diastereomers) 1.66-1.87 (m, 6H), 2.20 (s, 1H), 2.75 (m, 2H), 3.40 (m, 2H), 3.84 (m, 2H), 5.27 and 5.34 (two m, 1H), 7.05 (s, 1H), 7.19 (t, 1H, J = 4.0 Hz), 7.30 (t, 1H, J = 8.0 Hz), 7.38 (d, 1H, J = 8.0 Hz), 7.46 (d, 1H, J = 8.0 Hz), 8.06 and 8.12 (two s, 1H)

| 1301 | | 1-(4-aminophenyl)-2-(5H-imidazo[5,1-a]isoindol-5-yl)ethanone | 87 |

¹H NMR 3.35 (dd, 1H, J = 18.6 Hz, 9.6 Hz), 3.61 (dd, 1H, J = 18.6 Hz, 9.6 Hz), 4.13 (br s, 2H), 5.84 (dd, 1H, J = 18.6 Hz, 9.6 Hz), 6.65 (d, 2H, J = 8.7 Hz), 7.18 (s, 1H), 7.24-7.29 (m, 1H), 7.37-7.58 (m, 3H), 7.74-7.82 (m, 3H)

| 1369 | | 1-(3-aminophenyl)-2-(5H-imidazo[5,1-a]isoindol-5-yl)ethanol | 58 |

(MeOH-d₄) 2.32 (t, 2H, J = 6.3 Hz), 4.89-4.94 (m, 1H), 5.30 and 5.38 (two m, 1H), 6.64 (d, 1H, J =7.8 Hz), 6.71-6.77 (m, 2H), 7.05-7.10 (m, 1H), 7.28-7.41 (m, 2H), 7.51-7.58 (m, 2H), 7.66 (s, 1H).

Example 46

5-(2-Cyclohexyl-2-hydroxyethyl)-5H-imidazo[5,1-a]isoindol-9-ol

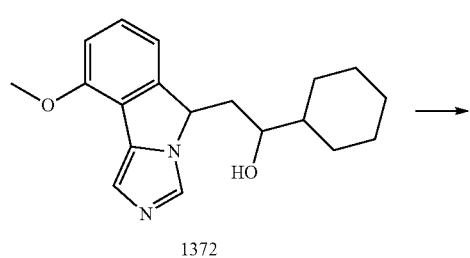

1372

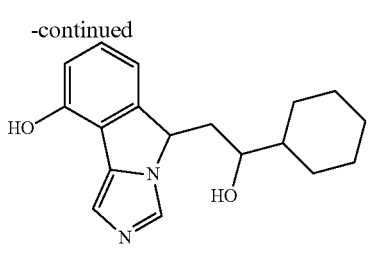

1373

To a solution of 1372 (28 mg, 0.09 mmol) in DCM (3 mL) at 0° C. was added BBr₃ (1 M in DCM, 0.27 mL, 0.27 mmol) dropwise and the mixture was allowed to stir at 0° C. for 2 h. Saturated aqueous NaHCO₃ was added and the aqueous layer was extracted with DCM (2×10 mL). The combined organic layers were dried (Na₂SO₄) and concentrated under reduced pressure. The residue was purified by flash column chromatography to afford 1373 (15 mg, 56%). ¹H NMR MeOH-d₄: (mixture of diastereomers) 1.04-1.12 (m, 1H), 1.15-1.33 (m, 4H), 1.62-1.86 (m, 5H), 2.00-2.07 (m, 1H), 3.55 and 3.70 (two m, 1H), 5.38 and 5.44 (two m, 1H), 6.80 and 6.81 (two d, 1H, J=8.0 Hz), 6.90 and 6.99 (two d, 1H, J=7.6 Hz), 7.03 and 7.05 (two s, 1H), 7.12-7.16 (m, 1H), 7.93 and 7.99 (two s, 1H).
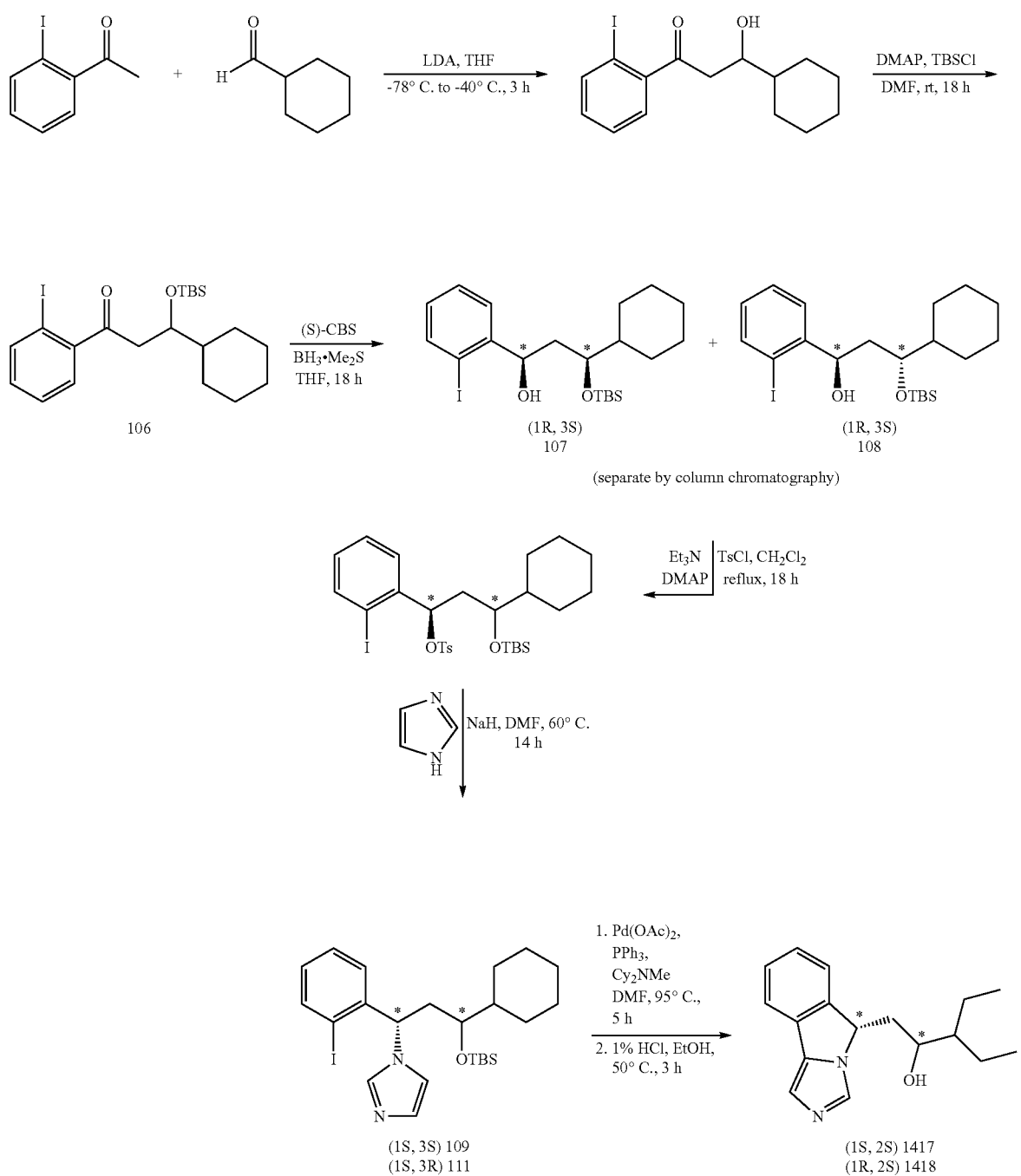
Scheme 3. Enantioselective Synthesis of (S)-1-cyclohexyl-2-((S)-5H-imidazo[5,1-a]isoindol-5-yl)ethanol (1417) and (R)-1-cyclohexyl-2-((S)-5H-imidazo[5,1-a]isoindol-5-yl)ethanol (1418)

Example 47

3-Cyclohexyl-3-hydroxy-1-(2-iodophenyl)propan-1-one

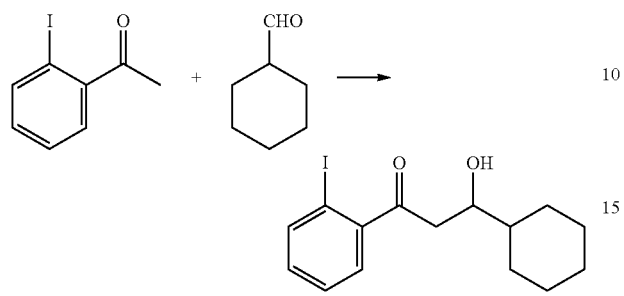

To a solution of diisopropylamine (1.6 mL, 11.1 mmol) in THF (38 mL) at 0° C. was added n-BuLi (4.1 mL, 10.2 mmol) under an atmosphere of $N_2$. After 30 min the solution was cooled to −30° C. and a solution of 1-(2-iodophenyl)ethanone (2.27 g, 9.23 mmol) in THF (6 mL) was added dropwise to the mixture and was stirred for 45 min at −30° C. The mixture was cooled to −78° C. and cyclohexylcarboxaldehyde (1.2 mL, 9.69 mmol) was added dropwise and the mixture was allowed to warm to −40° C. over 2 h. The reaction was quenched by the addition of saturated aqueous $NH_4Cl$. The aqueous layer was extracted with EtOAc (2×50 mL). The combined organic layers were washed with brine, dried ($Na_2SO_4$), filtered and concentrated. The residue was purified by flash column chromatography to afford the title compound as yellow oil (2.56 g, 78%). $^1$H NMR: 1.02-1.27 (m, 4H), 1.41-1.49 (m, 1H), 1.66-1.76 (m, 4H), 1.89 (d, 1H, J=12.4 Hz), 2.88 (d, 1H, J=3.2 Hz), 2.98 (dd, 1H, J=9.2 Hz, 17.2 Hz), 3.13 (dd, 1H, J=2.0 Hz, 17.2 Hz), 3.99-4.01 (m, 1H), 7.11-7.15 (m, 1H), 7.42 (d, 2H, J=4.4 Hz), 7.93 (d, 1H, J=8.0 Hz).

Example 48

3-(tert-Butyldimethylsilyloxy)-3-cyclohexyl-1-(2-iodophenyl)propan-1-one

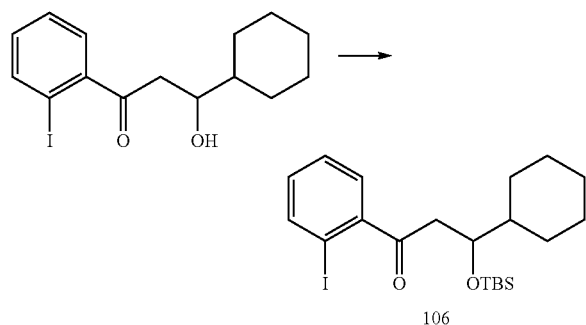

To a solution of 3-Cyclohexyl-3-hydroxy-1-(2-iodophenyl)propan-1-one (2.56 g, 7.15 mmol) and DMAP (1.05 g, 8.58 mmol) in DMF (40 mL) was added TBSCl (1.62, 10.7). The reaction mixture was stirred at rt for 18 h and poured into water (40 mL). The aqueous layer was extracted with EtOAc (2×50 mL) and the combined organic layers were washed with water (2×20 mL), brine (10 mL), dried ($Na_2SO_4$), filtered and concentrated. The crude was purified by flash column chromatography to afford 106 as clear oil (3.15 g, 93%). $^1$H NMR: 0.01 (s, 3H), 0.08 (s, 3H), 0.86 (s, 9H), 1.12-1.24 (m, 6H), 1.43-1.52 (dt, 1H, J=3.6 Hz, 15.2 Hz), 1.65-1.76 (m, 4H), 2.91 (dd, 1H, J=6.8 Hz, 22.0 Hz), 3.1 (dd, 1H, J=9.4 Hz, 22.0 Hz), 4.19-4.24 (m, 1H), 7.11 (dt, 1H, J=2.4 Hz, 10.0 Hz), 7.40 (t, 1H, J=9.6 Hz), 7.48 (dd, 1H, J=2.4 Hz, 10.4 Hz), 7.92 (d, 1H, J=10.4 Hz).

Example 49

(1R,3R)-3-(tert-Butyldimethylsilyloxy)-3-cyclohexyl-1-(2-iodophenyl)propan-1-ol and (1R,3S)-3-(tert-butyldimethylsilyloxy)-3-cyclohexyl-1-(2-iodophenyl)propan-1-ol

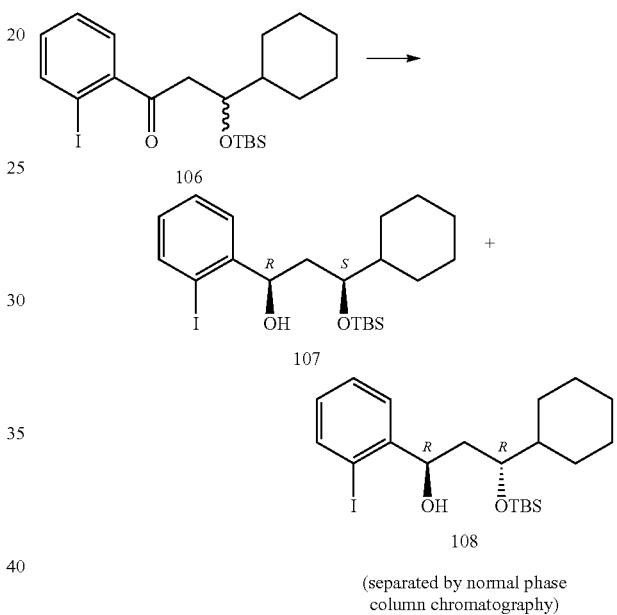

(separated by normal phase column chromatography)

A mixture of 106 (3.15 g, 6.67 mmol), $BH_3.SMe_2$ (0.63 mL, 6.67 mmol) and S-2-methyl-CBS-oxazaborolidine (370 mg, 1.33 mmol) in THF (50 ml) was stirred at room temperature for 16 h. Aqueous 6 M HCl (4 mL) was added and the mixture was stirred for 5 minutes. The mixture was poured into water (20 mL) and the aqueous layer was extracted with EtOAc (2×40 mL). The combined organic layers were washed with brine (20 mL), dried ($Na_2SO_4$), filtered and concentrated. The residue was purified by flash column chromatography (3%-6% EtOAc/hexanes gradient). The two diastereomers 107 and 108 were separated in this manner. The stereochemistry was confirmed by developing 107 and 108 on a normal phase analytical silica gel TLC plate against an authentic sample of 108. An authentic sample of 108 was prepared independently by an enantioselective aldol reaction as outlined in Scheme 4. $^1$H NMR: (1R,3S): 0.15 (s, 3H), 0.18 (s, 3H), 0.87 (s, 9H), 1.08-1.27 (m, 5H), 1.52-1.68 (m, 4H), 1.75-1.89 (m, 4H), 4.02-4.10 (m, 1H), 4.91 (d, 1H, J=9.6 Hz), 6.95 (t, 1H, J=6.8 Hz), 7.37 (t, 1H, J=7.4 Hz), 7.61 (d, 1H, J=6.8 Hz), 7.78 (d, 1H, J=7.2 Hz). $^1$H NMR: (1R,3R): 0.12 (s, 3H), 0.16 (s, 3H), 0.88-0.93 (m, 2H), 0.97 (s, 9H), 1.12-1.17 (m, 1H), 1.27-1.31 (m, 2H), 1.57-1.79 (m, 5H), 1.91-2.07 (m, 3H), 3.70-3.72 (m, 1H), 4.19 (s, 1H), 5.20 (d, 1H, J=10.4 Hz), 6.94 (t, 1H, J=6.8 Hz), 7.38 (t, 1H, J=7.4 Hz), 7.60 (d, 1H, J=7.2 Hz), 7.77 (d, 1H, J=7.2 Hz).

Example 50

(1R,3S)-3-(tert-Butyldimethylsilyloxy)-3-cyclohexyl-1-(2-iodophenyl)propyl-4-methylbenzenesulfonate

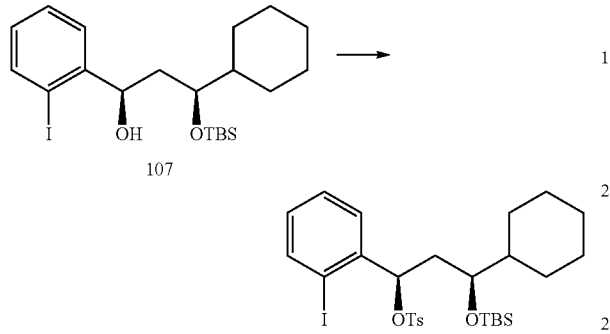

To a solution of 107 or 108 (300 mg, 0.63 mmol) in dichloromethane (5 mL) was added triethylamine (0.18 mL, 1.26 mmol) and DMAP (85 mg, 0.70 mmol. The reaction mixture was stirred at room temperature for 5 min and p-toluenesulfonyl chloride (145 mg, 0.76 mmol) was added. The reaction mixture was refluxed for 18 h. The solvent was removed under reduced pressure. The residue was dissolved in EtOAc (30 ml) and the organic layer was washed with water (10 ml), satd aq NaHCO$_3$ (15 mL) and brine. The organic layer was dried (Na$_2$SO$_4$), filtered and concentrated. The title compound was used in the next step without further purification.

Example 51

(1R,3R)-3-(tert-Butyldimethylsilyloxy)-3-cyclohexyl-1-(2-iodophenyl)propyl-4-methylbenzenesulfonate

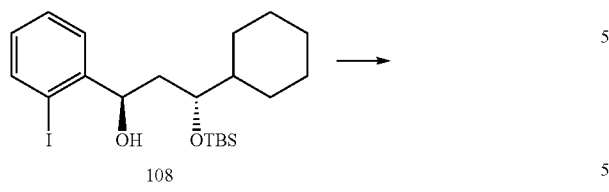

(1R,3R)-3-(tert-Butyldimethylsilyloxy)-3-cyclohexyl-1-(2-iodophenyl)propyl-4-methylbenzenesulfonate was prepared as described in the above procedure. The title compound was used in the next step without further purification.

Example 52

1-((1S,3S)-3-(tert-Butyldimethylsilyloxy)-3-cyclohexyl-1-(2-iodophenyl)propyl)-1H-imidazole

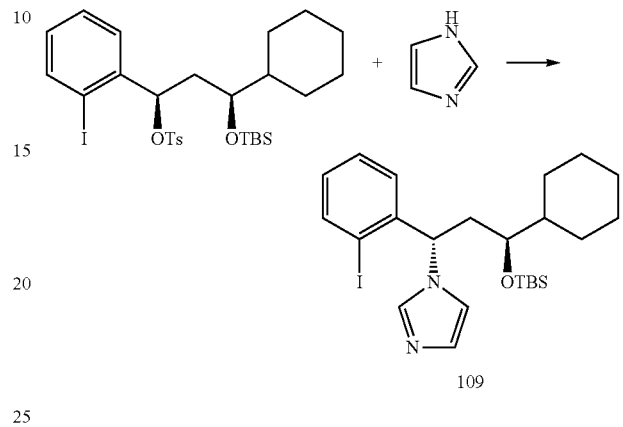

To a suspension of NaH (55 mg, 2.17 mmol) in dry DMF (4 mL) was added imidazole (148 mg, 2.17 mmol). The solution was stirred for 2 h and a solution of (1R,3S)-3-(tert-butyldimethylsilyloxy)-3-cyclohexyl-1-(2-iodophenyl)propyl 4-methylbenzenesulfonate (341 mg, 0.54 mmol) in DMF (2 mL) was added. The reaction mixture was heated at 60° C. for 14 h. The reaction mixture was poured into water (10 mL) and the aqueous layer was extracted with EtOAc (2×20 mL). The combined organic layers were washed with water (2×10 mL), brine (10 mL), dried (Na$_2$SO$_4$), filtered and concentrated. The residue was purified by flash column chromatography to afford 109 as clear gel (130 mg, 46%). $^1$H NMR: (1S, 3S) 0.03 (s, 3H), 0.05 (s, 3H), 0.97 (s, 9H), 1.11-1.31 (m, 5H), 1.53-1.59 (m, 2H), 1.68-1.79 (m, 4H), 2.20-2.23 (m, 2H), 3.59-3.62 (m, 1H), 5.75-5.79 (m, 1H), 7.01-7.13 (m, 3H), 7.17 (s, 1H), 7.34-7.37 (m, 1H), 7.73 (s, 1H), 7.93 (d, 1H, J=7.8 Hz).

Example 53

1-((1S,3R)-3-(tert-Butyldimethylsilyloxy)-3-cyclohexyl-1-(2-iodophenyl)propyl)-1H-imidazole (78)

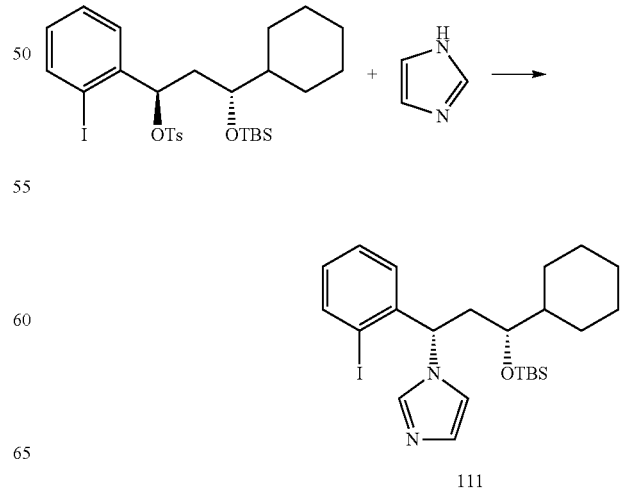

Compound III was prepared as described for compound 109 in the above procedure. 111 was isolated as a clear gel (42% over two steps). ¹H NMR: (1S,3R) 0.05 (s, 3H), 0.07 (s, 3H), 0.97 (s, 9H), 1.12-1.29 (m, 5H), 1.47-1.50 (m, 1H), 1.69-1.77 (m, 3H), 1.82-1.85 (m, 2H), 2.20-2.28 (m, 1H), 2.39-2.47 (m, 1H), 3.56-3.60 (m, 1H), 5.63 (t, 1H, J=7.4 Hz), 6.97-6.98 (m, 1H), 7.04-7.11 (m, 2H), 7.31-7.34 (m, 2H), 7.45 (dt, 1H, J=1.0 Hz, 7.6 Hz), 7.64 (s, 1H), 7.96 (dd, 1H, J=1.2 Hz, 8.0 Hz).

Example 54

(S)-5-((S)-2-(tert-Butyldimethylsilyloxy)-2-cyclohexylethyl)-5H-imidazo[5,1-a]isoindole

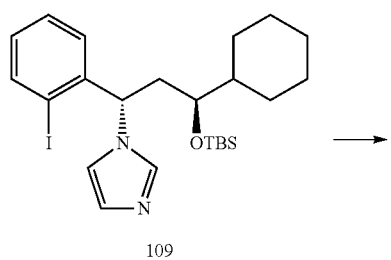
109

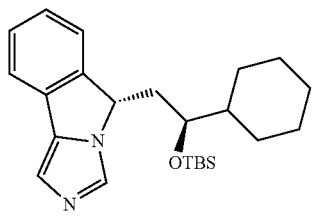
109a

To a vial containing 109 (65 mg, 0.12 mmol) was added dicyclohexylmethylamine (0.04 mL, 0.19 mmol), PPh₃ (13 mg, 0.05 mmol) and DMF (4 mL). The mixture was degassed for 10 min and Pd(OAc)₂ (6 mg, 25 mol) was added. The mixture was heated at 95° C. for 5 h. After cooling to rt, the mixture was diluted with ethyl acetate (15 mL) and passed through a Celite pad. The filter cake was washed with ethyl acetate. The organic layer was washed with water (3×10 mL), brine (10 mL), dried (Na₂SO₄), filtered and concentrated. The crude residue was used directly in the next step.

Example 55

(S)-5-((R)-2-((tert-butyldimethylsilyl)oxy)-2-cyclohexylethyl)-5H-imidazo[5,1-a]isoindole

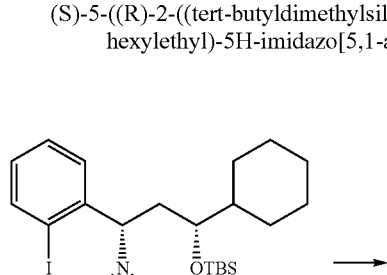
111

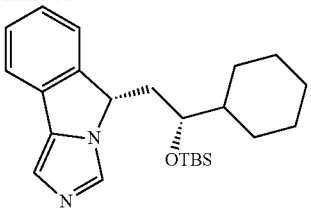
111a

Compound 111a was prepared as described in the above procedure. The crude residue was used directly in the next step.

Example 56

(S)-1-cyclohexyl-2-((S)-5H-imidazo[5,1-a]isoindol-5-yl)ethanol (1417)

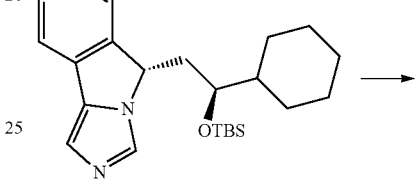
109a

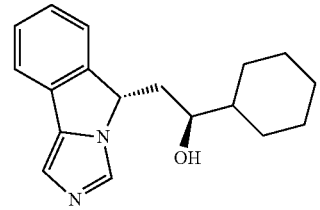
1417

To a vial containing crude 109a (60 mg, 0.15 mmol) was added 1% HCl in ethanol (2 mL). The reaction mixture was heated at 50° C. for 3 h and poured into saturated aqueous NaHCO₃ (5 mL). The aqueous layer was extracted with dichloromethane (2×15 mL). The combined organic layers were dried (Na₂SO₄), filtered and concentrated. The residue was purified by flash column chromatography to afford 1417 as a white solid (17 mg, 47% over 2 steps). ¹H NMR: (1S,2S) 1.02-1.28 (m, 5H), 1.40-1.42 (m, 1H), 1.67-1.83 (m, 4H), 1.91 (d, 1H, J=12.4 Hz), 2.22-2.30 (m, 1H), 2.82 (br s, 1H), 3.80-3.83 (m, 1H), 5.52 (dd, 1H, J=3.0 Hz, 10.8 Hz), 7.20 (s, 1H), 7.25-7.29 (m, 1H), 7.36-7.40 (m, 2H), 7.56 (d, 1H, J=7.6 Hz), 7.84 (s, 1H). Absolute configuration of this diasteromer was confirmed by X-ray crystallography of HBr:1417 salt crystals (FIG. 1).

Example 57

(R)-1-cyclohexyl-2-((S)-5H-imidazo[5,1-a]isoindol-5-yl)ethanol (1418)

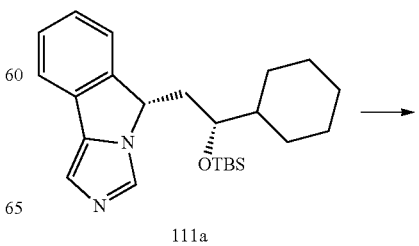
111a

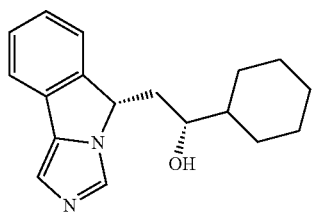

1418

Compound 1418 was prepared as described for compound 111a in the above procedure. 1418 was isolated as a colorless solid (42% over 2 steps). $^1$H NMR: (1S,2R) 0.97-1.26 (m, 5H), 1.32-1.39 (m, 1H), 1.63-1.67 (m, 2H), 1.71-1.80 (m, 3H), 2.00-2.06 (m, 1H), 2.10-2.18 (m, 1H), 2.55 (br s, 1H), 3.70-3.74 (m, 1H), 5.35 (t, 1H, J=7.6 Hz), 7.14 (s, 1H), 7.19-7.23 (m, 1H), 7.34 (t, 1H, J=7.6 Hz), 7.42 (d, 1H, J=7.4 Hz), 7.52 (d, 1H, J=7.4 Hz), 7.78 (s, 1H).

Example 58

(trans)-1-hydroxy-2-(5H-imidazo[5,1-a]isoindol-5-yl)ethyl)cyclohexanecarboxylic acid (1436)

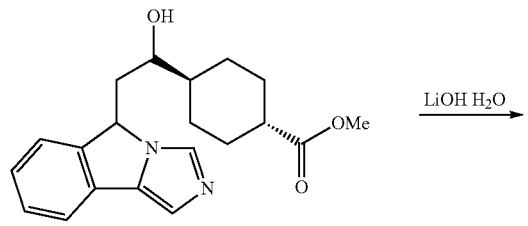

1436

To a solution of 1426 (268 mg, 0.79 mmol) in THF:Water 3:1 (4 mL) was added lithium hydroxide monohydrate (99 mg, 2.36 mmol). The solution was allowed to stir for 18 h. The THF was removed under reduced pressure and the solution was neutralized to pH=5 with 1M HCl. The solution was concentrated under reduced pressure and to the remaining residue was added 20% MeOH/DCM. The residue was filtered through a plug of silica gel and the plug was eluted with 200 mL 20% MeOH/DCM. The solution was concentrated to afford the NLG-1436 as a light yellow solid 193 mg (75%). $^1$H NMR (DMSO-d6): 0.83-0.85 (m, 1H), 1.05-1.25 (m, 4H), 1.41-1.45 (m, 2H), 1.85-1.88 (m, 3H), 2.03-2.21 (m, 2H), 3.61-3.64 (m, 1H), 5.35-5.42 (m, 1H), 7.11 and 7.13 (two s, 1H), 7.27 (t, 1H, J=7.0 Hz), 7.37 (t, 1H, J=7.4 Hz), 7.49 and 7.56 (two d, 1H, J=7.5 Hz), 7.59 (d, 1H, J=7.5 Hz), 7.88 and 7.92 (two s, 1H), 11.98 (br s, 1H).

Example 59

1-((trans)-4-(hydroxymethyl)cyclohexyl)-2-(5H-imidazo[5,1-a]isoindol-5-yl)ethanol (NLG-1430)

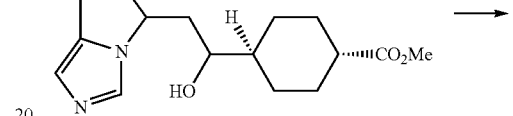

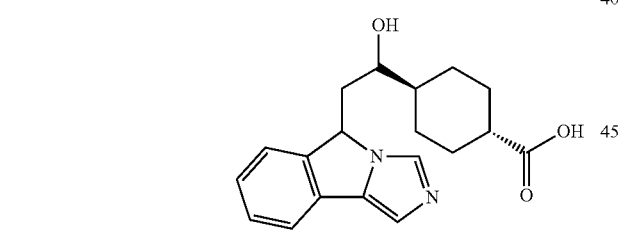

1430

To a solution of 1426 (100 mg, 0.30 mmol) in THF:EtOH (3 mL, 1:2 ratio) at rt, was added NaBH$_4$ (48.1 mg, 1.27 mmol) and LiCl (53.9 mg, 1.27 mmol). The reaction mixture was stirred overnight. The solvents were removed under reduced pressure and the crude residue was diluted with sat'd NH$_4$Cl (20 mL). The product was extracted with EtOAc (3×10 mL). The combined organic extract was dried over Na2SO4 and the solvent was removed under reduced pressure. The crude product was purified by silica flash chromatography to afford 1430 (78 mg, 85%). $^1$H NMR (a mixture of diastereomers) 0.94-1.13 (m, 4H), 1.14-2.18 (m, 10H), 3.45 (d, J=6.3 Hz, 2H), 3.73-3.78 (m, 1H), 5.30-5.38 (m, 1H), 7.17 (s, 1H), 7.22-7.27 (m merged with CHCl$_3$, 1H), 7.33-7.44 (m, 2H), 7.54 (d, J=7.6 Hz, 1H), 7.83 (d, J=10.4 Hz, 1H).

Example 60

(trans)-1-hydroxy-2-(5H-imidazo[5,1-a]isoindol-5-yl)ethyl)-N-(2-methylsulfonamido)ethyl)cyclohexanecarboxamide (1432)

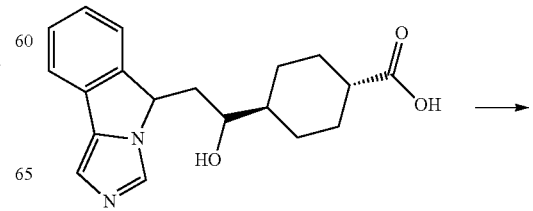

-continued

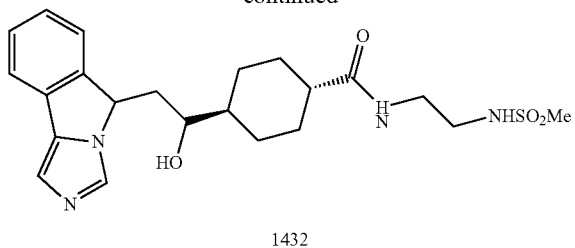

1432

To a vial containing N-(2-aminoethyl)methanesulfonamide dihydrochloride (56.4 mg, 0.27 mmol) in DMF (4 mL) was added 1436 (83 mg, 0.25 mmol), DIPEA (197 mg, 1.53 mmol) and HATU (106 mg, 0.28 mmol). The reaction was stirred at RT for 18 h and concentrated. The residue was purified by column chromatography on silica gel using hexanes/EtOAc 10%->60% gradient. The compound was isolated as a light yellow solid 72 mg (64%). $^1$H NMR: (CD3OD) 1.04-1.14 (m, 2H), 1.38-1.46 (m, 3H), 1.73-1.96 (m, 4H), 2.11-217 (m, 2H), 2.32-2.38 (m, 1H), 2.93 and 2.97 (two s, 3H), 3.15 (t, 1.7H, J=6.4 Hz), 3.29-3.31 (m overlap with, 1H), 3.54-3.58 and 3.78-3.80 (two m, 1H), 5.57-5.66 (t and dd, 1H, J=6.3 and J=2.6, 9.2H), 7.33-7.47 (m, 3H), 7.52 and 7.60 (two d, 1H, J=7.6 Hz), 7.68-7.71 (m, 0.8H), 7.91 (s, 0.4H), 8.21 (dd, 0.6H, J=1.1, 8.4 Hz), 8.44 (s, 0.4H), 8.53-8.57 (m, 1H).

Example 61

(cis)-4-(2-(6-fluoro-5H-imidazo[5,1-a]isoindol-5-yl)-1-hydroxyethyl)cyclohexanol

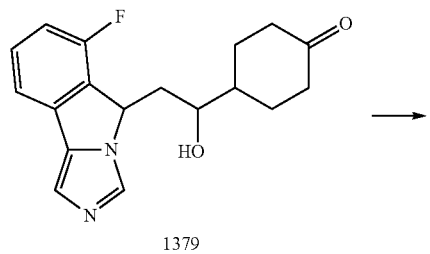

1379

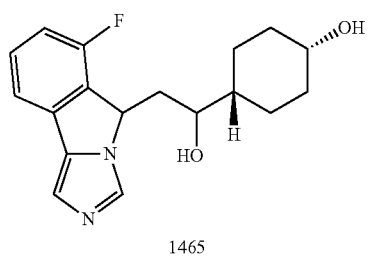

1465

To a solution of NLG-1379 (60 mg, (0.19 mmol) in dry THF (5 mL) at −78° C. under a nitrogen atmosphere was added lithium trisiamylborohydride solution (1.0 M in THF) (0.38 mL, 0.38 mmol). The resulting mixture was stirred vigorously for 3 h at −78° C. and then allowed to warm to room temperature (1 h). The reaction mixture was quenched with 1:1 H$_2$O/EtOH (4 mL). The reaction was acidified with 6 N HCl followed by basification with sat'd K$_2$CO$_3$ solution. The aqueous layer was extracted with dichloromethane (5×15 mL). The combined organic layers were dried over Na$_2$SO$_4$, filtered and concentrated under reduced pressure to afford a crude residue. The residue was purified by column chromatography to afford 1465 35 mg (58%). Mixture of diastereomers $^1$H NMR: 1.45-2.15 (m, 10H), 2.35-2.51 (m, 1H), 3.66-3.79 (two m, 1H), 4.03 (br s, 1H), 5.48 (t, 1H, J=5.1 Hz, isomer), 5.67 (dd, 1H, J=10.6, 2.8 Hz), 6.91-6.95 (m, 1H), 7.19 (d, 1H, J=5.4 Hz), 7.25-7.39 (m, 2H), 7.88 (two, s, 1H).

The mixtures of four diastereomers (1465) were separated by preparative chiral super critical fluid chromatography (SFC) to afford the pure diasteromers 1482-1485. SFC was performed on RegisPack 5 column in isopropanol/CO2: 0.2% DEA.

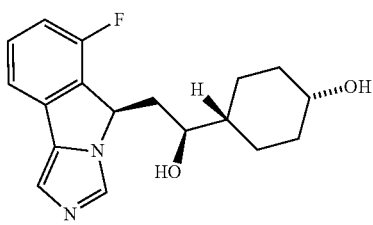

1482

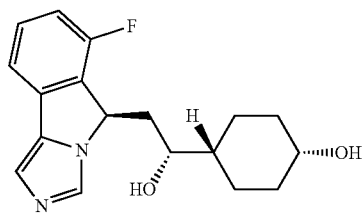

1483

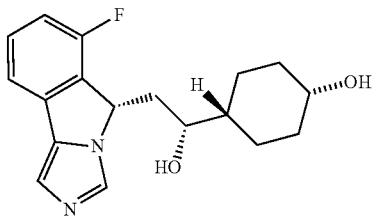

1484

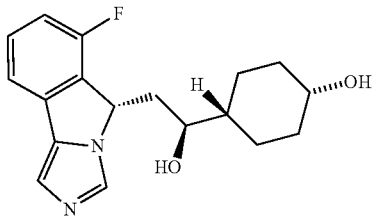

1485

1482 and 1484 $^1$H NMR (CD$_3$OD) δ 1.16 (d, J=6.1 Hz, 1H), 1.23 (d, J=17.8 Hz, 2H), 1.28 (s, 1H), 1.37-1.65 (m, 6H), 1.73 (s, 2H), 1.90-2.14 (m, 1H), 2.48 (d, J=15.2 Hz, 1H), 3.55 (s, 1H), 3.90 (s, 1H), 5.58 (s, 1H), 6.91-7.08 (m, 1H), 7.16 (s, 1H), 7.41 (s, 2H), 7.96 (d, J=28.8 Hz, 1H).

1483 and 1485 $^1$H NMR: (CD$_3$OD) δ 1.15 (d, J=6.4 Hz, 1H), 1.26 (d, J=24.4 Hz, 2H) 1.41-1.79 (m, 8H) 2.35-2.50 (m, 1H), 3.65 (d, J=7.8 Hz, 1H), 3.90 (s, 1H), 5.69 (dd, J=10.1, 2.4 Hz, 1H), 6.93-7.08 (m, 1H), 7.18 (s, 1H), 7.41 (dd, J=5.2, 3.5 Hz, 2H), 7.94 (s, 1H).

Example 62

2-(6-fluoro-5H-imidazo[5,1-a]isoindol-5-yl)-1-((trans)-4-hydroxycyclohexyl)ethanone

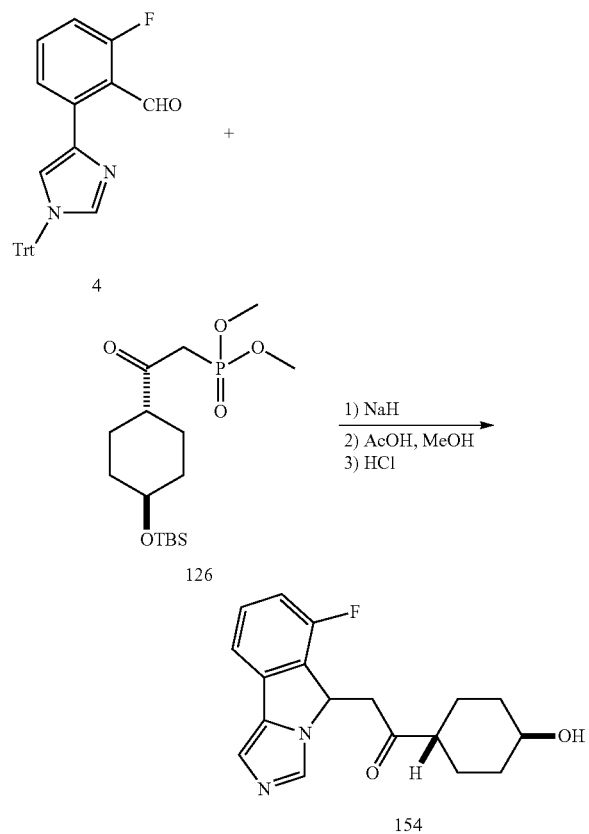

To a suspension of NaH (1.11 g, 46.2 mmol) in THF (150 mL) at −10° C. was added a solution of 126 (18.5 g, 50.8 mmol) in THF (75 mL) dropwise and the mixture was stirred for 45 min at 0° C. Aldehyde 4 (20.0 g, 46.4 mmol) was added as a solution in THF (120 mL) dropwise over a period of 15 min. After stirring for 1 h at 0° C. the reaction mixture was allowed to warm to rt and was stirred overnight. The solvent was distilled off under reduced pressure and the crude was diluted with sat'd NH$_4$Cl (80 mL), water (100 mL) and EtOAc (100 mL). The solution was partitioned in a separatory funnel and the organic layer was collected. The aqueous layer was extracted with EtOAc (3×150 mL) and the combined organic fractions were washed with brine and dried over Na$_2$SO$_4$. The solution was filtered and concentrated under reduced pressure to afford the crude product. The crude was stirred in a mixture of acetic acid (20 mL) and MeOH (170 mL) at 90° C. for 1.5 h. After cooling to 50° C. the reaction mixture was treated with 6N HCl (20 mL) and stirred for 30 minutes. After cooling to rt the solvent was distilled off and sat'd NaHCO$_3$ (200 mL) was added to the residue followed by CH$_2$Cl$_2$ (200 mL). The layers were separated and the aqueous layer was extracted with CH$_2$Cl$_2$ (2×100 mL). The combined organic layers were dried over Na$_2$SO$_4$ and the solvent evaporated under reduced pressure to afford the crude product which was purified by using flash silica gel column chromatography to afford 154 (13.8 g, 95%).

Example 63

(trans)-4-(2-(6-fluoro-5H-imidazo[5,1-a]isoindol-5-yl)-1-hydroxyethyl)cyclohexanol (1475)

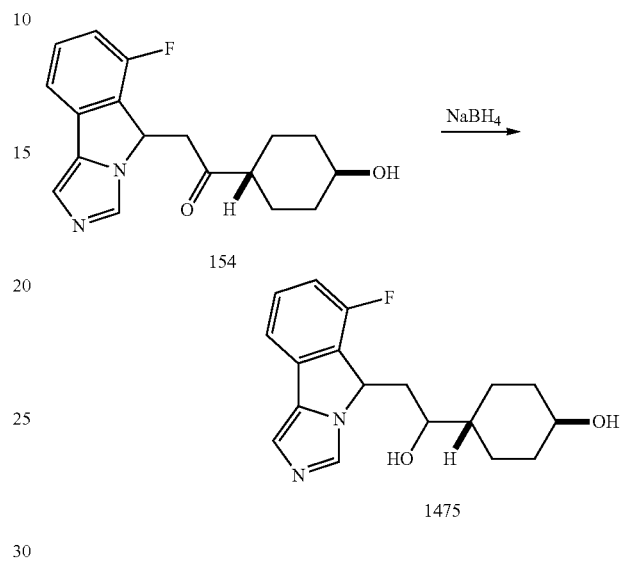

To a solution of 154 (13.8 g, 43.9 mmol) in MeOH (150 mL) at −10 to 0° C., was added NaBH$_4$ (4.98 g, 131.71 mmol) in small portions and the solution was allowed to stir for 4 h. The solvent was distilled off under reduced pressure and the mixture was diluted by addition of saturated NH$_4$Cl solution (200 mL) and dichloromethane (200 mL) and the mixture was stirred for 25 min. The organic layer was separated and the aqueous layer was extracted with a mixture of 5% 2,2,2-trifluorethanol in CH$_2$Cl$_2$ (5×75 mL). The combined organic extract was washed with brine, dried (MgSO4) and concentrated under reduced pressure to afford the crude. Purification by column chromatography afforded 1475 as a white solid (13.24 g, 95%). $^1$H NMR (a mixture of diastereomers): 1.07-2.52 (m, 11H), 3.48-3.68 (two m, 2H), 5.45 (t, 1H, J=6.0 Hz), 5.65 (dd, 1H, J=9.0, 3.0 Hz), 6.89-6.96 (m, 1H), 7.16 (s, 1H), 7.29-7.38 (m, 2H), 7.80 and 7.88 (two s, 1H).

The mixtures of the four diastereomers were separated by preparative chiral super critical fluid chromatography to afford the pure diasteromers 1486-1489. Separation by SFC was performed by a first passage through an AD-H column (Regis Technologies, Inc.) to separate compounds 1487, 1486+1488 and 1489. The peak comprising a mixture of 1486+1488 was separated by SFC in a Whelk-O1 column (Regis Technologies, Inc). All separations were done in isopropanol:CO2 (10:90)+DEA 0.1%.

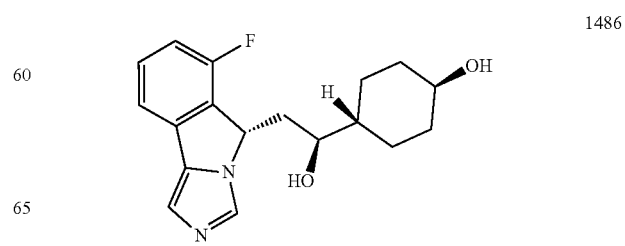

-continued

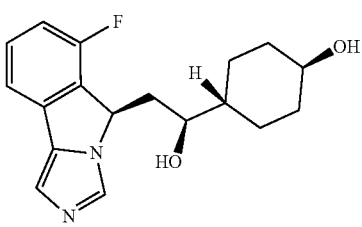
1487

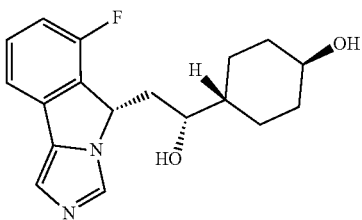
1488

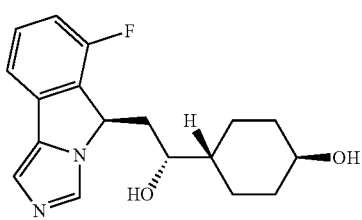
1489

NLG-1486 and NLG-1489 ¹H NMR: 1.03-1.26 (m, 6H), 1.43-1.47 (m, 2H), 1.93-1.96 (m, 2H), 2.45-2.50 (m, 3H), 3.48 (s, 1H), 3.61 (s, 1H), 5.62 (d, J=8.9 Hz, 1H), 6.91 (t, J=8.6 Hz, 1H), 7.12 (s, 1H), 7.26-7.30 (in merged with CHCl₃, 2H), 7.79 (s, 1H).

NLG-1487 and NLG-1488 ¹H NMR: 0.95-1.33 (m, 6H), 1.61-1.64 (m, 1H), 1.79-1.82 (m, 1H), 1.91-2.04 (m, 4H), 2.28 (d, J=14.4 Hz, 1H), 3.42-3.45 (m, 1H), 3.62 (s, 1H), 5.37 (t, J=4.9 Hz, 1H), 6.88 (t, J=8.9 Hz), 7.05 (s, 1H), 7.24-7.31 (in merged with CHCl₃, 2H), 7.84 (s, 1H).

Synthesis of ProDrugs of 1304

Example 64

Sodium 1-cyclohexyl-2-(5H-imidazo[5,1-a]isoindol-5-yl)ethyl phosphate (1434)

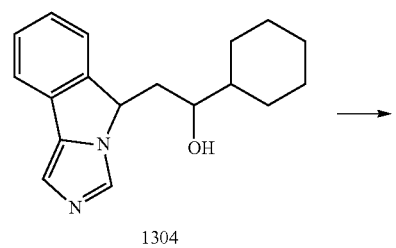
1304

-continued

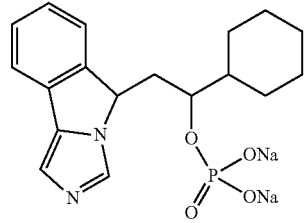
1434

To a solution of 1304 (150 mg, 0.53 mmol) and pyridine (85.7 µL, 1.1 mmol) in dichloromethane (4 mL) at 0° C. was added POCl₃ (99.3 µL, 1.06 mmol) and the solution was allowed to warm to rt. After stirring overnight the reaction was quenched with NaHCO3 sat'd (5 mL), and stirred for 15 minutes. The solvents were evaporated under reduced pressure and the solid was washed with THF (2×15 mL). The solvent was removed under reduced pressure to afford the crude residue. The residue was dissolved in DCM (5 mL) and passed through a plug of Na₂SO₄ to remove water. The solvent was evaporated under reduced pressure to afford 1434.

(33%). ¹H NMR (a mixture of diastereomers): (CD₃OD) 1.15-1.41 (m, 6H), 1.59-1.82 (m, 5H), 1.98-2.04 (m, 1H), 2.56-2.86 (two m, 1H), 3.57-3.58 and 4.08-4.11 (two m, 1H), 5.29-5.54 (two m, 1H), 7.11 and 7.16 (two s, 1H), 7.25-7.47 (m, 3H), 7.53-7.60 (m, 1H), 7.83 and 7.95 (two s, 1H).

Example 65

1-cyclohexyl-2-(5H-imidazo[5,1-a]isoindol-5-yl)ethyl acetate

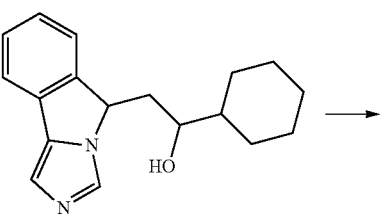

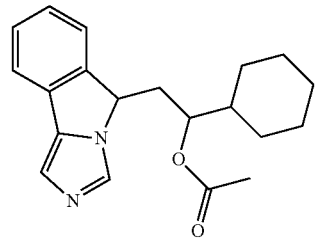

A solution of 1304 (80 mg, 0.28 mmol) and 4-dimethylaminopyridine (1.04 mg, 8.5 µmol) in pyridine (3 ml) was treated with acetic anhydride (32 µL, 0.34 mmol) at RT and the reaction was stirred overnight. The solution was concentrated in vacuo and the residue was dissolved in dichloromethane (10 ml) and washed successively with water (3×10 ml) and dried over Na₂SO₄. The solution was concentrated and the crude was purified by flash column chromatography to afford the desired product as yellow gel (75 mg, 82%). ¹H NMR (a mixture of diastereomers): 0.76-1.25 (m, 5H), 1.30-

1.75 (m, 6H), 1.78-2.20 (m, 4H), 2.26-2.40 (m, 1H), 4.96-5.12 (m, 2H), 7.17-7.39 (m, 4H), 7.51-7.53 (m, 1H), 7.71 and 8.00 (two s, 1H).

Example 66

4-(1-cyclohexyl-2-(5H-imidazo[5,1-a]isoindol-5-yl)ethoxy)-4-oxobutanoic acid (1428)

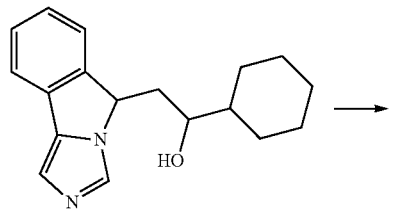

1304

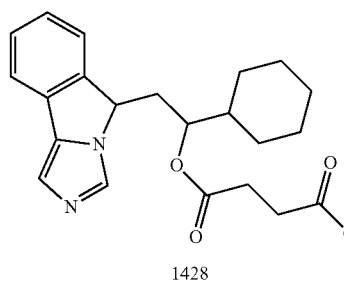

1428

A solution of 1304 (48 mg, 0.17 mmol) and 4-dimethylaminopyridine (0.83 mg, 6.8 µmol) in dichloromethane (3 ml) was treated with succinic anhydride (19 mg, 0.19 mmol) and DIPEA (33 µL, 0.19 mmol) at RT and the reaction was stirred overnight. The solution was poured into saturated NH₄Cl (10 mL) and extracted with dichloromethane (3×10 ml). The combined organic layers were dried over Na₂SO₄ and concentrated. The crude product was crystallized from ethanol/chloroform (1:4) to afford 1428 as white solid (62 mg, 95%). ¹H NMR (a mixture of diastereomers): 0.93-1.65 (m, 11H), 1.90-2.32 (m, 1H), 2.50-2.90 (m, 3H), 2.92-3.05 (m, 1H), 3.57 and 3.73 (m, 1H), 5.20-5.22 (m, 1H), 5.29-5.33 (m, 1H), 6.41-6.78 (m, 1H), 7.16-8.00 (m, 5H), 12.20-12.80 (br s, 1H).

Example 67

1-cyclohexyl-2-(5H-imidazo[5,1-a]isoindol-5-yl)ethyl benzoate (1431)

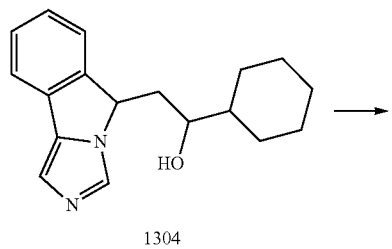

1304

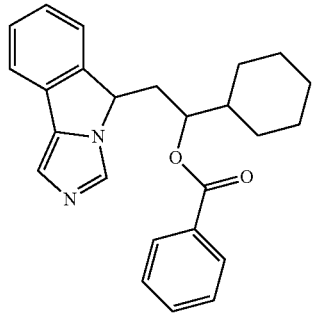

1431

A solution of 1304 (76 mg, 0.27 mmol) and 4-dimethylaminopyridine (1.0 mg, 8.1 mol) in pyridine (3 ml) was treated with benzoic anhydride (73 mg, 0.32 mmol) at RT and the reaction was stirred overnight. The solution was concentrated in vacuo and the residue was dissolved in dichloromethane (10 ml) and washed successively with saturated NaHCO₃ (10 mL), water (10 ml) and dried over Na₂SO₄. The solution was concentrated and the crude was purified by flash column chromatography to afford 1431 (25 mg, 23%). ¹H NMR (a mixture of diastereomers): 0.88-1.25 (m, 7H), 1.62-1.90 (m, 4H), 2.15-2.25 (m, 1H), 2.49-2.58 (m, 1H), 5.19-5.21 (m, 1H), 5.34-5.37 (m, 1H), 7.16-7.28 (m, 4H), 7.40-7.64 (m, 4H), 7.80 (s, 1H), 8.00-8.02 (d, J=6.3 Hz, 1H), 8.12-8.14 (d, J=5.7 Hz, 1H).

Example 68

1-cyclohexyl-2-(5H-imidazo[5,1-a]isoindol-5-yl)ethyl phenylcarbamate (1427)

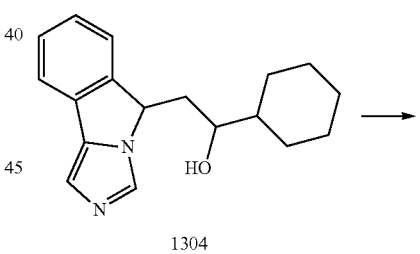

1304

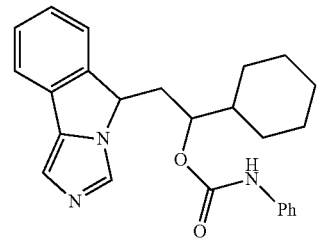

1427

To a solution of 1304 (40 mg, 0.14 mmol) in THF (5 mL) was added triethylamine (43 µL, 0.31 mmol) followed by phenylisocyanate (17 µL, 0.16 mmol). The reaction mixture was stirred at RT for 18 h and concentrated. The crude product was purified using flash column chromatography (4:1 EtOAc:MeOH) to afford 1427 as colorless gel (19 mg, 34%). ¹H NMR (a mixture of diastereomers): 1.02-1.04 (m, 5H), 1.56-

1.70 (m, 6H), 2.10-2.14 (m; 1H), 2.31-2.40 (m, 1H), 5.02-5.10 (m, 1H), 5.18-5.24 (m, 1H), 7.04-7.08 (m, 1H), 7.18-7.35 (m, 6H), 7.39-7.41 (m, 2H), 7.50 (d, J=4 Hz, 1H), 7.65 (d, J=8 Hz, 1H), 7.74 (s, 1H).

Example 69

General Procedure for the Synthesis of Prodrugs of 1304

To a vial containing 1304 (0.5 mmol) in dichloromethane (5 mL) was added the appropriate carboxylic acid (1.1 mmol), diisopropylethyl amine (3.0 mmol) and HATU (1.3 mmol). The reaction mixture was stirred at rt for 48 h and poured into saturated aqueous $NaHCO_3$ (10 mL) and the aqueous layer was extracted with dichloromethane (2×20 mL). The combined organic layers were dried over $Na_2SO_4$, and concentrated. The crude product was dissolved in dichloromethane (6 mL) and TFA (2 mL) was added. The reaction mixture was stirred at room temperature for 2 h and concentrated. The residue was dissolved in water and solid $K_2CO_3$ was added until the solution was basic. The aqueous solution was extracted with dichloromethane (2×20 mL). The combined organic layers were dried over $Na_2SO_4$, filtered and concentrated to afford 1433, 1440, 1442 and 1443.

| # | Compound | Name | Yield (%) |
|---|---|---|---|
| 1440 | (structure) | (2S)-1-cyclohexyl-2-(5H-imidazo[5,1-a]isoindol-5-yl)ethyl 2-aminopropanoate | 87 |

$^1$H NMR (a mixture of diastereomers) 0.96-1.06 (m, 2H), 1.09-1.19 (m, 3H), 1.27 and 1.30 (two d, 3H, J = 7.0 Hz), 1.41-1.53 (m, 3H), 1.63-1.77 (m, 5H), 2.10-2.16 and 2.23-2.26 (two m, 1H), 2.37-2.45 (m, 1H), 3.21 and 3.50 (two q, 1H, J = 7.0 Hz), 4.86-4.90, 5.06-5.09 and 5.15-5.17 (three m, 2H), 7.19 (d, 1H, J = 3.2 Hz), 7.24-7.27 (m, 1H, merged with chloroform), 7.37 (dt, 1H, J = 2.8, 7.6 Hz), 7.49-7.55 (m, 2H), 7.69 (s, 1H)

| # | Compound | Name | Yield (%) |
|---|---|---|---|
| 1442 | (structure) | (2S)-1-cyclohexyl-2-(5H-imidazo[5,1-a]isoindol-5-yl)ethyl pyrrolidine-2-carboxylate dihydrochloride | 77 |

$^1$H NMR (a mixture of diastereomers) (CD$_3$OD) 0.90-1.17 (m, 5H), 1.4-1.75 (m, 10H), 2.11-2.18 (m, 2H), 2.36-2.42 (m, 1H), 2.82 (br s, 1H), 2.89-3.0 (m, 2H), 3.54-3.60 and 3.72-3.75 and 3.81-3.83 (three m, 1H), 4.93-5.25 (four m, 2H), 7.16 (s, 1H, J = 3.6 Hz), 7.22-7.16 (m, 1H), 7.35 (t, 1H, J = 7.40 Hz), 7.48-7.52 (m, 2H), 7.69 (d, 1H, J = 8.40 Hz)

| # | Compound | Name | Yield (%) |
|---|---|---|---|
| 1443 | (structure) | (2S)-5-(1-cyclohexyl-2-(5H-imidazo[5,1-a]isoindol-5-yl)ethyl) 1-methyl 2-aminopentanedioate dihydrochloride | 73 |

$^1$H NMR (a mixture of diastereomers) (DMOS-d6) 0.85-0.88 (m, 2H), 1.02-1.12 (m, 3H), 1.34-1.38 (m, 1H), 1.53-1.67 (m, 5H), 2.14-2.20 (m, 2H), 2.60-2.73 (m, 2H), 3.41-3.53 (m, 2H), 3.74 and 3.87 (two s, 3H), 4.44-4.52 (m, 1H), 5.81-5.3 (m, 1H), 7.50-7.53 (m, 2H), 7.69-7.70 (m, 1H), 7.81-7.72 (m, 1H), 7.95 (d, 1H, J= 6.4 Hz), 8.66 (br s, 3H), 9.52 (s, 1H)

-continued

| # | Compound | Name | Yield (%) |
|---|---|---|---|
| 1433 | | (2S)-1-(1-cyclohexyl-2-(5H-imidazo[5,1-a]isoindol-5-yl)ethoxy)-3-methyl-1-oxobutan-2-aminium chloride hydrochloride | 40 |

¹H NMR (a mixture of diastereomers) (DMOS-d6) 0.86-0.98 (m, 6H), 1.01-1.12 (m, 4H), 1.42 and 1.44 (two s, 9H), 1.58-1.87 (m, 6H), 2.0-2.16 (m, 2H), 2.33-2.43 (m, 1H), 4.04-4.07 and 4.08-4.15 (two m, 1H), 4.91-5.29 (three m, 3H), 7.17 (s, 1H), 7.21-7.28 (m, 2H), 7.31-7.40 (m, 2H), 7.70 (s, 1H)

Biological Example 1

Human IDO Protein Cloning, Expression and Purification

Expression vectors for human indoleamine-2,3-dioxygenase (IDO) protein were prepared by amplification of a 1219 by fragment of the sequence present in vector phIDO6His cDNA with primers 5'-ggagcatgctaATGGCACACGCTATG-GAAAAC-3' (SEQ ID NO: 1) and 5'-gagagatctACCTTCCT-TCAAAAGGGATTTC-3' (SEQ ID NO: 2) and cloning the SphI-BglII 1213 by fragment into pQE70 (Qiagen), to yield vector pQE70-hIDO. This construct adds 2 extra amino acids and a 6-Histidine tag to the C-terminus of the natural human IDO protein while preserving intact the natural start codon and N-terminus amino acid sequence. The amplified allele of human IDO shows two polymorphisms with respect to the sequence deposited in accession file P14902 of SwissProt database. These polymorphisms result in a P110S and E119G amino acid changes.

Plasmid pQE70-hIDO was transformed into M15 (pREP4) cells (Qiagen) and clones were selected in LB-agar plates supplemented with carbenicillin 50 µg/mL and kanamycin 30 g/mL. Protein expression was carried out by growing an overnight culture of the M15pREP4/pQE70-hIDO clone in 100 mL LB supplemented with 100 µg/mL carbenicillin, 50 µg/mL kanamycin and 50 µg/mL of L-tryptophan (LBCKT medium). 40 mL of this culture were inoculated into 750 mL of LBCKT for 4 hours at 37° C. This culture was diluted 1:10 into LBCKT medium and cultured for another 2 hours at 37° C. until OD600 was higher than 0.8. At this point the cultures were inoculated with Hemin to 7 M and L-Tryptophan to 75 µg/mL and incubated at 37° C. for 2 h. Induction of protein expression was carried out by supplementing the cultures with IPTG to 1 mM, PMSF to 200 µM, EDTA to 1 mM and L-tryptophan to 50 µg/mL. Incubation was continued for additional 16 h at 25° C. Cells were collected by centrifugation, and the cell pellets were washed with PBS buffer supplemented with 200 µM PMSF and 1 mM EDTA and stored at −80° C. until protein purification.

The equivalent of 16 L of culture were processed in one batch of purification. Cell pellets were thawed, resuspended in 50 mM potassium phosphate buffer pH 7.0, 200 µM PMSF, 1 mM EDTA, 1 mg/mL lysozyme to 10 mL per liter of bacterial culture and incubated 30 minutes on ice. Cells were then lysed by sonication. Cell lysates were centrifuged 20 min at 20000 g and the supernatant was filtered through 0.45 µm filters. The filtered supernatant was loaded onto a 60 mL phosphocellulose column equilibrated with 50 mM potassium phosphate buffer pH 6.5 (KPB) at 1-3 mL/min. The column was washed with 3 volumes of 50 mM KPB, 3 volumes of 100 mM. KPB and the protein was eluted with 15 volumes of a linear gradient of 100-500 mM KPB. Fractions were collected and IDO activity assay was performed by measuring kynurenine production. This was carried out by mixing 50 µL of each fraction with 100 µL of reaction mix to yield a final concentration of 50 mM KPB buffer, 20 mM ascorbic acid, 200 µg/mL catalase, 20 µM methylene blue and 400 µM L-tryptophan. Fractions demonstrating IDO activity were loaded onto a Ni-NTA purification column (15 mL). This affinity purification column was washed with 10 volumes of 250 mM KPB, 150 mM NaCl, 50 mM imidazole pH 8, and eluted with 10 volumes of buffer containing 250 mM KPB, 150 mM NaCl and a 50 to 250 mM imidazole linear gradient. Collected fractions were assayed by IDO enzymatic assay described above and the positive fractions were pooled and concentrated by ultrafiltration and dialyzed against a buffer containing 250 mM KPB, 50% glycerol. This process yields-8-10 mg of pure protein (>98%) with a specific activity of 170 mol/h/mg.

Biological Example 2

Testing of IDO Inhibitory Compounds by Enzymatic IDO Assay

The $IC_{50}$ values for each compound were determined by testing the activity of IDO in a mixture containing 50 mM potassium phosphate buffer at pH 6.5; 70 nM purified human IDO protein, 200 µM L-tryptophan, 20 mM ascorbate, 20 µM methylene blue, 0.1% DMSO. The inhibitors were initially diluted in DMSO at 100 mM and were diluted in potassium phosphate 50 mM, added to the reaction mixture at final concentrations raging from 1 mM to 5 nM and preincubated with the enzyme for 5 min at 25° C. The reaction was started by addition of L-tryptophan to 200 µM and incubated 15 min at 37° C. The reaction was stopped by addition of 0.5 vol of 30% trichloroacetic acid and incubated 30 min at 60° C. to hydrolyze N-formylkynurenine to kynurenine. The reaction was centrifuged at 3400 g for 5 min to remove precipitated protein and the supernatant was reacted with 2% (w/v) of p-dimethylaminobenzaldehyde in acetic acid. The reaction was incubated 10 min at 25° C. and read at 480 nm in a spectrophotometer. Control samples with no IDO inhibitor, or with no IDO enzyme or with the reference inhibitors 1-methyl-tryptophan (200 M) and menadione (1.2 µM) were used as controls to set the parameters for the non-linear regressions necessary for determination of the $IC_{50}$ for each compound.

Nonlinear regressions and determination of the $IC_{50}$ values were performed using the GraphPad Prism 4 software. Compounds with an $IC_{50}$ of less than 500 M were considered as active inhibitors in this assay.

Biological Example 3

Determination of IDO Inhibitory Activity and Toxicity in Cell Based IDO/Kynurenine Assay 293-T-REx™ cells (Invitrogen) constitutively express a tet operator binding repressor protein and are maintained in DMEM, 10% FBS, 1× Penicillin+Streptomycin, 2 mM L-glutamine, 5 µg/mL blasticidin at 37° C. with a 5% $CO_2$ in air atmosphere and typically split prior to confluency. Cells were passed by splitting the culture 1/10—by removing media by aspiration, washing 1× with PBS, incubating with 0.25% trypsin/EDTA until the cells detach, disbursing the cells in fresh growth media, and plating at 1/10 dilutions in fresh growth media. For long term cryopreservation, cells are detached from the plate as described above, collected by centrifugation, resuspended in freeze medium (growth medium, 10% DMSO), stored in 1.8 mL cyropreservation vials (~2–5×106 cells per vial), in liquid nitrogen vapor storage tanks.

IDO1-expressing 293-T-Rex™ cell lines were generated by stable transfection of plasmid pcDNA-tetO-IDO expressing human IDO or murine IDO under the control of the doxycycline-inducible CMV-tet promoter. Transfected cells were selected in DBZ medium (DMEM, 10% FBS, 1× Penicillin+Streptomycin, 2 mM L-glutamine, 5 µg/mL blasticidin and 25 µg/mL Zeocin) at 37° C. with a 5% $CO_2$ in air atmosphere. Individual clones were isolated by limiting dilution cloning from these populations. These clones were assayed for IDO activity and the clones that showed the highest levels of IDO activity inducible by doxycycline were used for subsequent cell based IDO assays.

To setup an IDO cell based activity assay, IDO-293-T-Rex cells were harvested and resuspended in DBZ media at $10^6$ cells/mL, and split into poly-D-lysine coated 96-well plates at 100,000 cells per well. 100 µL of Neutral medium (DBZ medium, 200 µM L-tryptophan) or Induction media (Neutral medium supplemented with 5 µM doxycycline) are added to the cells and incubated 28 h at 37° C. After the IDO induction period, medium is removed and replaced with Induction or Neutral medium containing different concentrations of each inhibitor (1 mM to 0.5 nM). The cells incubated in Neutral medium serve as negative control of the assay. The cells incubated in Induction medium and without inhibitor serve as the positive control of the assay. The incubation is carried out for 16 h at 37° C. in a cell culture incubator. 200 µL of medium are transferred to U-bottom polypropylene 96-well plates containing 25 µL of 30% TCA, incubated 30 minutes at 60° C. and centrifuged at 3400 g for 5 minutes. 150 µL of the clear supernatant is transferred to a polystyrene 96-well plate containing 50 µL of 4% (w/v) of p-dimethylaminobenzaldehyde in acetic acid, incubated for 10 min. Kynurenine concentration is determined by measuring the absorbance at 480 nm.

To measure the toxicity of each compound after 16 h incubation with cells, cell viability is measured via a WST-1 assay (Roche) according to instructions from the manufacturer. Briefly, after the incubation with each compound, medium is aspirated and replaced with 100 mL of WST-1 reagent, and incubated 30 min at 37° C. Absorbance at 540 nm is correlated with the number of viable cells. Determination of $IC_{50}$ (Kynurenine assay) or $LD_{50}$ (WST-1 assay) is performed via non-linear regression analysis using GraphPad Prism software.

Biological Example 4

Reversal of IDO-Mediated Suppression of T-Cell Proliferation by IDO Inhibitors

Human monocytes were collected from peripheral mononuclear cells by leukoapheresis and cultured overnight at $10^6$ cells/well in a 96-well plate in RPMI 1640 medium supplemented with 10% fetal calf serum and 2 mM L-glutamine. Adherent cells were retained and cultured for 7 days with 200 ng/ml IL-4, 100 ng/ml GM-CSF. Cells were matured for 2 days with a cytokine cocktail containing TNF-α, IL-1β, IL-6 and PGE2 for additional 2 days to induce dendritic cell maturation. At the end of maturation, loosely adherent cells were detached by gentle aspiration and plated in V-bottom 96 well plates, at 5000 cells/well. These cells are >80% IDO+ dendritic cells. Human allogeneic T cells ($3\times10^5$) from normal donors were resuspended in RPMI 1640 supplemented with 100-200 U/mL IL-2 and 100 ng/mL anti-CD3 antibody and added to the wells. Serial dilutions of IDO compounds dissolved in phenol red-free RPMI was added to yield a final concentration of IDO1 between 500 and 1 µM. After incubation for 2-4 days, T cell proliferation was measured by BrdU incorporation assay after an overnight pulse with BrdU labeling mix (Roche Molecular Biochemicals). At the en of the pulse, the cells were fixed and incubated with 100 µL/well anti-BrdU-POD antibody following the instructions from the manufacturer. Plates were read in a microplate reader.

Alternatively, testing of IDO inhibitors in an in vitro mouse model of IDO-mediated suppression of T cell proliferation is performed by the following procedure. C57bl6 mice are inoculated with $1\times10^6$ B78H1-GMCSF tumor cells in the right flank. After 10-12 days, tumor draining lymph nodes are collected and cells are stained with anti-CD11c and anti-B220 monoclonal antibodies. Cells are sorted by high-speed fluorescence activated cell sorting and the CD11c+/B220+ plasmacytoid dendritic cells are collected and seeded at 2000 cells/well in 96 well V-bottom plates. Splenocytes are collected from BM3 transgenic mice (in CBA background) and collected by nylon wool enrichment. BM3 T cells ($10^5$ cells/well) are added to each well in 200 µL of RPMI, 10% FCS, 50 µM β-mercaptoetanol. Alternatively, T cells are obtained from spleens of OT-I transgenic mice and added to the culture in combination with OVA peptide. IDO inhibitors are added dissolved in RPMI at final concentrations ranging from 1 mM to 10 nM. After 3 days of stimulation, cells are pulsed by 16 h with BrdU or $^3$H-thymidine. Cells are collected, fixed and tested for BrdU incorporation following the instructions from the BrdU labeling kit manufacturer (Roche Diagnostics). If $^3$H-tymidine is used to measure T cell proliferation, cells are harvested and dpm counts are measured in a scintillation counter following procedures widely known in the art. Control CD11c$^+$ cells taken from the contralateral lymph node or CD11c$^+$/B220$^-$ cells (IDO$^-$ population) from the TDLN are used as positive control for proliferation.

Biological Example 5

Pharmacological Value

Pharmacological values for compounds tested according to one or more of the preceding examples are reported in the following table, including, Human IDO $IC_{50}$: this is the concentration of the compound at which we observe 50% of enzymatic activity using recombinant human IDO under the assay conditions described in one of the examples;

IC$_{50}$ values are reported in ranges: A: <1 µM, B: 1-10 µM, C: 10-100 µM; D: >100 µM.

| No. | Structure | Name | hIDO IC$_{50}$ |
|---|---|---|---|
| 1254 | 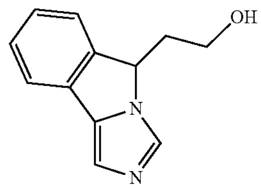 [SMILES: OCCC1c2ccccc2-c2cncn21] | 2-(5H-imidazo[5,1-a]isoindol-5-yl)ethanol | B |
| 1256 | 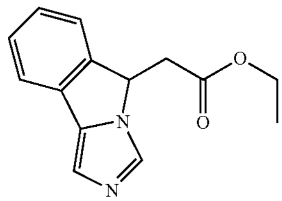 [SMILES: CCOC(=O)CC1c2ccccc2-c2cncn21] | ethyl 2-(5H-imidazo[5,1-a]isoindol-5-yl)acetate | B |
| 1258 | 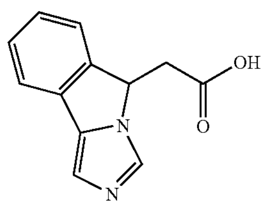 [SMILES: O=C(O)CC1c2ccccc2-c2cncn21] | 2-(5H-imidazo[5,1-a]isoindol-5-yl)acetic acid | D |
| 1259 | 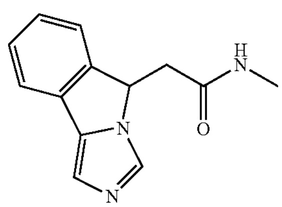 [SMILES: CNC(=O)CC1c2ccccc2-c2cncn21] | 2-(5H-imidazo[5,1-a]isoindol-5-yl)-N-methylacetamide | D |
| 1273 | 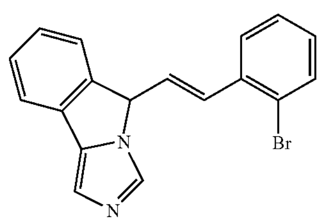 [SMILES: Brc1ccccc1/C=C/C1c2ccccc2-c2cncn21] | (E)-5-(2-bromostyryl)-5H-imidazo[5,1-a]isoindole | C |
| 1286 | 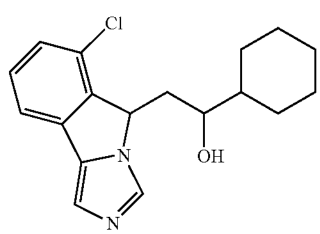 [SMILES: OC(CC1c2c(Cl)cccc2-c2cncn21)C1CCCCC1] | 2-(6-chloro-5H-imidazo[5,1-a]isoindol-5-yl)-1-cyclohexylethanol | A |
| 1287 | 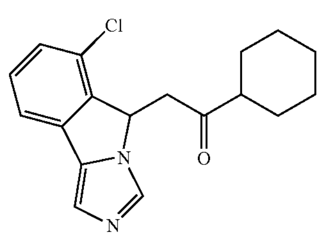 [SMILES: O=C(CC1c2c(Cl)cccc2-c2cncn21)C1CCCCC1] | 2-(6-chloro-5H-imidazo[5,1-a]isoindol-5-yl)-1-cyclohexylethanone | B |

-continued

| No. | Structure | Name | hIDO IC$_{50}$ |
|---|---|---|---|
| 1288 | 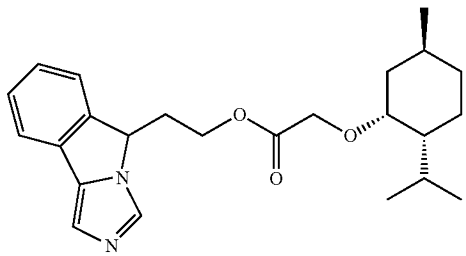 [SMILES: CC(C)[C@H]1CC[C@H](C)C[C@H]1OCC(=O)OCCC1c2ccccc2-c2cncn21] | 2-(5H-imidazo[5,1-a]isoindol-5-yl)ethyl 2-(((1R,2R,5S)-2-isopropyl-5-methylcyclohexyl)oxy)acetate | B |
| 1299 | 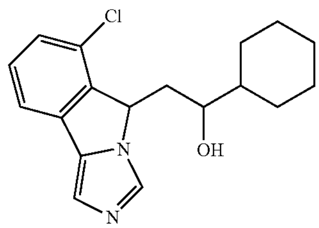 [SMILES: OC(CC1c2c(Cl)cccc2-c2cncn21)C1CCCCC1] | 2-(6-chloro-5H-imidazo[5,1-a]isoindol-5-yl)-1-cyclohexylethanol | A |
| 1300 | 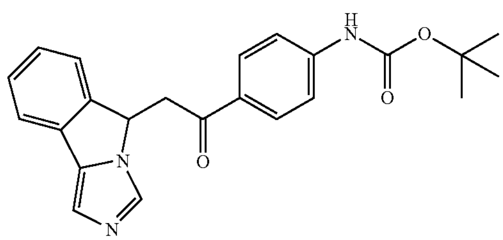 [SMILES: CC(C)(C)OC(=O)Nc1ccc(C(=O)CC2c3ccccc3-c3cncn32)cc1] | tert-butyl (4-(2-(5H-imidazo[5,1-a]isoindol-5-yl)acetyl)phenyl)carbamate | B |
| 1301 | 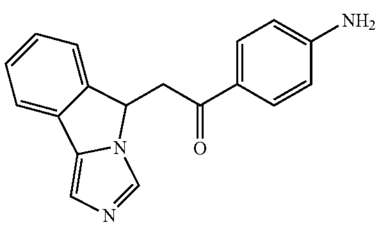 [SMILES: Nc1ccc(C(=O)CC2c3ccccc3-c3cncn32)cc1] | 1-(4-aminophenyl)-2-(5H-imidazo[5,1-a]isoindol-5-yl)ethanone | C |
| 1302 | 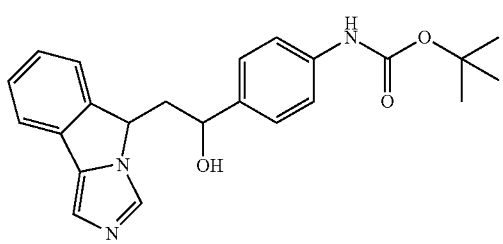 [SMILES: CC(C)(C)OC(=O)Nc1ccc(C(O)CC2c3ccccc3-c3cncn32)cc1] | tert-butyl (4-(1-hydroxy-2-(5H-imidazo[5,1-a]isoindol-5-yl)ethyl)phenyl)carbamate | A |
| 1303 | 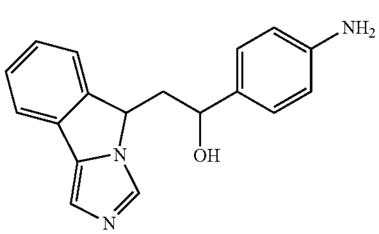 [SMILES: Nc1ccc(C(O)CC2c3ccccc3-c3cncn32)cc1] | 1-(4-aminophenyl)-2-(5H-imidazo[5,1-a]isoindol-5-yl)ethanol | C |

| No. | Structure | Name | hIDO IC$_{50}$ |
|---|---|---|---|
| 1304 | 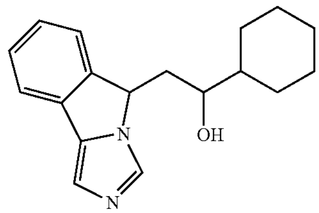 [SMILES: OC(CC1c2ccccc2-c2cncn21)C1CCCCC1] | 1-cyclohexyl-2-(5H-imidazo[5,1-a]isoindol-5-yl)ethanol | A |
| 1306 | 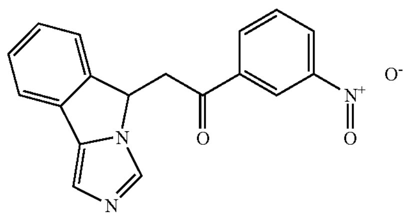 | 2-(5H-imidazo[5,1-a]isoindol-5-yl)-1-(3-nitrophenyl)ethanone | B |
| 1307 | 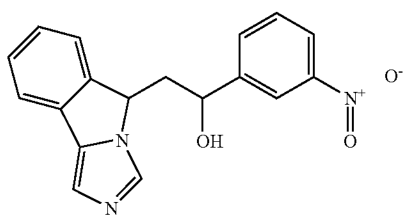 | 2-(5H-imidazo[5,1-a]isoindol-5-yl)-1-(3-nitrophenyl)ethanol | A |
| 1326 | 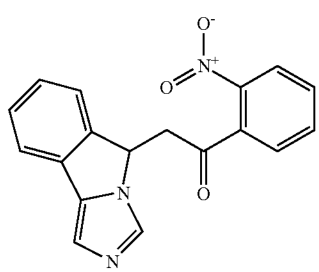 [SMILES: O=C(CC1c2ccccc2-c2cncn21)c1ccccc1[N+](=O)[O-]] | 2-(5H-imidazo[5,1-a]isoindol-5-yl)-1-(2-nitrophenyl)ethanone | B |
| 1327 | 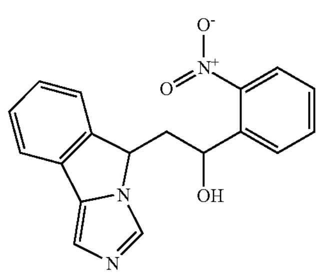 [SMILES: O=[N+]([O-])c1ccccc1C(O)CC1c2ccccc2-c2cncn21] | 2-(5H-imidazo[5,1-a]isoindol-5-yl)-1-(2-nitrophenyl)ethanol | A |
| 1328 | 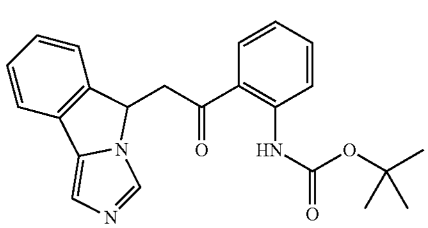 [SMILES: CC(C)(C)OC(=O)Nc1ccccc1C(=O)CC1c2ccccc2-c2cncn21] | tert-butyl (2-(2-(5H-imidazo[5,1-a]isoindol-5-yl)acetyl)phenyl)carbamate | B |

-continued

| No. | Structure | Name | hIDO IC$_{50}$ |
|---|---|---|---|
| 1329 | 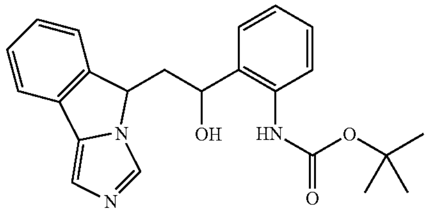 [SMILES: CC(C)(C)OC(=O)Nc1ccccc1C(O)CC1c2ccccc2-c2cncn21] | tert-butyl (2-(1-hydroxy-2-(5H-imidazo[5,1-a]isoindol-5-yl)ethyl)phenyl)carbamate | B |
| 1330 | 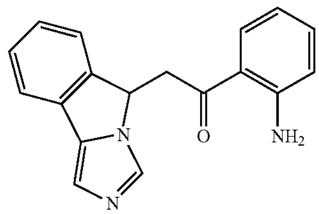 [SMILES: Nc1ccccc1C(=O)CC1c2ccccc2-c2cncn21] | 1-(2-aminophenyl)-2-(5H-imidazo[5,1-a]isoindol-5-yl)ethanone | B |
| 1331 | 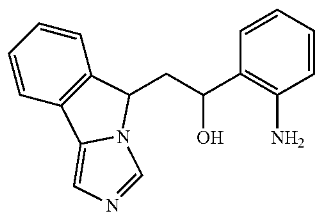 [SMILES: Nc1ccccc1C(O)CC1c2ccccc2-c2cncn21] | 1-(2-aminophenyl)-2-(5H-imidazo[5,1-a]isoindol-5-yl)ethanol | A |
| 1334 | 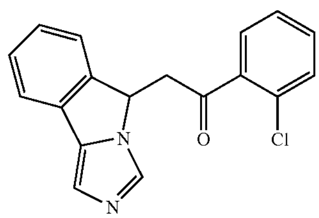 [SMILES: O=C(CC1c2ccccc2-c2cncn21)c1ccccc1Cl] | 1-(2-chlorophenyl)-2-(5H-imidazo[5,1-a]isoindol-5-yl)ethanone | B |
| 1335 | 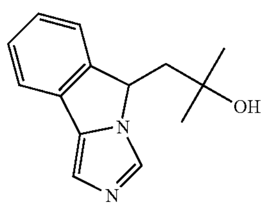 [SMILES: CC(C)(O)CC1c2ccccc2-c2cncn21] | 1-(5H-imidazo[5,1-a]isoindol-5-yl)-2-methylpropan-2-ol | B |
| 1336 | 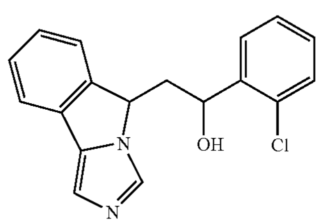 [SMILES: OC(CC1c2ccccc2-c2cncn21)c1ccccc1Cl] | 1-(2-chlorophenyl)-2-(5H-imidazo[5,1-a]isoindol-5-yl)ethanol | A |
| 1343 | 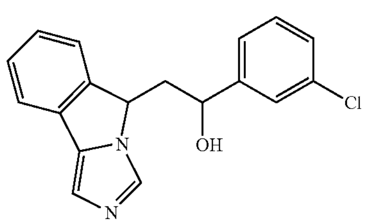 [SMILES: OC(CC1c2ccccc2-c2cncn21)c1cccc(Cl)c1] | 1-(3-chlorophenyl)-2-(5H-imidazo[5,1-a]isoindol-5-yl)ethanol | A |

-continued

| No. | Name | hIDO IC$_{50}$ |
|---|---|---|
| 1348 | 2-(5H-imidazo[5,1-a]isoindol-5-yl)-1-phenylethanone | B |
| 1349 | 2-(5H-imidazo[5,1-a]isoindol-5-yl)-1-phenylethanol | A |
| 1352 | 1-(2,4-dimethylfuran-3-yl)-2-(6-fluoro-5H-imidazo[5,1-a]isoindol-5-yl)ethanol; | B |
| 1353 | 1-(3-chlorophenyl)-2-(5H-imidazo[5,1-a]isoindol-5-yl)ethanone | B |
| 1356 | 1-cyclohexyl-2-(6-fluoro-5H-imidazo[5,1-a]isoindol-5-yl)ethanone | B |
| 1357 | 1-cyclohexyl-2-(6-fluoro-5H-imidazo[5,1-a]isoindol-5-yl)ethanol | A |
| 1358 | 2-(5H-imidazo[5,1-a]isoindol-5-yl)-1-(tetrahydro-2H-pyran-4-yl)ethanol | A |

-continued

| No. | Structure | Name | hIDO IC$_{50}$ |
|---|---|---|---|
| 1359 | 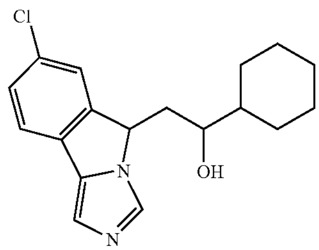 [SMILES: OC(CC1c2cc(Cl)ccc2-c2cncn21)C1CCCCC1] | 2-(7-chloro-5H-imidazo[5,1-a]isoindol-5-yl)-1-cyclohexylethanol | A |
| 1360 | 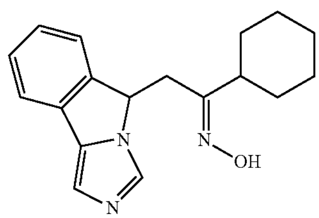 [SMILES: O/N=C(/CC1c2ccccc2-c2cncn21)C1CCCCC1] | (Z)-1-cyclohexyl-2-(5H-imidazo[5,1-a]isoindol-5-yl)ethanone oxime | B |
| 1362 | 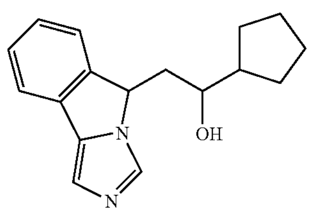 [SMILES: OC(CC1c2ccccc2-c2cncn21)C1CCCC1] | 1-cyclopentyl-2-(5H-imidazo[5,1-a]isoindol-5-yl)ethanol | A |
| 1363 | 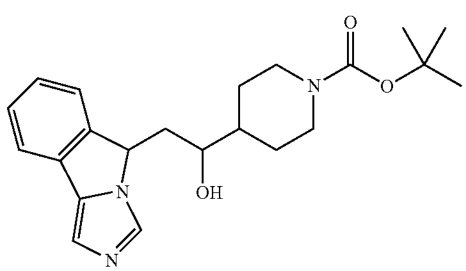 [SMILES: CC(C)(C)OC(=O)N1CCC(C(O)CC2c3ccccc3-c3cncn32)CC1] | tert-butyl 4-(1-hydroxy-2-(5H-imidazo[5,1-a]isoindol-5-yl)ethyl)piperidine-1-carboxylate | A |
| 1364 | 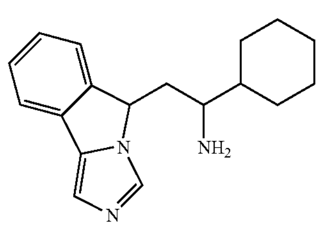 [SMILES: NC(CC1c2ccccc2-c2cncn21)C1CCCCC1] | 1-cyclohexyl-2-(5H-imidazo[5,1-a]isoindol-5-yl)ethanamine | B |
| 1367 | 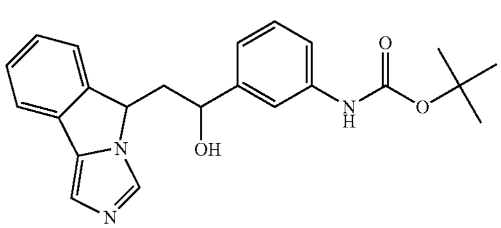 [SMILES: CC(C)(C)OC(=O)Nc1cccc(C(O)CC2c3ccccc3-c3cncn32)c1] | tert-butyl (3-(1-hydroxy-2-(5H-imidazo[5,1-a]isoindol-5-yl)ethyl)phenyl)carbamate | B |

| No. | Structure | Name | hIDO IC$_{50}$ |
|---|---|---|---|
| 1369 | 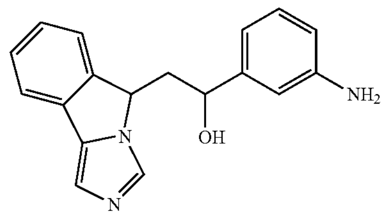 [SMILES: Nc1cccc(C(O)CC2c3ccccc3-c3cncn32)c1] | 1-(3-aminophenyl)-2-(5H-imidazo[5,1-a]isoindol-5-yl)ethanol | B |
| 1370 | 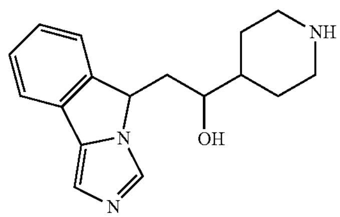 [SMILES: OC(CC1c2ccccc2-c2cncn21)C1CCNCC1] | 2-(5H-imidazo[5,1-a]isoindol-5-yl)-1-(piperidin-4-yl)ethanol | D |
| 1371 | 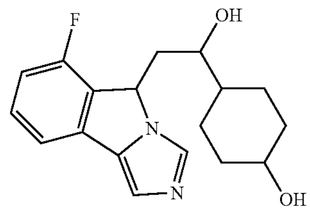 [SMILES: OC1CCC(C(O)CC2c3c(F)cccc3-c3cncn32)CC1] | 4-(2-(6-fluoro-5H-imidazo[5,1-a]isoindol-5-yl)-1-hydroxyethyl)cyclohexanol; | A |
| 1372 | 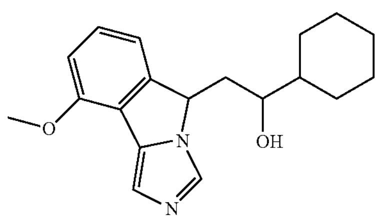 [SMILES: COc1cccc2c1-c1cncn1C2CC(O)C1CCCCC1] | 1-cyclohexyl-2-(9-methoxy-5H-imidazo[5,1-a]isoindol-5-yl)ethanol | C |
| 1373 | 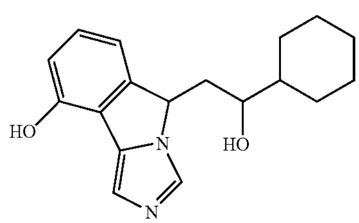 [SMILES: Oc1cccc2c1-c1cncn1C2CC(O)C1CCCCC1] | 5-(2-cyclohexyl-2-hydroxyethyl)-5H-imidazo[5,1-a]isoindol-9-ol | C |
| 1374 | 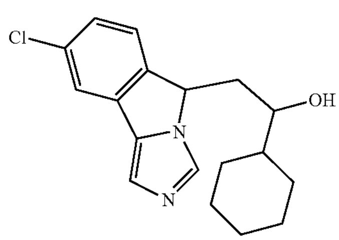 [SMILES: OC(CC1c2ccc(Cl)cc2-c2cncn21)C1CCCCC1] | 2-(8-chloro-5H-imidazo[5,1-a]isoindol-5-yl)-1-cyclohexylethanol; | B |
| 1375 | 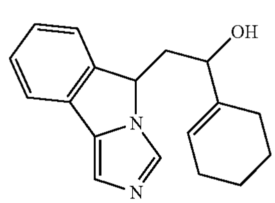 [SMILES: OC(CC1c2ccccc2-c2cncn21)C1=CCCCC1] | 1-(cyclohex-1-en-1-yl)-2-(5H-imidazo[5,1-a]isoindol-5-yl)ethanol; | B |

| No. | Structure | Name | hIDO IC$_{50}$ |
|---|---|---|---|
| 1376 | 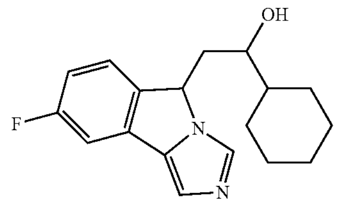 [SMILES: OC(CC1c2ccc(F)cc2-c2cncn21)C1CCCCC1] | 1-cyclohexyl-2-(8-fluoro-5H-imidazo[5,1-a]isoindol-5-yl)ethanol; | B |
| 1378 | 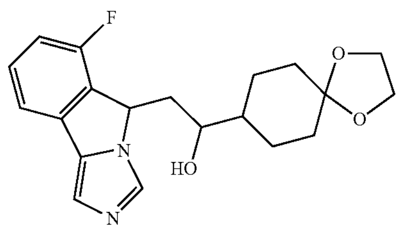 [SMILES: OC(CC1c2c(F)cccc2-c2cncn21)C1CCC2(CC1)OCCO2] | 2-(6-fluoro-5H-imidazo[5,1-a]isoindol-5-yl)-1-(1,4-dioxaspiro[4.5]decan-8-yl)ethanol; | B |
| 1379 | 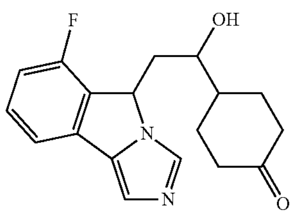 [SMILES: O=C1CCC(C(O)CC2c3c(F)cccc3-c3cncn32)CC1] | 4-(2-(6-fluoro-5H-imidazo[5,1-a]isoindol-5-yl)-1-hydroxyethyl)cyclohexanone; | A |
| 1381 | 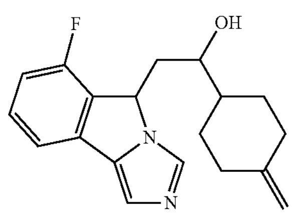 [SMILES: C=C1CCC(C(O)CC2c3c(F)cccc3-c3cncn32)CC1] | 2-(6-fluoro-5H-imidazo[5,1-a]isoindol-5-yl)-1-(4-methylenecyclohexyl)ethanol; | A |
| 1382 | 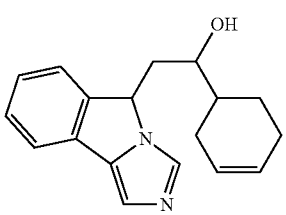 [SMILES: OC(CC1c2ccccc2-c2cncn21)C1CC=CCC1] | 1-(cyclohex-3-en-1-yl)-2-(5H-imidazo[5,1-a]isoindol-5-yl)ethanol; | A |
| 1383 | 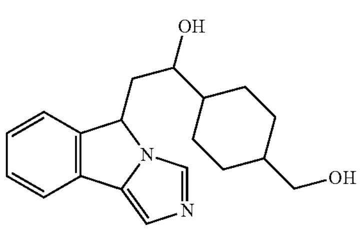 [SMILES: OCC1CCC(C(O)CC2c3ccccc3-c3cncn32)CC1] | 1-(4-(hydroxymethyl)cyclohexyl)-2-(5H-imidazo[5,1-a]isoindol-5-yl)ethanol; | A |

-continued

| No. | Structure | Name | hIDO IC$_{50}$ |
|---|---|---|---|
| 1384 | 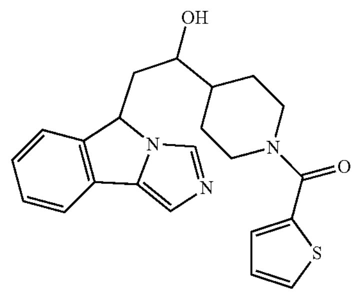 [SMILES: O=C(c1cccs1)N1CCC(C(O)CC2c3ccccc3-c3cncn32)CC1] | (4-(1-hydroxy-2-(5H-imidazo[5,1-a]isoindol-5-yl)ethyl)piperidin-1-yl)(thiophen-2-yl)methanone; | A |
| 1385 | 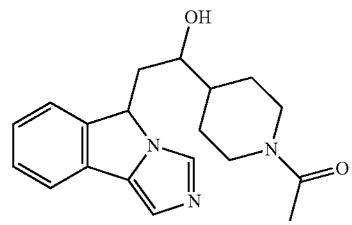 [SMILES: CC(=O)N1CCC(C(O)CC2c3ccccc3-c3cncn32)CC1] | 1-(4-(1-hydroxy-2-(5H-imidazo[5,1-a]isoindol-5-yl)ethyl)piperidin-1-yl)ethanone; | B |
| 1386 | 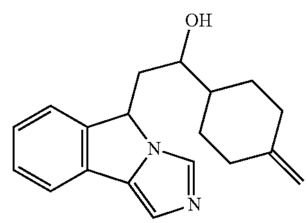 [SMILES: C=C1CCC(C(O)CC2c3ccccc3-c3cncn32)CC1] | 2-(5H-imidazo[5,1-a]isoindol-5-yl)-1-(4-methylenecyclohexyl)ethanol; | A |
| 1387 | 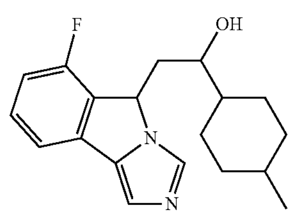 [SMILES: CC1CCC(C(O)CC2c3c(F)cccc3-c3cncn32)CC1] | 2-(6-fluoro-5H-imidazo[5,1-a]isoindol-5-yl)-1-(4-methylcyclohexyl)ethanol; | A |
| 1388 | 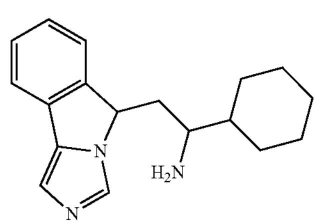 [SMILES: NC(CC1c2ccccc2-c2cncn21)C1CCCCC1] | 1-cyclohexyl-2-(5H-imidazo[5,1-a]isoindol-5-yl)ethanamine | B |
| 1389 | 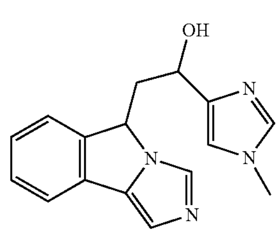 [SMILES: Cn1cnc(C(O)CC2c3ccccc3-c3cncn32)c1] | 2-(5H-imidazo[5,1-a]isoindol-5-yl)-1-(1-methyl-1H-imidazol-4-yl)ethanol; | D |

-continued

| No. | Structure | Name | hIDO IC$_{50}$ |
|---|---|---|---|
| 1390 | 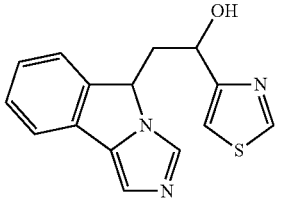 [SMILES: OC(CC1c2ccccc2-c2cncn21)c1cscn1] | 2-(5H-imidazo[5,1-a]isoindol-5-yl)-1-(thiazol-4-yl)ethanol; | C |
| 1391 | 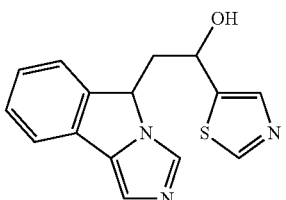 | 2-(5H-imidazo[5,1-a]isoindol-5-yl)-1-(thiazol-5-yl)ethanol; | B |
| 1392 | 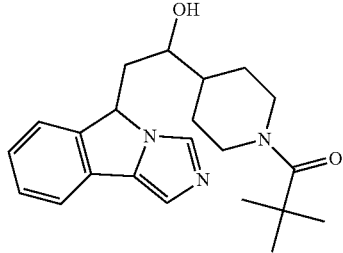 [SMILES: CC(C)(C)C(=O)N1CCC(C(O)CC2c3ccccc3-c3cncn32)CC1] | 1-(4-(1-hydroxy-2-(5H-imidazo[5,1-a]isoindol-5-yl)ethyl)piperidin-1-yl)-2,2-dimethylpropan-1-one; | B |
| 1393 | 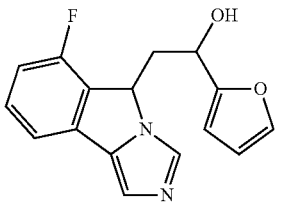 [SMILES: OC(CC1c2c(F)cccc2-c2cncn21)c1ccco1] | 2-(6-fluoro-5H-imidazo[5,1-a]isoindol-5-yl)-1-(furan-2-yl)ethanol; | B |
| 1394 | 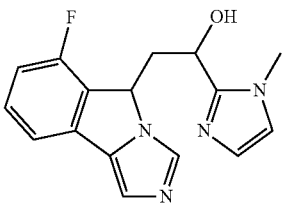 [SMILES: Cn1ccnc1C(O)CC1c2c(F)cccc2-c2cncn21] | 2-(6-fluoro-5H-imidazo[5,1-a]isoindol-5-yl)-1-(1-methyl-1H-imidazol-2-yl)ethanol; | C |
| 1398 | 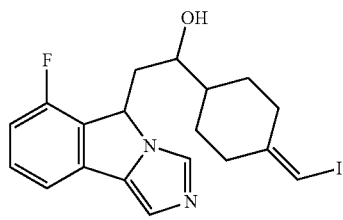 [SMILES: OC(CC1c2c(F)cccc2-c2cncn21)C1CCC(=CI)CC1] | 2-(6-fluoro-5H-imidazo[5,1-a]isoindol-5-yl)-1-(4-(iodomethylene)cyclohexyl)ethanol; | A |
| 1400 | 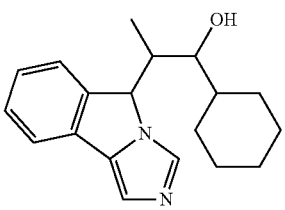 [SMILES: CC(C(O)C1CCCCC1)C1c2ccccc2-c2cncn21] | 1-cyclohexyl-2-(5H-imidazo[5,1-a]isoindol-5-yl)propan-1-ol; | B |

-continued

| No. | Structure | Name | hIDO IC$_{50}$ |
|---|---|---|---|
| 1402 | 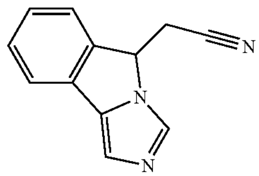 [SMILES: N#CCC1c2ccccc2-c2cncn21] | 2-(5H-imidazo[5,1-a]isoindol-5-yl)acetonitrile; | C |
| 1403 | 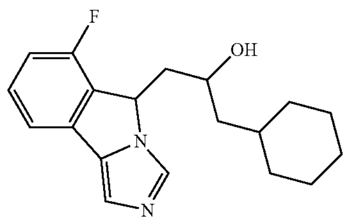 [SMILES: OC(CC1CCCCC1)CC1c2c(F)cccc2-c2cncn21] | 1-cyclohexyl-3-(6-fluoro-5H-imidazo[5,1-a]isoindol-5-yl)propan-2-ol; | A |
| 1404 | 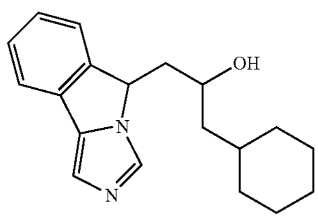 [SMILES: OC(CC1CCCCC1)CC1c2ccccc2-c2cncn21] | 1-cyclohexyl-3-(5H-imidazo[5,1-a]isoindol-5-yl)propan-2-ol; | A |
| 1405 | 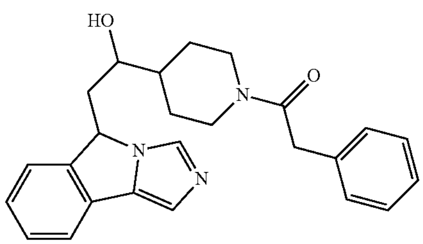 [SMILES: O=C(Cc1ccccc1)N1CCC(C(O)CC2c3ccccc3-c3cncn32)CC1] | 1-(4-(1-hydroxy-2-(5H-imidazo[5,1-a]isoindol-5-yl)ethyl)piperidin-1-yl)-2-phenylethanone; | A |
| 1406 | 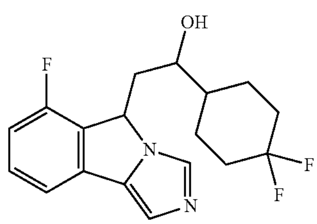 [SMILES: OC(CC1c2c(F)cccc2-c2cncn21)C1CCC(F)(F)CC1] | 1-(4,4-difluorocyclohexyl)-2-(6-fluoro-5H-imidazo[5,1-a]isoindol-5-yl)ethanol; | A |
| 1407 | 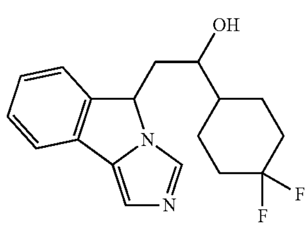 [SMILES: OC(CC1c2ccccc2-c2cncn21)C1CCC(F)(F)CC1] | 1-(4,4-difluorocyclohexyl)-2-(5H-imidazo[5,1-a]isoindol-5-yl)ethanol; | A |
| 1409 | 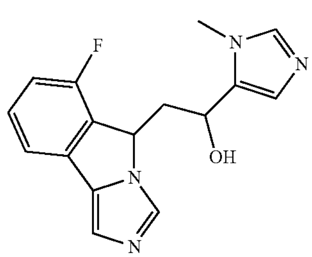 [SMILES: Cn1cncc1C(O)CC1c2c(F)cccc2-c2cncn21] | 2-(6-fluoro-5H-imidazo[5,1-a]isoindol-5-yl)-1-(1-methyl-1H-imidazol-5-yl)ethanol; | C |

-continued

| No. | Structure | Name | hIDO IC$_{50}$ |
|---|---|---|---|
| 1410 | 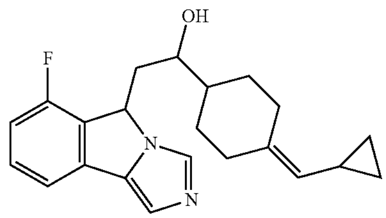 [SMILES: OC(CC1c2c(F)cccc2-c2cncn21)C1CCC(=CC2CC2)CC1] | 1-(4-(cyclopropylmethylene)cyclohexyl)-2-(6-fluoro-5H-imidazo[5,1-a]isoindol-5-yl)ethanol; | A |
| 1411 | 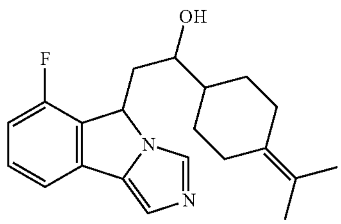 [SMILES: CC(C)=C1CCC(C(O)CC2c3c(F)cccc3-c3cncn32)CC1] | 2-(6-fluoro-5H-imidazo[5,1-a]isoindol-5-yl)-1-(4-(propan-2-ylidene)cyclohexyl)ethanol; | A |
| 1412 | 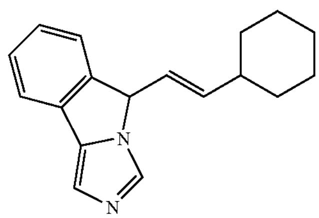 [SMILES: C(=C\C1c2ccccc2-c2cncn21)/C1CCCCC1] | (E)-5-(2-cyclohexylvinyl)-5H-imidazo[5,1-a]isoindole; | A |
| 1413 | 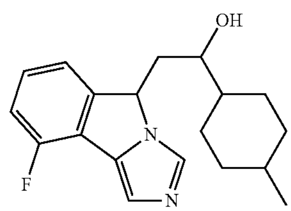 [SMILES: CC1CCC(C(O)CC2c3cccc(F)c3-c3cncn32)CC1] | 2-(9-fluoro-5H-imidazo[5,1-a]isoindol-5-yl)-1-(4-methylcyclohexyl)ethanol; | A |
| 1414 | 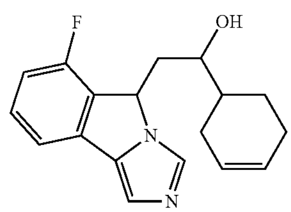 [SMILES: OC(CC1c2c(F)cccc2-c2cncn21)C1CC=CCC1] | 1-(cyclohex-3-en-1-yl)-2-(6-fluoro-5H-imidazo[5,1-a]isoindol-5-yl)ethanol; | A |
| 1415 | 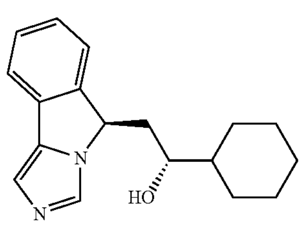 [SMILES: O[C@H](C[C@@H]1c2ccccc2-c2cncn21)C1CCCCC1] | (R)-1-cyclohexyl-2-((R)-5H-imidazo[5,1-a]isoindol-5-yl)ethanol | B |
| 1416 | 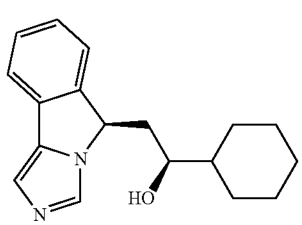 [SMILES: O[C@@H](C[C@@H]1c2ccccc2-c2cncn21)C1CCCCC1] | (S)-1-cyclohexyl-2-((R)-5H-imidazo[5,1-a]isoindol-5-yl)ethanol | B |

-continued

| No. | Structure | Name | hIDO IC$_{50}$ |
|---|---|---|---|
| 1417 | 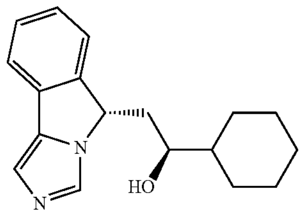 [SMILES: O[C@@H](C[C@H]1c2ccccc2-c2cncn21)C1CCCCC1] | (S)-1-cyclohexyl-2-((S)-5H-imidazo[5,1-a]isoindol-5-yl)ethanol | A |
| 1418 | 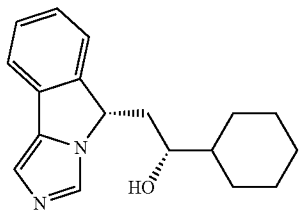 [SMILES: O[C@H](C[C@H]1c2ccccc2-c2cncn21)C1CCCCC1] | (R)-1-cyclohexyl-2-((S)-5H-imidazo[5,1-a]isoindol-5-yl)ethanol | A |
| 1419 | 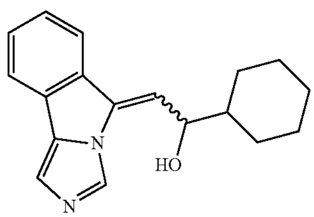 [SMILES: OC(C=c1c2ccccc2c2cncn12)C1CCCCC1] | 1-cyclohexyl-2-(5H-imidazo[5,1-a]isoindol-5-ylidene)ethanol | B |
| 1420 | 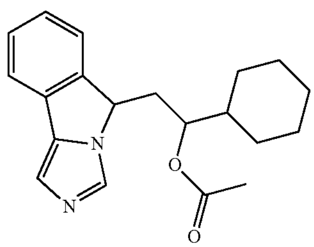 [SMILES: CC(=O)OC(CC1c2ccccc2-c2cncn21)C1CCCCC1] | 1-cyclohexyl-2-(5H-imidazo[5,1-a]isoindol-5-yl)ethyl acetate | C |
| 1421 | 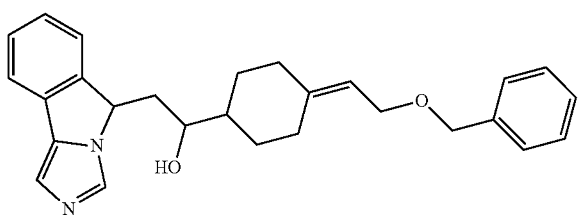 [SMILES: OC(CC1c2ccccc2-c2cncn21)C1CCC(=CCOCc2ccccc2)CC1] | 1-(4-(2-(benzyloxy)ethylidene)cyclohexyl)-2-(5H-imidazo[5,1-a]isoindol-5-yl)ethanol | A |
| 1422 | 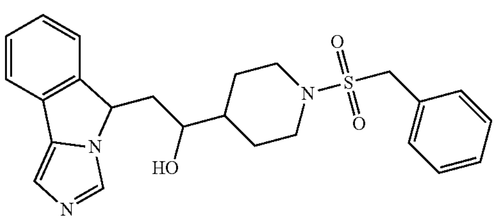 [SMILES: O=S(=O)(Cc1ccccc1)N1CCC(C(O)CC2c3ccccc3-c3cncn32)CC1] | 1-(1-(benzylsulfonyl)piperidin-4-yl)-2-(5H-imidazo[5,1-a]isoindol-5-yl)ethanol | A |
| 1423 | 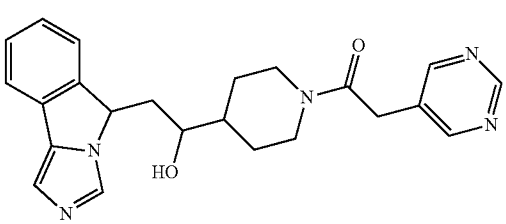 [SMILES: O=C(Cc1cncnc1)N1CCC(C(O)CC2c3ccccc3-c3cncn32)CC1] | 1-(4-(1-hydroxy-2-(5H-imidazo[5,1-a]isoindol-5-yl)ethyl)piperidin-1-yl)-2-(pyrimidin-5-yl)ethanone | A |

-continued

| No. | Structure | Name | hIDO IC$_{50}$ |
|---|---|---|---|
| 1424 | 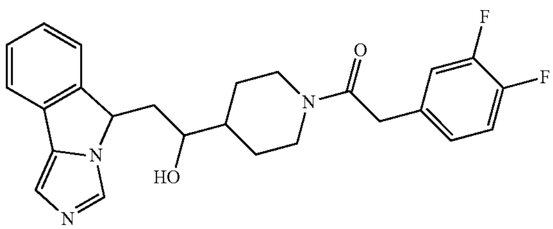 [SMILES: O=C(Cc1ccc(F)c(F)c1)N1CCC(C(O)CC2c3ccccc3-c3cncn32)CC1] | 2-(3,4-difluorophenyl)-1-(4-(1-hydroxy-2-(5H-imidazo[5,1-a]isoindol-5-yl)ethyl)piperidin-1-yl)ethanone | A |
| 1425 | 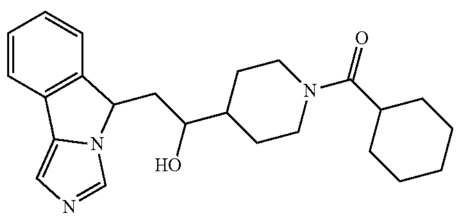 [SMILES: O=C(C1CCCCC1)N1CCC(C(O)CC2c3ccccc3-c3cncn32)CC1] | cyclohexyl(4-(1-hydroxy-2-(5H-imidazo[5,1-a]isoindol-5-yl)ethyl)piperidin-1-yl)methanone | A |
| 1426 | 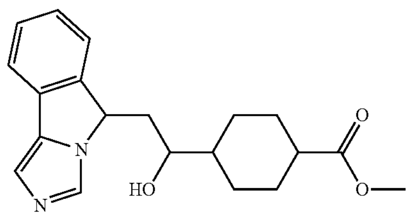 [SMILES: COC(=O)C1CCC(C(O)CC2c3ccccc3-c3cncn32)CC1] | methyl 4-(1-hydroxy-2-(5H-imidazo[5,1-a]isoindol-5-yl)ethyl)cyclohexanecarboxylate | A |
| 1427 | 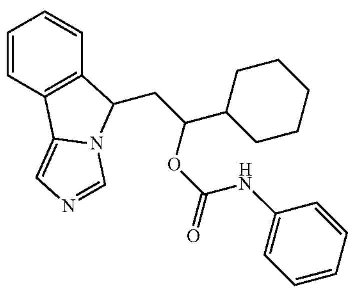 [SMILES: O=C(Nc1ccccc1)OC(CC1c2ccccc2-c2cncn21)C1CCCCC1] | 1-cyclohexyl-2-(5H-imidazo[5,1-a]isoindol-5-yl)ethyl phenylcarbamate | B |
| 1428 | 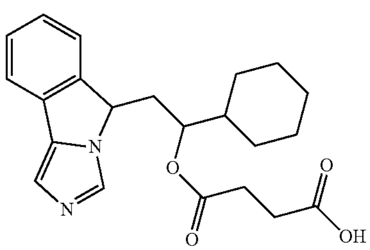 [SMILES: O=C(O)CCC(=O)OC(CC1c2ccccc2-c2cncn21)C1CCCCC1] | 4-(1-cyclohexyl-2-(5H-imidazo[5,1-a]isoindol-5-yl)ethoxy)-4-oxobutanoic acid | B |
| 1429 | 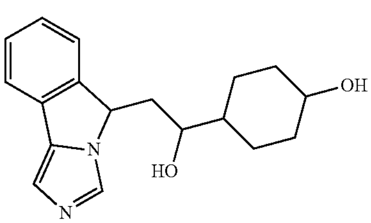 [SMILES: OC1CCC(C(O)CC2c3ccccc3-c3cncn32)CC1] | 4-(1-hydroxy-2-(5H-imidazo[5,1-a]isoindol-5-yl)ethyl)cyclohexanol | A |

| No. | Structure | Name | hIDO IC$_{50}$ |
|---|---|---|---|
| 1430 | 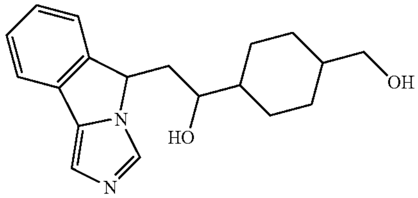 [SMILES: OCC1CCC(C(O)CC2c3ccccc3-c3cncn32)CC1] | 1-(4-(hydroxymethyl)cyclohexyl)-2-(5H-imidazo[5,1-a]isoindol-5-yl)ethanol | A |
| 1431 | 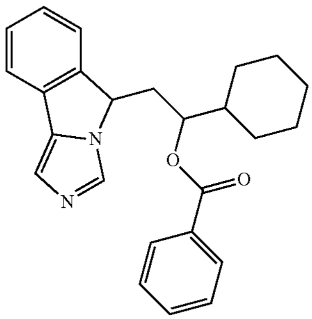 [SMILES: O=C(OC(CC1c2ccccc2-c2cncn21)C1CCCCC1)c1ccccc1] | 1-cyclohexyl-2-(5H-imidazo[5,1-a]isoindol-5-yl)ethyl benzoate | C |
| 1432 | 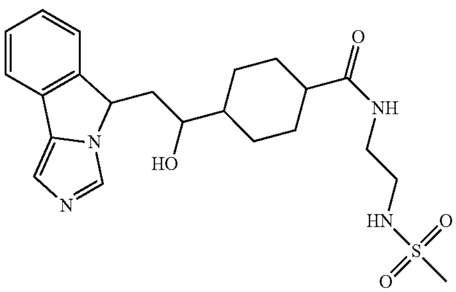 [SMILES: CS(=O)(=O)NCCNC(=O)C1CCC(C(O)CC2c3ccccc3-c3cncn32)CC1] | 4-(1-hydroxy-2-(5H-imidazo[5,1-a]isoindol-5-yl)ethyl)-N-(2-(methylsulfonamido)ethyl)cyclohexanecarboxamide | B |
| 1433 | 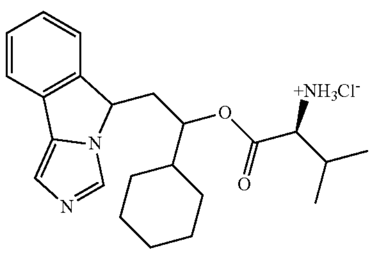 | (2S)-1-(1-cyclohexyl-2-(5H-imidazo[5,1-a]isoindol-5-yl)ethoxy)-3-methyl-1-oxobutan-2-aminium chloride | C |
| 1434 | 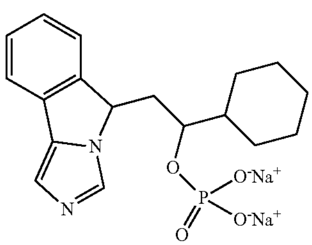 | sodium 1-cyclohexyl-2-(5H-imidazo[5,1-a]isoindol-5-yl)ethyl phosphate | A |
| 1436 | 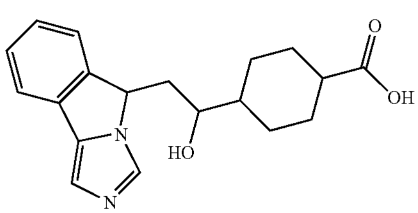 [SMILES: O=C(O)C1CCC(C(O)CC2c3ccccc3-c3cncn32)CC1] | 4-(1-hydroxy-2-(5H-imidazo[5,1-a]isoindol-5-yl)ethyl)cyclohexanecarboxylic acid | B |

-continued

| No. | Structure | Name | hIDO IC$_{50}$ |
|---|---|---|---|
| 1437 | 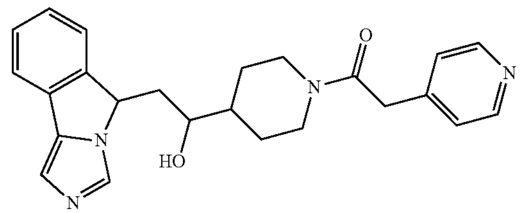 [SMILES: O=C(Cc1ccncc1)N1CCC(C(O)CC2c3ccccc3-c3cncn32)CC1] | 1-(4-(1-hydroxy-2-(5H-imidazo[5,1-a]isoindol-5-yl)ethyl)piperidin-1-yl)-2-(pyridin-4-yl)ethanone | A |
| 1438 | 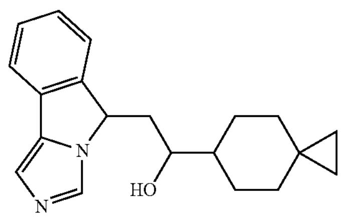 [SMILES: OC(CC1c2ccccc2-c2cncn21)C1CCC2(CC1)CC2] | 2-(5H-imidazo[5,1-a]isoindol-5-yl)-1-(spiro[2.5]octan-6-yl)ethanol | C |
| 1439 | 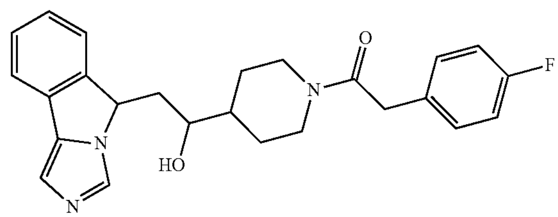 [SMILES: O=C(Cc1ccc(F)cc1)N1CCC(C(O)CC2c3ccccc3-c3cncn32)CC1] | 2-(4-fluorophenyl)-1-(4-(1-hydroxy-2-(5H-imidazo[5,1-a]isoindol-5-yl)ethyl)piperidin-1-yl)ethanone | A |
| 1440 | 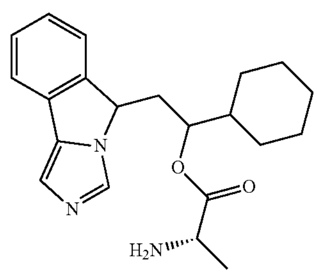 [SMILES: C[C@H](N)C(=O)OC(CC1c2ccccc2-c2cncn21)C1CCCCC1] | (2S)-1-cyclohexyl-2-(5H-imidazo[5,1-a]isoindol-5-yl)ethyl 2-aminopropanoate | C |
| 1441 | 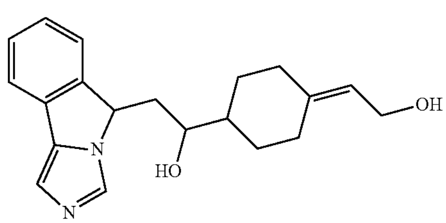 [SMILES: OCC=C1CCC(C(O)CC2c3ccccc3-c3cncn32)CC1] | 1-(4-(2-hydroxyethylidene)cyclohexyl)-2-(5H-imidazo[5,1-a]isoindol-5-yl)ethanol | A |
| 1442 | 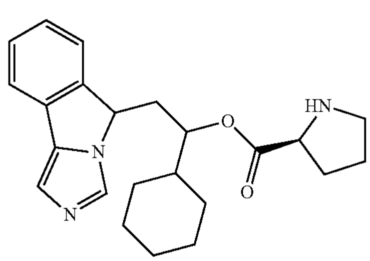 [SMILES: O=C(OC(CC1c2ccccc2-c2cncn21)C1CCCCC1)[C@@H]1CCCN1] | (2S)-1-cyclohexyl-2-(5H-imidazo[5,1-a]isoindol-5-yl)ethyl pyrrolidine-2-carboxylate | B |

-continued

| No. | Structure | Name | hIDO IC$_{50}$ |
|---|---|---|---|
| 1443 | 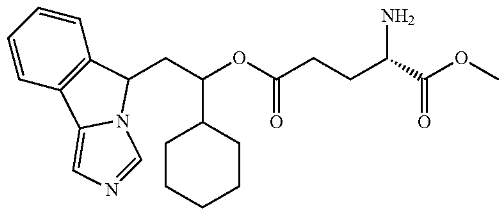 [SMILES: COC(=O)[C@@H](N)CCC(=O)OC(CC1c2ccccc2-c2cncn21)C1CCCCC1] | (2S)-5-(1-cyclohexyl-2-(5H-imidazo[5,1-a]isoindol-5-yl)ethyl) 1-methyl 2-aminopentanedioate | C |
| 1447 | 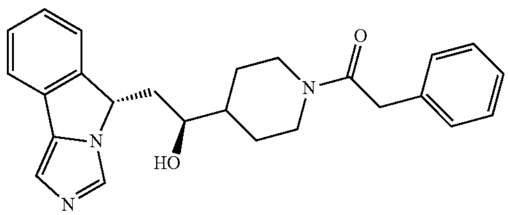 [SMILES: O=C(Cc1ccccc1)N1CCC([C@@H](O)C[C@H]2c3ccccc3-c3cncn32)CC1] | 1-(4-((S)-1-hydroxy-2-((S)-5H-imidazo[5,1-a]isoindol-5-yl)ethyl)piperidin-1-yl)-2-phenylethanone | A |
| 1448 | 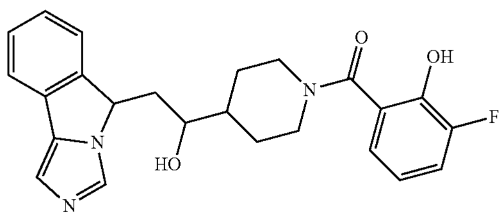 [SMILES: O=C(c1cccc(F)c1O)N1CCC(C(O)CC2c3ccccc3-c3cncn32)CC1] | (3-fluoro-2-hydroxyphenyl)(4-(1-hydroxy-2-(5H-imidazo[5,1-a]isoindol-5-yl)ethyl)piperidin-1-yl)methanone | A |
| 1449 | 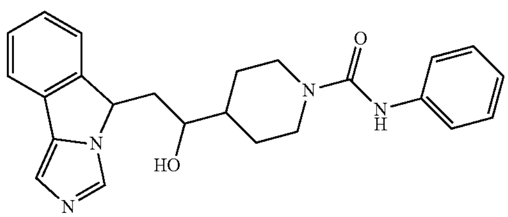 [SMILES: O=C(Nc1ccccc1)N1CCC(C(O)CC2c3ccccc3-c3cncn32)CC1] | 4-(1-hydroxy-2-(5H-imidazo[5,1-a]isoindol-5-yl)ethyl)-N-phenylpiperidine-1-carboxamide | A |
| 1450 | 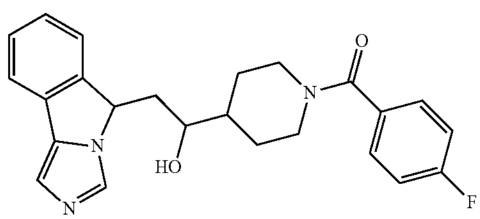 [SMILES: O=C(c1ccc(F)cc1)N1CCC(C(O)CC2c3ccccc3-c3cncn32)CC1] | (4-fluorophenyl)(4-(1-hydroxy-2-(5H-imidazo[5,1-a]isoindol-5-yl)ethyl)piperidin-1-yl)methanone | B |
| 1451 | 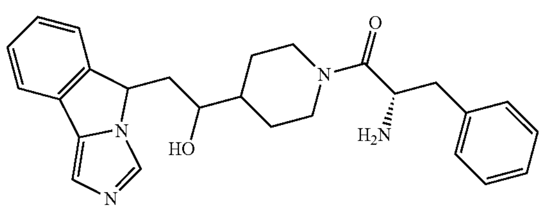 [SMILES: N[C@@H](Cc1ccccc1)C(=O)N1CCC(C(O)CC2c3ccccc3-c3cncn32)CC1] | (2S)-2-amino-1-(4-(1-hydroxy-2-(5H-imidazo[5,1-a]isoindol-5-yl)ethyl)piperidin-1-yl)-3-phenylpropan-1-one | B |
| 1454 | 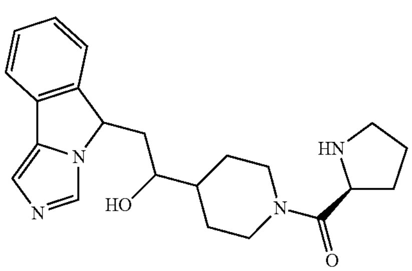 [SMILES: O=C([C@@H]1CCCN1)N1CCC(C(O)CC2c3ccccc3-c3cncn32)CC1] | (4-(1-hydroxy-2-(5H-imidazo[5,1-a]isoindol-5-yl)ethyl)piperidin-1-yl)((S)-pyrrolidin-2-yl)methanone | D |

-continued

| No. | Structure | Name | hIDO IC$_{50}$ |
|---|---|---|---|
| 1455 | 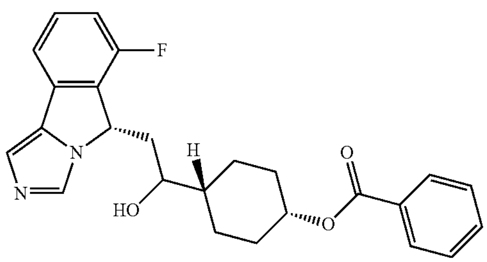 [SMILES: O=C(O[C@H]1CC[C@@H](C(O)C[C@H]2c3c(F)cccc3-c3cncn32)CC1)c1ccccc1] | (1R,4s)-4-(2-((S)-6-fluoro-5H-imidazo[5,1-a]isoindol-5-yl)-1-hydroxyethyl)cyclohexyl benzoate | A |
| 1456 | 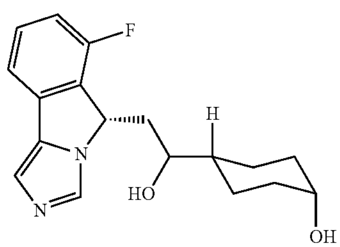 [SMILES: OC1CCC(C(O)C[C@H]2c3c(F)cccc3-c3cncn32)CC1] | (1R,4s)-4-(2-((S)-6-fluoro-5H-imidazo[5,1-a]isoindol-5-yl)-1-hydroxyethyl)cyclohexanol | A |
| 1458 | 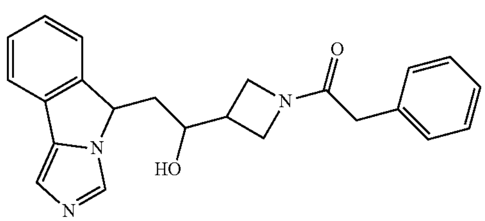 [SMILES: O=C(Cc1ccccc1)N1CC(C(O)CC2c3ccccc3-c3cncn32)C1] | 1-(3-(1-hydroxy-2-(5H-imidazo[5,1-a]isoindol-5-yl)ethyl)azetidin-1-yl)-2-phenylethanone | A |
| 1459 | 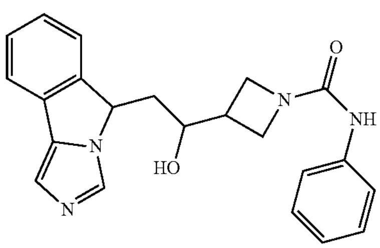 [SMILES: O=C(Nc1ccccc1)N1CC(C(O)CC2c3ccccc3-c3cncn32)C1] | 3-(1-hydroxy-2-(5H-imidazo[5,1-a]isoindol-5-yl)ethyl)-N-phenylazetidine-1-carboxamide | A |
| 1460 | 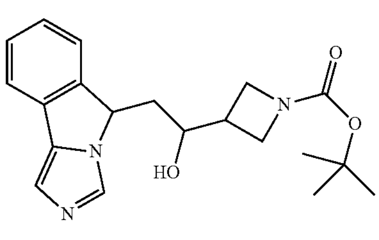 [SMILES: CC(C)(C)OC(=O)N1CC(C(O)CC2c3ccccc3-c3cncn32)C1] | tert-butyl 3-(1-hydroxy-2-(5H-imidazo[5,1-a]isoindol-5-yl)ethyl)azetidine-1-carboxylate | A |
| 1461 | 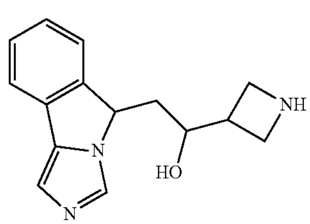 [SMILES: OC(CC1c2ccccc2-c2cncn21)C1CNC1] | 1-(azetidin-3-yl)-2-(5H-imidazo[5,1-a]isoindol-5-yl)ethanol | C |

-continued

| No. | Structure | Name | hIDO IC$_{50}$ |
|---|---|---|---|
| 1469 | 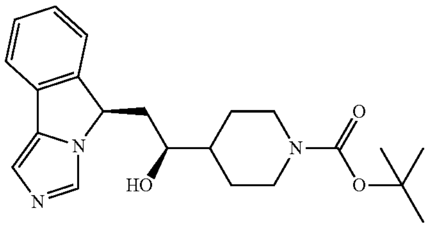 [SMILES: CC(C)(C)OC(=O)N1CCC([C@@H](O)C[C@@H]2c3ccccc3-c3cncn32)CC1] | tert-butyl 4-((S)-1-hydroxy-2-((R)-5H-imidazo[5,1-a]isoindol-5-yl)ethyl)piperidine-1-carboxylate | B |
| 1470 | 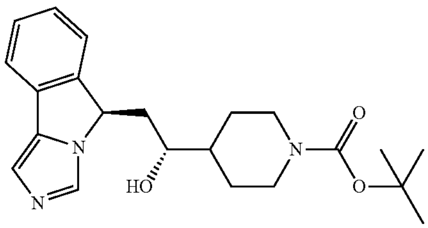 [SMILES: CC(C)(C)OC(=O)N1CCC([C@H](O)C[C@@H]2c3ccccc3-c3cncn32)CC1] | tert-butyl 4-((R)-1-hydroxy-2-((R)-5H-imidazo[5,1-a]isoindol-5-yl)ethyl)piperidine-1-carboxylate | B |
| 1471 | 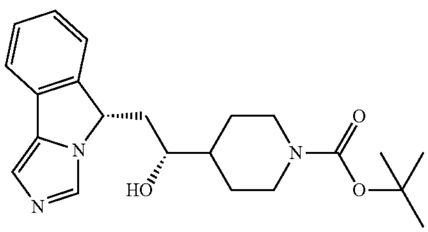 [SMILES: CC(C)(C)OC(=O)N1CCC([C@H](O)C[C@H]2c3ccccc3-c3cncn32)CC1] | tert-butyl 4-((R)-1-hydroxy-2-((S)-5H-imidazo[5,1-a]isoindol-5-yl)ethyl)piperidine-1-carboxylate | A |
| 1472 | 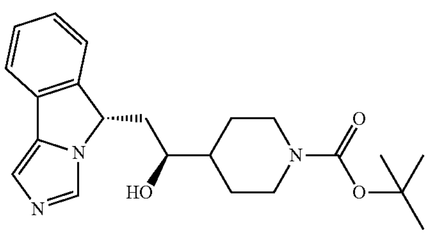 [SMILES: CC(C)(C)OC(=O)N1CCC([C@@H](O)C[C@H]2c3ccccc3-c3cncn32)CC1] | tert-butyl 4-((S)-1-hydroxy-2-((S)-5H-imidazo[5,1-a]isoindol-5-yl)ethyl)piperidine-1-carboxylate | A |
| 1473 | 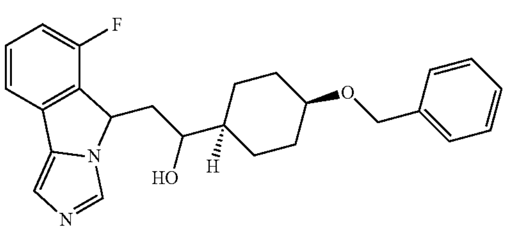 [SMILES: OC(CC1c2c(F)cccc2-c2cncn21)[C@H]1CC[C@@H](OCc2ccccc2)CC1] | 1-((1s,4s)-4-(benzyloxy)cyclohexyl)-2-(6-fluoro-5H-imidazo[5,1-a]isoindol-5-yl)ethanol | A |
| 1474 | 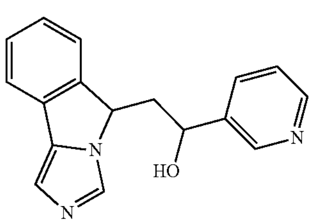 [SMILES: OC(CC1c2ccccc2-c2cncn21)c1cccnc1] | 2-(5H-imidazo[5,1-a]isoindol-5-yl)-1-(pyridin-3-yl)ethanol | B |

-continued

| No. | Structure | Name | hIDO IC$_{50}$ |
|---|---|---|---|
| 1475 | 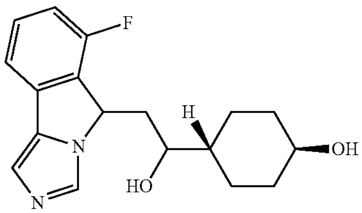 | (1r,4r)-4-(2-(6-fluoro-5H-imidazo[5,1-a]isoindol-5-yl)-1-hydroxyethyl)cyclohexanol | A |
| 1476 | 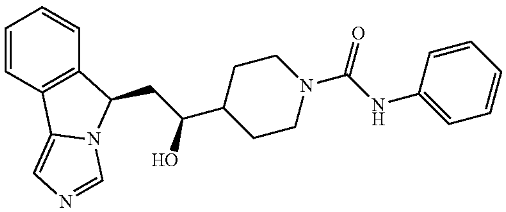 | 4-((S)-1-hydroxy-2-((R)-5H-imidazo[5,1-a]isoindol-5-yl)ethyl)-N-phenylpiperidine-1-carboxamide | B |
| 1477 | 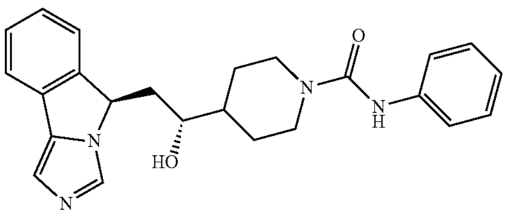 [SMILES: O=C(Nc1ccccc1)N1CCC([C@H](O)C[C@@H]2c3ccccc3-c3cncn32)CC1] | 4-((R)-1-hydroxy-2-((R)-5H-imidazo[5,1-a]isoindol-5-yl)ethyl)-N-phenylpiperidine-1-carboxamide | B |
| 1478 | 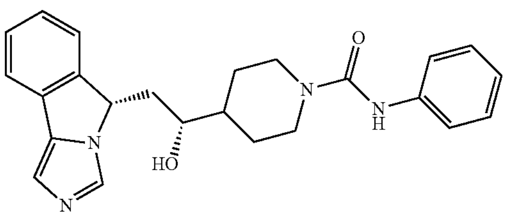 [SMILES: O=C(Nc1ccccc1)N1CCC([C@H](O)C[C@H]2c3ccccc3-c3cncn32)CC1] | 4-((R)-1-hydroxy-2-((S)-5H-imidazo[5,1-a]isoindol-5-yl)ethyl)-N-phenylpiperidine-1-carboxamide | A |
| 1479 | 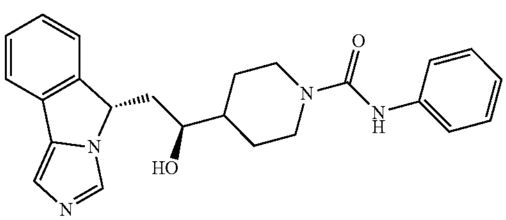 [SMILES: O=C(Nc1ccccc1)N1CCC([C@@H](O)C[C@H]2c3ccccc3-c3cncn32)CC1] | 4-((S)-1-hydroxy-2-((S)-5H-imidazo[5,1-a]isoindol-5-yl)ethyl)-N-phenylpiperidine-1-carboxamide | A |
| 1480 | 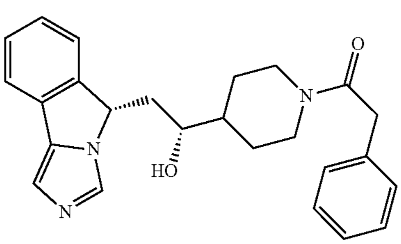 [SMILES: O=C(Cc1ccccc1)N1CCC([C@H](O)C[C@H]2c3ccccc3-c3cncn32)CC1] | 1-(4-((R)-1-hydroxy-2-((S)-5H-imidazo[5,1-a]isoindol-5-yl)ethyl)piperidin-1-yl)-2-phenylethanone | A |
| 1481 | 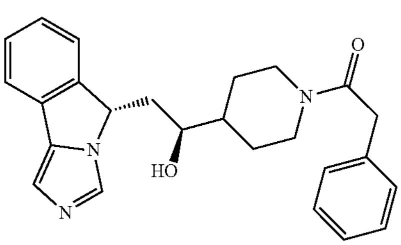 [SMILES: O=C(Cc1ccccc1)N1CCC([C@@H](O)C[C@H]2c3ccccc3-c3cncn32)CC1] | 1-(4-((S)-1-hydroxy-2-((S)-5H-imidazo[5,1-a]isoindol-5-yl)ethyl)piperidin-1-yl)-2-phenylethanone | A |

-continued

| No. | Structure | Name | hIDO IC$_{50}$ |
|---|---|---|---|
| 1482 | 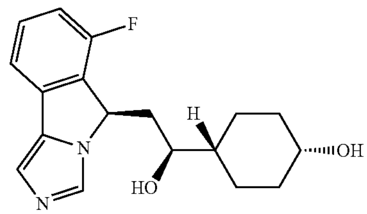 [SMILES: O[C@@H](C[C@@H]1c2c(F)cccc2-c2cncn21)[C@H]1CC[C@@H](O)CC1] | (1R,4s)-4-((S)-2-((R)-6-fluoro-5H-imidazo[5,1-a]isoindol-5-yl)-1-hydroxyethyl)cyclohexanol | B |
| 1483 | 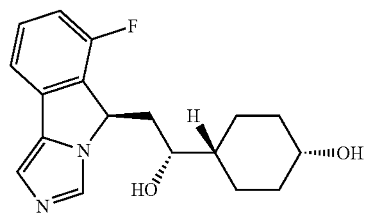 [SMILES: O[C@H](C[C@@H]1c2c(F)cccc2-c2cncn21)[C@H]1CC[C@@H](O)CC1] | (1S,4s)-4-((R)-2-((R)-6-fluoro-5H-imidazo[5,1-a]isoindol-5-yl)-1-hydroxyethyl)cyclohexanol | B |
| 1484 | 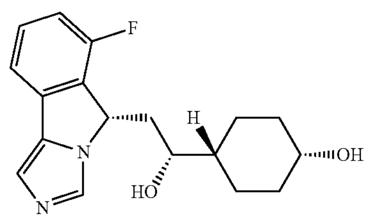 [SMILES: O[C@H](C[C@H]1c2c(F)cccc2-c2cncn21)[C@H]1CC[C@@H](O)CC1] | (1S,4s)-4-((R)-2-((S)-6-fluoro-5H-imidazo[5,1-a]isoindol-5-yl)-1-hydroxyethyl)cyclohexanol | A |
| 1485 | 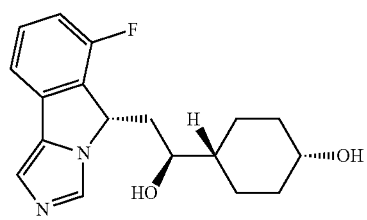 [SMILES: O[C@@H](C[C@H]1c2c(F)cccc2-c2cncn21)[C@H]1CC[C@@H](O)CC1] | (1R,4s)-4-((S)-2-((S)-6-fluoro-5H-imidazo[5,1-a]isoindol-5-yl)-1-hydroxyethyl)cyclohexanol | A |
| 1486 | 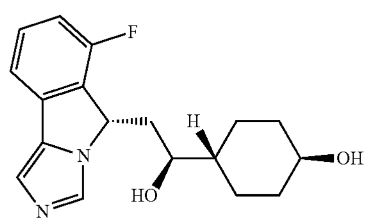 [SMILES: O[C@@H](C[C@H]1c2c(F)cccc2-c2cncn21)[C@H]1CC[C@H](O)CC1] | (1S,4r)-4-((S)-2-((S)-6-fluoro-5H-imidazo[5,1-a]isoindol-5-yl)-1-hydroxyethyl)cyclohexanol | A |
| 1487 | 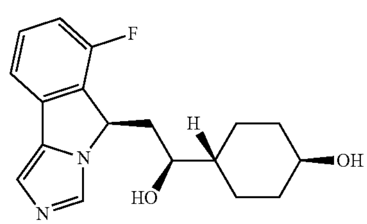 [SMILES: O[C@@H](C[C@@H]1c2c(F)cccc2-c2cncn21)[C@H]1CC[C@H](O)CC1] | (1S,4r)-4-((S)-2-((R)-6-fluoro-5H-imidazo[5,1-a]isoindol-5-yl)-1-hydroxyethyl)cyclohexanol | B |
| 1488 | 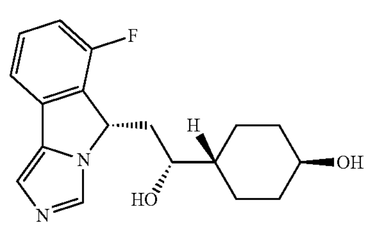 [SMILES: O[C@H](C[C@H]1c2c(F)cccc2-c2cncn21)[C@H]1CC[C@H](O)CC1] | (1R,4r)-4-((R)-2-((S)-6-fluoro-5H-imidazo[5,1-a]isoindol-5-yl)-1-hydroxyethyl)cyclohexanol | A |

-continued

| No. | Structure | Name | hIDO IC$_{50}$ |
|---|---|---|---|
| 1489 | 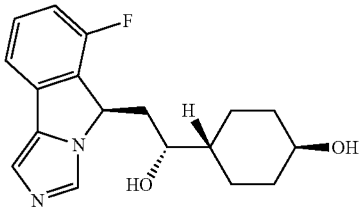 [SMILES: O[C@H](C[C@@H]1c2c(F)cccc2-c2cncn21)[C@H]1CC[C@H](O)CC1] | (1R,4r)-4-((R)-2-((R)-6-fluoro-5H-imidazo[5,1-a]isoindol-5-yl)-1-hydroxyethyl)cyclohexanol | B |
| 1490 | 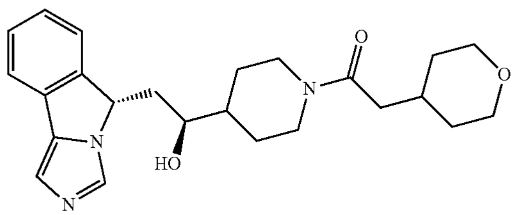 [SMILES: O=C(CC1CCOCC1)N1CCC([C@@H](O)C[C@H]2c3ccccc3-c3cncn32)CC1] | 1-(4-((S)-1-hydroxy-2-((S)-5H-imidazo[5,1-a]isoindol-5-yl)ethyl)piperidin-1-yl)-2-(tetrahydro-2H-pyran-4-yl)ethanone | A |
| 1491 | 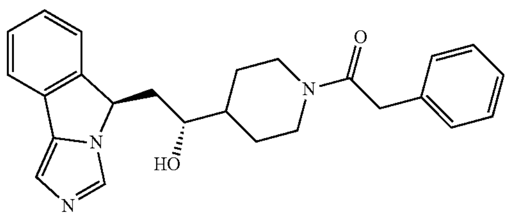 [SMILES: O=C(Cc1ccccc1)N1CCC([C@H](O)C[C@@H]2c3ccccc3-c3cncn32)CC1] | 1-(4-((R)-1-hydroxy-2-((R)-5H-imidazo[5,1-a]isoindol-5-yl)ethyl)piperidin-1-yl)-2-phenylethanone | B |
| 1492 | 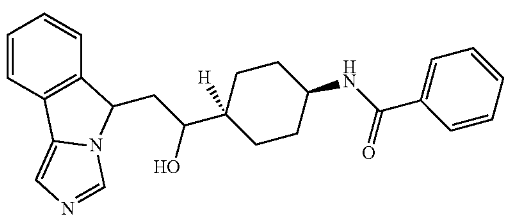 [SMILES: O=C(N[C@H]1CC[C@@H](C(O)CC2c3ccccc3-c3cncn32)CC1)c1ccccc1] | N-((1s,4s)-4-(1-hydroxy-2-(5H-imidazo[5,1-a]isoindol-5-yl)ethyl)cyclohexyl)benzamide | A |
| 1493 | 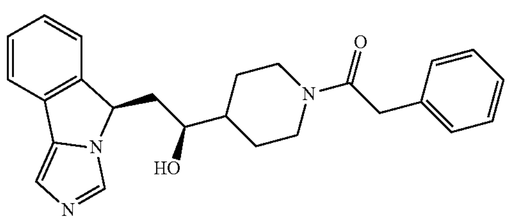 [SMILES: O=C(Cc1ccccc1)N1CCC([C@@H](O)C[C@@H]2c3ccccc3-c3cncn32)CC1] | 1-(4-((S)-1-hydroxy-2-((R)-5H-imidazo[5,1-a]isoindol-5-yl)ethyl)piperidin-1-yl)-2-phenylethanone | B |
| 1494 | 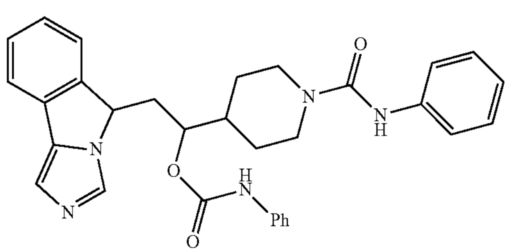 [SMILES: O=C(Nc1ccccc1)OC(CC1c2ccccc2-c2cncn21)C1CCN(C(=O)Nc2ccccc2)CC1] | 2-(5H-imidazo[5,1-a]isoindol-5-yl)-1-(1-(phenylcarbamoyl)piperidin-4-yl)ethyl phenylcarbamate | C |
| 1495 | 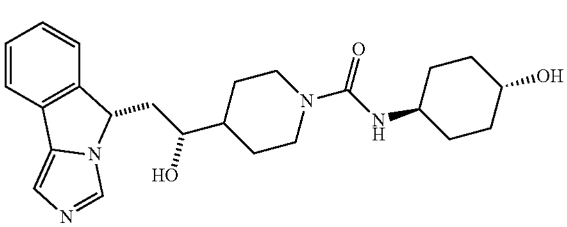 [SMILES: O=C(N[C@H]1CC[C@H](O)CC1)N1CCC([C@H](O)C[C@H]2c3ccccc3-c3cncn32)CC1] | 4-((R)-1-hydroxy-2-((S)-5H-imidazo[5,1-a]isoindol-5-yl)ethyl)-N-((1r,4R)-4-hydroxycyclohexyl)piperidine-1-carboxamide | A |

-continued

| No. | Structure | Name | hIDO IC$_{50}$ |
|---|---|---|---|
| 1496 | 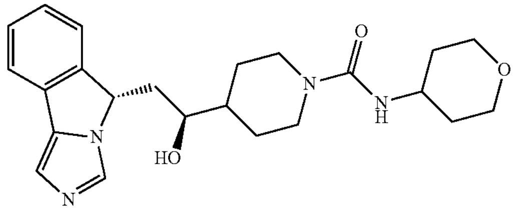 [SMILES: O=C(NC1CCOCC1)N1CCC([C@@H](O)C[C@H]2c3ccccc3-c3cncn32)CC1] | 4-((S)-1-hydroxy-2-((S)-5H-imidazo[5,1-a]isoindol-5-yl)ethyl)-N-(tetrahydro-2H-pyran-4-yl)piperidine-1-carboxamide | A |
| 1497 | 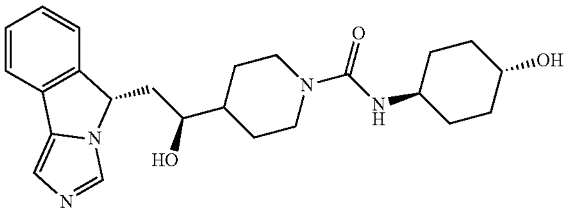 [SMILES: O=C(N[C@H]1CC[C@H](O)CC1)N1CCC([C@@H](O)C[C@H]2c3ccccc3-c3cncn32)CC1] | 4-((S)-1-hydroxy-2-((S)-5H-imidazo[5,1-a]isoindol-5-yl)ethyl)-N-((1r,4S)-4-hydroxycyclohexyl)piperidine-1-carboxamide | A |
| 1498 | 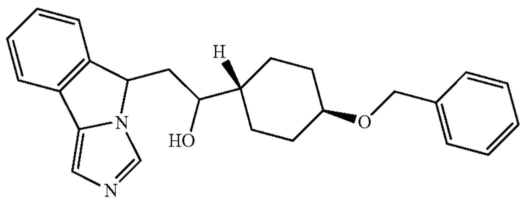 [SMILES: OC(CC1c2ccccc2-c2cncn21)[C@H]1CC[C@H](OCc2ccccc2)CC1] | 1-((1r,4r)-4-(benzyloxy)cyclohexyl)-2-(5H-imidazo[5,1-a]isoindol-5-yl)ethanol | A |
| 1499 | 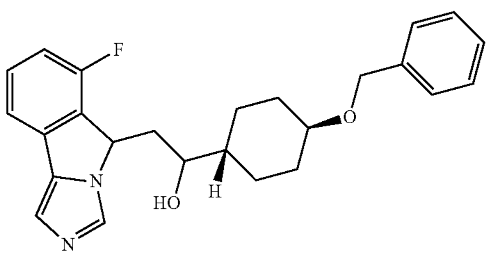 [SMILES: OC(CC1c2c(F)cccc2-c2cncn21)[C@H]1CC[C@H](OCc2ccccc2)CC1] | 1-((1r,4r)-4-(benzyloxy)cyclohexyl)-2-(6-fluoro-5H-imidazo[5,1-a]isoindol-5-yl)ethanol | A |
| 1500 | 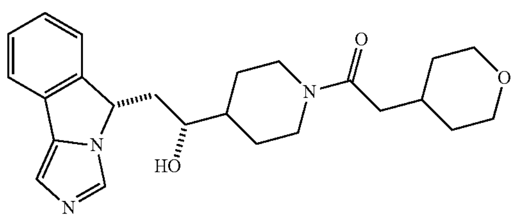 [SMILES: O=C(CC1CCOCC1)N1CCC([C@H](O)C[C@H]2c3ccccc3-c3cncn32)CC1] | 1-(4-((R)-1-hydroxy-2-((S)-5H-imidazo[5,1-a]isoindol-5-yl)ethyl)piperidin-1-yl)-2-(tetrahydro-2H-pyran-4-yl)ethanone | A |
| 1501 | 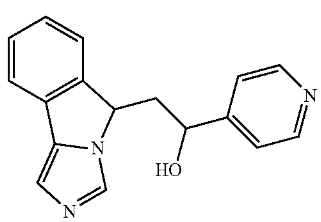 [SMILES: OC(CC1c2ccccc2-c2cncn21)c1ccncc1] | 2-(5H-imidazo[5,1-a]isoindol-5-yl)-1-(pyridin-4-yl)ethanol | A |
| 1502 | 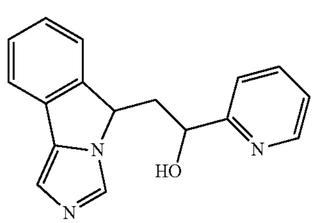 [SMILES: OC(CC1c2ccccc2-c2cncn21)c1ccccn1] | 2-(5H-imidazo[5,1-a]isoindol-5-yl)-1-(pyridin-2-yl)ethanol | B |

-continued

| No. | Structure | Name | hIDO IC$_{50}$ |
|---|---|---|---|
| 1503 | 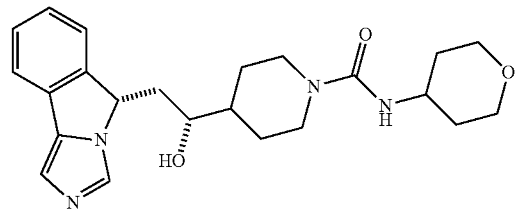 [SMILES: O=C(NC1CCOCC1)N1CCC([C@H](O)C[C@H]2c3ccccc3-c3cncn32)CC1] | 4-((R)-1-hydroxy-2-((S)-5H-imidazo[5,1-a]isoindol-5-yl)ethyl)-N-(tetrahydro-2H-pyran-4-yl)piperidine-1-carboxamide | A |
| 1504 | 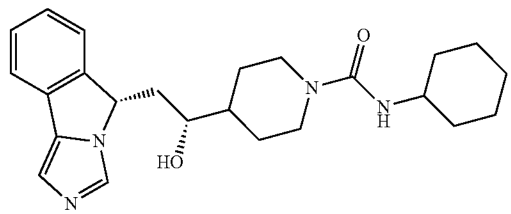 [SMILES: O=C(NC1CCCCC1)N1CCC([C@H](O)C[C@H]2c3ccccc3-c3cncn32)CC1] | N-cyclohexyl-4-((R)-1-hydroxy-2-((S)-5H-imidazo[5,1-a]isoindol-5-yl)ethyl)piperidine-1-carboxamide | A |
| 1505 | 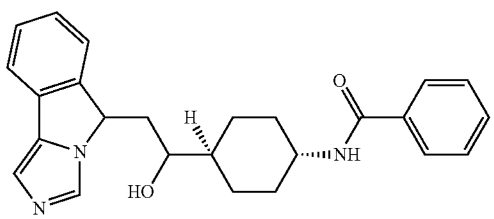 [SMILES: O=C(N[C@H]1CC[C@H](C(O)CC2c3ccccc3-c3cncn32)CC1)c1ccccc1] | N-((1r,4r)-4-(1-hydroxy-2-(5H-imidazo[5,1-a]isoindol-5-yl)ethyl)cyclohexyl)benzamide | A |
| 1506 | 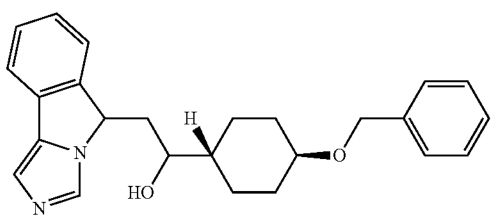 [SMILES: OC(CC1c2ccccc2-c2cncn21)[C@H]1CC[C@H](OCc2ccccc2)CC1] | 1-((1r,4r)-4-(benzyloxy)cyclohexyl)-2-(5H-imidazo[5,1-a]isoindol-5-yl)ethanol | A |
| 1507 | 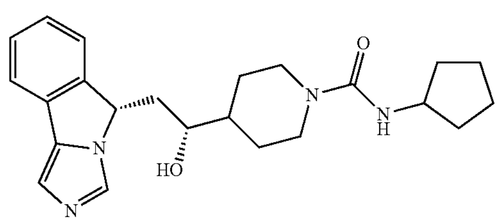 [SMILES: O=C(NC1CCCC1)N1CCC([C@H](O)C[C@H]2c3ccccc3-c3cncn32)CC1] | N-cyclopentyl-4-((R)-1-hydroxy-2-((S)-5H-imidazo[5,1-a]isoindol-5-yl)ethyl)piperidine-1-carboxamide | A |
| 1508 | 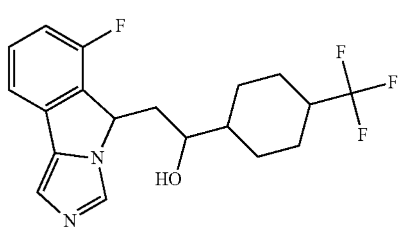 [SMILES: OC(CC1c2c(F)cccc2-c2cncn21)C1CCC(C(F)(F)F)CC1] | 2-(6-fluoro-5H-imidazo[5,1-a]isoindol-5-yl)-1-(4-(trifluoromethyl)cyclohexyl)ethanol | A |
| 1509 | 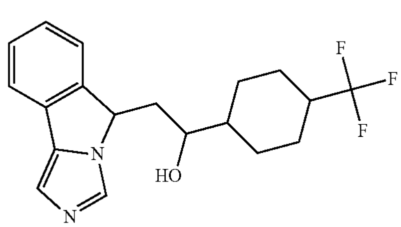 [SMILES: OC(CC1c2ccccc2-c2cncn21)C1CCC(C(F)(F)F)CC1] | 2-(5H-imidazo[5,1-a]isoindol-5-yl)-1-(4-(trifluoromethyl)cyclohexyl)ethanol | A |

| No. | Structure | Name | hIDO IC$_{50}$ |
|---|---|---|---|
| 1511 | 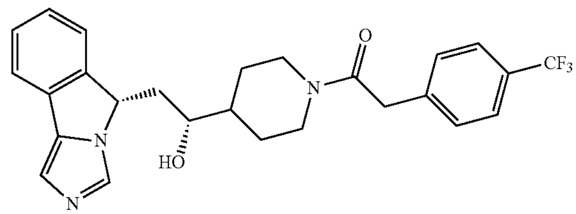 [SMILES: O=C(Cc1ccc(C(F)(F)F)cc1)N1CCC([C@H](O)C[C@H]2c3ccccc3-c3cncn32)CC1] | 1-(4-((R)-1-hydroxy-2-((S)-5H-imidazo[5,1-a]isoindol-5-yl)ethyl)piperidin-1-yl)-2-(4-(trifluoromethyl)phenyl)ethanone | A |
| 1512 | 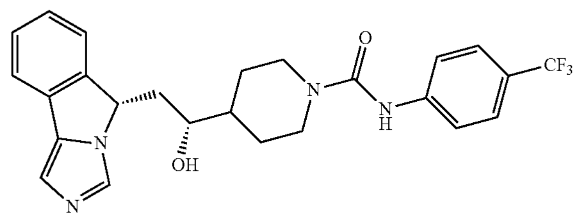 [SMILES: O=C(Nc1ccc(C(F)(F)F)cc1)N1CCC([C@H](O)C[C@H]2c3ccccc3-c3cncn32)CC1] | 4-((R)-1-hydroxy-2-((S)-5H-imidazo[5,1-a]isoindol-5-yl)ethyl)-N-(4-(trifluoromethyl)phenyl)piperidine-1-carboxamide | A |
| 1513 | 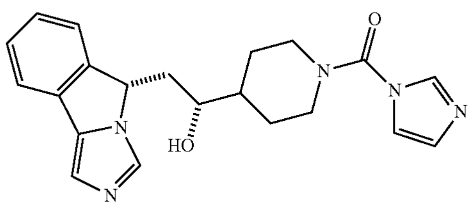 [SMILES: O=C(N1CCC([C@H](O)C[C@H]2c3ccccc3-c3cncn32)CC1)n1ccnc1] | (4-((R)-1-hydroxy-2-((S)-5H-imidazo[5,1-a]isoindol-5-yl)ethyl)piperidin-1-yl)(1H-imidazol-1-yl)methanone | |

Biological Example 6

In Vivo Testing of IDO Inhibitors for Antitumor Activity in Combination with Chemotherapeutic Agents In vivo anti-tumor efficacy can be tested using modified tumor allograft protocols. For instance, it has been described in the literature that IDO inhibition can syngerize with cytotoxic chemotherapy in immune-competent mice. Due to different susceptibilities of different tumor cell lines to chemotherapeutic drugs and to immune mediated rejection, each IDO inhibitor is tested alone and in combination with 2 different chemotherapeutic drugs in 4 different animal tumor models, represented by 4 different mouse tumor cell lines, of different tissue origin (colorectal, bladder, mammary and lung carcinoma), implanted subcutaneously in syngeneic strains of mice. These cell lines have been selected based on their known susceptibility to chemotherapeutic drugs, their partial response to IDO inhibitors as single agents, their presumed pattern of IDO expression according to their tissue of origin, and their ability to elicit an immune reaction.

For every animal tumor model, 2 different chemotherapeutic drugs are tested in separate groups of mice according to the following list: 1] LLC tumor: cyclophosphamide and paclitaxel; 2] EMT6 tumor: cyclophosphamide and paclitaxel; 3] CT26 tumor: cyclophosphamide and doxorubicin; and 4] MB49 tumor: cyclophosphamide and gemcitabine.

The following chemotherapeutic drugs are used, at the indicated doses. The maximum tolerated dose for the following chemotherapeutic agents in mice depends on the formulation, concentration, frequency of administration, route of administration and number of doses. The chemotherapeutic drugs administered in conjunction with each IDO inhibitor drug are: 1] Paclitaxel: 20 mg/kg/day i.p, every 4 days, 4 times (q4dx4) (in Cremophor); 2] Doxorubicin: 5 mg/kg, once a week for 3 weeks (q7dx3); 3] Cyclophosphamide (CTX): 100 mg/kg, I.P., every 4 days, 4 times (q4dx4); 4] Gemcitabine: 80 mg/kg every 4 days, 4 times, i.p. (q4dx4).

All animals receive a subcutaneous injection of a tumor forming dose of live tumor cells (~50000-1000000 cells) suspended in 0.1 mL of PBS or saline on day 1. Subcutaneous injection forms a localized tumor that allows monitoring tumor growth over time.

To mimic the effect of IDO inhibitor drugs as therapeutic compositions, administration of IDO inhibitor drugs begins at day 5-8 after tumor inoculation. Dosing, route of administration, dosing frequency varies depending on the toxicity and pharmacokinetics profile of each drug. Duration of the treatment is 2 weeks. Most preferably, drug is administered continuously via oral gavage or dissolution in the drinking water. Alternatively, subcutaneous slow release pellets or osmotic pumps containing 100 mg of each drug are implanted under the skin by surgical procedure. IDO inhibitor drug are administered at the maximum tolerated dose or at a concentration corresponding to the LD$_{50}$.

To test antitumor activity compounds 1357 and 1304, 200000 LLC murine tumor cells were injected subcutaneously into syngeneic C57B16 mice on day 0. Each treatement group consists of 10 mice. On day 7, once the tumor is established and IDO expression is induced in plasmacytoid dendritic cells at the tumor draining lymph nodes, a group of 10 mice were surgically implanted (subcutaneously and on the opposite flank to the tumor), with osmotic pumps loaded with 200 uL of a 30 mg/mL solution of compounds 1357 or 1304 in cremaphor:EtOH:saline (10:10:80). These pumps release 1 uL of solution per hour for a period of 8 days, achieveing a steady state plasma concentration of drug of ~0.5-3 micromolar. From days 15 to 24 compound administrations continued via two s.c. daily doses of 1 mg each. In the case of compound 1304, mice were optionally treated with cyclophosphamide 100 mg/kg by intraperitoneal injection on days 9, 13 and 15 post-tumor innoculation, either as a single agent or in combination with compound 1304. The results of these tests indicate that compounds 1357 and 1304 have a significant antitumor effect either as a single agent or when administered in combination with chemotherapy. The therapeutic effect is observed as a reduced rate of tumor growth, which has an impact on median survival time and in overall survival fraction.

The average tumor volume over time of two groups of 10 mice each was studied. The control group was treated with vehicle, while the treatment groups received osmotic pumps with compound 1357 as described above. The tumor volumes were fitted to an exponential growth equation and the fitted parameters were compared using GraphPad software. The data indicate a statistically significant differences between the two curves (p<0.0001).

A survival plot of the same groups of mice described immediately above was generated. The logrank test indicates a statistically significant difference in median survival time when animals were treated with compound 1357 as a single agent.

The average tumor volume over time of four groups of 10 mice each was studied. The control group was treated with vehicle, while the treatment groups received either cyclophosphamide chemotherapy, osmotic pumps with compound 1304, or a combination therapy of cyclophosphamide with compound 1304. The data shows that this tumor is very sensitive to the effects of treatment with compound 1304 either as a single agent or in combination with chemotherapy.

A survival plot of the same groups of mice described immediately above was generated. The logrank test indicated a statistically significant difference in median survival time when animals were treated with compound 1304, either as a single agent or in combination with cyclophosphamide. The long term survival fraction observed for treatment with 1304 is exceptionally high, with 70-80% of the mice being tumor free after 60 days.

We claim:
1. A compound of the formula,

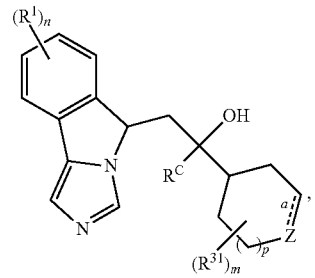

or a pharmaceutically acceptable salt thereof, wherein
bond a is a single bond or a double bond;
n is 0 or 1;
each $R^1$ is independently halogen, —OR, —N(R)$_2$, or —SR;
m is 0, 1, or 2;
p is 0 or 1;
when a is a single bond, then Z is —C($R^{36}$)$_2$— or —C(=$R^{32}$)—,
when a is a double bond, then Z is —C($R^{36}$)=;
each $R^{36}$ is independently hydrogen or $R^{31}$;
each $R^{31}$ is independently halogen, cyano, nitro, $C_{1-6}$alkyl, —$C_{1-6}$alkyl-$R^{33}$, $C_{1-6}$haloalkyl, —OR, —N(R)$_2$, —SR, —C(O)OR, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, —N(R)C(O)N(R)$_2$, wherein $R^{33}$ is —OR, —N(R)$_2$, or —SR;
$R^{32}$ is oxo, =C($R^{34}$)$_2$, =(spiro-$C_{3-8}$cycloalkyl), or =(spiro-(3-10 membered heterocyclyl)), wherein each $R^{34}$ is independently hydrogen, halogen, $C_{1-6}$alkyl, or $C_{3-8}$cycloalkyl;
$R^C$ is hydrogen or $C_{1-6}$alkyl; and
each R is independently hydrogen, $C_{1-6}$alkyl, $C_{1-6}$haloalkyl, phenyl, 5- or 6-membered heteroaryl, $C_{3-8}$cy-

SEQUENCE LISTING

<160> NUMBER OF SEQ ID NOS: 2

<210> SEQ ID NO 1
<211> LENGTH: 32
<212> TYPE: DNA
<213> ORGANISM: Artificial Sequence
<220> FEATURE:
<223> OTHER INFORMATION: Synthetic primer

<400> SEQUENCE: 1
ggagcatgct aatggcacac gctatggaaa ac                              32

<210> SEQ ID NO 2
<211> LENGTH: 31
<212> TYPE: DNA
<213> ORGANISM: Artificial Sequence
<220> FEATURE:
<223> OTHER INFORMATION: Synthetic primer

<400> SEQUENCE: 2
gagagatcta ccttccttca aagggattt c                                31 cloalkyl, C$_{3-8}$cycloalkenyl, 3-8 membered heterocyclyl, benzyl, (5- or 6-membered heteroaryl)C$_{1-6}$alkyl-, C$_{3-8}$cycloalkylC$_{1-6}$alkyl-, C$_{3-8}$cycloalkenylC$_{1-6}$alkyl-, or (3-8 membered heterocyclyl)C$_{1-6}$alkyl-.

2. The compound of claim 1, or a pharmaceutically acceptable salt thereof, wherein bond a is a single bond and Z is —C(R$^{36}$)$_2$—.

3. The compound of claim 1, or a pharmaceutically acceptable salt thereof, wherein
m is 0;
bond a is a single bond; and
each R$^{36}$ is independently hydrogen, halogen, C$_{1-6}$alkyl, —C$_{1-6}$alkyl-OH, C$_{1-6}$haloalkyl, or —OH, and
R$^{32}$ is oxo, =C(R$^{34}$)$_2$, =(spiro-C$_{3-8}$cycloalkyl), or =(spiro-(3-8 membered heterocyclyl)), wherein each R$^{34}$ is independently hydrogen, halogen, C$_{1-6}$alkyl, or C$_{3-8}$cycloalkyl.

4. The compound of claim 1, of the formula,

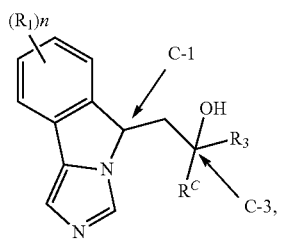

or a pharmaceutically acceptable salt thereof, wherein the stereoisomeric configuration of carbon-1 (C-1) and carbon-3 (C-3) are respectively (R, R), and wherein R$^3$ is

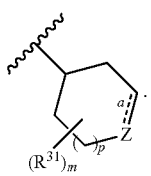

5. The compound of claim 1, of the formula,

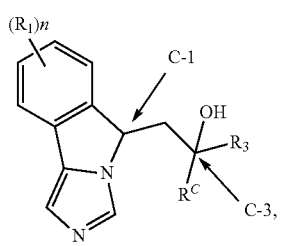

or a pharmaceutically acceptable salt thereof, wherein the stereoisomeric configuration of carbon-1 and carbon-3 are respectively (R, S), and wherein R$^3$ is

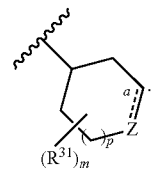

6. The compound of claim 1, of the formula,

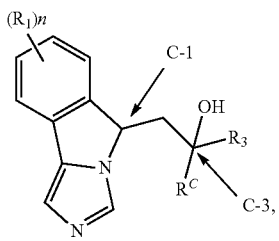

or a pharmaceutically acceptable salt thereof, wherein the stereoisomeric configuration of carbon-1 and carbon-3 are respectively (S, R), and wherein R$^3$ is

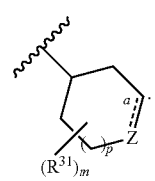

7. The compound of claim 1, of the formula,

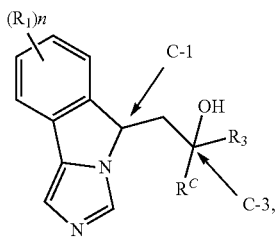

or a pharmaceutically acceptable salt thereof, wherein the stereoisomeric configuration of carbon-1 and carbon-3 are respectively (S, S), and wherein R$^3$ is

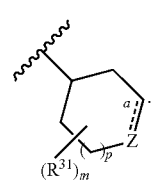

8. The compound of claim 1, of the formula,

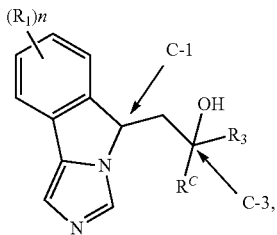

or a pharmaceutically acceptable salt thereof, wherein the stereoisomeric configuration of carbon-1 and carbon-3 are respectively (S, R) or (S,S), and wherein $R^3$ is cyclohexyl and $R^{31}$ is OR.

9. The compound of claim 8, or a pharmaceutically acceptable salt thereof, wherein the stereoisomeric configuration of carbon-1 and carbon-3 are respectively (S, R), and $R^1$ is fluoro or chloro.

10. The compound of claim 6, of the formula,

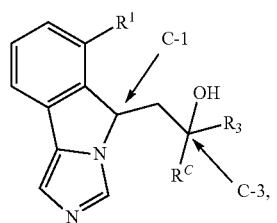

or a pharmaceutically acceptable salt thereof, wherein
the stereoisomeric configuration of carbon-1 and carbon-3 are respectively (S, R);
$R^1$ is fluoro or chloro;
$R^C$ is hydrogen;
a is a single bond;
m is 0;
p is 0 or 1;
Z is $—C(R^{36})_2—$;
each $R^{31}$ is independently halogen, $C_{1-6}$alkyl, $—C_{1-6}$alkyl-$R^{33}$, $C_{1-6}$haloalkyl, $—OR$, $—N(R)_2$, $—C(O)OR$, $—C(O)N(R)_2$, $—N(R)C(O)R$, wherein $R^{33}$ is $—OR$, or $—N(R)_2$; and
each R is independently hydrogen or $C_{1-6}$alkyl.

11. The compound of claim 1, that is
2-(6-chloro-5H-imidazo[5,1-a]isoindol-5-yl)-1-cyclohexylethanol;
1-cyclohexyl-2-(5H-imidazo[5,1-a]isoindol-5-yl)ethanol;
1-cyclohexyl-2-(6-fluoro-5H-imidazo[5,1-a]isoindol-5-yl)ethanol;
2-(7-chloro-5H-imidazo[5,1-a]isoindol-5-yl)-1-cyclohexylethanol;
1-cyclopentyl-2-(5H-imidazo[5,1-a]isoindol-5-yl)ethanol;
4-(2-(6-fluoro-5H-imidazo[5,1-a]isoindol-5-yl)-1-hydroxyethyl)cyclohexanol;
4-(2-(6-fluoro-5H-imidazo[5,1-a]isoindol-5-yl)-1-hydroxyethyl)cyclohexanone;
2-(6-fluoro-5H-imidazo[5,1-a]isoindol-5-yl)-1-(4-methylenecyclohexyl)ethanol;
1-(cyclohex-3-en-1-yl)-2-(5H-imidazo[5,1-a]isoindol-5-yl)ethanol;
1-(4-(hydroxymethyl)cyclohexyl)-2-(5H-imidazo[5,1-a]isoindol-5-yl)ethanol;
2-(5H-imidazo[5,1-a]isoindol-5-yl)-1-(4-methylenecyclohexyl)ethanol;
2-(6-fluoro-5H-imidazo[5,1-a]isoindol-5-yl)-1-(4-methylcyclohexyl)ethanol;
2-(6-fluoro-5H-imidazo[5,1-a]isoindol-5-yl)-1-(4-(iodomethylene)cyclohexyl)ethanol;
1-(4,4-difluorocyclohexyl)-2-(6-fluoro-5H-imidazo[5,1-a]isoindol-5-yl)ethanol;
1-(4,4-difluorocyclohexyl)-2-(5H-imidazo[5,1-a]isoindol-5-yl)ethanol;
1-(4-(cyclopropylmethylene)cyclohexyl)-2-(6-fluoro-5H-imidazo[5,1-a]isoindol-5-yl)ethanol;
2-(6-fluoro-5H-imidazo[5,1-a]isoindol-5-yl)-1-(4-(propan-2-ylidene)cyclohexyl)ethanol;
2-(9-fluoro-5H-imidazo[5,1-a]isoindol-5-yl)-1-(4-methylcyclohexyl)ethanol;
1-(cyclohex-3-en-1-yl)-2-(6-fluoro-5H-imidazo[5,1-a]isoindol-5-yl)ethanol;
(R)-1-cyclohexyl-2-((S)-5H-imidazo[5,1-a]isoindol-5-yl)ethanol;
(S)-1-cyclohexyl-2-((S)-5H-imidazo[5,1-a]isoindol-5-yl)ethanol;
cyclohexyl(4-(1-hydroxy-2-(5H-imidazo[5,1-a]isoindol-5-yl)ethyl)piperidin-1-yl)methanone;
methyl 4-(1-hydroxy-2-(5H-imidazo[5,1-a]isoindol-5-yl)ethyl) cyclohexanecarboxylate;
4-(1-hydroxy-2-(5H-imidazo[5,1-a]isoindol-5-yl)ethyl) cyclohexanol;
1-(4-(2-hydroxyethylidene)cyclohexyl)-2-(5H-imidazo[5,1-a]isoindol-5-yl)ethanol;
(1R,4s)-4-(2-((S)-6-fluoro-5H-imidazo[5,1-a]isoindol-5-yl)-1-hydroxyethyl) cyclohexyl benzoate;
(1R,4s)-4-(2-((S)-6-fluoro-5H-imidazo[5,1-a]isoindol-5-yl)-1-hydroxyethyl) cyclohexanol;
1-((1s,4s)-4-(benzyloxy)cyclohexyl)-2-(6-fluoro-5H-imidazo[5,1-a]isoindol-5-yl)ethanol;
(1r,4r)-4-(2-(6-fluoro-5H-imidazo[5,1-a]isoindol-5-yl)-1-hydroxyethyl)cyclohexanol;
(1S,4s)-4-((R)-2-((S)-6-fluoro-5H-imidazo[5,1-a]isoindol-5-yl)-1-hydroxyethyl)cyclohexanol;
(1R,4s)-4-((S)-2-((S)-6-fluoro-5H-imidazo[5,1-a]isoindol-5-yl)-1-hydroxyethyl)cyclohexanol;
(1S,4r)-4-((S)-2-((S)-6-fluoro-5H-imidazo[5,1-a]isoindol-5-yl)-1-hydroxyethyl)cyclohexanol;
(1R,4r)-4-((R)-2-((S)-6-fluoro-5H-imidazo[5,1-a]isoindol-5-yl)-1-hydroxyethyl)cyclohexanol;
N-((1s,4s)-4-(1-hydroxy-2-(5H-imidazo[5,1-a]isoindol-5-yl)ethyl)cyclohexyl)benzamide;
1-((1r,4r)-4-(benzyloxy)cyclohexyl)-2-(5H-imidazo[5,1-a]isoindol-5-yl)ethanol;
1-((1r,4r)-4-(benzyloxy)cyclohexyl)-2-(6-fluoro-5H-imidazo[5,1-a]isoindol-5-yl)ethanol;
N-((1r,4r)-4-(1-hydroxy-2-(5H-imidazo[5,1-a]isoindol-5-yl)ethyl)cyclohexyl)benzamide;
2-(6-fluoro-5H-imidazo[5,1-a]isoindol-5-yl)-1-(4-(trifluoromethyl)cyclohexyl)ethanol;
2-(5H-imidazo[5,1-a]isoindol-5-yl)-1-(4-(trifluoromethyl)cyclohexyl)ethanol;
or a pharmaceutically acceptable salt thereof.

12. A compound selected from the group consisting of
1-cyclohexyl-2-(5H-imidazo[5,1-a]isoindol-5-yl)ethanol;
(S)-1-cyclohexyl-2-((S)-5H-imidazo[5,1-a]isoindol-5-yl)ethanol;
(1R,4r)-4-((R)-2-((S)-6-fluoro-5H-imidazo[5,1-a]isoindol-5-yl)-1-hydroxyethyl)cyclohexanol;
or a pharmaceutically acceptable salt thereof.

13. A pharmaceutical composition comprising the compound of claim 1, or a pharmaceutically acceptable salt thereof, and a pharmaceutically acceptable diluent, excipient, or carrier.

14. A pharmaceutical composition comprising the compound of claim 9, or a pharmaceutically acceptable salt thereof, and a pharmaceutically acceptable diluent, excipient, or carrier.

15. A pharmaceutical composition comprising the compound of claim 10, or a pharmaceutically acceptable salt thereof, and a pharmaceutically acceptable diluent, excipient, or carrier.

16. A pharmaceutical composition comprising the compound of claim 11, or a pharmaceutically acceptable salt thereof, and a pharmaceutically acceptable diluent, excipient, or carrier.

17. A pharmaceutical composition comprising the compound of claim 12, or a pharmaceutically acceptable salt thereof, and a pharmaceutically acceptable diluent, excipient, or carrier.

18. A compound that is (S)-1-cyclohexyl-2((S)-5H-imidazo[5,1-a]isoindol-5-yl)ethanol, or a pharmaceutically acceptable salt thereof.

19. A compound that is (1R,4r)-4-((R)-2-((S)-6-fluoro-5H-imidazo[5,1-a]isoindol-5-yl)-1-hydroxyethyl)cyclohexanol, or a pharmaceutically acceptable salt thereof.

20. A pharmaceutical composition comprising the compound of claim 18, or a pharmaceutically acceptable salt thereof, and a pharmaceutically acceptable diluent, excipient, or carrier.

21. A pharmaceutical composition comprising the compound of claim 19, or a pharmaceutically acceptable salt thereof, and a pharmaceutically acceptable diluent, excipient, or carrier.

22. A compound that is a hydrochloric, phosphoric, hydrobromic, sulfuric, sulfinic, formic, toluenesulfonic, methanesulfonic, nitric, benzoic, citric, tartaric, maleic, hydroiodic, or acetic acid salt of (S)-1-cyclohexyl-2-((S)-5H-imidazo[5,1-a]isoindol-5-yl)ethanol.

23. A compound that is a phosphoric acid salt of (S)-1-cyclohexyl-2-((S)-5H-imidazo[5,1-a]isoindol-5-yl)ethanol.

24. A compound that is a hydrochloric, phosphoric, hydrobromic, sulfuric, sulfinic, formic, toluenesulfonic, methanesulfonic, nitric, benzoic, citric, tartaric, maleic, hydroiodic, or acetic acid salt of (1R,4r)-4-((R)-2-((S)-6-fluoro-5H-imidazo[5,1-a]isoindol-5-yl)-1-hydroxyethyl)cyclohexanol.

25. A compound that is a phosphoric acid salt of (1R,4r)-4-((R)-2-((S)-6-fluoro-5H-imidazo[5,1-a]isoindol-5-yl)-1-hydroxyethyl)cyclohexanol.

26. A pharmaceutical composition comprising the compound of claim 22 and a pharmaceutically acceptable diluent, excipient, or carrier.

27. A pharmaceutical composition comprising the compound of claim 23 and a pharmaceutically acceptable diluent, excipient, or carrier.

28. A pharmaceutical composition comprising the compound of claim 24 and a pharmaceutically acceptable diluent, excipient, or carrier.

29. A pharmaceutical composition comprising the compound of claim 25 and a pharmaceutically acceptable diluent, excipient, or carrier.

* * * * *